(12) United States Patent
Cook, II et al.

(10) Patent No.: US 7,863,291 B2
(45) Date of Patent: Jan. 4, 2011

(54) QUINUCLIDINE COMPOUNDS AS ALPHA-7 NICOTINIC ACETYLCHOLINE RECEPTOR LIGANDS

(75) Inventors: James H. Cook, II, East Hampton, CT (US); Ivar M. McDonald, East Haddam, CT (US); Dalton King, Hamden, CT (US); Richard E. Olson, Orange, CT (US); Nenghui Wang, Guilford, CT (US); Christiana I. Iwuagwu, Hamden, CT (US); F. Christopher Zusi, Hamden, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/423,299

(22) Filed: Apr. 14, 2009

(65) Prior Publication Data

US 2009/0270405 A1    Oct. 29, 2009

Related U.S. Application Data

(60) Provisional application No. 61/047,211, filed on Apr. 23, 2008.

(51) Int. Cl.
*A01N 43/90* (2006.01)
(52) U.S. Cl. .................. 514/305; 544/322; 544/356; 546/133; 546/143; 546/268.1; 548/216
(58) Field of Classification Search .............. 514/305; 544/322, 356; 546/133, 143, 268.1; 548/216
See application file for complete search history.

(56) References Cited

U.S. PATENT DOCUMENTS 5,053,412 A    10/1991    Fisher et al.

2007/0004715 A1    1/2007    Huang et al.

FOREIGN PATENT DOCUMENTS

| EP | 0 337 547 | 10/1989 |
|---|---|---|
| EP | 0 452 101 | 10/1991 |
| WO | WO 96/06098 | 2/1996 |
| WO | WO 03/092580 | 11/2003 |
| WO | WO 2005/005435 | 1/2005 |
| WO | WO 2006/065209 | 6/2006 |
| WO | WO 2008/000469 | 1/2008 |

OTHER PUBLICATIONS

Swain, C.J. et al., "Novel 5-HT$_3$ Antagonists: Indol-3-ylspiro(azabicycloalkane-3,5'(4'H)-oxazoles)", Journal of Medicinal Chemistry, vol. 35, No. 6, pp. 1019-1031 (1992).
Tatsumi, R. et al., "(R)-3'-(3-Methylbenzo[b]thiophen-5-yl)spiro[1-azabicyclo[2,2,2]octane-3,5'-oxazolidin]-2'-one, a Novel and Potent α7 Nicotinic Acetylcholine Receptor Partial Agonist Displays Cognitive Enhancing Properties", Journal of Medicinal Chemistry, vol. 49, No. 14, pp. 4374-4383 (2006).

*Primary Examiner*—James O Wilson
*Assistant Examiner*—Douglas M Willis
(74) *Attorney, Agent, or Firm*—James Epperson; Aldo A. Algieri

(57) ABSTRACT

The disclosure provides compounds of formula I, including their salts, as well as compositions and methods of using the compounds. The compounds are ligands for the nicotinic α7 receptor and may be useful for the treatment of various disorders of the central nervous system, especially affective and neurodegenerative disorders.

I

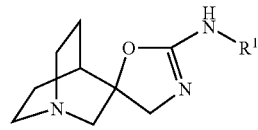

14 Claims, No Drawings

QUINUCLIDINE COMPOUNDS AS ALPHA-7 NICOTINIC ACETYLCHOLINE RECEPTOR LIGANDS

CROSS-REFERENCE TO RELATED APPLICATIONS

This patent application claims the benefit of U.S. provisional patent application No. 61/047,211 filed Apr. 23, 2008.

BACKGROUND OF THE INVENTION

The disclosure generally relates to compounds of formula I, including their salts, as well as compositions and methods of using the compounds. The compounds are ligands for the nicotinic α7 receptor and may be useful for the treatment of various disorders of the central nervous system, especially affective and neurodegenerative disorders.

Schizophrenia is a serious mental disorder, affecting approximately 1% of the population. Its progressive course results in major impairment of mental and social functioning and often leads to the development of other pathologies. Susceptibility often runs in families, with both genetic and environmental factors thought to be important. The direct and indirect costs of the disease are estimated in the tens of billion dollars annually in the U.S. alone.

Patients with schizophrenia have an elevated risk of suicide (approximately a 10% lifetime risk). They have a 2.5 fold increase in all-cause mortality, resulting in a 20% lowered life expectancy. The onset of illness can result in cascade of unhealthy lifestyle factors and behaviors that elevate the risk of various conditions and consequently the risk of death.

The onset of schizophrenia is most often in late adolescence or early adulthood, and episodes recur throughout life. The disease is characterized by the expression of three distinct symptom domains: positive, negative and cognitive. Psychotic or positive symptoms include delusions, hallucinations, thought disorder and paranoia. Negative symptoms include negative affect, social withdrawal, and anhedonia. Cognitive dysfunction includes deficits in attention, working memory and executive function. The pathophysiology of schizophrenia is not well understood, however, most experts believe it is a multi-factorial disorder in which biological, genetic and environmental factors play a role. Most current therapies target the dopaminergic system and have resulted in the suggestion that an excess of dopaminergic neurotransmission underlies at least some aspects of schizophrenia. This theory received further support from findings that drugs which increase the levels of dopamine cause psychoses similar to the positive symptoms of the disease. Also, post mortem analysis of brains from schizophrenic patients indicate increased numbers of D2 dopamine receptors. Although newer antipsychotic agents, known as atypical antipsychotics, which are active at several additional neurotransmitter receptors, have been introduced in the past decade, these agents still share efficacy against the D2 dopamine receptor. All currently-used agents also have major limitations. Although positive symptoms are generally reduced in a majority of patients, these drugs do little to relieve the negative symptoms and cognitive deficits that are common and often most debilitating. In addition, antipsychotic agents have a number of unwanted and limiting side effects.

Nicotine is among the few agents which have a positive effect on cognitive function. Many schizophrenics smoke; the rate in patients is 2-4 times that of the general population, and up to 90% in schizophrenics who have been institutionalized do smoke. This smoking habit has been characterized as a form of self-medication.

Alzheimer's disease is a progressive neurodegenerative disorder, resulting in the general loss of cognitive functions. The incidence increases with age, to the degree that 25-50% of all individuals over 85 are estimated to suffer from some degree of dementia. A diagnosis of Alzheimer's implies that the remaining life expectancy is reduced by half, compared to normal adults.

Clinical signs of Alzheimer's disease are progressive cognitive deterioration, decreased ability to perform the activities of daily living and neuropsychiatric symptoms or behavioral changes. In the advanced stages of the disease, deterioration of musculature and mobility may lead to inability to feed oneself, and eventually to the patient becoming bedridden. Language becomes severely disorganized, and then is lost altogether. Patients are not able to perform even simple tasks independently and require constant supervision. The cost of institutional care makes up nearly 70% of the cost of the disease. Therefore, therapies which increase cognitive function and delay institutionalization are greatly needed.

Nicotinic acetylcholine receptors (nAChR's) are pentameric ligand-gated ion channels which are widely expressed through the central and peripheral nervous system. These channels are fast-desensitizing calcium channels which, when open, increase the intracellular concentration of the $Ca^{++}$ ion. Although there are 12 individual receptors, the most abundant nicotinic receptors in the brain are α4β2 and α7. The α4β2 complex has been identified as the "high affinity" nicotine site. The homo-pentameric α7 receptor selectively binds the natural product, α-bungarotoxin, which has allowed its relatively facile localization and measurement. The α7 receptor is primarily expressed in the cortex, hippocampus and subcortical limbic regions and commonly occurs presynaptically. The localization of α7 nAChRs in areas involved with learning and memory has led to studies using both knockout mice and pharmacological manipulation. It is involved in sensory gating, memory, and neuronal plasticity. Compounds which selectively bind to the α7 receptor have been shown to improve learning and memory functions in normal and aged animals, reverse scopolamine-induced memory deficits, reverse pharmacologically-induced gating deficits, and to possess some anxiolytic properties. The α7 receptor has also been shown to be involved in the reduction of inflammation via the vagus nerve.

Alzheimer's disease has been shown in several studies to be accompanied by a reduction in nicotinic receptors in the cortex and hippocampus. Nicotine injections or nicotine skin patches have been reported to significantly improve attention, memory and learning in Alzheimer's disease patients. While there is a progressive loss of nicotinic receptors during the course of Alzheimer's disease, the α7 neurons are relatively spared, compared to the more abundant α4 receptors. Recently, the administration of selective nicotinic α7 agonists has been shown to increase cognitive functioning in Alzheimer's patients when dosed as long as 8 weeks.

The following references provide general reviews of the nicotinic receptor system and α7 receptors and ligands: Picciotto and Zoli, *J. Neurobio.* (2002) 53:641-655; Brening, et al, *Ann. Reports in Med. Chem.* (2005) 40:3-16; Dani and Bertrand, *Ann. Rev. Pharm. Tox.* (2007) 47:699-729; Olincy and Stevens, *Biochem. Pharmacol.* (2007) 74:1192-1201; Broad, et al, *Drugs Future* (2007) 32 (2):161-70; de Jonge and Ulloa, *Brit. J. Pharmacol.* (2007) 151:915-929; Romanelli, et al, *Chem Med Chem* (2007) 2(6):746-767.

Ligands for the nicotinic α7 receptor have been disclosed. See EP 452,101, EP 337,547, WO 2003/092580, WO 2004/000,469, US patent application publication 2007004715, and C. J. Swain, et al., *J. Med. Chem.*, (1992) 35:1019-1031.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds formula I, including pharmaceutically acceptable salts, and compositions and methods of treatment using these compounds. The compounds may be useful for the treatment of various disorders of the central nervous system:

One aspect of the invention is a compound of formula I, or a stereoisomer thereof,

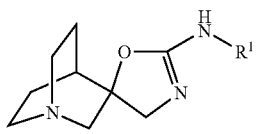

I wherein:

$R^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, quinoxalinyl, quinazolinyl, naphthyridinyl, indazolyl, indolyl, 2-indolonyl, benzisoxazolyl, benzoisothiazolyl, benzoxazolyl, benzothiazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, and tetrahydrobenzothiazolyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$;

$R^2$ is hydrogen, $C_{1-4}$alkyl, $C_{1-4}$hydroxyalkyl, or $C_{1-4}$aminoalkyl;

$R^3$ is hydrogen, $C_{1-4}$alkyl, $C_{1-4}$hydroxyalkyl, or $C_{1-4}$aminoalkyl;

or $R_2$ and $R_3$ taken together with the nitrogen atom to which they are attached is axetidinyl, pyrrolidinyl, piperidinyl, piperazinyl, N—($C_{1-4}$alkyl)piperazinyl, morpholinyl, or homopiperidinyl;

or a pharmaceutically acceptable salt thereof.

Another aspect of the invention is stereoisomer of formula I according to formula Ia.

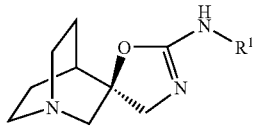

Ia

Another aspect of the invention is a compound of formula I or Ia where $R^1$ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, (pyrrolidinylCO)thiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, methoxypyridinylpyridazinyl, pyrimidinyl, (bromo)(isopropyl)pyrimidinyl, (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, and phenylpyrazinyl, and dimethyltriazinyl; or a pharmaceutically acceptable salt thereof.

Another aspect of the invention is a compound of formula I or Ia where $R^1$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, (pyrrolidinylCO)benzothiazolyl, methylsulfonylbenzothiazolyl, chlorothiazolopyridinyl, dimethylthiazolopyridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, chlorotriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy) thiazolopyrimidinyl, quinolinyl, bromoquinolinyl, fluoroquinolinyl, methylquinolinyl, (methyl)(methoxy) quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, and 7,8-dihydroquinazolin-5(6H)-onyl; or a pharmaceutically acceptable salt thereof.

Another aspect of the invention is a compound of formula I or Ia where $R^1$ is selected from the group consisting of phenylthiazolyl, (chloro)(methyl)pyridinyl, (bromo)(phenyl) pyrimidinyl, methoxypyrimidinyl, difluoromethoxypyrimidinyl, difluoroethoxypyrimidinyl, cyclopentoxypyrimidinyl, (methylphenyl)pyrimidinyl, (methoxyphenyl) pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinoinyl, and quinazolinyl or a pharmaceutically acceptable salt thereof.

Another aspect of the invention is a compound or formula I or Ia where $R^1$ is selected from the group consisting of thiazolyl, pyridinyl, pyridazinyl, pyrimidinyl, pyrazinyl, benzothiazolyl, thiazolopyridinyl, indazolyl, benzimidazolyl, isoquinoinyl, and quinazolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I or Ia where $R^1$ is selected from the group consisting of pyridinyl, pyrimidinyl, pyrazinyl, thiazolopyridinyl, and isoquinoinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound or formula I or Ia where $R^1$ is selected from the group consisting of pyridinyl and isoquinoinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$; or a pharmaceutically acceptable salt thereof.

Another aspect of the invention is a compound selected from the group consisting of

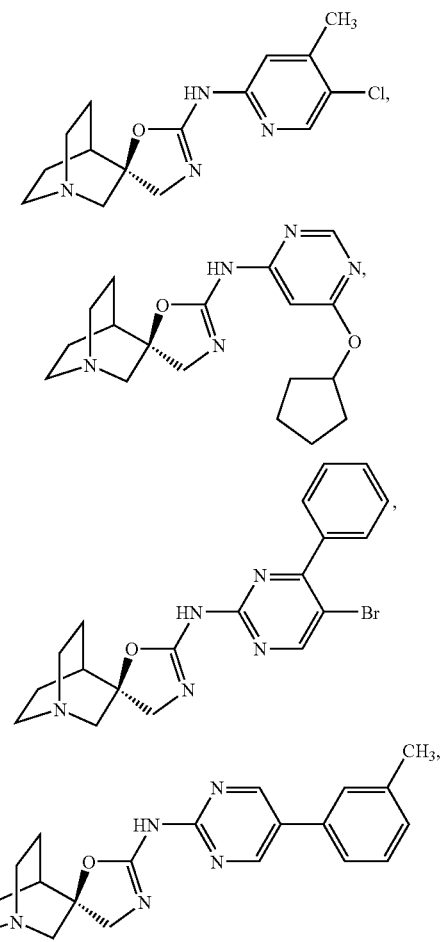

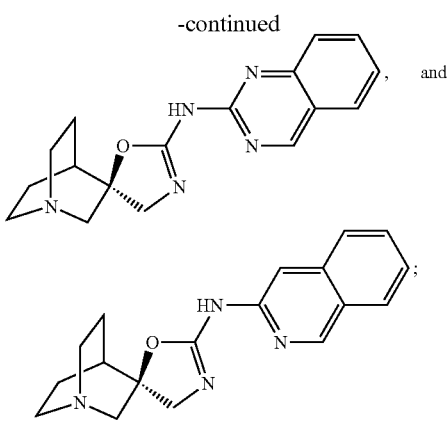

or a pharmaceutically acceptable salt thereof.

Another aspect of the invention is a compound of formula I where $R_1$ is selected from the group consisting of thiazole, thiadiazole, isoxazole, oxazole, pyrazole, imidazole, pyridine, pyrazine, pyridazine, pyrimidine, quinoline, isoquinoline, quinoxaline, indazole, indole, 2-indolone, benzothiazole, benzimidazole, benzoxazole, benzo(d)isothiazole, benzisoxazole, isothiazolo-[5,4-b]pyridine, (1,2,4)-triazolo[1,5-a]pyridine, thiazolo[5,4-b]pyridine and tetrahydrobenzothiazole in which each group is optionally substituted with one or two substituents selected from the group consisting of $C_{1-4}$alkyl, $C_{1-4}$alkoxy, halogen, hydroxy, cyano, trifluoromethyl, difluoromethyl, fluoromethyl, trifluoromethoxy, difluoromethoxy, $C_{1-4}$alkylsulfonyl, furyl, morpholino, methylenedioxy, pyridyl, $C_{1-4}$alkylphenyl, halophenyl, dimethylaminophenyl, $C_{1-4}$alkylamido, —$CONR_2R_3$ in which $R_2$ and $R_3$ each are independently hydrogen, $C_{1-4}$alkyl, hydroxy $C_{1-4}$alkyl, amino $C_{1-4}$alkyl or $R_2$ and $R_3$ taken together with the atom to which they are attached are $C_{3-6}$ cycloalkyl; phenyl, substituted phenyl, phenylmethyl, substituted phenylmethyl in which said substituted phenyl and substituted phenylmethyl are substituted with substituents independently selected from the group consisting of halogen, $C_{1-4}$alkyl, $C_{1-4}$alkoxy, trifluoromethyl and trifluromethoxy; or a pharmaceutically acceptable salt thereof.

For a compound of formula I or Ia, the scope of any instance of a variable substituent, including $R^1$, $R^2$, and $R^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 4 carbons. "Alkenyl" means a straight or branched alkyl group composed of 2 to 4 carbons with at least one double bond. "Alkynyl" means a straight or branched alkyl group composed of 2 to 4 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art.

The invention includes all tautomeric forms of the compounds. An example of a tautomeric pair is shown below.

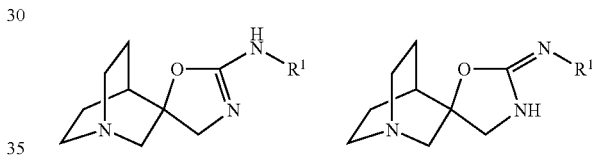

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Some of the compounds may be prepared using the reactions and techniques described in this section. The reactions are performed in solvents appropriate to the reagents and materials employed and are suitable for the transformations being effected. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Abbreviations used in the schemes generally follow conventions used in the art. Chemical abbreviations used in the specification and examples are defined as follows: "NaH-MDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "$Et_2O$" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

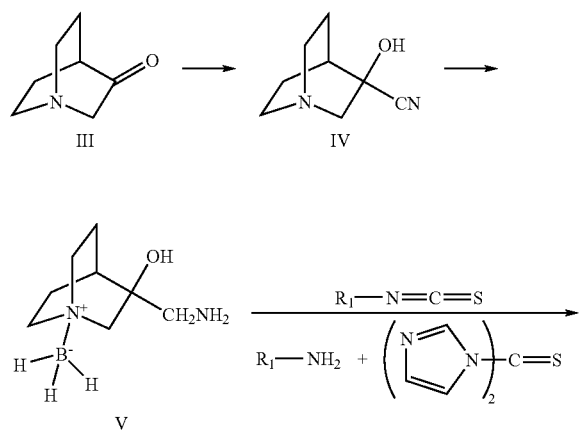

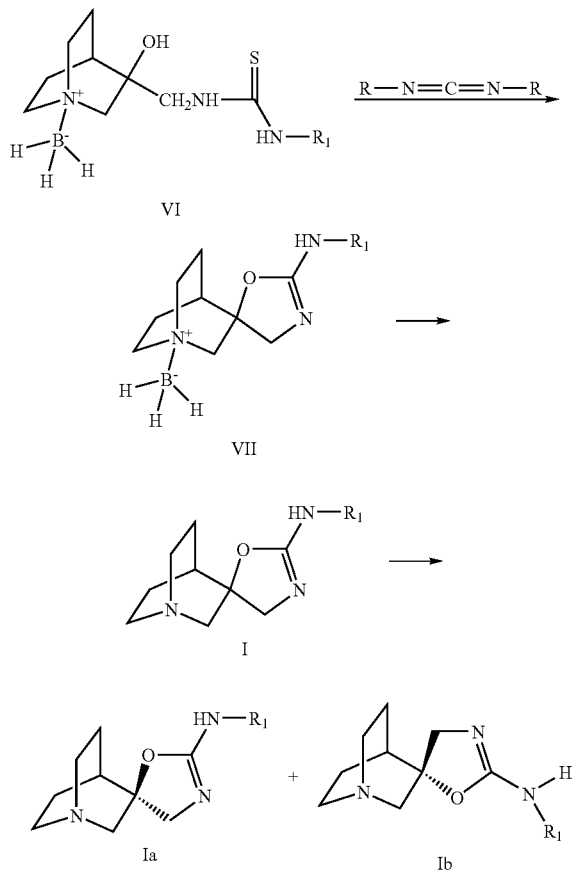

Compounds of Formula I are prepared as illustrated in Reaction Scheme 1. The ketone of Formula III (3-quinuclidone) is known, is commercially available, or may be prepared by methods known to those skilled in the art. The ketone can be converted to the corresponding cyanohydrin of Formula IV by reaction with sodium or potassium cyanide plus an acid. The compound of Formula IV can be reduced to the corresponding amino-methyl compound (borane complex) of Formula V by reaction with borane/tetrahydrofuran complex.

The compound of Formula V can be reacted with heteroaryl isothiocyanates directly in an inert solvent to give the thioureas of Formula VI. Alternatively, the heteroarylamine can be reacted with thiocarbonyl-diimidazole to give an activated species which can be used without isolation to convert the compound of Formula V to the compound of Formula VI. The heteroarylamine may be prepared by methods known to those skilled in the art.

The thiourea of Formula VI can be cyclized using, for example, di-isopropyl carbodiimide to give the oxazoline of Formula VII which may be deprotected via treatment with acid to give the racemic final product of the compound of Formula I. The compound of Formula I may be resolved into pure enantiomer compounds of Formula Ia and Formula Ib by means known in the art, for example, via chiral chromatography.

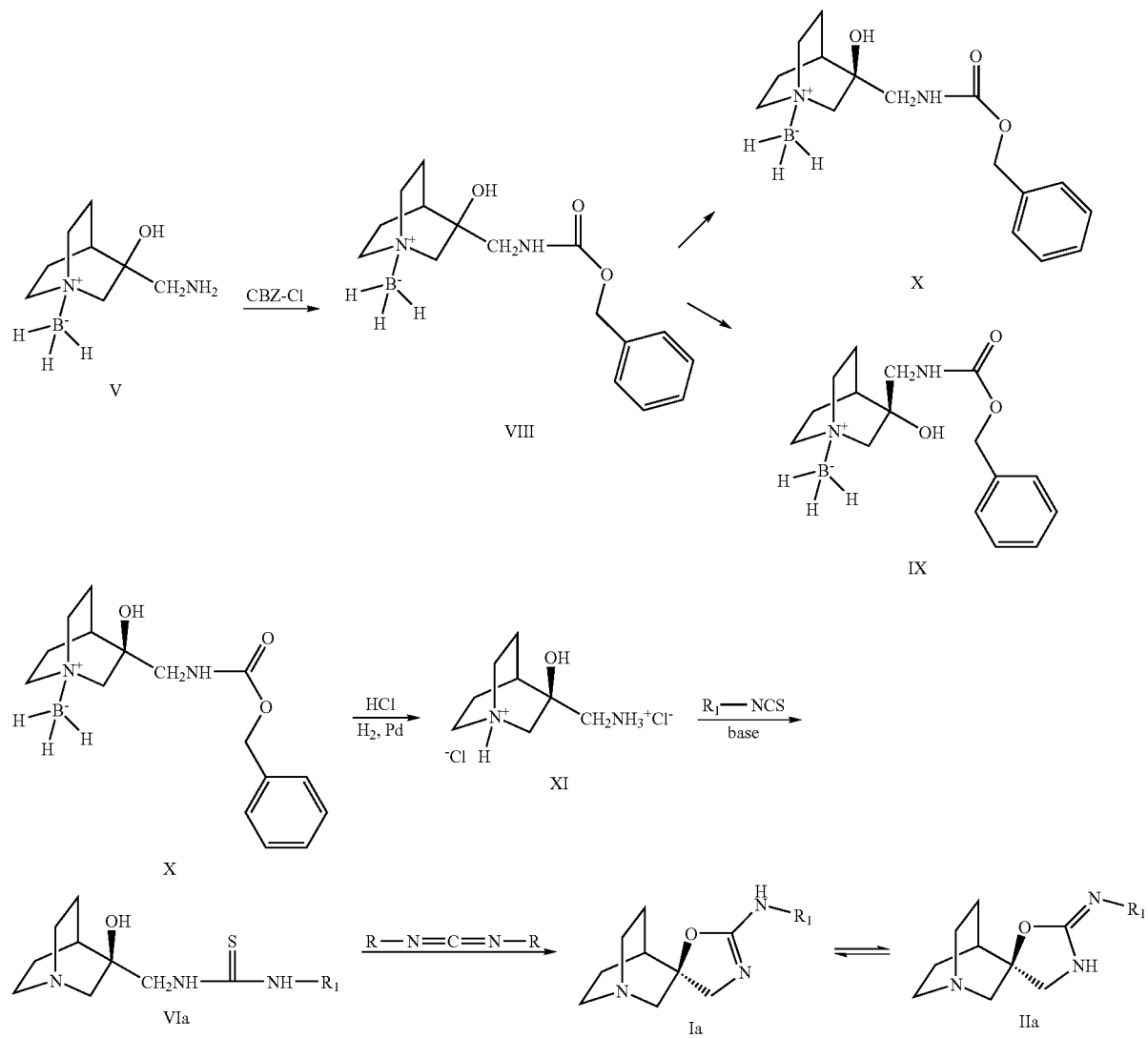

Scheme 2.

Alternatively, the free amino group of the quinuclidine of Formula V can be blocked with, for example, carbobenzyloxy-chloride ("CBZ-Cl") to give the compound of Formula VIII, as illustrated in Reaction Scheme 2.

The racemic compound of Formula VIII can be resolved into its enantiomers, Formula IX and Formula X by, for example, chiral chromatography. Either the compound of Formula IX or Formula X, and preferably the compound of Formula X, can then be carried on as shown in Reaction Scheme 2.

The borane group in the compound of Formula X can be removed, for example, by treatment with dilute hydrochloric acid, and the carbobenzyloxy group can be removed, for example, by catalytic hydrogenation to give the chiral quinuclidine amine of Formula XI. Similarly to Reaction Scheme 1, the amine salt of Formula XI can be reacted with isothiocyanates to give the thiourea of Formula VIa, which can then be reacted with dialkyl carbodiimides or mixed thioureas (as from reaction with thiocarbonyl diimidazole) to give the chiral oxazoline quinuclidine compounds of Formula Ia, and its tautomer, Formula IIa.

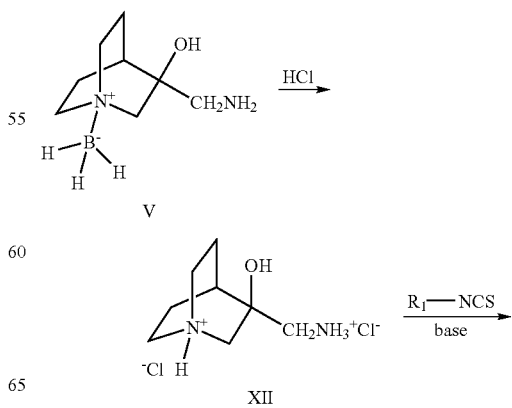

Scheme 2a.

-continued

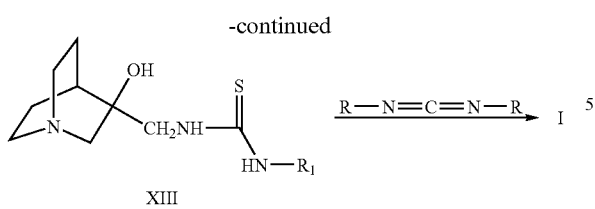

XIII

Alternatively, the borane group of V may be removed with hydrochloric acid to give dihydrochloride salt XII, which can be reacted in the presence of base with an isothiocyanate to give intermediate thiourea XIII, which can then be cyclized as in Reaction Schemes 1-2 to give I. XII may also be prepared by other methods, as referenced in U.S. Pat. No. 5,137,895 (Aug. 11, 1992).

Scheme 3.

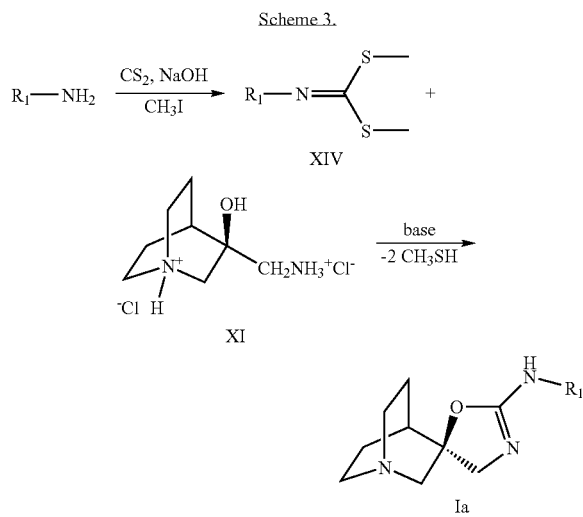

Additionally, the (hetero)aromatic amines may be reacted with carbon disulfide, sodium hydroxide, and methyl iodide to give intermediate dimethyl carbonimidodithioates XIV. These are reacted with dihydrochloride XI in the presence of base to eliminate two moles of methanethiol and generate desired products Ia directly.

Biological Methods

I) α7 Nicotinic Acetycholine Receptor Binding. Membranes were prepared for binding using HEK293 cells stably expressing the rat α7 nicotinic acetycholine receptor (rat α7 nAChR). Cells were homogenized at 4° C. in hypotonic lysis buffer consisting of 10 mM Tris (pH 7.4), 5 mM EDTA and protease inhibitors and centrifuged at 32000×g for 20 minutes. The pellet was washed once in membrane wash buffer consisting of 50 mM Tris (pH 7.4), 1 mM EDTA and protease inhibitors and centrifuged at 32000×g for 20 minutes. This pellet was then resuspended in assay buffer consisting 50 mM $KH_2PO_4$ (pH 7.4 at 25° C.), 1 mM EDTA, 0.005% Triton-X 100 and 0.1% (v/v) Sigma Protease Inhibitor Cocktail. Aliquots were then frozen in dry ice/ethanol and kept at −80° C. until the day of the assay.

II) A $Ca^{2+}$-Sensitive, Fluorescence-Based Assay α7 for Nicotinic Acetylcholine Receptor Channel Function In Mammalian Cells ("FLIPR"). Summary: Lead compounds are evaluated for agonist activity at α-7, α3β4, α4αβ2, and α1β1δ1ε sub-types of nicotinic ACh receptor ion channels expressed in mammalian HEK 293 cells. Agonist potency and efficacy values are determined from kinetic fluorescence $Ca^{2+}$ influx measurements made using a 384 well FLIPR (Fluorescence Image Plate Reader). The utility of fluorescent indicators for measuring changes in intracellular divalent cation concentrations, particularly $Ca^{2+}$, for drug discovery endeavors is well documented (Rudiger, R., et al., Nature Reviews, 2003, 4:579-586; Gonzalez J. E., et al., Receptors and Channels, 2002, 8:283-295). In this assay, channel expressing HEK cell lines seeded in 384 well assay plates are loaded with a membrane permeant fluorescent $Ca^{2+}$ indicator dye, whose 510 nm green emission signal increases in response to elevation of intracellular $Ca^{2+}$ concentration. The basal fluorescence from the cells is monitored in real time, followed by the acute addition of test compounds. If the compound is an agonist at any of the non-selective cation channels, the latter open and allow the movement of extracellular $Ca^{2+}$ ions into the cell cytoplasm, where they bind to the $Ca^{2+}$ indicator dye, and produce an increase in fluorescence output signal, which is detected by a cooled CCD imaging camera.

Materials and Methods: Reagents: The acetomethoxy (AM) ester of the $Ca^{2+}$ indicator dye Fluo-4 was obtained from InVitrogen, (Carlsbad, Calif.). Acetylcholine and all buffer constituents were purchased from Sigma Chemical Company, St. Louis, Mo. G418 and Minimal Essential Medium were purchased from InVitrogen Life Technologies, Carlsbad, Calif. Fetal bovine serum was purchased from (InVitrogen, Carlsbad, Calif.).

Cell Culture: HEK-293 cells were grown in Minimal Essential Medium containing 10% (v/v) fetal bovine serum at 37° C. in a 5% $CO_2$ incubator. HEK-293 cells stably expressing the ion channels were grown in the same medium with the addition of 500 μg/ml G418.

$Ca^{2+}$ flux assays of $Ca^{2+}$ channels expressed in HEK-293 cells: HEK-293 cells expressing the ion channels of interest were plated in 384 well, black-walled, clear-bottomed, poly-D-lysine coated plates at a density of ~20,000 cells/well in 20 μl of Minimal Essential Medium containing 10% (v/v) fetal bovine serum and incubated for 2 days at 29° C. in a 5% $CO_2$ incubator. Prior to assay, cells were loaded with the Fluo-4 AM ester. Cell loading was accomplished by removing the culture medium and replacing it with 30 μl/well of the AM ester of the dye (5 μM) mixed with Hanks Balanced Salt Solution (#14175-095) containing 20 mM HEPES, 2.5 mM probenecid, 0.5 mM $CaCl_2$, 1 mM MgCl2 and 10 μM atropine. Dye loading was allowed to proceed for 90 minutes at room temperature at which time the dye loading solution was removed and replaced with 40 μl/well of Hanks buffer. Cells loaded with dye were loaded onto a FLIPR384 (Molecular Devices, Sunnyvale, Calif.). Fluo-4 dye was excited using the 488 nm line of an argon laser. Emission was filtered using a 540+/−30 nm bandpass filter. For evaluation of the effects of test compounds using the $Ca^{2+}$ flux assay, compounds to be tested were provided in assay ready plates. For nicotinic receptor ion channel expressing cells, the assay was initiated by the addition of 20 μl/well of Hanks buffer containing test compounds. For all assays, data were collected at 1 Hz for 10 seconds (baseline), at which time the compound containing stimulus buffers are added, and further measurements collected at 0.33 Hz for 3 min.

Data Analysis: The statistical robustness of the nicotinic receptor $Ca^{2+}$ flux assays is determined from blanks and totals wells. The totals wells define maximal channel activation for each compound test plate (Maximum efficacious dose of acetylcholine), and the blanks wells which contain matched DMSO only, define zero channel activation. The raw fluorescence units data files generated on the FLIPR plate reader are automatically exported and processed by in-house data analysis tools. The reduced percent activation data for each concentration of test compound are fit using MathIQ fitting engine (ID Business Solutions Limited, Surrey, UK). Data were analyzed by fitting maximum amplitudes of change in fluorescence, for $Ca^{2+}$ flux for a given condition of test compound. Potencies ($EC_{50}$ values) of compounds are calculated from the average of three assay wells from a twenty point CRC. Test compound efficacy values (Ymax values) are expressed relative to a maximal response to acetylcholine in the total wells.

III) Fos quantification assay: Male Wistar rats are treated with drug (1-10 mg/kg) or vehicle (2 ml/kg, sc). Two hours after treatments, the rats are rapidly decapitated and discrete brain regions of interest are isolated on ice and weighed and flash frozen with liquid nitrogen and stored at −80 deg. C. Further processing of the brain tissue for nuclear extracts as well as for Fos quantification are in accordance with the protocol prescribed by a commercially available ELISA-based chemiluminiscence detection kit (catalog #89860, EZ-detect c-Fos Trans kit, Pierce Biotechnology Inc., Rockford, Ill.).

IV) MK-801 Disrupted Set-Shift Assay in rats: This assay uses a modification of the protocol described by Stefani et al. (*Behavioral Neuroscience*, 2003, 117: 728-737). Test compounds are assessed for their ability to reverse an MK-801-induced performance deficit (0.03 mg/kg, i.p., single dose) in this assay.

The activity of specific compounds described herein and tested in the above assay (II) is provided in Table 1.

TABLE 1

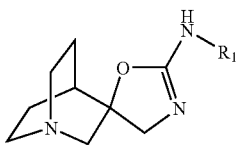

| Example Number | $R_1$ | FLIPR α7-HI ($EC_{50}$, nM) | FLIPR α7-HI ($EC_{50}$, nM) |
|---|---|---|---|
| 1 | 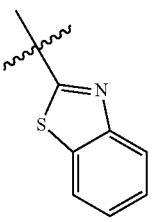 | | +++ |
| 1a | 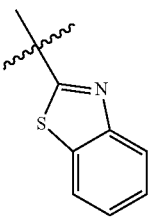 | | + |
| 1b | 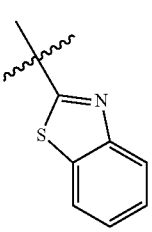 | | +++ |
| 2 | 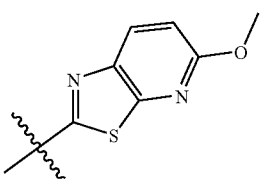 | | ++ |

TABLE 1-continued

| Example Number | R₁ | FLIPR α7-HI (EC₅₀, nM) | FLIPR α7-HI (EC₅₀, nM) |
|---|---|---|---|
| 2a | 5-methoxy-thiazolo[5,4-b]pyridin-2-yl | | + |
| 2b | 5-methoxy-thiazolo[4,5-b]pyridin-2-yl | | ++ |
| 3 | 6-(pyrrolidin-1-ylcarbonyl)benzothiazol-2-yl | 3840 | + |
| 4 | 5-phenylthiazol-2-yl | | +++ |
| 4a | 5-phenylthiazol-2-yl | | + |

TABLE 1-continued
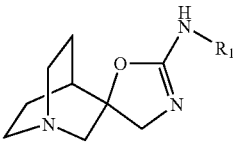
| Example Number | R₁ | FLIPR α7-HI (EC₅₀, nM) | FLIPR α7-HI (EC₅₀, nM) |
|---|---|---|---|
| 4b | 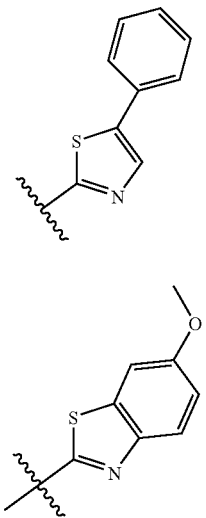 | 230 | ++ |
| 5 | 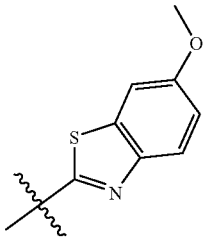 |  | ++ |
| 5a | 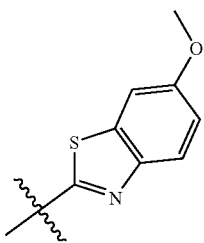 |  | + |
| 5b | 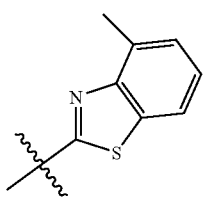 |  | +++ |
| 6 |  |  | ++ |

TABLE 1-continued

| Example Number | R₁ | FLIPR α7-HI (EC₅₀, nM) | FLIPR α7-HI (EC₅₀, nM) |
|---|---|---|---|
| 6a | 4-methylbenzothiazol-2-yl | 4340 | + |
| 6b | 4-methylbenzothiazol-2-yl | | +++ |
| 7 | 4-chlorobenzothiazol-2-yl | | ++ |
| 7a | 4-chlorobenzothiazol-2-yl | | + |
| 7b | 4-chlorobenzothiazol-2-yl | | +++ |
| 8 | 1H-benzimidazol-2-yl | | ++ |

TABLE 1-continued

| Example Number | R₁ | FLIPR α7-HI (EC$_{50}$, nM) | FLIPR α7-HI (EC$_{50}$, nM) |
|---|---|---|---|
| 8a | benzimidazol-2-yl (NH) | 120 | ++ |
| 8b | benzimidazol-2-yl (NH) | | + |
| 9 | 6-chlorobenzothiazol-2-yl | | ++ |
| 9a | 6-chlorobenzothiazol-2-yl | 7315 | + |
| 9b | 6-chlorobenzothiazol-2-yl | | +++ |
| 10 | 1-methylbenzimidazol-2-yl | | ++ |
| 10a | 1-methylbenzimidazol-2-yl | | ++ |

TABLE 1-continued
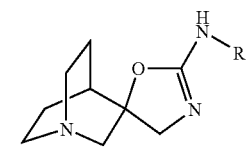
| Example Number | R$_1$ | FLIPR α7-HI (EC$_{50}$, nM) | FLIPR α7-HI (EC$_{50}$, nM) |
|---|---|---|---|
| 10b | 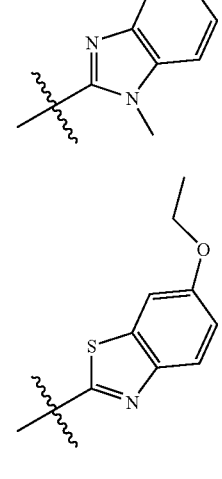 | | ++ |
| 11 | 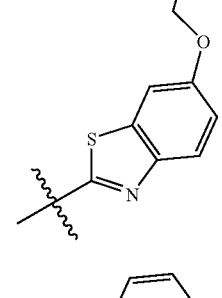 | | ++ |
| 11b | 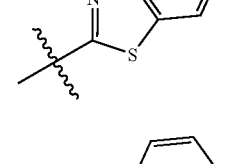 | 213 | ++ |
| 12 | 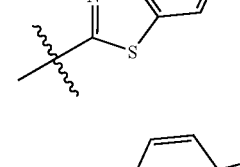 | | ++ |
| 12a | | | ++ |
| 12b | 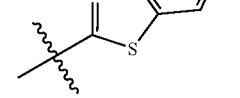 | | + |

TABLE 1-continued
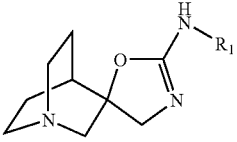
| Example Number | R$_1$ | FLIPR α7-HI (EC$_{50}$, nM) | FLIPR α7-HI (EC$_{50}$, nM) |
|---|---|---|---|
| 13 | 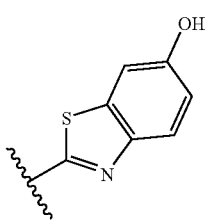 | | +++ |
| 13a | 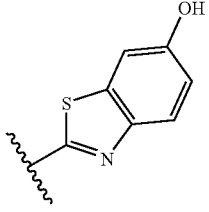 | | ++ |
| 13b | 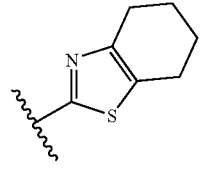 | | +++ |
| 14 | 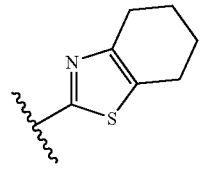 | | ++ |
| 14b | 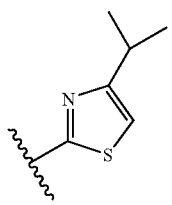 | | ++ |
| 15 | | | ++ |

TABLE 1-continued

| Example Number | R₁ | FLIPR α7-HI (EC$_{50}$, nM) | FLIPR α7-HI (EC$_{50}$, nM) |
|---|---|---|---|
| 15a | 4-isopropyl-thiazol-2-yl | 6345 | + |
| 15b | 4-isopropyl-thiazol-2-yl | | ++ |
| 16 | 2-thiazolyl (methyl) | | ++ |
| 16a | 2-thiazolyl | 3174 | + |
| 16b | 2-thiazolyl (methyl) | | ++ |
| 17 | 4-(4-methoxyphenyl)-5-methyl-thiazol-2-yl | | ++ |
| 18 | pyridin-3-yl | 3930 | + |
| 19 | pyridin-2-yl | | ++ |

TABLE 1-continued
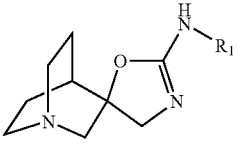
| Example Number | R₁ | FLIPR α7-HI (EC₅₀, nM) | FLIPR α7-HI (EC₅₀, nM) |
|---|---|---|---|
| 20 | 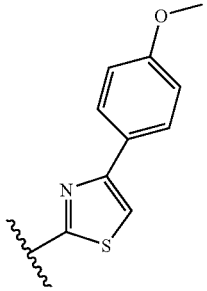 | | ++ |
| 20a | 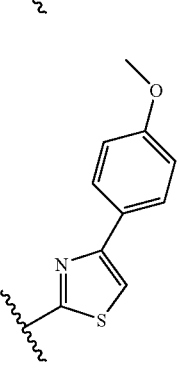 | | ++ |
| 20b | 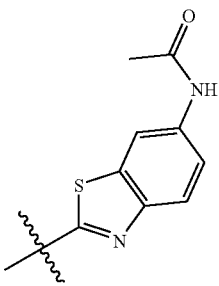 | 318 | ++ |
| 21 |  | | +++ |

TABLE 1-continued

[Structure shown at top of table]

| Example Number | R₁ | FLIPR α7-HI (EC₅₀, nM) | FLIPR α7-HI (EC₅₀, nM) |
|---|---|---|---|
| 22 | benzothiazole with OCHF₂ substituent | | ++ |
| 23 | methoxy-pyrimidine | | +++ |
| 24 | methoxy-[1,2,4]triazolo[1,5-a]pyridine | | +++ |
| 25 | pyrazine-CF₃ | 510 | ++ |
| 26 | 6-fluoro-1H-indazol-3-yl | | +++ |
| 27 | furo[3,2-c]pyridine | | +++ |
| 28 | 5-phenylpyridin-3-yl | 4010 | + |

TABLE 1-continued

| Example Number | R₁ | FLIPR α7-HI (EC$_{50}$, nM) | FLIPR α7-HI (EC$_{50}$, nM) |
|---|---|---|---|
| 29 | (4-phenylpyridin-2-yl) | | ++ |
| 30 | (6-phenylpyridin-2-yl) | | ++ |
| 31 | (6-(difluoromethoxy)-1-methyl-1H-indazol-3-yl) | | ++ |
| 32 | (5-(difluoromethoxy)thiazolo[5,4-b]pyridin-2-yl) | | ++ |
| 34 | (6-(pyrrolidin-1-yl)pyrazin-2-yl) | | + |
| 35 | (6-(2-oxopyrrolidin-1-yl)pyrazin-2-yl) | 4035 | + |
| 36 | (6-(pyridin-3-yl)pyrazin-2-yl) | | ++ |
| 37 | (6-(6-methoxypyridin-3-yl)pyrazin-2-yl) | | + |

TABLE 1-continued

| Example Number | R₁ | FLIPR α7-HI (EC₅₀, nM) | FLIPR α7-HI (EC₅₀, nM) |
|---|---|---|---|
| 38 | methoxyquinoxalin-2-yl | | +++ |
| 39 | 5-(difluoromethoxy)pyrimidin-2-yl | | +++ |
| 40 | 4,5-dimethylpyrimidin-2-yl | | +++ |
| 41 | 6-phenylpyrimidin-4-yl | | +++ |
| 42 | 6-(4-methoxyphenyl)pyrimidin-4-yl | | +++ |
| 43 | 6-(6-methoxypyridin-3-yl)pyrimidin-4-yl | | +++ |

TABLE 1-continued

| Example Number | R₁ | FLIPR α7-HI (EC₅₀, nM) | FLIPR α7-HI (EC₅₀, nM) |
|---|---|---|---|
| 44 | naphthyl-pyrimidine | | ++ |
| 45 | 4-phenylthiazole | | ++ |
| 46 | 6-morpholinobenzothiazole | 2000 | + |
| 47 | 6-fluorobenzothiazole | | +++ |
| 48 | 6-trifluoromethylbenzothiazole | 790 | ++ |
| 49 | 6-trifluoromethoxybenzothiazole | 3330 | + |

TABLE 1-continued

| Example Number | R₁ | FLIPR α7-HI (EC₅₀, nM) | FLIPR α7-HI (EC₅₀, nM) |
|---|---|---|---|
| 50 | 7-fluoro-benzothiazol-2-yl | | +++ |
| 51 | 6-fluoro-benzothiazol-2-yl | | NT[b] |
| 52 | 5,6-difluoro-benzothiazol-2-yl | 325 | ++ |
| 53 | 6-methoxy-benzothiazol-2-yl | | + |
| 54 | 7-methoxy-benzothiazol-2-yl | | + |
| 55 | 5,6-dimethoxy-benzothiazol-2-yl | | + |

TABLE 1-continued

| Example Number | R₁ | FLIPR α7-HI (EC₅₀, nM) | FLIPR α7-HI (EC₅₀, nM) |
|---|---|---|---|
| 56 | 5-phenyl-1,3,4-thiadiazol-2-yl | | + |
| 57 | N,N-dimethylbenzothiazole-6-carboxamide-2-yl | 3900 | + |
| 58 | 6-(piperidine-1-carbonyl)benzothiazol-2-yl | | + |
| 59 | 5-(4-fluorophenyl)-1,3,4-thiadiazol-2-yl | 4240 | + |
| 60 | 5-(furan-2-yl)-1,3,4-thiadiazol-2-yl | 2550 | + |
| 61 | 6-bromobenzothiazol-2-yl | | ++ |

TABLE 1-continued

| Example Number | R₁ | FLIPR α7-HI (EC$_{50}$, nM) | FLIPR α7-HI (EC$_{50}$, nM) |
|---|---|---|---|
| 62 | 6-(methylsulfonyl)benzothiazol-2-yl | | + |
| 63 | 2-methylbenzothiazol-5-yl | 2600 | + |
| 64 | 5-bromothiazol-2-yl | | +++ |
| 65 | 6-chloro-5-methoxybenzothiazol-2-yl | | + |
| 66 | 6-chloro-[1,2,4]triazolo[1,5-a]pyridin-2-yl | 360 | ++ |
| 67 | 3,5-dimethylisoxazol-4-yl | | + |
| 68 | 1,4-dimethyl-1H-pyrazol-5-yl | | + |

TABLE 1-continued

| Example Number | R₁ | FLIPR α7-HI (EC₅₀, nM) | FLIPR α7-HI (EC₅₀, nM) |
|---|---|---|---|
| 70 | (benzothiazole-CN) | | ++ |
| 71 | (benzothiazole) | | + |
| 72 | (benzothiazole) | | + |
| 73 | (quinoline) | 7550 | + |
| 74 | (methyl-triazolopyridine) | | +++ |
| 75 | (quinoxaline) | | + |
| 76 | (methoxy-benzimidazole) | | ++ |

TABLE 1-continued

| Example Number | R₁ | FLIPR α7-HI (EC₅₀, nM) | FLIPR α7-HI (EC₅₀, nM) |
|---|---|---|---|
| 77 | 6-fluoro-1H-benzimidazol-2-yl | 355 | ++ |
| 78 | 1H-indazol-6-yl | | + |
| 81 | 2-(4-ethylphenyl)-1,3-benzoxazol-6-yl | | NT[b] |
| 82 | 2-[4-(dimethylamino)phenyl]-1,3-benzoxazol-6-yl | | NT[b] |
| 83 | 6-(trifluoromethyl)-[1,2,4]triazolo[1,5-a]pyridin-2-yl | 240 | ++ |
| 85 | quinolin-6-yl | | + |
| 86 | 2-oxo-2,3-dihydro-1H-indol-5-yl | | + |
| 87 | [1,2,4]triazolo[1,5-a]pyridin-2-yl | | +++ |

TABLE 1-continued

| Example Number | R₁ | FLIPR α7-HI (EC$_{50}$, nM) | FLIPR α7-HI (EC$_{50}$, nM) |
|---|---|---|---|
| 88 | (2-pyridyl-thiazol-2-yl) | | ++ |
| 89 | (4,6-dimethyl-benzothiazol-2-yl) | | +++ |
| 90 | (6-acetamido-benzothiazol-2-yl) | 130 | ++ |
| 91 | (6-ethyl-benzothiazol-2-yl) | | ++ |
| 92 | (5-methyl-thiazol-2-yl) | | +++ |
| 93 | (5-(pyrrolidine-1-carbonyl)-thiazol-2-yl) | | ++ |

TABLE 1-continued

| Example Number | R₁ | FLIPR α7-HI (EC₅₀, nM) | FLIPR α7-HI (EC₅₀, nM) |
|---|---|---|---|
| 94 | (6-methyl-[1,2,4]triazolo[1,5-a]pyridin-2-yl) | | +++ |
| 95 | (pyrazin-2-yl) | | ++ |
| 96 | (1-methyl-5-phenyl-1H-imidazol-2-yl) | | + |
| 97 | (8-methyl-[1,2,4]triazolo[1,5-a]pyridin-2-yl) | | ++ |
| 98 | (4-methyl-5-(N,N-dimethylcarbamoyl)thiazol-2-yl) | | + |
| 99 | (4-methoxypyrimidin-2-yl) | | ++ |
| 100 | (5-methoxypyrimidin-2-yl) | | +++ |
| 101 | (pyrimidin-2-yl) | | ++ |

TABLE 1-continued

| Example Number | R₁ | FLIPR α7-HI (EC₅₀, nM) | FLIPR α7-HI (EC₅₀, nM) |
|---|---|---|---|
| 102 | 7,4-dimethyl-benzothiazol-2-yl | | +++ |
| 103 | 6-methyl-4-chloro-benzothiazol-2-yl | 280 | ++ |
| 104 | 6-(difluoromethoxy)-benzothiazol-2-yl | | ++ |
| 105 | 5-benzyl-thiazol-2-yl | | ++ |
| 106 | 5-methyl-pyrazin-2-yl | | ++ |
| 107 | 5-bromo-pyrazin-2-yl | | ++ |

TABLE 1-continued

| Example Number | R₁ | FLIPR α7-HI (EC₅₀, nM) | FLIPR α7-HI (EC₅₀, nM) |
|---|---|---|---|
| 108 | 4-chlorophenyl-thiazolyl | | NT[b] |
| 109 | 4-methyl-thiazolyl | | ++ |
| 110 | 4-tert-butyl-thiazolyl | 450 | ++ |
| 111 | 5-(4-methoxybenzyl)-thiazolyl | | ++ |
| 112 | 7-methoxy-4-methyl-benzothiazolyl | | +++ |
| 113 | 1H-indazol-3-yl | | +++ |

TABLE 1-continued

| Example Number | R₁ | FLIPR α7-HI (EC₅₀, nM) | FLIPR α7-HI (EC₅₀, nM) |
|---|---|---|---|
| 114 | | | ++ |
| 115 | | | + |
| 116 | | | + |
| 117 | | | ++ |
| 118 | | | + |
| 119 | | | +++ |
| 120 | | 875 | ++ |
| 121 | | | + |

TABLE 1-continued

| Example Number | R₁ | FLIPR α7-HI (EC₅₀, nM) | FLIPR α7-HI (EC₅₀, nM) |
|---|---|---|---|
| 122 | isoquinolin-3-yl | | +++ |
| 123 | 2,6-dimethylpyrimidin-4-yl | | + |
| 124 | 6-methylpyridazin-3-yl | | + |
| 125 | 7-methoxy-[1,2,4]triazolo[1,5-a]pyridin-2-yl | 17 | +++ |
| 126 | pyrimidin-2-yl | | +++ |
| 127 | 6-chloropyrazin-2-yl | | + |
| 128 | 5-chloropyrazin-2-yl | | +++ |
| 129 | 4-(4-methoxyphenyl)-5-methylthiazol-2-yl | | ++ |
| 130 | 5-bromo-3-methoxypyrazin-2-yl | | ++ |

TABLE 1-continued
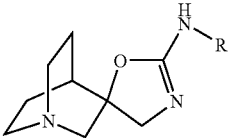
| Example Number | R₁ | FLIPR α7-HI (EC₅₀, nM) | FLIPR α7-HI (EC₅₀, nM) |
|---|---|---|---|
| 131 | 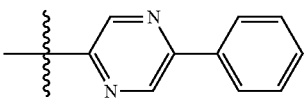 | | + |
| 132 | 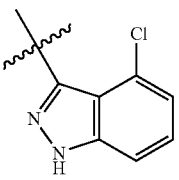 | | ++ |
| 133 | 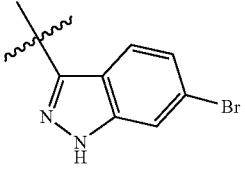 | | +++ |
| 134 | 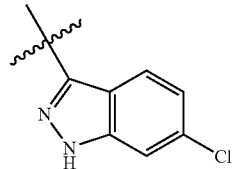 | | +++ |
| 135 | 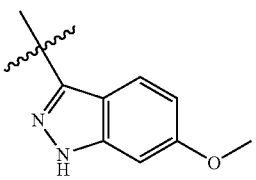 | | +++ |
| 136 | 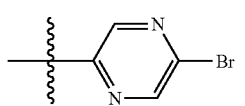 | | +++ |
| 137 | 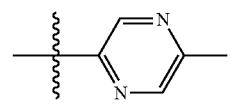 | 137 | ++ |
| 138 | 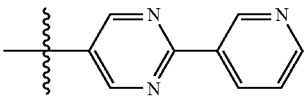 | | + |
| 139 | 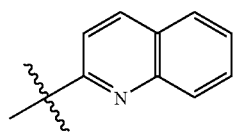 | 16 | +++ |

TABLE 1-continued

| Example Number | R₁ | FLIPR α7-HI (EC$_{50}$, nM) | FLIPR α7-HI (EC$_{50}$, nM) |
|---|---|---|---|
| 140 | 6-fluoroquinolin-2-yl | | ++ |
| 141 | 5-bromopyrimidin-2-yl | 4 | +++ |
| 142 | 6-chloropyrimidin-4-yl | | ++ |
| 143 | 5-(thiophen-2-yl)-1H-pyrazol-3-yl | | ++ |
| 144 | 6-(difluoromethoxy)pyrimidin-4-yl | | +++ |
| 145 | 4,6-dimethylisothiazolo[5,4-b]pyridin-3-yl | | + |
| 146 | isoquinolin-1-yl | | ++ |
| 147 | quinazolin-4-yl | | ++ |

TABLE 1-continued
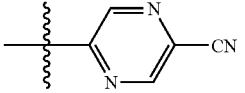
| Example Number | R₁ | FLIPR α7-HI (EC$_{50}$, nM) | FLIPR α7-HI (EC$_{50}$, nM) |
|---|---|---|---|
| 148 | 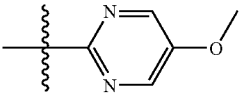 | | + |
| 149 | 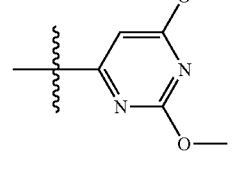 | 17 | +++ |
| 150 | 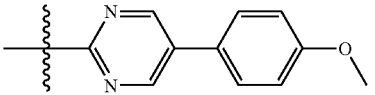 | | ++ |
| 151 | 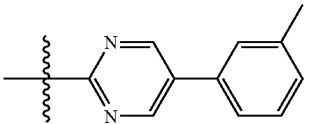 | | ++ |
| 152 | 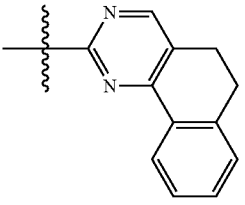 | 233 | ++ |
| 153 | 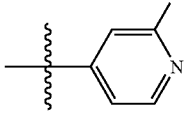 | | ++ |
| 154 | 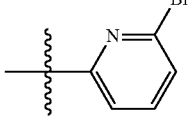 | | + |
| 155 | 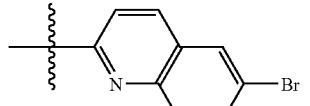 | | ++ |
| 156 | | | ++ |

TABLE 1-continued
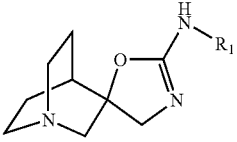
| Example Number | R₁ | FLIPR α7-HI (EC$_{50}$, nM) | FLIPR α7-HI (EC$_{50}$, nM) |
|---|---|---|---|
| 157 | 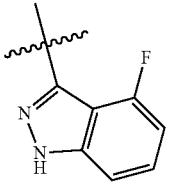 | | ++ |
| 158 | 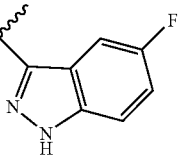 | 135 | ++ |
| 159 | 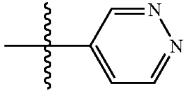 | | +++ |
| 160 | 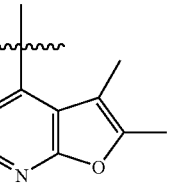 | | + |
| 161 | 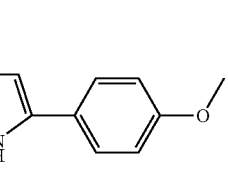 | | + |
| 162 | 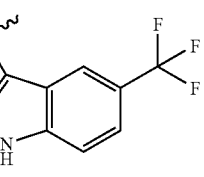 | | + |
| 163 | | | +++ |

TABLE 1-continued

| Example Number | R₁ | FLIPR α7-HI (EC₅₀, nM) | FLIPR α7-HI (EC₅₀, nM) |
|---|---|---|---|
| 164 | 6-(trifluoromethyl)-1H-indazol-3-yl | | ++ |
| 165 | 1H-indazol-3-yl | 13 | +++ |
| 166 | 4-(4-methoxyphenyl)pyrimidin-2-yl | 11 | +++ |
| 167 | 5,6-dimethylthieno[2,3-d]pyrimidin-4-yl | | + |
| 168 | 6-bromoquinazolin-2-yl | | +++ |
| 169 | pyrimidin-5-yl | | + |
| 170 | 5-methoxypyrazin-2-yl | | +++ |
| 171 | 5-bromo-4,6-dimethylpyrimidin-2-yl | | +++ |

TABLE 1-continued
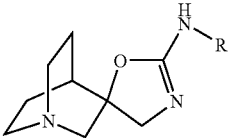
| Example Number | R₁ | FLIPR α7-HI (EC₅₀, nM) | FLIPR α7-HI (EC₅₀, nM) |
|---|---|---|---|
| 172 | 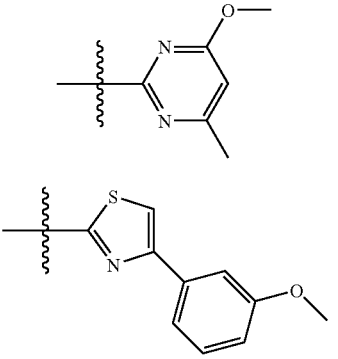 | | ++ |
| 173 | 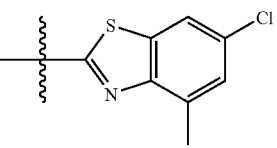 | | ++ |
| 174 | 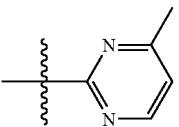 | 245 | ++ |
| 175 | 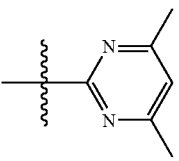 | | ++ |
| 176 | 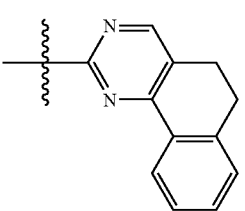 | | ++ |
| 177 | 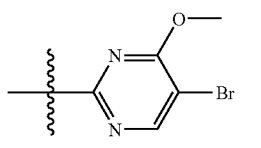 | | +++ |
| 178 | 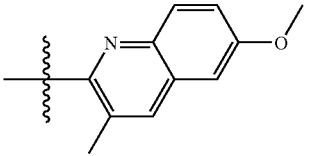 | 17 | +++ |
| 179 | | | ++ |

TABLE 1-continued
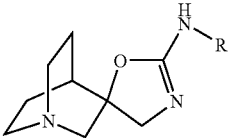
| Example Number | R₁ | FLIPR α7-HI (EC$_{50}$, nM) | FLIPR α7-HI (EC$_{50}$, nM) |
|---|---|---|---|
| 180 | 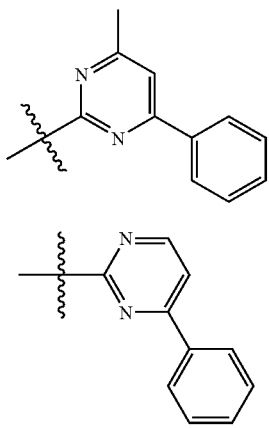 | | ++ |
| 181 | 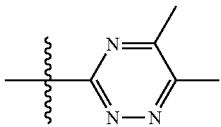 | 13 | +++ |
| 182 | 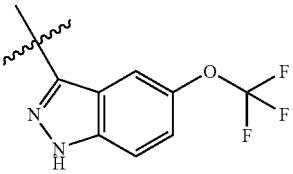 | | ++ |
| 183 | 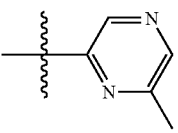 | | +++ |
| 184 | 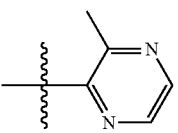 | | + |
| 185 | 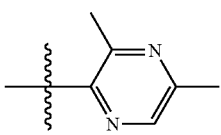 | | + |
| 186 | | | ++ |
| 187 | 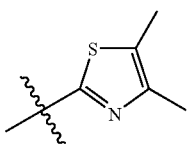 | 424 | ++ |

TABLE 1-continued
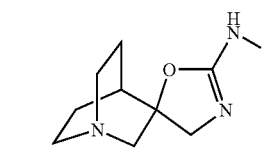
| Example Number | R₁ | FLIPR α7-HI (EC$_{50}$, nM) | FLIPR α7-HI (EC$_{50}$, nM) |
|---|---|---|---|
| 188 | 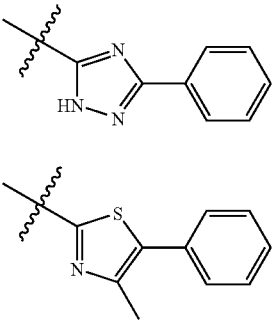 | | + |
| 189 | 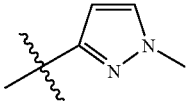 | | ++ |
| 190 | 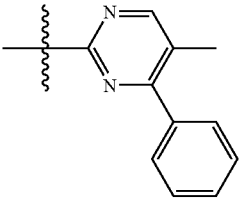 | | + |
| 191 | 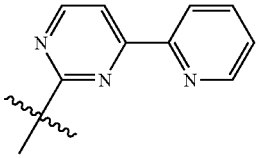 | | +++ |
| 192 | 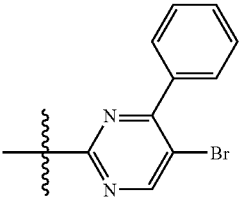 | | ++ |
| 193 | 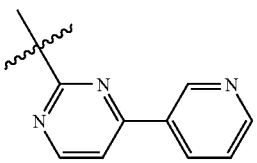 | 17 | +++ |
| 194 |  | 18 | +++ |

TABLE 1-continued
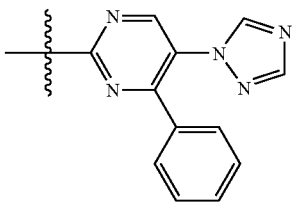
| Example Number | R₁ | FLIPR α7-HI (EC$_{50}$, nM) | FLIPR α7-HI (EC$_{50}$, nM) |
|---|---|---|---|
| 195 | 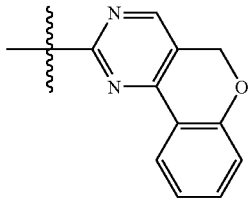 |  | + |
| 196 | 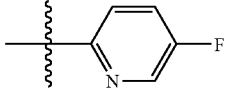 | 13 | +++ |
| 197 | 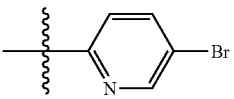 |  | +++ |
| 198 | 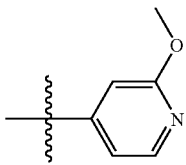 | 15 | +++ |
| 199 | 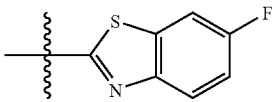 |  | + |
| 200 | 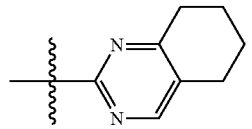 |  | +++ |
| 201 | 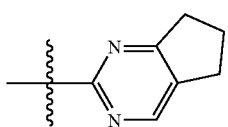 |  | +++ |
| 202 |  | 16 | +++ |

TABLE 1-continued

| Example Number | R₁ | FLIPR α7-HI (EC₅₀, nM) | FLIPR α7-HI (EC₅₀, nM) |
|---|---|---|---|
| 203 | | | +++ |
| 204 | | | ++ |
| 205 | | | ++ |
| 206 | | | + |
| 207 | | | ++ |
| 208 | | | + |
| 209 | | | +++ |
| 210 | | 9 | +++ |

TABLE 1-continued
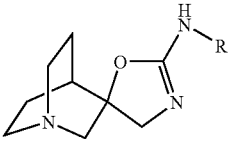
| Example Number | R₁ | FLIPR α7-HI (EC$_{50}$, nM) | FLIPR α7-HI (EC$_{50}$, nM) |
|---|---|---|---|
| 211 | 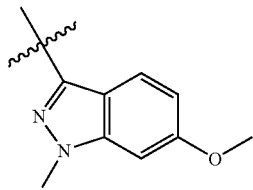 | | ++ |
| 212 | 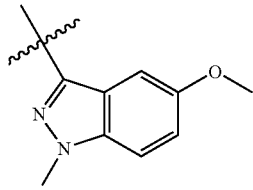 | | + |
| 213 | 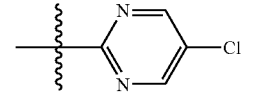 | 9 | +++ |
| 214 | 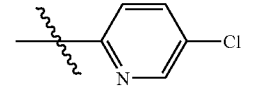 | | +++ |
| 215 | 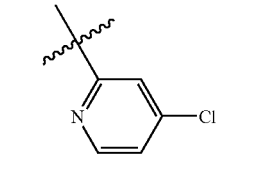 | | +++ |
| 216 | 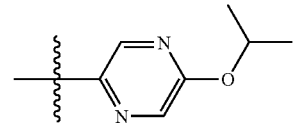 | | + |
| 217 | 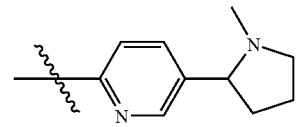 | | + |
| 218 | 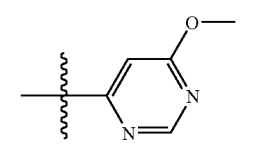 | 285 | ++ |

TABLE 1-continued
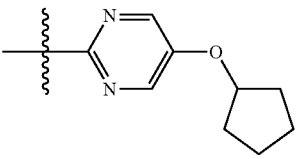
| Example Number | R₁ | FLIPR α7-HI (EC₅₀, nM) | FLIPR α7-HI (EC₅₀, nM) |
|---|---|---|---|
| 219 | 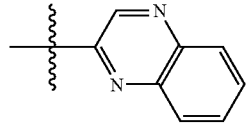 | | + |
| 220 | 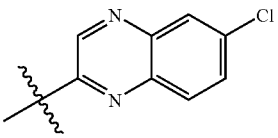 | | +++ |
| 221 | 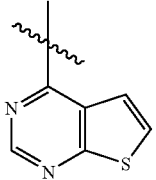 | | ++ |
| 222 | 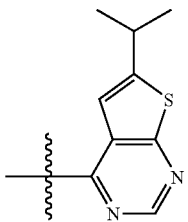 | | ++ |
| 223 | 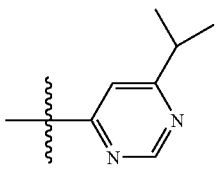 | | ++ |
| 224 | 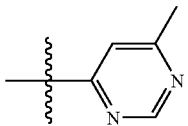 | | ++ |
| 225 | 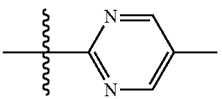 | | ++ |
| 226 | | | +++ |

TABLE 1-continued

| Example Number | R₁ | FLIPR α7-HI (EC₅₀, nM) | FLIPR α7-HI (EC₅₀, nM) |
|---|---|---|---|
| 227 | 5-ethylpyrimidin-2-yl | | ++ |
| 228 | 6-(2,2,2-trifluoroethoxy)pyrimidin-4-yl | | +++ |
| 229 | 5-bromo-4-isopropylpyrimidin-2-yl | | +++ |
| 230 | 5-bromo-4-(pyridin-3-yl)pyrimidin-2-yl | | +++ |
| 231 | 6-(cyclopentyloxy)pyrimidin-4-yl | | ++ |
| 232 | 6-isopropoxypyrimidin-4-yl | | ++ |
| 233 | 6-(2,2-difluoroethoxy)pyrimidin-4-yl | | +++ |

TABLE 1-continued

| Example Number | R₁ | FLIPR α7-HI (EC$_{50}$, nM) | FLIPR α7-HI (EC$_{50}$, nM) |
|---|---|---|---|
| 234 | 2-pyridyl | | +++ |
| 235 | 4-pyridyl | | + |
| 236 | 5-benzyloxy-thiazolo[5,4-b]pyridin-2-yl | | + |
| 237 | 5-oxo-4,5-dihydro-thiazolo[5,4-b]pyridin-2-yl | | +++ |
| 238 | 6-(3-methoxyphenyl)pyrimidin-4-yl | 16 | +++ |
| 239 | 2,7-naphthyridin-3-yl | 15 | +++ |
| 240 | 6-phenoxypyrimidin-4-yl | | ++ |

TABLE 1-continued
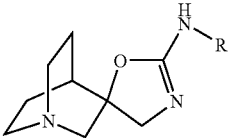
| Example Number | R₁ | FLIPR α7-HI (EC$_{50}$, nM) | FLIPR α7-HI (EC$_{50}$, nM) |
|---|---|---|---|
| 241 | 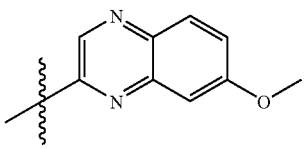 | | + |
| 242 | 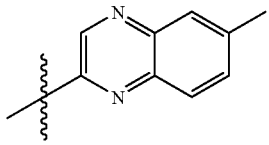 | | ++ |
| 243 | 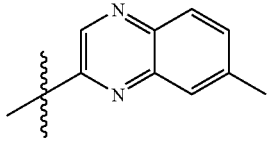 | | + |
| 244 | 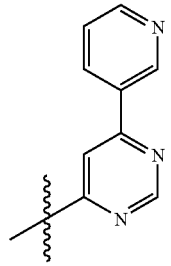 | | +++ |
| 245 | 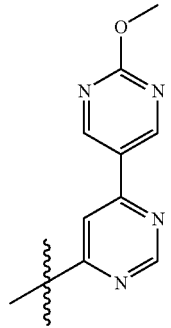 | | +++ |
| 246 | 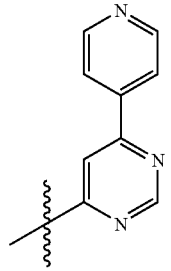 | | +++ |

TABLE 1-continued
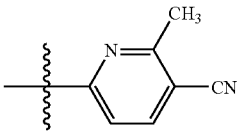
| Example Number | R₁ | FLIPR α7-HI (EC$_{50}$, nM) | FLIPR α7-HI (EC$_{50}$, nM) |
|---|---|---|---|
| 247 | 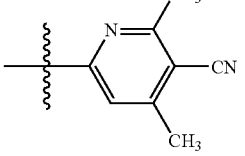 | | ++ |
| 248 | 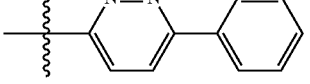 | | ++ |
| 249 | 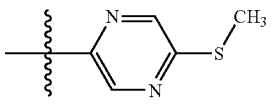 | | + |
| 250 | 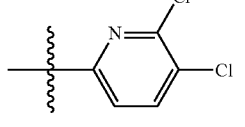 | | +++ |
| 251 | 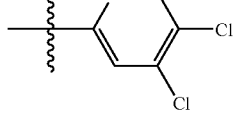 | | +++ |
| 252 | 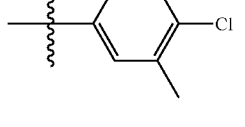 | | +++ |
| 253 | 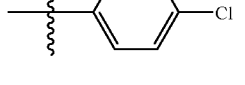 | | +++ |
| 254 | 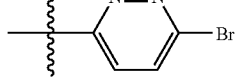 | | ++ |
| 255 | | | ++ |

TABLE 1-continued
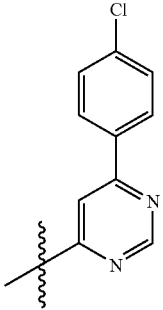
| Example Number | R₁ | FLIPR α7-HI (EC$_{50}$, nM) | FLIPR α7-HI (EC$_{50}$, nM) |
|---|---|---|---|
| 256 | 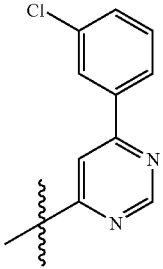 | | +++ |
| 257 | 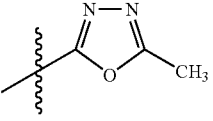 | | +++ |
| 258 | 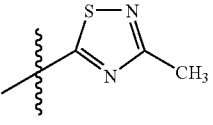 | | + |
| 259 | 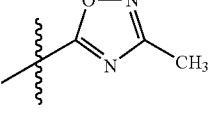 | | + |
| 260 | 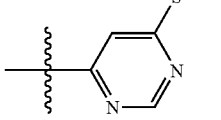 | | ++ |
| 261 | 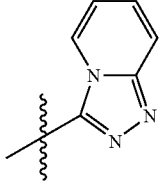 | | +++ |
| 262 | | | + |

TABLE 1-continued
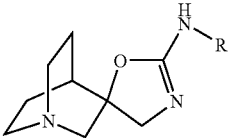
| Example Number | R₁ | FLIPR α7-HI (EC₅₀, nM) | FLIPR α7-HI (EC₅₀, nM) |
|---|---|---|---|
| 263 | 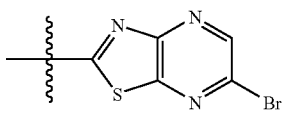 | | +++ |
| 264 | 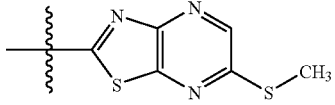 | | ++ |
| 265 | 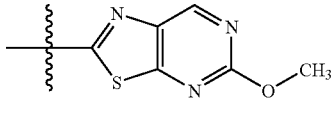 | | +++ |
| 266 | 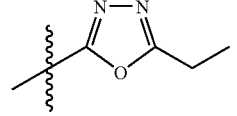 | | + |
| 267 | 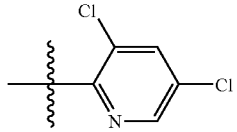 | | +++ |
| 268 | 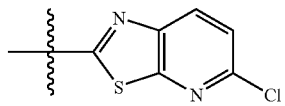 | | +++ |
| 269 | 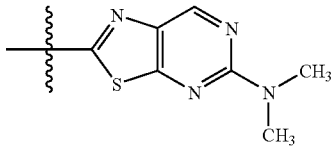 | | + |
| 270 | 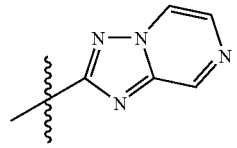 | | +++ |
| 271 | 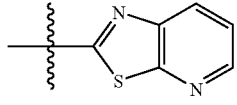 | | +++ |
| 272 | 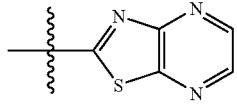 | | +++ |

TABLE 1-continued
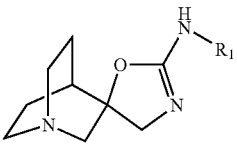
| Example Number | R₁ | FLIPR α7-HI (EC$_{50}$, nM) | FLIPR α7-HI (EC$_{50}$, nM) |
|---|---|---|---|
| 273 | 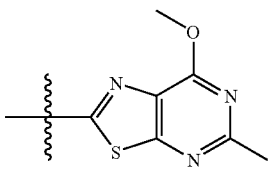 | | + |
| 274 | 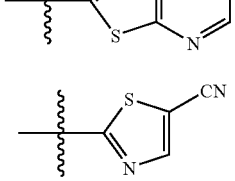 | | + |
| 275 | 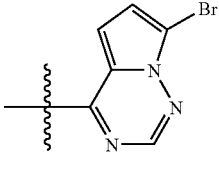 | | ++ |
| 276 | 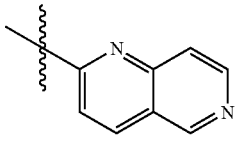 | | +++ |
| 277 | 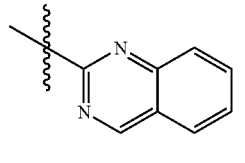 | | +++ |
| 278 | 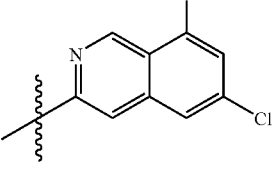 | | +++ |
| 279 | 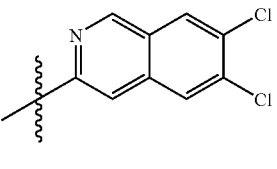 | | ++ |
| 280 | | | |

TABLE 1-continued
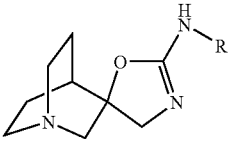
| Example Number | R$_1$ | FLIPR α7-HI (EC$_{50}$, nM) | FLIPR α7-HI (EC$_{50}$, nM) |
|---|---|---|---|
| 281 | 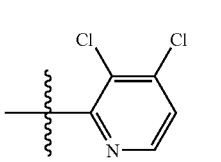 | | +++ |
| 282 | 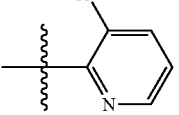 | | ++ |
| 283 | 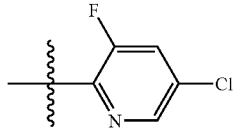 | | ++ |
| 284 | 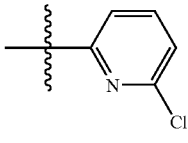 | | +++ |
| 285 | 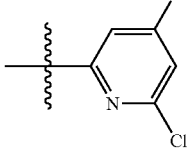 | | ++ |
| 286 | 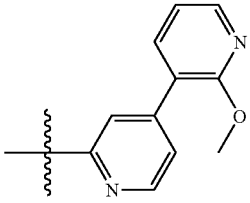 | | ++ |
| 287 | 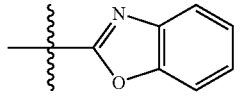 | | ++ |
| 288 | | | +++ |

TABLE 1-continued
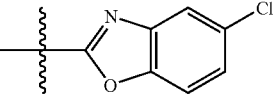
| Example Number | R₁ | FLIPR α7-HI (EC$_{50}$, nM) | FLIPR α7-HI (EC$_{50}$, nM) |
|---|---|---|---|
| 289 | 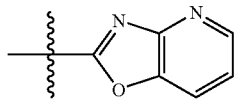 | | +++ |
| 290 | 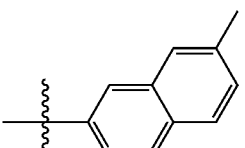 | | +++ |
| 291 | 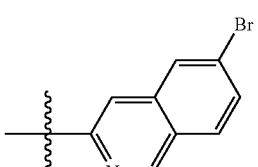 | | +++ |
| 292 | 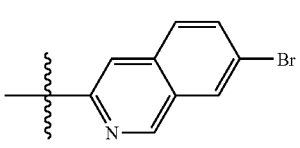 | | +++ |
| 293 | 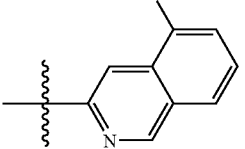 | | ++ |
| 294 | 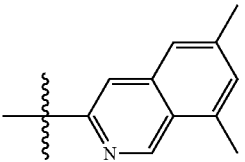 | | +++ |
| 295 |  | | ++ |
[a]Activity based on EC$_{50}$ nM values:
+++ = <100 nM
++ = 100-1000 nM
+ = 1000-100000 nM
[b]NT = Not tested
NA = Not active (>1000000 nM)

Pharmaceutical Compositions and Methods of Treatment

Compounds of formula I bind to alpha 7 and can be useful in treating affective disorders and neurodegenerative disorders. Therefore, another aspect of the invention is a composition comprising a compound of formula I, or a pharmaceutically acceptable salt thereof, and a pharmaceutically acceptable carrier.

Another aspect of the invention is the use of a compound of formula I in the manufacture of a medicament for the treatment of affective disorders or neurodegenerative disorders.

Another aspect of the invention is the use of a compound of formula I in the manufacture of a medicament for the treatment of schizophrenia or Alzheimer's Disease.

Another aspect of the invention is a method of treating affective disorders or neurodegenerative disorders comprising administering to a patient a therapeutically effective amount of a compound of formula I.

Another aspect of the invention is a method of treating schizophrenia or Alzheimer's Disease comprising administering to a patient a therapeutically effective amount of a compound of formula I.

Another aspect of the invention is a method of treating schizophrenia comprising administering to a patient a therapeutically effective amount of a compound of formula I.

Another aspect of the invention is a method of treating Alzheimer's Disease comprising administering to a patient a therapeutically effective amount of a compound of formula I.

"Patient" means a person suitable for therapy as understood by practitioners in the field of affective disorders and neurodegenerative disorders.

"Treatment," "therapy," and related terms are used as understood by practitioners in the field of affective disorders and neurodegenerative disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS $^1$H-NMR spectra were run on a Bruker 500, 400, or 300 MHz instrument and chemical shifts were reported in ppm ($\delta$) with reference to tetramethylsilane ($\delta$=0.0). All evaporations were carried out under reduced pressure. Unless otherwise stated, LC/MS analyses were carried out on a Shimadzu instrument using a Phenomenex-Luna 4.6×50 mm S10 reverse phase column employing a flow rate of 4 mL/min using a 0.1% TFA in methanol/water gradient [0-100% in 3 min, with 4 min run time] and a UV detector set at 220 nm or Gemini C18 4.6×50 mm 5u reverse phase column employing a flow rate of 5 mL/min using a 10 mM ammonium acetate acetonitrile/water gradient [5-95% in 3 min, with 4 min run time] and a UV detector set at 220 nm (negative-ion mass spectrometry). Unless otherwise stated, purification could be done by preparative C-18 column employing gradients of methanol-water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient.

EXAMPLE 1

N-(benzo[d]thiazol-2-yl)-4H-1'-azaspiro[oxazole-5, 3'-bicyclo[2.2.2]octan]-2-amine

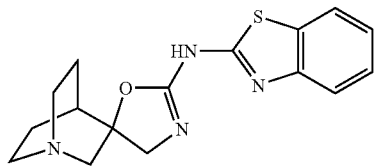

Step A: N-(Benzo[d]thiazol-2-yl)-$^1$H-imidazole-1-carbothioamide

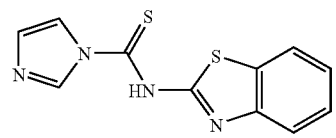

To benzo[d]thiazol-2-amine (20 g, 133 mmol) in acetonitrile (300 mL) was added 1,1'-thiocarbonyldiimidazole (30.8 g, 173 mmol). The reaction was stirred at 50° C. for 24 hours. The reaction was cooled to room temperature and the precipitate was filtered and washed with acetonitrile (2×50 mL). The yellow powder was dried in a vacuum oven (40° C.) for 2 hours. The product, N-(benzo[d]thiazol-2-yl)-$^1$H-imidazole-1-carbothioamide (28.9 g, 111 mmol), was taken directly to the next step without any further purification.

Step B: (3-((3-Benzo[d]thiazol-2-ylthioureido)methyl)-3-hydroxy-1-ammoniobicyclo[2.2.2]octan-1-yl)trihydroborate

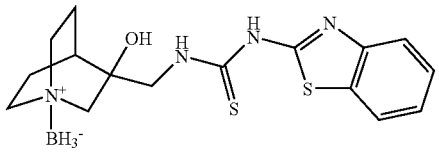

To N-(benzo[d]thiazol-2-yl)-$^1$H-imidazole-1-carbothioamide (9.2 g, 35 mmol) in N,N-dimethylformamide (100 mL) was added (3-(aminomethyl)-3-hydroxy-1-ammoniobicyclo[2.2.2]octan-1-yl)trihydroborate (6.0 g, 35 mmol) which was synthesized according to Swain C. J., et. al., *J. Med. Chem.*, 35:1019-1031 (1992). The reaction was stirred at 65° C. for 15 hours. The reaction was cooled and concentrated to yield the crude product. The crude material was purified via flash chromatography (50-100% ethyl acetate/hexanes) yielding the first spot/fractions detected by TLC as the product. The fractions were combined and concentrated to yield (3-((3-benzo[d]thiazol-2-ylthioureido)methyl)-3-hydroxy-1-ammoniobicyclo[2.2.2]octan-1-yl)trihydroborate (10.6 g, 29.1 mmol, 83% yield) as an off-white powder. $^1$H NMR (500 MHz, DMSO-$d_6$) δ ppm 11.88 (s, 1 H), 10.30 (s, 1 H), 7.94 (d, J=7.63 Hz, 1 H), 7.55-7.74 (m, 1 H), 7.37-7.53 (m, J=7.32, 7.32 Hz, 1 H), 7.16-7.37 (m, J=7.63, 7.63 Hz, 1 H), 5.39 (s, 1 H), 3.85 (d, 2H), 2.65-3.08 (m, 6 H), 1.99-2.22 (m, 1 H), 1.79-1.97 (m, 2 H), 1.66-1.79 (m, 1 H), 1.08-1.63 (m, 4 H). MS (LC/MS) R.T.=3.40; [M+H]$^+$=363.1

Step C: (2-(Benzo[d]thiazol-2-ylamino)-4H-1'-ammoniospiro[oxazole-5,3'-bicyclo[2.2.2]octane]-1'-yl)trihydroborate

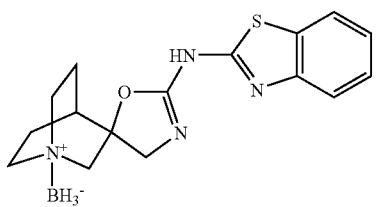

To (3-((3-benzo[d]thiazol-2-ylthioureido)methyl)-3-hydroxy-1-ammoniobicyclo[2.2.2]octan-1-yl)trihydroborate (10.6 g, 29.1 mmol) in N,N-dimethylformamide (100 mL) was added N,N'-diisopropylcarbodiimide (11.4 mL, 72.8 mmol). The reaction was stirred at 70° C. for 4 hours. The reaction was concentrated to yield a crude residue. A small amount of ethyl acetate (20 mL) was added and the suspension was sonicated. The solids were filtered and washed with small portions of ethyl acetate (2×10 mL). The solids were dried in a vacuum oven (80° C.) to yield (2-(benzo[d]thiazol-2-ylamino)-4H-1'-ammoniospiro[oxazole-5,3'-bicyclo[2.2.2]octane]-1'-yl)trihydroborate (6.83 g, 20.8 mmol, 72% yield) as a white powder. $^1$H NMR (500 MHz, DMSO-$d_6$) δ ppm 9.09 (br. s., 1 H) 7.81 (d, J=7.63 Hz, 1 H) 7.63 (d, J=7.93 Hz, 1 H) 7.30-7.40 (m, 1 H) 7.15-7.24 (m, 1 H) 3.88 (d, J=10.38 Hz, 1 H) 3.77 (d, J=10.38 Hz, 1 H) 3.25-3.37 (m, 1 H) 3.17 (dd, J=14.95, 1.83 Hz, 1 H) 2.99-3.10 (m, 1 H) 2.79-2.98 (m, 3 H) 2.27 (br. s., 1 H) 1.98-2.11 (m, 1 H) 1.71-1.88 (m, 3 H) 1.45 (br. s., 3 H). MS (LC/MS) R.T.=2.44; [M+H−BH$_3$]$^+$=315.1.

Step D: N-(Benzo[d]thiazol-2-yl)-4H-1'-azaspiro[oxazole-5,3'-bicyclo[2.2.2]octan]-2-amine

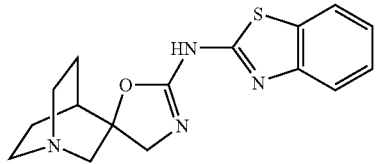

To (2-(benzo[d]thiazol-2-ylamino)-4H-1'-ammoniospiro[oxazole-5,3'-bicyclo[2.2.2]octane]-1'-yl)trihydroborate (6.6 g, 20.1 mmol) in acetone (9 mL) was added 3M HCl (50.3 mL, 151 mmol). The reaction was stirred at room temperature for 4 hours. The reaction was complete by TLC (lower spot). Ethyl acetate was added and the aqueous layer was then separated. The aqueous layer was neutralized with 1N sodium hydroxide. The product was extracted with ethyl acetate (2×150 mL). The organics were combined, dried with magnesium sulfate, filtered, and concentrated in vacuo to afford a white powder. A small amount of ethyl acetate (20 mL) was added to the powder. The solids were sonicated and filtered to yield racemic N-(benzo[d]thiazol-2-yl)-4H-1'-azaspiro[oxazole-5,3'-bicyclo[2.2.2]octan]-2-amine (5.13 g, 16.3 mmol, 81% yield) as a white powder. $^1$H NMR (500 MHz, DMSO-$d_6$) δ ppm 9.02 (br. s., 1 H) 7.79 (d, J=7.02 Hz, 1 H) 7.62 (d, J=7.63 Hz, 1 H) 7.29-7.38 (m, 1 H) 7.15-7.22 (m, 1 H) 3.90 (d, J=10.07 Hz, 1 H) 3.65 (d, J=10.07 Hz, 1 H) 2.98-3.10 (m, 2 H) 2.73-2.88 (m, 2 H) 2.67 (t, J=7.78 Hz, 2H) 2.07 (br. s., 1 H) 1.93 (br. s., 1 H) 1.42-1.67 (m, 3 H). MS (LC/MS) R.T.=1.15; [M+H]$^+$=315.3.

The enantiomers were separated using a Chiralpak AD-H (3×25 cm, 5 uM) column with a mobile phase consisting of CO$_2$/(methanol/ACN/DEA=70/30/0.1 (v/v/v))=77/23. The wavelength was set at 300 nM. The separated peaks were concentrated in vacuo to yield white powders. The first peak off the column was (S)—N-(benzo[d]thiazol-2-yl)-4H-1'-azaspiro[oxazole-5,3'-bicyclo[2.2.2]octan]-2-amine (1.45 g, 4.61 mmol, 29.4% yield). (1a; S-isomer): $^1$H NMR (400 MHz, DMSO-$d_6$) δ ppm 9.03 (br. s., 1 H) 7.78 (d, J=7.05 Hz, 1 H) 7.61 (d, J=7.55 Hz, 1 H) 7.27-7.37 (m, 1 H) 7.11-7.23 (m, 1 H) 3.89 (d, J=10.07 Hz, 1 H) 3.64 (d, J=10.07 Hz, 1 H) 2.96-3.09 (m, 2 H) 2.71-2.88 (m, 2 H) 2.66 (t, J=7.81 Hz, 2 H) 2.02-2.11 (m, 1 H) 1.85-1.97 (m, 1 H) 1.41-1.65 (m, 3 H). MS (LC/MS) R.T.=1.15; [M+H]$^+$=315.3. Optical rotation (1.23 mg/mL, DMSO)=+5.20°. The second peak was (R)—N-(benzo[d]thiazol-2-yl)-4H-1'-azaspiro[oxazole-5,3'-bicyclo[2.2.2]octan]-2-amine (1.21 g, 3.85 mmol, 24.5% yield). (1b; R-isomer): $^1$H NMR (500 MHz, DMSO-$d_6$) δ ppm 9.02 (br. s., 1 H) 7.79 (d, J=7.32 Hz, 1 H) 7.62 (d, J=7.63 Hz, 1 H) 7.33 (t, J=7.63 Hz, 1 H) 7.18 (t, J=7.48 Hz, 1 H) 3.90 (d, J=10.07 Hz, 1 H) 3.65 (d, J=10.07 Hz, 1 H) 2.98-3.10 (m, 2 H) 2.73-2.87 (m, 2 H) 2.67 (t, J=7.63 Hz, 2 H) 2.08 (br. s., 1 H) 1.93 (br. s., 1 H) 1.42-1.67 (m, 3 H). MS (LC/MS) R.T.=1.15; [M+H]$^+$=315.3; Optical rotation (3.9 mg/mL, DMSO)=−3.92°.

EXAMPLE 2

N-(5-Methoxythiazolo[5,4-b]pyridin-2-yl)-4H-1'-azaspiro[oxazole-5,3'-bicyclo[2.2.2]octan]-2-amine

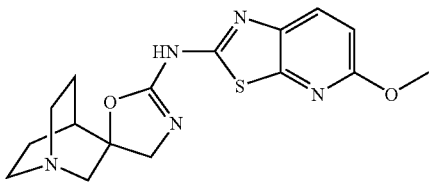

Step A: 5-Methoxythiazolo[5,4-b]pyridin-2-amine

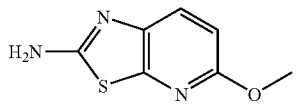

In a 500 ml, 3-neck flask equipped with a mechanical stirrer, dropping funnel and thermometer, acetic acid (100 mL) was added and cooled in an ice bath. Potassium thiocyanate (40 g, 412 mmol) and 6-methoxypyridin-3-amine (6.2 g, 49.9 mmol) were added to the reaction mixture. The reaction was cooled in an ice-salt bath until the reaction temperature reached <0° C. A solution of bromine (8 mL, 156 mmol) in acetic acid (30.0 mL) was added dropwise over 2 hours at a rate that maintained the reaction temperature <0° C. Mechanical stirring was required. After the addition was complete, the mixture was left to stir and allowed to slowly warm to room temperature overnight. Water (30 mL) was then added and the mixture was heated to 85° C. in an oil bath. This mixture was then filtered while still hot. The orange filter cake was returned to the reaction flask, and an additional 50 ml acetic acid was added. The mixture was heated again to 85° C., and then filtered while still hot once more. The combined filtrates were cooled in an ice bath and neutralized to pH 8 with conc. ammonium hydroxide. A purple precipitate formed which was then collected by filtration to afford 5 g of crude material. This crude material was recrystallized from methanol (40 mL) to yield 5-methoxythiazolo[5,4-b]pyridin-2-amine (3 g, 16.55 mmol, 33.1% yield) as purple crystals. $^1$H NMR (300 MHz, DMSO-$d_6$) δ ppm 7.60 (1 H, d, J=8.42 Hz), 7.41 (2 H, s), 6.67 (1 H, d, J=8.78 Hz), 3.81 (3 H, s).

Step B: (3-Hydroxy-3-((3-(5-methoxythiazolo[5,4-b]pyridin-2-yl)thioureido)methyl)-1-ammoniobicyclo[2.2.2]octan-1-yl)trihydroborate

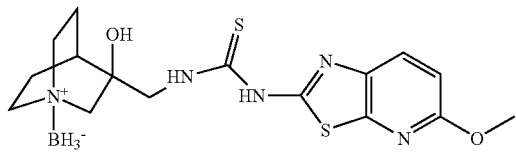

5-Methoxythiazolo[5,4-b]pyridin-2-amine (2.4 g, 13.24 mmol) was divided among 5×20 mL screw-cap vials. To each vial was added acetonitrile (10 mL) and thiocarbonyl diimidazole (600 mg). All vials were heated at 60° C. overnight. The reaction vials were combined and concentrated to yield crude N-(5-methoxythiazolo[5,4-b]pyridin-2-yl)-1H-imidazole-1-carbothioamide product.

This crude product was suspended in N,N-dimethylformamide (50 ml) and (3-(aminomethyl)-3-hydroxy-1-ammoniobicyclo[2.2.2]octan-1-yl)trihydroborate (2.7 g, 15.88 mmol) was then added. The reaction was heated at 70° C. for 4 hours. LC/MS showed essentially complete conversion. The reaction was cooled to room temperature and then poured into water. The product was extracted first with toluene, and then with chloroform. The organics were combined, washed with water and brine, dried over sodium sulfate, filtered and concentrated in vacuo to afford crude material. This crude material was purified via flash chromatography (20-100% ethyl acetate-hexane). The product fractions were collected and concentrated in vacuo to afford (3-hydroxy-3-((3-(5-methoxythiazolo[5,4-b]pyridin-2-yl)thioureido)methyl)-1-ammoniobicyclo[2.2.2]octan-1-yl)trihydroborate (1.36 g, 3.46 mmol, 26.1% yield). $^1$HNMR showed a 1:0.55 molar ratio of (3-hydroxy-3-((3-(5-methoxythiazolo[5,4-b]pyridin-2-yl)thioureido)methyl)-1-ammoniobicyclo[2.2.2]octan-1-yl)trihydroborate (1.36 g, 3.46 mmol, 26.1% yield) to 5-methoxythiazolo[5,4-b]pyridin-2-amine (0.34 g, 1.876 mmol, 14.17% yield). The mixture was taken directly to the next step without any further purification. MS (LC/MS) R.T.=3.23; [M+H]$^+$=392.1.

Step C: (2-(5-Methoxy-3a,7a-dihydrothiazolo[5,4-b]pyridin-2-ylamino)-4H-1'-ammoniospiro[oxazole-5,3'-bicyclo[2.2.2]octane]-1'-yl)trihydroborate

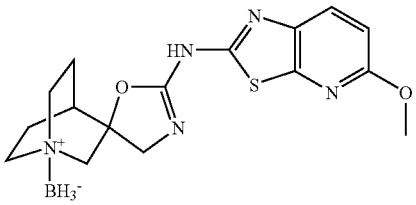

To (3-hydroxy-3-((3-(5-methoxythiazolo[5,4-b]pyridin-2-yl)thioureido)methyl)-1-ammoniobicyclo[2.2.2]octan-1-yl)trihydroborate (1.7 g, 3.46 mmol) in N,N-dimethylformamide (10 mL) was added N,N'-diisopropylcarbodiimide (1.89 mL, 12.10 mmol). The reaction was stirred at 70° C. for 2 hours. The mixture was cooled and then poured into water. The product was extracted with toluene and chloroform. The organic layers were combined, washed with brine, dried over sodium sulfate, filtered and concentrated in vacuo to afford crude material. This solid material was triturated with ether. The solids were then filtered and dried to yield (2-(5-methoxy-3a,7a-dihydrothiazolo[5,4-b]pyridin-2-ylamino)-4H-1'-ammoniospiro[oxazole-5,3'-bicyclo[2.2.2]octane]-1'-yl)trihydroborate (700 mg, 1.94 mmol, 56.0% yield). $^1$H NMR (300 MHz, DMSO-$d_6$) δ ppm 8.98 (1 H, s), 7.86 (1 H, d, J=8.78 Hz), 6.81 (1 H, d, J=8.42 Hz), 3.87 (3 H, s), 3.83 (1 H, s), 3.68-3.78 (1 H, m), 3.31 (1 H, s), 3.15-3.29 (1 H, m), 2.78-3.14 (4 H, m), 2.26 (1 H, br. s.), 2.04 (1 H, br. s.), 1.63-1.89 (3 H, m).

Step D: N-(5-Methoxythiazolo[5,4-b]pyridin-2-yl)-4H-1'-azaspiro[oxazole-5,3'-bicyclo[2.2.2]octan]-2-amine

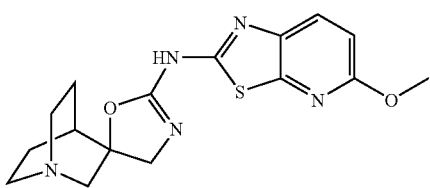

To (2-(5-methoxythiazolo[5,4-b]pyridin-2-ylamino)-4H-1'-ammoniospiro[oxazole-5,3'-bicyclo[2.2.2]octane]-1'-yl) trihydroborate (780 mg, 2.17 mmol) in acetone (10 mL) was added 3M HCl (10 mL, 329 mmol). The reaction was stirred at room temperature for 2 hours. Chloroform and water were added and the aqueous layer was then separated. The aqueous layer was neutralized with sodium bicarbonate. The product was extracted with chloroform (2×). The organics were combined, dried over sodium sulfate, filtered and concentrated in vacuo to afford racemic N-(5-methoxythiazolo[5,4-b]pyridin-2-yl)-4H-1'-azaspiro[oxazole-5,3'-bicyclo[2.2.2]octan]-2-amine (588 mg, 1.70 mmol, 78% yield) as a white powder. $^1$H NMR (500 MHz, DMSO-d$_6$) δ ppm 8.90 (1 H, br. s.), 7.82-7.86 (1 H, m), 6.80 (1H, d, J=8.85 Hz), 3.84-3.89 (4 H, m), 3.61 (1 H, d, J=10.07 Hz), 3.03 (2 H, d, J=5.19 Hz), 2.73-2.86 (2 H, m), 2.66 (2 H, t, J=7.78 Hz), 2.07 (1 H, br. s.), 1.92 (1 H, br. s.), 1.45-1.65 (3 H, m). MS (LC/MS) R.T.=1.29; [M+H]$^+$=346.1.

The enantiomers were separated using a Chiralpak AD-H (30×250 mm, 5 µm) column with a mobile phase consisting of 35% methanol (0.1% DEA) in CO$_2$. The wavelength was set at 300 nM. The separated peaks were concentrated in vacuo to yield white powders. The first peak off the column was (S)—N-(5-methoxythiazolo[5,4-b]pyridin-2-yl)-4H-1'-azaspiro[oxazole-5,3'-bicyclo[2.2.2]octan]-2-amine (212 mg, 0.61 mmol, 36.1% yield). (2a; S-isomer): $^1$H NMR (500 MHz, DMSO-d$_6$) δ ppm 8.89 (1 H, br. s.), 7.84 (1 H, d, J=8.85 Hz), 6.77-6.82 (1 H, m), 3.84-3.89 (4 H, m), 3.61 (1 H, d, J=10.07 Hz), 3.03 (2 H, d, J=5.19 Hz), 2.74-2.86 (2 H, m), 2.66 (2 H, t, J=7.63 Hz), 2.06 (1 H, br. s.), 1.92 (1 H, br. s.), 1.44-1.65 (3 H, m). MS (LC/MS) R.T.=1.47; [M+H]$^+$=346.2. Optical rotation (3.57 mg/ml, DMSO)=−2.58°. The second peak was (R)—N-(5-methoxythiazolo[5,4-b]pyridin-2-yl)-4H-1'-azaspiro[oxazole-5,3'-bicyclo[2.2.2]octan]-2-amine (242 mg, 0.70 mmol, 41.2% yield). (2b; R-isomer): $^1$H NMR (500 MHz, DMSO-d$_6$) δ ppm 8.89 (1 H, br. s.), 7.84 (1H, d, J=8.85 Hz), 6.79 (1 H, d, J=8.55 Hz), 3.82-3.90 (4 H, m), 3.61 (1 H, d, J=10.07 Hz), 3.03 (2 H, d, J=5.49 Hz), 2.74-2.86 (2 H, m), 2.66 (2 H, t, J=7.78 Hz), 2.06 (1 H, br. s.), 1.92 (1 H, br. s.), 1.42-1.67 (3 H, m). MS (LC/MS) R.T.=1.30; [M+H]$^+$=346.2. Optical rotation (3.29 mg/ml, DMSO)=+2.43°.

EXAMPLE 3

(2-(5H-1'-Azaspiro[oxazole-4,3'-bicyclo[2.2.2]octane]-2-ylamine)benzo[d]thiazol-6-yl)pyrrolidin-1-yl)methanone

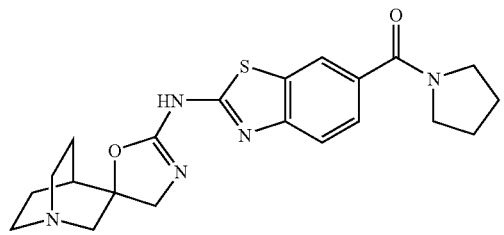

Step A: tert-Butyl 6-(pyrrolidine-1-carbonyl)benzo[d]thiazol-2-ylcarbamate

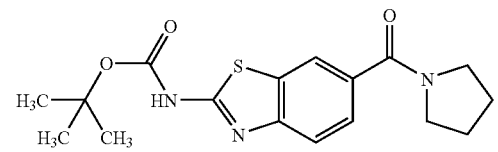

In a 250 ml flask was added 2-(tert-butoxycarbonyl-amino)benzo[d]thiazole-6-carboxylic acid (1.0 g, 3.4 mmol) and pyrrolidine (0.559 mL, 6.8 mmol) in tetrahydrofuran (50 mL). To this solution was added EDC (1.3 g, 6.8 mmol), 1-hydroxybenzotriaxole (1.041 g, 6.8 mmol) and Hunig's Base (2.37 mL, 13.59 mmol). The reaction was stirred at 25° C. for 1 hour. The reaction was then poured into water and dichloromethane. The water was extracted 3 times with dichloromethane and the organic layers were combined and concentrated. The residue was taken up in a small amount of dichloromethane and precipitated out with diethyl ether/hexanes. The flask was put in the freezer for 1 hour and filtered. The white precipitate was collected to yield tert-butyl 6-(pyrrolidine-1-carbonyl)benzo[d]thiazol-2-ylcarbamate (1.09 g, 3.14 mmol, 92% yield). $^1$H NMR (500 MHz, DMSO-d$_6$) δ ppm 11.95 (s, 1 H), 8.14 (s, 1 H), 7.61-7.77 (m, J=8.39, 1.98 Hz, 1 H), 7.46-7.63 (m, 1 H), 3.39-3.63 (m, 4 H), 1.74-2.00 (m, 4 H), 1.45-1.62 (m, 9 H). MS (LC/MS) R.T.=3.40; [M+H]$^+$=363.1.

Step B: (2-Aminobenzo[d]thiazol-6-yl)(pyrrolidin-1-yl)methone

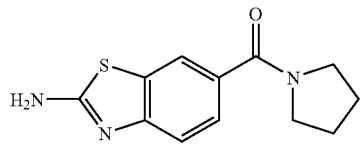

tert-Butyl 6-(pyrrolidine-1-carbonyl)benzo[d]thiazol-2-ylcarbamate (1.09 g, 3.14 mmol) was dissolved in dichloromethane (10 mL) and TFA (3 mL, 38.9 mmol) and the reaction was stirred at 25° C. overnight. The reaction was poured into a separatory funnel and carefully neutralized with sodium bicarbonate. The liquid was extracted 3 times with chloroform/methanol (4:1). The organic layers were concentrated to a white residue and triturated in diethyl ether. The precipitate was collected to yield (2-aminobenzo[d]thiazol-6-yl)(pyrrolidin-1-yl)methone (0.497 g, 2.0 mmol, 64%). $^1$H NMR (400 MHz, DMSO-$d_6$) δ ppm 7.86 (d, J=1.51 Hz, 1 H), 7.65 (s, 2 H), 7.35-7.46 (m, 1 H), 7.26-7.35 (m, 1 H), 3.41-3.57 (m, 4H), 1.64-1.97 (m, 4 H). MS (LC/MS) R.T.=1.39; [M+H]$^+$=248.1.

Step C: (2-(5H-1'-Azaspiro[oxazole-4,3'-bicyclo[2.2.2]octane]-2-ylamine)benzo[d]thiazol-6-yl)pyrrolidin-1-yl)methanone

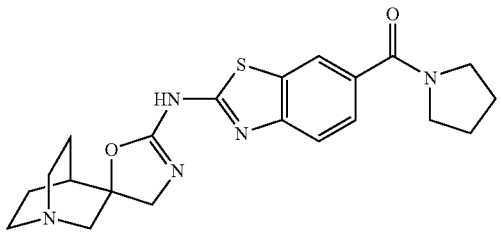

(2-(5H-1'-Azaspiro[oxazole-4,3'-bicyclo[2.2.2]octane]-2-ylamine)benzo-[d]thiazol-6-yl)pyrrolidin-1-yl)methanone was prepared by following the general procedures of Example 1, Steps A-D and using (2-aminobenzo[d]thiazol-6-yl)(pyrrolidin-1-yl)methone (Example 3, Step B) as the starting material. $^1$H NMR (400 MHz, DMSO-$d_6$) δ ppm 9.05 (br. s., 1 H) 7.99 (d, J=1.76 Hz, 1H) 7.60 (d, J=8.31 Hz, 1 H) 7.48 (dd, J=8.31, 1.76 Hz, 1 H) 3.90 (d, J=10.07 Hz, 1 H) 3.65 (d, J=10.07 Hz, 1 H) 3.42-3.52 (m, 4H) 3.04 (s, 2 H) 2.75-2.87 (m, 2 H) 2.67 (t, J=7.81 Hz, 2 H) 2.08 (br. s., 1 H) 1.76-1.98 (m, 5 H) 1.41-1.65 (m, 3 H). MS (LC/MS) R.T.=1.33; [M+H]$^+$=412.2.

EXAMPLE 4

N-(5-Phenylthiazol-2-yl)-4H-1'-azaspiro[oxazole-5,3'-bicyclo[2.2.2]octan]-2-amine

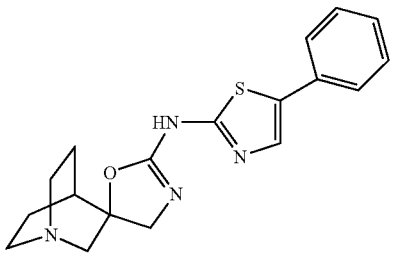

Step A: (3-Hydroxy-3-((3-(5-phenylthiazol-2-yl)thioureido)methyl)-1-ammoniobicyclo[2.2.2]octan-1-yl)trihydroborate

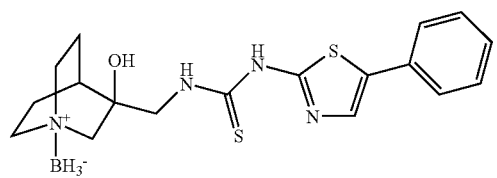

To 5-phenylthiazol-2-amine (0.52 g, 2.9 mmol) in acetonitrile (6 mL) was added 1,1'-thiocarbonyldiimidazole (0.68 g, 3.8 mmol). The reaction mixture was stirred at 65° C. for 2 hours. The precipitate was filtered and washed with acetonitrile (2×20 mL) to yield intermediate N-(5-phenylthiazol-2-yl)-$^1$H-imidazole-1-carbothioamide. The intermediate was taken up in N,N-dimethylformamide (30 mL) and treated with (3-(aminomethyl)-3-hydroxy-1-ammoniobicyclo[2.2.2]octan-1-yl)trihydroborate (0.5 g, 2.9 mmol). The reaction mixture was stirred for 5 hours at 65° C. The reaction was concentrated in vacuo and purified via silica gel chromatography (30-100% ethyl acetate/hexane). The product fractions were combined and concentrated in vacuo to yield (3-hydroxy-3-((3-(5-phenylthiazol-2-yl)thioureido)methyl)-1-ammoniobicyclo[2.2.2]octan-1-yl)trihydroborate (0.85 g, 2.19 mmol, 74.4% yield) as a white powder. LC/MS confirmed product with loss of $BH_3$ in the LC/MS conditions: retention time 3.26 (M+1–$BH_3$=375.33).

Step B: (2-(5-Phenylthiazol-2-ylamino)-4H-1'-ammoniospiro-[oxazole-5,3'-bicyclo[2.2.2]octane]-1'-yl)trihydroborate

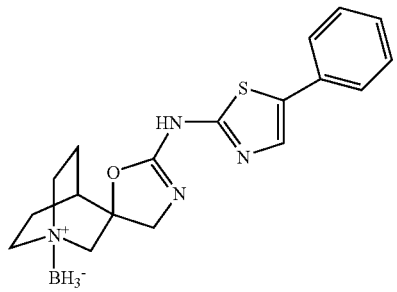

To (3-hydroxy-3-((3-(5-phenylthiazol-2-yl)thioureido)methyl)-1-ammoniobicyclo[2.2.2]octan-1-yl)trihydroborate (0.8 g, 2.1 mmol) in N,N-dimethylformamide (20 mL) was added N,N'-diisopropylcarbodiimide (1.12 mL, 7.2 mmol). The reaction mixture was stirred at 70° C. for 4 hours. The reaction was concentrated in vacuo and purified via silica gel chromatography (40-100% ethyl acetate/hexane). The combined product fractions were concentrated in vacuo to yield (2-(5-phenylthiazol-2-ylamino)-4H-1'-ammoniospiro[oxazole-5,3'-bicyclo[2.2.2]octane]-1'-yl)trihydroborate (0.51 g, 1.44 mmol, 70% yield) as a white powder. LCMS-mass corresponds to $BH_3$ lost in the LC/MS conditions: retention time 2.46 (M+1–$BH_3$=341.36).

Step C: N-(5-Phenylthiazol-2-yl)-4H-1'-azaspiro[oxazole-5,3'-bicyclo[2.2.2]octan]-2-amine

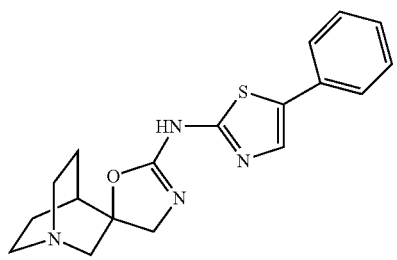

To (2-(5-phenylthiazol-2-ylamino)-4H-1'-ammoniospiro[oxazole-5,3'-bicyclo[2.2.2]octane]-1'-yl)trihydroborate (0.56 g, 1.58 mmol) in acetone (9 mL) was added 3 M HCl (3.95 mL, 11.86 mmol). The reaction mixture was stirred at room temperature for 4 hours and then neutralized with 1N sodium hydroxide. The product was extracted with ethyl acetate (2×20 mL), followed by chloroform (2×20 mL). The organics were combined, dried with magnesium sulfate, filtered, and concentrated in vacuo to afford a white powder. The crude product was purified by reverse phase HPLC (Phenomenex Luna 30×100 mm; 220 wavelength; gradient time 10 min; flow rate 40 ml/min; solvent A; 10% methanol-90% water-0.1% TFA, solvent B; 90% methanol-10% water-0.1% TFA). The fractions were combined, neutralized with 1N sodium hydroxide and extracted with ethyl acetate (2×30 mL) and chloroform (2×30 mL). The organics were combined, dried with magnesium sulfate, filtered and concentrated in vacuo to yield N-(5-phenylthiazol-2-yl)-4H-1'-azaspiro[oxazole-5,3'-bicyclo[2.2.2]octan]-2-amine (0.4 g, 1.175 mmol, 74.3% yield) as a white powder. $^1$H NMR (500 MHz, DMSO-$d_6$) δ ppm 8.63 (1 H, br. s.), 7.71 (1 H, s), 7.52 (2 H, d, J=7.32 Hz), 7.37 (2 H, t, J=7.78 Hz), 7.25 (1 H, t, J=7.32 Hz), 3.82 (1 H, d, J=10.07 Hz), 3.57 (1 H, d, J=9.77 Hz), 3.02 (2 H, d, J=4.27 Hz), 2.79 (2 H, t, J=7.63 Hz), 2.66 (2 H, t, J=7.63 Hz), 2.04 (1 H, br. s.), 1.92-197 (1 H, m), 1.44-1.65 (3 H, m). MS (LC/MS) R.T.=1.52; [M+H]$^+$=341.3.

The enantiomers were separated using a Chiralpak AS-H (30×250mm, 5 μm) column with a mobile phase consisting of 30% methanol (0.1% DEA) in $CO_2$ and UV monitored at 300 nm. The separated peaks were concentrated in vacuo to yield white powders. The first peak off the column yielded 0.4 g, 1.15 mmol, 32.7% (4a, S-isomer): $^1$H NMR (500 MHz, DMSO-$d_6$) δ ppm 8.69 (s, 1 H), 7.69-7.87 (m, 1 H), 7.52-7.66 (m, J=10.99 Hz, 2 H), 7.37-7.51 (m, 2 H), 7.21-7.38 (m, 2 H), 3.52-4.00 (m, 2 H), 2.98-3.23 (m, 2 H), 2.78-2.94 (m, 2 H), 2.64-2.78 (m, 2 H), 1.88-2.19 (m, J=60.43 Hz, 2 H), 1.40-1.77 (m, 3 H). MS (LC/MS) R.T.=1.77; [M+H]$^+$=341.1. The second peak yielded 0.4 g, 1.15 mmol, 32.7%. (4b, R-isomer):L M.P. 187-9° C. $^1$H NMR (500 MHz, DMSO-$d_6$) δ ppm 8.64 (s, 1 H), 7.62-7.84 (m, 1 H), 7.44-7.61 (m, 2 H), 7.33-7.46 (m, 2 H), 7.18-7.31 (m, 1 H), 3.50-3.99 (m, 2 H), 2.94-3.14 (m, 2 H), 2.74-2.91 (m, 2 H), 2.61-2.72 (m, 2 H), 2.05 (s, 1 H), 1.82-2.00 (m, 1 H), 1.34-1.72 (m, 3 H). MS (LC/MS) R.T.=1.78; [M+H]$^+$=341.1.

EXAMPLE 5

N-(6-Methoxybenzo[d]thiazol-2-yl)-4H-1'-azaspiro[oxazole-5,3'-bicyclo[2.2.2]octan]-2-amine Step A: N-(6-Methoxybenzo[d]thiazol-2-yl)-$^1$H-imidazole-1-carbothioamide

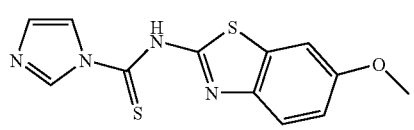

To 6-methoxybenzo[d]thiazol-2-amine (0.53 g, 2.94 mmol) in acetonitrile (20 mL) was added 1,1'-thiocarbonyldiimidazole (0.681 g, 3.82 mmol). The reaction mixture was stirred at 65° C. for 24 hours. The precipitate was filtered and washed with acetonitrile (2×20 mL) to yield the product. The product was taken directly to the next step without any further purification or characterization.

Step B: (3-Hydroxy-3-((3-(6-methoxybenzo[d]thiazol-2-yl)-thioureido)methyl)-1-ammoniobicyclo[2.2.2]octan-1-yl)trihydroborate

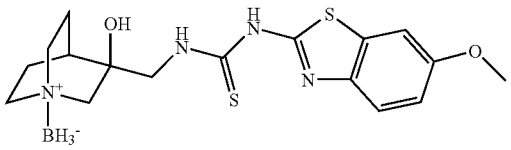

To N-(6-methoxybenzo[d]thiazol-2-yl)-$^1$H-imidazole-1-carbothioamide (0.82 g, 2.82 mmol) in N,N-dimethylformamide (20 mL) was added (3-(aminomethyl)-3-hydroxy-1-ammoniobicyclo[2.2.2]octan-1-yl)trihydroborate (0.48 g, 2.82 mmol). The reaction mixture was stirred at 65° C. for 6 hours. The reaction was concentrated in vacuo and then purified by silica gel chromatography (30%-100% ethyl acetate/hexanes). The pure fractions were combined and concentrated to yield (3-hydroxy-3-((3-(6-methoxybenzo[d]thiazol-2-yl)thioureido)methyl)-1-ammoniobicyclo[2.2.2]octan-1-yl)trihydroborate (0.7 g, 1.78 mmol, 63.2% yield) as a white powder. LC/MS confirmed product as loss of $BH_3$ in the LC/MS conditions: retention time 3.11 (M+1−$BH_3$=379.4).

Step C: (2-(6-Methoxybenzo[d]thiazol-2-ylamino)-4H-1'-ammoniospiro[oxazole-5,3'-bicyclo[2.2.2]octane]-1'-yl)trihydroborate

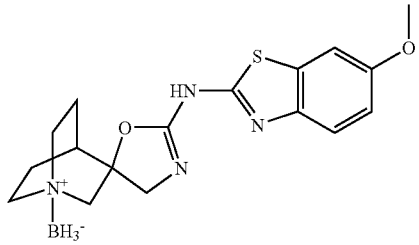

To (3-hydroxy-3-((3-(6-methoxybenzo[d]thiazol-2-yl)thioureido)methyl)-1-ammoniobicyclo[2.2.2]octan-1-yl)trihydroborate (0.68 g, 1.73 mmol) in N,N-dimethylformamide (20 mL) was added N,N'-diisopropylcarbodiimide (0.95 mL, 6.1 mmol). The reaction mixture was stirred at 70° C. for 4 hours. The reaction was concentrated and purified via silica gel chromatography (40-100% ethyl acetate/hexane). The product fractions were combined and concentrated in vacuo to yield (2-(6-methoxybenzo[d]thiazol-2-ylamino)-4H-1'-ammoniospiro[oxazole-5,3'-bicyclo[2.2.2]octane]-1'-yl)trihydroborate (0.35 g, 0.98 mmol, 56.4% yield) as a white powder. LC/MS MH$^+$-$BH_3$=345.2.

Step D: N-(6-Methoxybenzo[d]thiazol-2-yl)-4H-1'-azaspiro[oxazole-5,3'-bicyclo[2.2.2]octan]-2-amine

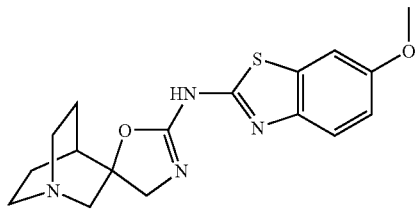

To (2-(6-methoxybenzo[d]thiazol-2-ylamino)-4H-1'-ammoniospiro[oxazole-5,3'-bicyclo[2.2.2]octane]-1'-yl)trihydroborate (0.33 g, 0.921 mmol) in acetone (9 mL) was added 3 M HCl (2.30 mL, 6.91 mmol). The reaction was stirred at room temperature for 4 hours and then neutralized with 1N sodium hydroxide. The product was extracted with ethyl acetate (2×20 mL), followed by chloroform (2×20 mL). The organics were combined, dried with magnesium sulfate, filtered, and concentrated in vacuo to afford a white powder. The crude product was purified by reverse phase HPLC (Phenomenex Luna 30×100 mm; 220 wavelength; gradient time 10 min; flow rate 40 ml/min; solvent A; 10% methanol-90% water-0.1% TFA, solvent B; 90% methanol-10% water-0.1% TFA). The fractions were combined, neutralized with 1N sodium hydroxide and extracted with ethyl acetate (2×30 mL). The organics were combined, dried with magnesium sulfate, filtered and concentrated in vacuo to yield N-(6-methoxybenzo[d]thiazol-2-yl)-4H-1'-azaspiro[oxazole-5,3'-bicyclo[2.2.2]octan]-2-amine (0.25 g, 0.73 mmol, 79% yield) as a white powder. $^1$H NMR (500 MHz, DMSO-$d_6$) δ ppm 8.88 (1 H, d, J=1.22 Hz), 7.48-7.52 (1 H, m), 7.40 (1 H, d, J=2.75 Hz), 6.92 (1 H, dd, J=8.70, 2.59 Hz), 3.87 (1 H, d, J=9.77 Hz), 3.77 (3 H, s), 3.61 (1 H, d, J=9.77 Hz), 3.03 (2 H, s), 2.75-2.86 (2 H, m), 2.67 (2 H, t, J=7.78 Hz), 2.06 (1 H, br. s.), 1.91 (1 H, br. s.), 1.41-1.65 (3 H, m). MS (LC/MS) R.T.=1.44; [M+H]$^+$=345.3.

The enantiomers were separated using a Chiralpak AD-H (30×250 mm, 5 μm) column with a mobile phase consisting of 23% methanol (0.1% DEA) in $CO_2$ and UV monitored at 220 nm. The separated peaks were concentrated in vacuo to yield white powders. The first peak off the column yielded 205.5 mg, 0.60 mmol, 34.1%. (5a, S-isomer): $^1$H NMR (400 MHz, DMSO-$d_6$) δ ppm 8.88 (1 H, br. s.), 7.50 (1 H, d, J=8.81 Hz), 7.40 (1 H, d, J=2.52 Hz), 6.92 (1 H, dd, J=8.81, 2.77 Hz), 3.87 (1 H, d, J=9.82 Hz), 3.77 (3 H, s), 3.58-3.65 (1 H, m), 3.02 (2 H, s), 2.74-2.86 (2 H, m), 2.66 (2 H, t, J=7.68 Hz), 2.03-2.08 (1 H, m), 1.91 (1 H, br. s.), 1.39-1.65 (3 H, m). MS (LC/MS) R.T.=1.40; [M+H]$^+$=345.2. The second peak yielded 206.9 mg, 0.6 mmol, 34%. (5b, R-isomer): $^1$H NMR (400 MHz, DMSO-$d_6$) δ ppm 8.88 (1 H, br. s.), 7.50 (1 H, d, J=8.56 Hz), 7.40 (1 H, d, J=2.52 Hz), 6.93 (1 H, dd, J=8.81, 2.52 Hz), 3.87 (1 H, d, J=10.07 Hz), 3.77 (3 H, s), 3.62 (1 H, d, J=10.07 Hz), 3.02 (2 H, s), 2.75-2.86 (2 H, m), 2.67 (2 H, t, J=7.68 Hz), 2.04-2.09 (1 H, m), 1.92 (1 H, br. s.), 1.42-1.66 (3 H, m). MS (LC/MS) R.T.=1.70; [M+H]$^+$=345.1.

EXAMPLE 6

N-(4-Methylbenzo[d]thiazol-2-yl)-4H-1'-azaspiro[oxazole-5,3'-bicyclo[2.2.2]octan]-2-amine

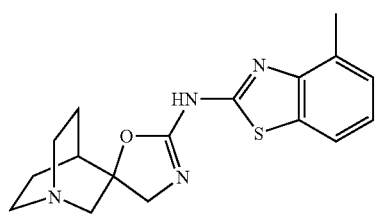

Step A: N-(4-Methylbenzo[d]thiazol-2-yl)-$^1$H-imidazole-1-carbothioamide

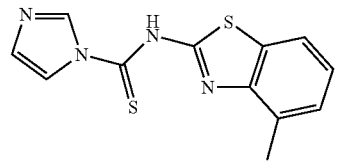

To 4-methylbenzo[d]thiazol-2-amine (1.1 g, 6.7 mmol) in acetonitrile (30 mL) was added 1,1'-thiocarbonyldiimidazole (1.552 g, 8.71 mmol). The reaction mixture was stirred at 50° C. for 18 hours. The reaction was cooled to room temperature and the precipitate was filtered and washed with acetonitrile (2×50 mL). The yellow powder was dried in a vacuum oven (50° C.) for 1 hour to yield N-(4-methylbenzo[d]thiazol-2-yl)-$^1$H-imidazole-1-carbothioamide (900 mg, 3.28 mmol, 49% yield) and then used in the next step without any further purification or characterization.

Step B: (3-Hydroxy-3-((3-(4-methylbenzo[d]thiazol-2-yl)thioureido)methyl)-1-ammoniobicyclo[2.2.2]octan-1-yl)trihydroborate

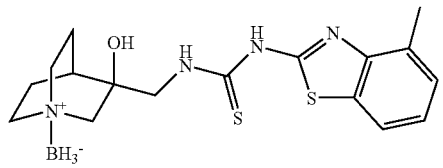

To N-(4-methylbenzo[d]thiazol-2-yl)-$^1$H-imidazole-1-carbothioamide (0.71 g, 2.59 mmol) in N,N-dimethylformamide (20 mL) was added (3-(aminomethyl)-3-hydroxy-1-ammoniobicyclo[2.2.2]octan-1-yl)trihydroborate (0.44 g, 2.59 mmol). The reaction mixture was stirred at 70° C. for 4 hours. The reaction was concentrated and purified via silica gel chromatography (40-100% ethyl acetate/hexanes). The product fractions were concentrated in vacuo to yield (3-hydroxy-3-((3-(4-methylbenzo[d]thiazol-2-yl)thioureido)methyl)-1-ammoniobicyclo[2.2.2]octan-1-yl)trihydroborate (0.65 g, 1.73 mmol, 66.7% yield) as a white powder. $^1$H NMR (500 MHz, DMSO-$d_6$) δ ppm 11.93 (1 H, s), 7.74 (1 H, d, J=7.63 Hz), 7.22-7.26 (1 H, m), 7.19 (1 H, t, J=7.63 Hz), 3.75-3.93 (2 H, m), 2.72-2.95 (6 H, m), 2.56 (3 H, s), 2.03-2.14 (1 H, m), 1.95 (1 H, br. s.), 1.78-1.87 (1 H, m), 1.73 (1 H, ddd, J=13.81, 9.23, 5.04 Hz), 1.56 (1 H, td, J=9.99, 7.78 Hz), 1.38 (2 H, br. s.). (LC/MS) R.T.=3.70; [M+H]$^+$=375.2.

Step C: (2-(4-Methylbenzo[d]thiazol-2-ylamino)-4H-1'-ammonio-spiro[oxazole-5,3'-bicyclo[2.2.2]octane]-1'-yl)trihydroborate

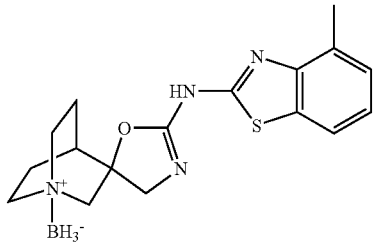

To (3-hydroxy-3-((3-(4-methylbenzo[d]thiazol-2-yl)thioureido)methyl)-1-ammoniobicyclo[2.2.2]octan-1-yl)trihydroborate (0.62 g, 1.65 mmol) in N,N-dimethylformamide (20 mL) was added N,N'-diisopropylcarbodiimide (0.33 mL, 2.14 mmol). The reaction mixture was stirred at 70° C. for 4 hours. The reaction was concentrated and purified via silica gel chromatography (40-100% ethyl acetate/hexanes). The product fractions were concentrated in vacuo to yield (2-(4-methylbenzo[d]thiazol-2-ylamino)-4H-1'-ammoniospiro[oxazole-5,3'-bicyclo[2.2.2]octane]-1'-yl)trihydroborate (0.4 g, 1.17 mmol, 70.9% yield) as a white powder. $^1$H NMR (500 MHz, DMSO-$d_6$) δ ppm 8.90 (s, 1 H), 7.61 (d, J=7.63 Hz, 1 H), 7.13-7.17 (m, 1 H), 7.09 (t, J=7.48 Hz, 1 H), 3.90 (d, J=10.38 Hz, 1 H), 3.77 (d, J=10.38 Hz, 1 H), 3.32 (s, 3 H), 3.30 (d, J=1.53 Hz, 1 H), 3.13-3.20 (m, 2 H), 3.00-3.09 (m, 1 H), 2.85-2.94 (m, 4 H), 2.57 (s, 4 H), 2.28 (s, 1 H), 2.06 (s, 1 H), 1.75-1.83 (m, 4 H), 1.45 (s, 1H). (LC/MS) R.T.=2.73; [M+H]$^+$=343.2.

Step D: N-(4-Methylbenzo[d]thiazol-2-yl)-4H-1'-azaspiro[oxazole-5,3'-bicyclo[2.2.2]octan]-2-amine

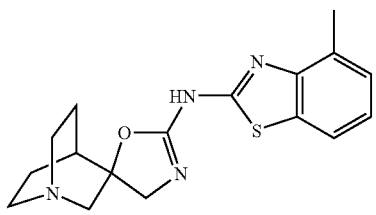

To (2-(4-methylbenzo[d]thiazol-2-ylamino)-4H-1'-ammoniospiro[oxazole-5,3'-bicyclo[2.2.2]octane]-1'-yl)trihydroborate (0.38 g, 1.11 mmol) in acetone (9 mL) was added 3 M HCl (2.78 mL, 8.33 mmol). The reaction mixture was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered and concentrated in vacuo to afford N-(4-methylbenzo[d]thiazol-2-yl)-4H-1'-azaspiro[oxazole-5,3'-bicyclo[2.2.2]octan]-2-amine (0.195 g, 0.594 mmol, 53.5% yield) as a white powder. $^1$H NMR (500 MHz, DMSO-$d_6$) δ ppm 8.84 (s, 1H), 7.60 (d, J=7.32 Hz, 1 H), 7.13-7.17 (m, 1 H), 7.08 (t, J=7.63 Hz, 1 H), 3.92 (d, J=10.07 Hz, 1 H), 3.66 (d, J=9.77 Hz, 1 H), 3.04 (s, 2 H), 2.76-2.85 (m, 2 H), 2.68 (t, J=7.48 Hz, 2 H), 2.56 (s, 3 H), 2.09 (s, 1 H), 1.93 (s, 1 H), 1.61 (d, J=3.05 Hz, 1 H), 1.60 (s, 1 H), 1.50 (dd, J=7.17, 2.59 Hz, 1 H). (LC/MS) R.T.=1.76; [M+H]$^+$=329.2.

The enantiomers were separated using a Chiralcel OJ-H (30×250 mm, 5 μm) column with a mobile phase consisting of 30% methanol (0.1% DEA) in $CO_2$ and UV monitored at 300 nm. The separated peaks were concentrated in vacuo to yield white powders. The first peak off the column yielded 0.07 g, 0.21 mmol, 38.9%. (6a, S-isomer): $^1$H NMR (500 MHz, DMSO-$d_6$) δ ppm 8.83 (br. s., 1 H) 7.59 (d, J=7.63 Hz, 1 H) 7.11-7.18 (m, 1 H) 7.08 (t, J=7.63 Hz, 1 H) 3.92 (d, J=10.38 Hz, 1 H) 3.66 (d, J=9.77 Hz, 1H) 3.04 (s, 2 H) 2.73-2.89 (m, 2 H) 2.61-2.72 (m, 2 H) 2.56 (s, 3 H) 2.09 (br. s., 1 H) 1.93 (br. s., 1 H) 1.43-1.71 (m, 3 H). MS (LCAMS) R.T.=1.75; [M+H]$^+$=329.1. The second peak yielded 0.07 g, 0.21 mmol, 38.1%. (6b, R-isomer): $^1$H NMR (500 MHz, DMSO-$d_6$) δ ppm 8.84 (br. s., 1 H) 7.59 (d, J=7.63 Hz, 1 H) 7.15 (d, J=7.20 Hz, 1 H) 7.08 (t, J=7.48 Hz, 1 H) 3.92 (d, J=9.77 Hz, 1 H 3.66 (d, J=10.07 Hz, 1 H) 3.00-3.09 (m, 2 H) 2.73-2.87 (m, 2 H) 2.62-2.72 (m, 2 H) 2.56 (s, 3 H) 2.05-2.12 (m, 1 H) 1.93 (br. s., 1 H) 1.56-1.67 (m, 2 H) 1.45-1.55 (m, 1 H). MS (LC/MS) R.T.=1.75; [M+H]$^+$=329.1.

EXAMPLE 7

N-(4-Chlorobenzo[d]thiazol-2-yl)-4H-1'-azaspiro[oxazole-5,3'-bicyclo[2.2.2]octan]-2-amine

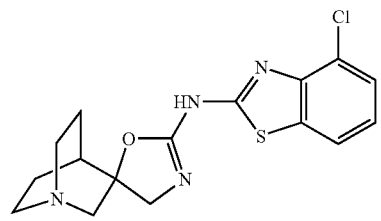

Step A: N-(4-Chlorobenzo[d]thiazol-2-yl)-$^1$H-imidazole-1-carbothioamide

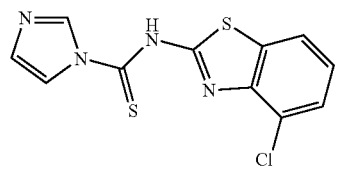

To 4-chlorobenzo[d]thiazol-2-amine (1.12 g, 6.07 mmol) in acetonitrile (30 mL) was added 1,1'-thiocarbonyldiimidazole (1.405 g, 7.89 mmol). The reaction mixture was stirred at 50° C. for 18 hours. The reaction was cooled to room temperature and the precipitate was filtered and washed with acetonitrile (2×50 mL). The yellow powder was dried in a vacuum oven (40° C.) for 1 hour to yield N-(4-chlorobenzo[d]thiazol-2-yl)-$^1$H-imidazole-1-carbothioamide (0.33 g, 1.12 mmol, 18.5% yield) and then used in the next step without any further purification or characterization.

Step B: (3-((3-(4-Chlorobenzo[d]thiazol-2-yl)thioureido)methyl)-3-hydroxy-1-ammoniobicyclo[2.2.2]octan-1-yl)trihydroborate

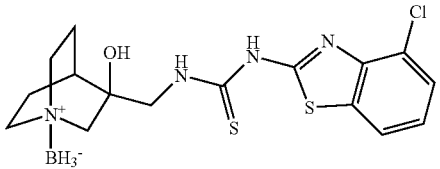

To N-(4-chlorobenzo[d]thiazol-2-yl)-¹H-imidazole-1-carbothioamide (0.3 g, 1.018 mmol) in N,N-dimethylformamide (20 mL) was added (3-(aminomethyl)-3-hydroxy-1-ammoniobicyclo[2.2.2]octan-1-yl)trihydroborate (0.173 g, 1.018 mmol). The reaction mixture was stirred at 70° C. for 4 hours. The reaction was concentrated and purified via silica gel chromatography (60-100% ethyl acetate/hexanes). The product fractions were concentrated in vacuo to yield (3-((3-(4-chlorobenzo[d]thiazol-2-yl)thioureido)methyl)-3-hydroxy-1-ammoniobicyclo[2.2.2]octan-1-yl)trihydroborate (0.25 g, 0.63 mmol, 61.9% yield) as a white powder. ¹H NMR (500 MHz, DMSO-$d_6$) δ ppm 12.19 (s, 1 H) 9.72 (br. s., 1 H) 7.93 (d, J=7.93 Hz, 1 H) 7.51 (d, J=7.93 Hz, 1 H) 7.26-7.32 (m, 1 H) 5.32 (s, 1 H) 3.88 (dd, J=13.73, 4.88 Hz, 1 H) 3.75 (dd, J=13.73, 4.88 Hz, 1 H) 2.73-2.95 (m, 6 H) 2.08 (br. s., 1 H) 1.96 (br. s., 1 H) 1.79-1.89 (m, 1 H) 1.68-1.78 (m, 1 H) 1.52-1.61 (m, 1 H) 1.39 (br. s., 3 H).

Step C: (2-(4-Chlorobenzo[d]thiazol-2-ylamino)-4H-1'-ammoniospiro[oxazole-5,3'-bicyclo[2.2.2]octane]-1'-yl)trihydroborate

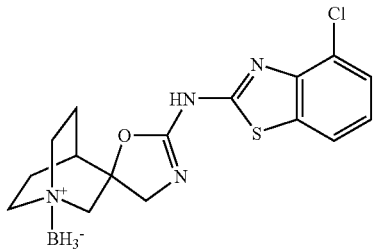

To (3-((3-(4-chlorobenzo[d]thiazol-2-yl)thioureido)methyl)-3-hydroxy-1-ammoniobicyclo[2.2.2]octan-1-yl)trihydroborate (0.23 g, 0.58 mmol) in N,N-dimethylformamide (20 mL) was added N,N'-diisopropylcarbodiimide (0.117 mL, 0.75 mmol). The reaction mixture was stirred at 70° C. for 4 hours. The reaction was concentrated and purified via silica gel chromatography (40-100% ethyl acetate/hexanes). The product fractions were concentrated in vacuo to yield (2-(4-chlorobenzo[d]thiazol-2-ylamino)-4H-1'-ammoniospiro[oxazole-5,3'-bicyclo[2.2.2]octane]-1'-yl)trihydroborate (0.1 g, 0.27 mmol, 47.6% yield) as a white powder. ¹H NMR (500 MHz, DMSO-$d_6$) δ ppm 8.95 (s, 1 H) 7.79 (d, J=7.93 Hz, 1 H) 7.42 (d, J=7.63 Hz, 1 H) 7.18 (t, J=7.93 Hz, 1 H) 3.92 (d, J=10.38 Hz, 1 H) 3.77 (d, J=10.38 Hz, 1 H) 3.26-3.38 (m, 1 H) 3.19 (dd, J=15.26, 1.53 Hz, 1 H) 3.01-3.11 (m, 1 H) 2.81-3.00 (m, 3 H) 2.31 (br. s., 1 H) 2.03-2.15 (m, 1 H) 1.70-1.89 (m, 3 H) 1.45 (br. s., 3 H).

Step D: N-(4-Chlorobenzo[d]thiazol-2-yl)-4H-1'-azaspiro[oxazole-5,3'-bicyclo[2.2.2]octan]-2-amine

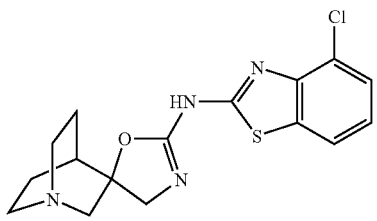

To (2-(4-chlorobenzo[d]thiazol-2-ylamino)-4H-1'-ammoniospiro[oxazole-5,3'-bicyclo[2.2.2]octane]-1'-yl)trihydroborate (0.08 g, 0.221 mmol) in acetone (9 mL) was added 3 M HCl (0.551 mL, 1.654 mmol). The reaction mixture was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered and concentrated in vacuo to afford N-(4-chlorobenzo[d]thiazol-2-yl)-4H-1'-azaspiro[oxazole-5,3'-bicyclo[2.2.2]octan]-2-amine (0.05 g, 0.14 mmol, 65.0% yield) as a white powder. ¹H NMR(500 MHz, DMSO-$d_6$) δ ppm 8.90 (br. s., 1 H) 7.77 (dd, J=7.78, 1.07 Hz, 1 H) 7.41 (dd, J=7.78, 1.07 Hz, 1 H) 7.17 (t, J=7.78 Hz, 1 H) 3.94 (d, J=10.07 Hz, 1 H) 3.67 (d, J=10.07 Hz, 1 H) 3.00-3.11 (m, 2 H) 2.76-2.88 (m, 2 H) 2.68 (t, J=7.63 Hz, 2 H) 2.11 (br. s., 1 H) 1.91-2.00 (m, 1 H) 1.47-1.67 (m, 3 H). MS (LC/MS) R.T.=2.11; [M+H]⁺=349.1.

The enantiomers were separated using a Chiralcel OJ-H (30×250 mm, 5 μm) column with a mobile phase consisting of 30% methanol (0.1% DEA) in $CO_2$. The wavelength was set at 220 nM. The separated peaks were concentrated in vacuo to yield white powders. The first peak off the column was (S)—N-(4-chlorobenzo[d]thiazol-2-yl)-4H-1'-azaspiro[oxazole-5,3'-bicyclo[2.2.2]octan]-2-amine (0.11 g, 0.30 mmol, 34.8% yield). (7a, S-isomer): ¹H NMR (500 MHz, DMSO-$d_6$) δ ppm 8.90 (br. s., 1 H) 7.77 (d, J=7.32 Hz, 1 H) 7.41 (d, J=7.93 Hz, 1 H) 7.17 (t, J=7.93 Hz, 1 H) 3.94 (d, J=10.07 Hz, 1 H) 3.67 (d, J=10.07 Hz, 1 H) 3.00-3.11 (m, 2 H) 2.76-2.90 (m, 2 H) 2.68 (t, J=7.78 Hz, 2 H) 2.11 (br. s., 1 H) 1.91-2.01 (m, 1 H) 1.47-1.68 (m, 3 H). MS (LC/MS) R.T.=2.06; [M+H]⁺=349.1. The second peak was (R)—N-(4-chlorobenzo[d]thiazol-2-yl)-4H-1'-azaspiro[oxazole-5,3'-bicyclo[2.2.2]octan]-2-amine (0.11 g, 0.30 mmol, 35.2% yield). (7b, R-isomer): ¹H NMR (500 MHz, DMSO-$d_6$) δ ppm 8.89 (br. s., 1 H) 7.77 (d, J=7.93 Hz, 1 H) 7.40 (d, J=7.93 Hz, 1 H) 7.16 (t, J=7.93 Hz, 1 H) 3.94 (d, J=10.07 Hz, 1 H) 3.67 (d, J=10.07 Hz, 1 H) 2.99-3.11 (m, 2 H) 2.74-2.88 (m, 2 H) 2.68 (t, J=7.78 Hz, 2 H) 2.11 (br. s., 1 H) 1.90-2.01 (m, 1 H) 1.44-1.68 (m, 3 H). MS (LC/MS) R.T.=2.07; [M+H]⁺=349.1.

EXAMPLE 8

N—(¹H-Benzo[d]imidazol-2-yl)-4H-1'-azaspiro[oxazole-5,3'-bicyclo[2.2.2]octan]-2-amine

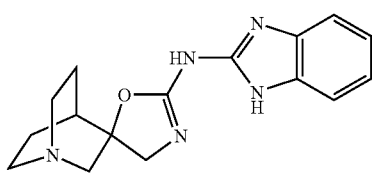

Step A: N-(¹H-Benzo[d]imidazol-2-yl)-¹H-imidazole-1-carbothioamide

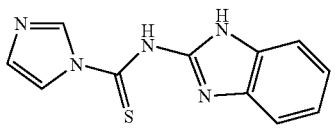

To ¹H-benzo[d]imidazol-2-amine (1.28 g, 9.61 mmol) in acetonitrile (30 mL) was added 1,1'-thiocarbonyldiimidazole (2.227 g, 12.5 mmol). The reaction mixture was stirred at 50° C. for 18 hours. The reaction was cooled to room temperature and the precipitate was filtered and washed with acetonitrile (2×50 mL). The yellow powder was dried in a vacuum oven (40° C.) for 1 hour to yield N—(¹H-benzo[d]imidazol-2-yl)-¹H-imidazole-1-carbothioamide (1.8 g, 7.4 mmol, 77% yield) and then used in the next step without any further purification or characterization.

Step B: (3-((3-¹H-Benzo[d]imidazol-2-ylthioureido)methyl)-3-hydroxy-1-ammoniobicyclo[2.2.2]octan-1-yl)trihydroborate

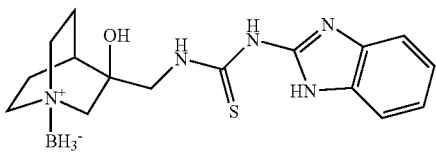

To N—(¹H-benzo[d]imidazol-2-yl)-¹H-imidazole-1-carbothioamide (1.07 g, 4.4 mmol) in N,N-dimethylformamide (20 mL) was added (3-(aminomethyl)-3-hydroxy-1-ammoniobicyclo[2.2.2]octan-1-yl)trihydroborate (0.748 g, 4.4 mmol). The reaction mixture was stirred at 70° C. for 4 hours. The reaction was concentrated and purified via silica gel chromatography (60-100% ethyl acetate/hexane). The product fractions were concentrated in vacuo to yield (3-((3-¹H-benzo[d]imidazol-2-ylthioureido)methyl)-3-hydroxy-1-ammoniobicyclo[2.2.2]octan-1-yl)trihydroborate (1.28 g, 3.71 mmol, 84% yield) as a white powder. ¹H NMR (500 MHz, DMSO-$d_6$) δ ppm 11.41 (s, 1 H), 11.16 (s, 1 H), 7.43 (d, J=3.05 Hz, 3 H), 7.13 (ddd, J=9.46, 3.81, 3.51 Hz, 3 H), 5.36 (s, 1 H), 4.01-4.07 (m, 3 H), 3.79 (dd, J=13.28, 4.12 Hz, 1 H), 2.83-2.92 (m, 6 H), 2.71 (d, J=14.04 Hz, 2 H), 2.04-2.13 (m, 2 H), 1.89-1.94 (m, 3 H), 1.74 (td, J=9.46, 5.49 Hz, 2 H), 1.51-1.59 (m, 2 H), 1.38 (s, 2 H), 1.31 (s, 1 H). LC/MS confirmed product as loss of $BH_3$ in the LC/MS conditions: retention time 2.75 (M+1−$BH_3$=332.2).

Step C: (2-(¹H-Benzo[d]imidazol-2-ylamino)-4H-1'-ammoniospiro-[oxazole-5,3'-bicyclo[2.2.2]octane]-1'-yl)trihydroborate

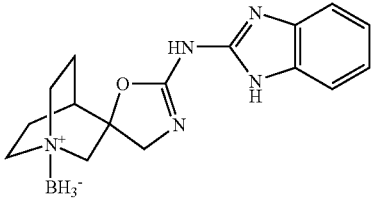

To (3-((3-¹H-benzo[d]imidazol-2-ylthioureido)methyl)-3-hydroxy-1-ammoniobicyclo[2.2.2]octan-1-yl)trihydroborate (1.0 g, 2.9 mmol) in N,N-dimethylformamide (20 mL) was added N,N'-diisopropylcarbodiimide (0.587 mL, 3.77 mmol). The reaction mixture was stirred at 70° C. for 4 hours. The reaction was concentrated and purified via silica gel chromatography (40-100% ethyl acetate/hexane). The product fractions were concentrated in vacuo to yield (2-(¹H-benzo[d]imidazol-2-ylamino)-4H-1'-ammoniospiro[oxazole-5,3'-bicyclo[2.2.2]octane]-1'-yl)trihydroborate (0.81 g, 2.6 mmol, 90% yield) as a white powder. ¹H NMR (500 MHz, DMSO-$d_6$) δ ppm 7.29 (s, 1 H), 6.99-7.05 (m, 2 H), 3.90 (t, J=9.77 Hz, 1 H), 3.75 (d, J=10.38 Hz, 1 H), 3.26-3.35 (m, 1 H), 3.13 (dd, J=14.95, 1.53 Hz, 1 H), 2.98-3.06 (m, 1 H), 2.84-2.92 (m, 3 H), 2.22 (s, 1 H), 1.98-2.05 (m, 1 H), 1.72-1.82 (m, 3 H), 1.45 (s, 1 H). LC/MS confirmed product as loss of $BH_3$ in the LC/MS conditions: retention time 2.29 (M+1−$BH_3$=298.2).

Step D: N—(¹H-Benzo[d]imidazol-2-yl)-4H-1'-azaspiro-[oxazole-5,3'-bicyclo[2.2.2]octan]-2-amine

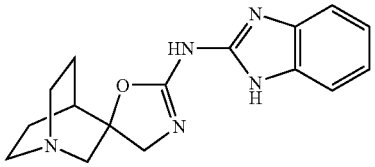

To (2-(¹H-benzo[d]imidazol-2-ylamino)-4H-1'-ammoniospiro[oxazole-5,3'-bicyclo[2.2.2]octane]-1'-yl)trihydroborate (0.77 g, 2.5 mmol) in acetone (9 mL) was added 3 M HCl (6.2 mL, 18.6 mmol). The reaction was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered and concentrated in vacuo to afford N—(¹H-benzo[d]imidazol-2-yl)-4H-1'-azaspiro[oxazole-5,3'-bicyclo[2.2.2]octan]-2-amine (0.5 g, 1.68 mmol, 68% yield) as a white powder. ¹H NMR (500 MHz, DMSO-$d_6$) δ ppm 11.45 (s, 1 H), 9.20 (s, 1 H), 7.32 (s, 1 H), 7.00 (dd, J=5.65, 2.90 Hz, 4 H), 3.91 (d, J=10.07 Hz, 2 H), 3.64 (d, J=10.07 Hz, 2 H), 2.98-3.05 (m, 4 H), 2.73-2.82 (m, 4 H), 2.67 (t, J=7.63 Hz, 4 H), 2.03 (d, J=2.75 Hz, 2 H), 1.85-1.92 (m, 2H), 1.54-1.63 (m, 4 H), 1.44-1.51 (m, 2 H). MS (LC/MS) R.T.=1.30; [M+H]⁺=298.2.

The enantiomers were separated using a Chiralpak AS-H (30×250 mm, 5 µm) column with a mobile phase consisting of 30% methanol (0.1% DEA) in $CO_2$ and UV monitored at 330 nm. The separated peaks were concentrated in vacuo to yield white powders. The first peak off the column yielded 0.11 g, 0.36 mmol, 33.0%. (8a; R-isomer): M.P. 255° C. (dec). $^1$H NMR (500 MHz, DMSO-d$_6$) δ ppm 11.43 (br. s., 1 H) 9.16 (br. s., 1 H) 7.14-7.53 (m, 2 H) 6.82-7.09 (m, 2 H) 3.91 (d, J=9.77 Hz, 1 H) 3.64 (d, J=10.07 Hz, 1 H) 2.96-3.09 (m, 2 H) 2.71-2.87 (m, 2 H) 2.62-2.73 (m, 2 H) 2.01-2.08 (m, 1 H) 1.81-1.97 (m, 1 H) 1.54-1.66 (m, 2 H) 1.40-1.53 (m, 1 H). MS (LC/MS) R.T.=1.26; [M+H]$^+$=298.2. The second peak yielded 0.11 g, 0.36 mmol, 33.0%. (8b; S-isomer): $^1$H NMR (500 MHz, DMSO-d$_6$) δ ppm 11.43 (br. s., 1 H) 9.20 (br. s., 1 H) 7.10-7.60 (m, 2 H) 6.83-7.11 (m, 2 H) 3.91 (d, J=9.77 Hz, 1 H) 3.64 (d, J=9.77 Hz, 1 H) 2.94-3.16 (m, 2 H) 2.71-2.86 (m, 2 H) 2.59-2.72 (m, 2 H) 1.97-2.09 (m, 1 H) 1.81-1.95 (m, 1 H) 1.53-1.71 (m, 2 H) 1.41-1.53 (m, 1 H). MS (LC/MS) R.T.=1.28; [M+H]$^+$=298.2.

EXAMPLE 9

N-(6-Chlorobenzo[d]thiazol-2-yl)-4H-1'-azaspiro[oxazole-5,3'-bicyclo[2.2.2]octan]-2-amine

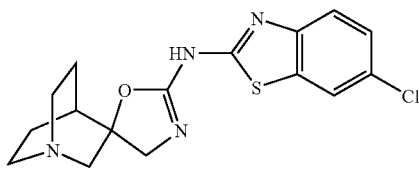

Step A: N-(6-Chlorobenzo[d]thiazol-2-yl)-$^1$H-imidazole-1-carbothioamide

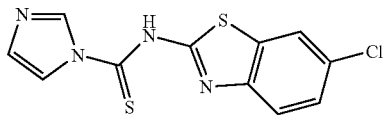

To 6-chlorobenzo[d]thiazol-2-amine (1.14 g, 6.17 mmol) in acetonitrile (30 mL) was added 1,1'-thiocarbonyldiimidazole (1.43 g, 8 mmol). The reaction was stirred at 50° C. for 18 hours. The reaction was cooled to room temperature and the precipitate was filtered and washed with acetonitrile (2×50 mL). The yellow powder was dried in a vacuum oven (40° C.) for 1 hour to yield N-(6-chlorobenzo[d]thiazol-2-yl)-$^1$H-imidazole-1-carbothioamide (1.16 g, 3.9 mmol, 64% yield) and then used in the next step without any further purification or characterization.

Step B: (3-((3-(6-Chlorobenzo[d]thiazol-2-yl)thioureido)methyl)-3-hydroxy-1-ammoniobicyclo[2.2.2]octan-1-yl)trihydroborate

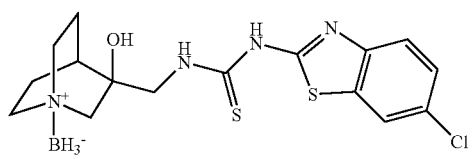

To N-(6-chlorobenzo[d]thiazol-2-yl)-$^1$H-imidazole-1-carbothioamide (0.86 g, 2.9 mmol) in N,N-dimethylformamide (20 mL) was added (3-(aminomethyl)-3-hydroxy-1-ammoniobicyclo[2.2.2]octan-1-yl)trihydroborate (0.5 g, 2.9 mmol). The reaction was stirred at 70° C. for 4 hours. The reaction was concentrated and purified via silica gel chromatography (60-100% ethyl acetate/hexanes). The product fractions were concentrated in vacuo to yield (3-((3-(6-chlorobenzo[d]thiazol-2-yl)thioureido)methyl)-3-hydroxy-1-ammoniobicyclo[2.2.2]octan-1-yl)trihydroborate (0.4 g, 1.01 mmol, 34.6% yield) as a white powder. $^1$H NMR (500 MHz, DMSO-d$_6$) δ ppm 11.92 (br. s., 1 H) 9.89 (br. s., 1 H) 8.08 (br. s., 1 H) 7.62 (br. s., 1 H) 7.40-7.50 (m, 1 H) 5.40 (br. s., 1 H) 3.88 (d, J=10.20 Hz, 1 H) 3.76 (d, J=10.20 Hz, 1 H) 2.67-3.02 (m, 6 H) 2.08 (br. s., 1 H) 1.80-1.95 (m, 2 H) 1.73 (br. s., 1 H) 1.01-1.63 (m, 4 H). MS (LC/MS) R.T.=3.87; [M+H]$^+$=395.1.

Step C: (2-(6-Chlorobenzo[d]thiazol-2-ylamino)-4H-1'-ammoniospiro[oxazole-5,3'-bicyclo[2.2.2]octane]-1'-yl)trihydroborate

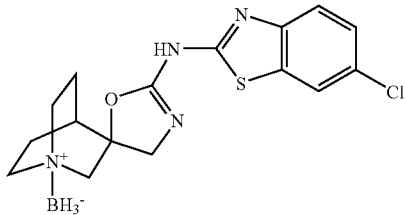

To (3-((3-(6-chlorobenzo[d]thiazol-2-yl)thioureido)methyl)-3-hydroxy-1-ammoniobicyclo[2.2.2]octan-1-yl)trihydroborate (0.37 g, 0.93 mmol) in N,N-dimethylformamide (20 mL) was added N,N'-diisopropylcarbodiimide (0.19 mL, 1.2 mmol). The reaction was stirred at 70° C. for 4 hours. The reaction was concentrated and purified via silica gel chromatography (40-100% ethyl acetate/hexane). The product fractions were concentrated in vacuo to yield (2-(6-chlorobenzo[d]thiazol-2-ylamino)-4H-1'-ammoniospiro[oxazole-5,3'-bicyclo[2.2.2]octane]-1'-yl)trihydroborate (0.12 g, 0.33 mmol, 35.5% yield) as a white powder. $^1$H NMR (500 MHz, DMSO-d$_6$) δ ppm 9.10 (br. s., 1 H) 7.95 (d, J=2.14 Hz, 1 H) 7.60 (d, J=8.55 Hz, 1 H) 7.36 (dd, J=8.55, 2.14 Hz, 1 H) 3.88 (d, J=10.38 Hz, 1 H) 3.76 (d, J=10.38 Hz, 1 H) 3.26-3.37 (m, 1 H) 3.17 (dd, J=14.95, 1.83 Hz, 1 H) 3.00-3.11 (m, 1 H) 2.80-2.97 (m, 3 H) 2.28 (br. s., 1 H) 2.00-2.11 (m, 1 H) 1.69-1.88 (m, 3H) 1.46 (br. s., 3H). LC/MS: retention time 2.94 (M+1−BH$_3$=349.1).

Step D: N-(6-Chlorobenzo[d]thiazol-2-yl)-4H-1'-azaspiro[oxazole-5,3'-bicyclo[2.2.2]octan]-2-amine

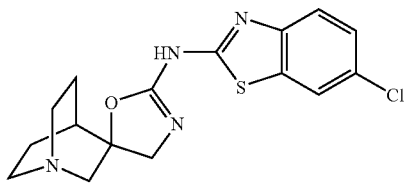

To (2-(6-chlorobenzo[d]thiazol-2-ylamino)-4H-1'-ammoniospiro[oxazole-5,3'-bicyclo[2.2.2]octane]-1'-yl)trihydroborate (0.1 g, 0.28 mmol) in acetone (9 mL) was added 3 M HCl (0.69 mL, 2.07 mmol). The reaction was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered and concentrated in vacuo to afford N-(6-chlorobenzo[d]thiazol-2-yl)-4H-1'-azaspiro[oxazole-5,3'-bicyclo[2.2.2]octan]-2-amine (0.06 g, 0.17 mmol, 62.4% yield) as a white powder. $^1$H NMR (500 MHz, DMSO-d$_6$) δ ppm 9.03 (br. s., 1 H) 7.93 (d, J=2.14 Hz, 1 H) 7.58 (d, J=8.55 Hz, 1 H) 7.35 (dd, J=8.55, 2.14 Hz, 1 H) 3.90 (d, J=10.07 Hz, 1 H) 3.65 (d, J=10.07 Hz, 1 H) 2.99-3.11 (m, 2 H) 2.73-2.89 (m, 2 H) 2.67 (t, J=7.63 Hz, 2 H) 2.08 (br. s., 1 H) 1.82-1.99 (m, 1 H) 1.43-1.67 (m, 3 H). MS (LC/MS) R.T.=2.07; [M+H]$^+$=349.1.

The enantiomers were separated using a Chiralpak AS-H (30×250 mm, 5 μm) column with a mobile phase consisting of 30% methanol (0.1% DEA) in CO$_2$ and UV monitored at 220 nm. The separated peaks were concentrated in vacuo to yield white powders. The first peak off the column yielded 0.034 g, 0.10 mmol, 36.2%. (9a; S-isomer): $^1$H NMR (500 MHz, DMSO-d$_6$) δ ppm 9.02 (br. s., 1 H) 7.93 (d, J=2.14 Hz, 1 H) 7.58 (d, J=8.55 Hz, 1 H) 7.35 (dd, J=8.55, 2.14 Hz, 1 H) 3.90 (d, J=10.07 Hz, 1 H) 3.65 (d, J=10.07 Hz, 1 H) 2.97-3.11 (m, 2 H) 2.73-2.89 (m, 2 H) 2.67 (t, J=7.48 Hz, 2 H) 2.08 (br. s., 1 H) 1.93 (br. s., 1 H) 1.43-1.69 (m, 3 H). MS (LC/MS) R.T.=2.05; [M+H]$^+$=349.1. Optical rotation=+4.00°. The second peak yielded 0.037 g, 0.10 mmol, 39.4%. (9b; R-isomer): $^1$H NMR(500 MHz, DMSO-d$_6$) δ ppm 9.02 (br. s., 1 H) 7.93 (d, J=2.14 Hz, 1 H) 7.58 (d, J=8.55 Hz, 1 H) 7.35 (dd, J=8.55, 2.44 Hz, 1 H) 3.90 (d, J=10.07 Hz, 1 H) 3.65 (d, J=10.07 Hz, 1 H) 2.93-3.13 (m, 2 H) 2.72-2.91 (m, 2 H) 2.62-2.73 (m, 2 H) 2.08 (br. s., 1 H) 1.93 (d, J=1.22 Hz, 1 H) 1.44-1.68 (m, 3 H). MS (LC/MS) R.T.=2.04; [M+H]$^+$=349.1. Optical rotation=−3.74°0.

EXAMPLE 10

N-(1-Methyl-$^1$H-benzo[d]imidazol-2-yl)-4H-1'-azaspiro[oxazole-5,3'-bicyclo[2.2.2]octan]-2-amine

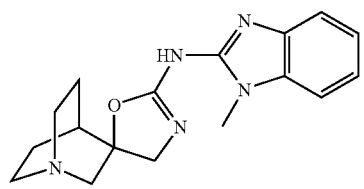

Step A: N-(1-Methyl-$^1$H-benzo[d]imidazol-2-yl)-$^1$H-imidazole-1-carbothioamide

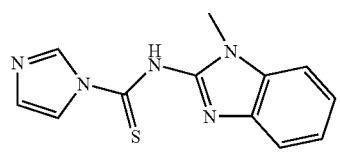

To 1-methyl-$^1$H-benzo[d]imidazol-2-amine (1.28 g, 8.7 mmol) in acetonitrile (30 mL) was added 1,1'-thiocarbonyldiimidazole (2.015 g, 11.31 mmol). The reaction was stirred at 50° C. for 18 hours. The reaction was cooled to room temperature and the precipitate was filtered and washed with acetonitrile (2×50 mL). The yellow powder was dried in a vacuum oven (40° C.) for 1 hour to yield N-(1-methyl-$^1$H-benzo[d]imidazol-2-yl)-$^1$H-imidazole-1-carbothioamide (1.6 g, 6.22 mmol, 71.5% yield) and then used in the next step without any further purification or characterization.

Step B: (3-Hydroxy-3-((3-(1-methyl-$^1$H-benzo[d]imidazol-2-yl)thioureido)methyl)-1-ammoniobicyclo[2.2.2]octan-1-yl)trihydroborate

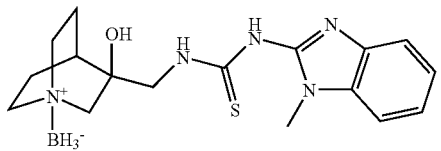

To N-(1-methyl-$^1$H-benzo[d]imidazol-2-yl)-$^1$H-imidazole-1-carbothioamide (1.04 g, 4.04 mmol) in N,N-dimethylformamide (20 mL) was added (3-(aminomethyl)-3-hydroxy-1-ammoniobicyclo[2.2.2]octan-1-yl)trihydroborate (0.687 g, 4.04 mmol). The reaction was stirred at 70° C. for 4 hours. The reaction was concentrated and purified via silica gel chromatography (60-100% ethyl acetate/hexane). The product fractions were concentrated in vacuo to yield (3-hydroxy-3-((3-(1-methyl-$^1$H-benzo[d]imidazol-2-yl)thioureido)methyl)-1-ammoniobicyclo[2.2.2]octan-1-yl)trihydroborate (1.28 g, 3.56 mmol, 88% yield) as a white powder. LC/MS confirmed product as loss of BH$_3$ in the LC/MS conditions: retention time 3.01 (M+1−BH$_3$=346.2).

Step C: (2-(1-Methyl-$^1$H-benzo[d]imidazol-2-ylamino)-4H-1'-ammoniospiro[oxazole-5,3'-bicyclo[2.2.2]octane]-1'-yl)trihydroborate

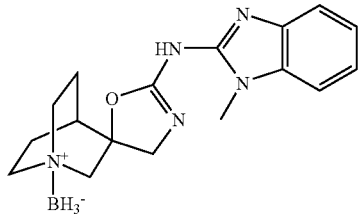

To (3-hydroxy-3-((3-(1-methyl-$^1$H-benzo[d]imidazol-2-yl)thioureido)methyl)-1-ammoniobicyclo[2.2.2]octan-1-yl)trihydroborate (1.19 g, 3.31 mmol) in N,N-dimethylformamide (20 mL) was added N,N'-diisopropylcarbodiimide (1.55 mL, 9.9 mmol). The reaction was stirred at 70° C. for 4 hours. The reaction was concentrated and purified via silica gel chromatography (40-100% ethyl acetate/hexane). The product fractions were concentrated in vacuo to yield (2-(1-methyl-$^1$H-benzo[d]imidazol-2-ylamino)-4H-1'-ammoniospiro[oxazole-5,3'-bicyclo[2.2.2]octane]-1'-yl)trihydroborate (0.94 g, 2.9 mmol, 87% yield) as a white powder. $^1$H NMR (400 MHz, DMSO-d$_6$) δ ppm 9.36 (br. s., 1 H) 7.34-7.44 (m, 1 H) 7.26-7.34 (m, 1 H) 7.00-7.12 (m, 2 H) 3.90 (d, J=10.32 Hz, 1 H) 3.77 (d, J=10.32 Hz, 1 H) 3.57 (s, 3 H) 3.28 (dd, J=14.86, 2.27 Hz, 1 H) 3.13 (dd, J=14.86, 1.51 Hz, 1 H) 2.95-3.08 (m, 1 H) 2.75-2.95 (m, 3 H) 2.22 (br. s., 1 H) 1.96-2.11 (m, 1 H) 1.67-1.89 (m, 3 H) 1.43 (br. s., 3 H). LC/MS: retention time 2.37 (M+1−BH$_3$=312.2).

Step D: N-(1-Methyl-¹H-benzo[d]imidazol-2-yl)-4H-1'-azaspiro[oxazole-5,3'-bicyclo[2.2.2]octan]-2-amine

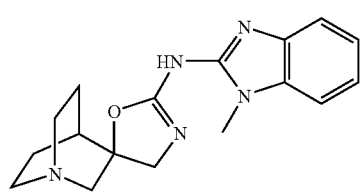

To (2-(1-methyl-¹H-benzo[d]imidazol-2-ylamino)-4H-1'-ammoniospiro[oxazole-5,3'-bicyclo[2.2.2]octane]-1'-yl)trihydroborate (0.92 g, 2.8 mmol) in acetone (9 mL) was added 3 M HCl (7.1 mL, 21.2 mmol). The reaction was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered, and concentrated in vacuo to afford N-(1-methyl-¹H-benzo[d]imidazol-2-yl)-4H-1'-azaspiro[oxazole-5,3'-bicyclo[2.2.2]octan]-2-amine (0.84 g, 2.7 mmol, 95% yield) as a white powder. $^1$H NMR (400 MHz, DMSO-$d_6$) δ ppm 9.24-9.39 (m, 1 H) 7.33-7.42 (m, 1 H) 7.25-7.33 (m, 1 H) 6.99-7.10 (m, 2 H) 3.92 (d, J=10.07 Hz, 1 H) 3.66 (d, J=10.07 Hz, 1 H) 3.57 (s, 3 H) 2.97-3.08 (m, 2 H) 2.78 (t, J=7.81 Hz, 2 H) 2.67 (t, J=7.81 Hz, 2 H) 2.01-2.09 (m, 1 H) 1.80-1.96 (m, 1 H) 1.40-1.66 (m, 3 H). MS (LC/MS) R.T.=1.49; [M+H]$^+$=312.2.

The enantiomers were separated using a Chiralcel OJ-H (30×250 mm, 5 µm) column with a mobile phase consisting of 22% methanol (0.1% DEA) in $CO_2$ and UV monitored at 300 nm. The separated peaks were concentrated in vacuo to yield white powders. The first peak off the column yielded 0.065 g, 0.205 mmol, 39.8%. (10a, R-isomer): $^1$H NMR (500 MHz, DMSO-$d_6$) δ ppm 9.31 (br. s., 1 H) 7.35-7.45 (m, 1 H) 7.26-7.34 (m, 1 H) 7.00-7.15 (m, 2 H) 3.93 (d, J=10.10 Hz, 1 H) 3.67 (d, J=10.10 Hz, 1 H) 3.59 (s, 3 H) 2.93-3.13 (m, 2 H) 2.74-2.89 (m, 2 H) 2.61-2.74 (m, 2 H) 2.05 (br. s., 1 H) 1.91 (br. s., 1 H) 1.38-1.68 (m, 3 H). MS (LC/MS) R.T.=1.37; [M+H]$^+$=312.2. Optical rotation=−16.02°. The second peak yielded 0.06 g, 0.19 mmol, 36.8%. (10b; S-isomer): $^1$H NMR (500 MHz, DMSO-$d_6$) δ ppm 9.31 (br. s., 1 H) 7.33-7.43 (m, 1 H) 7.25-7.33 (m, 1 H) 6.93-7.11 (m, 2 H) 3.93 (dd, J=9.92, 3.20 Hz, 1 H) 3.67 (dd, J=9.92, 3.20 Hz, 1 H) 3.58 (s, 3 H) 2.94-3.13 (m, 2H) 2.74-2.85 (m, 2 H) 2.59-2.72 (m, 2 H) 2.04 (br. s., 1 H) 1.90 (br. s., 1 H) 1.37-1.70 (m, 3 H). MS (LC/MS) R.T.=1.37; [M+H]$^+$=312.2. Optical rotation=+35.99°.

EXAMPLE 11

N-(6-Ethoxybenzo[d]thiazol-2-yl)-4H-1'-azaspiro[oxazole-5,3'-bicyclo[2.2.2]octan]-2-amine

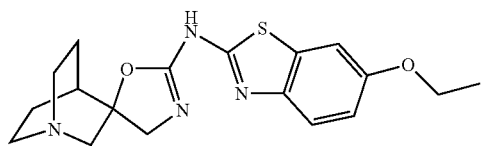

Step A: N-(6-Ethoxybenzo[d]thiazol-2-yl)-1H-imidazole-1-carbothioamide

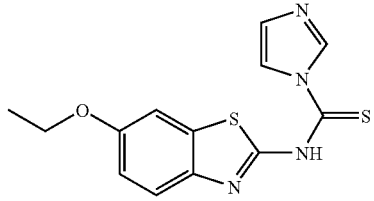

In a vial was placed 6-ethoxybenzo[d]thiazol-2-amine (1.5 g, 7.72 mmol) and di(¹H-imidazol-1-yl)methanethione (1.789 g, 10.04 mmol) in acetonitrile (15 mL). The reaction was heated to 80° C. overnight. The reaction mixture was filtered and the precipitate was collected to afford 2.4 grams (7.88 mmol, 102%) of rust-colored solids.

Step B: (3-((3-(6-Ethoxybenzo[d]thiazol-2-yl)thioureido)methyl)-3-hydroxy-1-ammoniobicyclo[2.2.2]octan-1-yl)trihydroborate

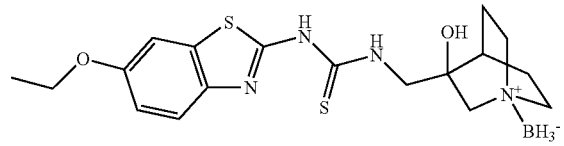

In a vial was placed N-(6-ethoxybenzo[d]thiazol-2-yl)-¹H-imidazole-1-carbothioamide (2.4 g, 7.88 mmol) and (3-(aminomethyl)-3-hydroxy-1-ammoniobicyclo[2.2.2]octan-1-yl)trihydroborate (1.341 g, 7.88 mmol) in N,N-dimethylformamide (8 mL). The reaction was heated to 80° C. After 2 hours the reaction was poured into water and chloroform and the organic was extracted and concentrated to a red oil. This material was used in the next reaction without any further purification or characterization.

Step C: (2-(6-Ethoxybenzo[d]thiazol-2-ylamino)-4H-1'-ammoniospiro-[oxazole-5,3'-bicyclo[2.2.2]octane]-1'-yl)trihydroborate

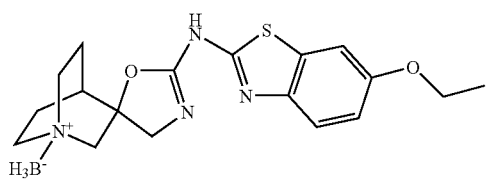

In a flask was placed (3-((3-(6-ethoxybenzo[d]thiazol-2-yl)thioureido)-methyl)-3-hydroxy-1-ammoniobicyclo[2.2.2]octan-1-yl)trihydroborate (3.2 g, 7.9 mmol) and N,N'-diisopropylcarbodiimide (4.3 mL, 27.6 mmol) in N,N-dimethylformamide (10 mL). The reaction was heated to 70° C. for 2 hours and then poured into water and chloroform. The organic was collected and concentrated to a residue. The residue was triturated in ether and the precipitate was collected via vacuum filtration to yield 1.11 grams (2.98 mmol, 37.8%) of gray powder.

Step D: N-(6-Ethoxybenzo[d]thiazol-2-yl)-4H-1'-azaspiro[oxazole-5,3'-bicyclo[2.2.2]octan]-2-amine

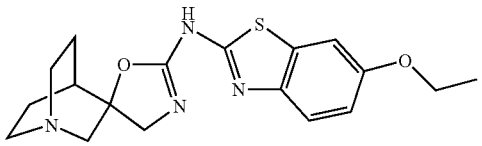

In a vial was placed (2-(6-ethoxybenzo[d]thiazol-2-ylamino)-4H-1'-ammoniospiro[oxazole-5,3'-bicyclo[2.2.2]octane]-1'-yl)trihydroborate (500 mg, 1.34 mmol) and HCl (8.06 mL, 24.17 mmol) in acetone (10 mL). The reaction was monitored by HPLC. After 2 hours, the reaction was complete by LC/MS. The reaction was poured into water and chloroform, and the organic layer was set aside. The aqueous layer was neutralized and extracted with chloroform (2×). The second chloroform fraction was concentrated to a white residue. The solid was triturated in ether and the precipitate collected to yield 314.4 mg (0.877 mmol, 65.3%) of the desired material. $^1$H NMR (400 MHz, DMSO-$d_6$) δ ppm 8.89 (1 H, br. s.), 7.50 (1 H, d, J=8.81 Hz), 7.38 (1 H, d, J=2.52 Hz), 6.91 (1 H, dd, J=8.81, 2.52 Hz), 4.03 (2 H, q, J=7.05 Hz), 3.87 (1 H, d, J=10.07 Hz), 3.62 (1 H, d, J=10.07 Hz), 3.02 (2 H, s), 2.78 (2 H, t, J=7.81 Hz), 2.66 (2 H, t, J=7.68 Hz), 2.05 (1 H, br. s.), 1.91 (1 H, br. s.), 1.42-1.67 (3 H, m), 1.33 (3 H, t, J=7.05 Hz). MS (LC/MS) R.T.=1.60; [M+H]$^+$=359.0.

The enantiomers were separated using a Chiralpak AS-H (30×250 mm, 5 µm) column with a mobile phase consisting of 30% methanol (0.1% DEA) in $CO_2$ and UV monitored at 300 nm. The separated peaks were concentrated in vacuo to yield white powders. The first peak off the column yielded 62.4 mg, 0.17 mmol, 31.2%. (11a; S-isomer): $^1$H NMR (500 MHz, DMSO-$d_6$) δ ppm 8.87 (1 H, br. s.), 7.49 (1 H, d, J=8.55 Hz), 7.38 (1 H, d, J=2.44 Hz), 6.91 (1 H, dd, J=8.85, 2.44 Hz), 4.03 (2 H, q, J=7.02 Hz), 3.87 (1 H, d, J=10.07 Hz), 3.61 (1 H, d, J=10.07 Hz), 3.02 (2H, s), 2.72-2.85 (2 H, m), 2.66 (2 H, t, J=7.63 Hz), 2.05 (1 H, br. s.), 1.91 (1 H, br. s.), 1.43-1.64 (3 H, m), 1.33 (3 H, t, J=7.02 Hz). MS (LC/MS) R.T.=1.81; [M+H]$^+$=359.1. The second peak yielded 58.9 mg, 0.164 mmol, 29.5%. (11b; R-isomer): $^1$H NMR (500 MHz, DMSO-$d_6$) δ ppm 8.86 (1 H, br. s.), 7.48 (1 H, d, J=8.85 Hz), 7.37 (1 H, d, J=2.44 Hz), 6.91 (1 H, d, J=2.75 Hz), 4.02 (2 H, q, J=7.02 Hz), 3.86 (1 H, d, J=9.77 Hz), 3.61 (1 H, d, J=9.77 Hz), 3.01 (2 H, s), 2.72-2.85 (2 H, m), 2.62-2.69 (2 H, m), 2.04 (1 H, d, J=2.44 Hz), 1.90 (1 H, d, J=4.27 Hz), 1.42-1.63 (3 H, m), 1.29-1.35 (3 H, m). MS (LC/MS) R.T.=1.52; [M+H]$^+$=359.1.

EXAMPLE 12

N-(6-Methylbenzo[d]thiazol-2-yl)-4H-1'-azaspiro[oxazole-5,3'-bicyclo[2.2.2]octan]-2-amine

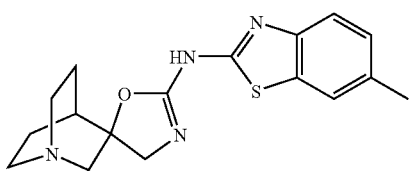

Step A: N-(6-Methylbenzo[d]thiazol-2-yl)-$^1$H-imidazole-1-carbothioamide

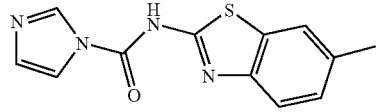

To 6-methylbenzo[d]thiazol-2-amine (1.0 g, 6.2 mmol) in acetonitrile (30 mL) was added 1,1'-thiocarbonyldiimidazole (1.44 g, 8.1 mmol). The reaction was stirred at 50° C. for 18 hours. The reaction was cooled to room temperature and the precipitate was filtered and washed with acetonitrile (2×50 mL). The yellow powder was dried in a vacuum oven (40° C.) for 1 hour to yield N-(6-methylbenzo[d]thiazol-2-yl)-$^1$H-imidazole-1-carbothioamide (1.06 g, 3.86 mmol, 62% yield) and then used in the next step without any further purification or characterization.

Step B: (3-Hydroxy-3-((3-(6-methylbenzo[d]thiazol-2-yl)thioureido)methyl)-1-ammoniobicyclo[2.2.2]octan-1-yl)trihydroborate

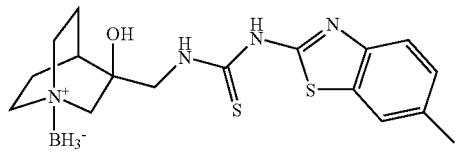

To N-(6-methylbenzo[d]thiazol-2-yl)-$^1$H-imidazole-1-carbothioamide (0.96 g, 3.5 mmol) in N,N-dimethylformamide (20 mL) was added (3-(aminomethyl)-3-hydroxy-1-ammoniobicyclo[2.2.2]octan-1-yl)trihydroborate (0.595 g, 3.5 mmol). The reaction was stirred at 70° C. for 4 hours. The reaction mixture was concentrated and purified via silica gel chromatography (40-100% ethyl acetate/hexanes). The product fractions were concentrated in vacuo to yield (3-hydroxy-3-((3-(6-methylbenzo[d]thiazol-2-yl)thioureido)methyl)-1-ammoniobicyclo[2.2.2]octan-1-yl)trihydroborate (0.88 g, 2.338 mmol, 66.8% yield) as a white powder. MS (LC/MS) R.T.=3.71; [M+H]$^+$=375.2.

Step C: (2-(6-Methylbenzo[d]thiazol-2-ylamino)-4H-1'-ammoniospiro[oxazole-5,3'-bicyclo[2.2.2]octane]-1'-yl)trihydroborate

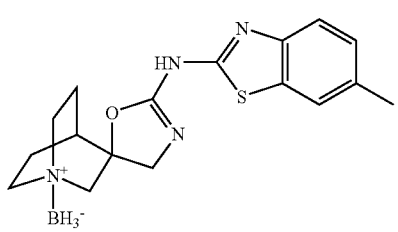

To (3-hydroxy-3-((3-(6-methylbenzo[d]thiazol-2-yl)thioureido)methyl)-1-ammoniobicyclo[2.2.2]octan-1-yl)trihydroborate (0.86 g, 2.285 mmol) in N,N-dimethylformamide (20 mL) was added N,N'-diisopropylcarbodiimide (0.288 g, 2.285 mmol). The reaction was stirred at 70° C. for 4 hours. The reaction was concentrated and ethyl acetate was added. The precipitate was filtered and washed with additional ethyl acetate. The powder was dried in a vacuum oven (70° C.) to yield (2-(6-methylbenzo[d]thiazol-2-ylamino)-4H-1'-ammoniospiro[oxazole-5,3'-bicyclo[2.2.2]octane]-1'-yl)trihydroborate (0.65 g, 1.899 mmol, 83% yield) as a white powder. $^{1}$H NMR (500 MHz, DMSO-$d_6$) δ ppm 9.03 (1 H, br. s.), 7.59 (1H, s), 7.51 (1 H, d, J=8.24 Hz), 7.15 (1 H, d, J=8.24 Hz), 3.86 (1 H, d, J=10.38 Hz), 3.74 (1 H, d, J=10.38 Hz), 3.29 (1 H, dd, J=15.26, 1.83 Hz), 3.14 (1H, d, J=15.26 Hz), 2.99-3.09 (1 H, m), 2.80-2.95 (3 H, m), 2.36 (3 H, s), 2.25 (1 H, br. s.), 2.03 (1 H, t, J=10.22 Hz), 1.70-1.85 (3 H, m). MS (LC/MS) R.T.=2.78; [M+H]$^+$=343.2.

Step D: N-(6-Methylbenzo[d]thiazol-2-yl)-4H-1'-azaspiro[oxazole-5,3'-bicyclo[2.2.2]octan]-2-amine

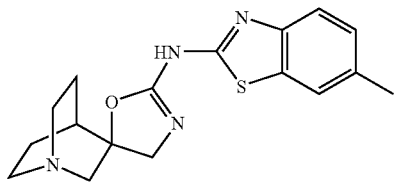

To (2-(6-methylbenzo[d]thiazol-2-ylamino)-4H-1'-ammoniospiro[oxazole-5,3'-bicyclo[2.2.2]octane]-1'-yl)trihydroborate (0.24 g, 0.70 mmol) in acetone (9 mL) was added 3 M HCl (1.753 mL, 5.26 mmol). The reaction mixture was stirred at room temperature for 4 hours. Ethyl acetate was added and the aqueous layer was collected and neutralized with 1N sodium hydroxide. The product was extracted with ethyl acetate (2×40 mL). The organics were combined, dried with magnesium sulfate, filtered and concentrated in vacuo to afford N-(6-methylbenzo[d]thiazol-2-yl)-4H-1'-azaspiro[oxazole-5,3'-bicyclo[2.2.2]octan]-2-amine (0.19 g, 0.58 mmol, 83% yield) as a white powder. $^{1}$H NMR (500 MHz, DMSO-$d_6$) δ ppm 8.96 (1H, br. s.), 7.57 (1 H, s), 7.49 (1 H, d, J=8.24 Hz), 7.13 (1 H, d, J=8.24 Hz), 3.88 (1 H, d, J=10.07 Hz), 3.63 (1 H, d, J=9.77 Hz), 2.98-3.04 (2 H, m), 2.72-2.85 (2 H, m), 2.66 (2 H, t, J=7.63 Hz), 2.36 (3H, s), 2.05 (1 H, d, J=2.14 Hz), 1.91 (1 H, br. s.), 1.53-1.64 (2 H, m), 1.42-1.53 (1 H, m). MS (LC/MS) R.T.=1.79; [M+H]$^+$=329.2.

The enantiomers were separated using a Chiralcel OJ-H (4.6×25 cm, 5 μm) column with 30% methanol (0.1% DEA) in CO$_2$ and UV monitored at 300 nm. The separated peaks were concentrated in vacuo to yield white powders. The first peak off the column yielded 0.11 g, 0.34 mmol, 55%. (12a; R-isomer): $^{1}$H NMR (500 MHz, DMSO-$d_6$) δ ppm 8.95 (s, 1 H), 7.57 (s, 2 H), 7.48 (d, J=8.24 Hz, 2 H), 7.13 (d, J=8.24 Hz, 2 H), 3.89 (d, J=10.38 Hz, 2 H), 3.63 (d, J=10.38 Hz, 2 H), 2.99-3.06 (m, 4 H), 2.75-2.84 (m, 4 H), 2.67 (t, J=7.63 Hz, 4 H), 2.37 (s, 7 H), 2.06 (s, 2 H), 1.92 (s, 2 H), 1.55-1.64 (m, 4 H), 1.49 (dd, J=9.77, 2.44 Hz, 2 H). MS (LC/MS) R.T.=1.80; [M+H]$^+$=329.2. Optical rotation=−4.52. The second peak yielded 0.11 g, 0.34 mmol, 55%. (12b; S-isomer): $^{1}$H NMR (500 MHz, DMSO-$d_6$) δ ppm 8.96 (s, 1 H), 7.58 (s, 1 H), 7.49 (d, J=8.24 Hz, 1 H), 7.14 (d, J=8.24 Hz, 1 H), 3.89 (d, J=10.07 Hz, 1 H), 3.63 (d, J=10.07 Hz, 1 H), 3.03 (d, J=2.44 Hz, 2 H), 2.75-2.84 (m, 2 H), 2.67 (t, J=7.78 Hz, 2 H), 2.37 (s, 3 H), 2.06 (s, 1 H), 1.92 (s, 1 H), 1.55-1.64 (m, 2 H), 1.49 (dd, J=9.77, 2.75 Hz, 1 H). MS (LC/MS) R.T.=1.80; [M+H]$^+$=329.2. Optical rotation=+10.08.

EXAMPLE 13

2-(4H-1'-Azaspiro[oxazole-5,3'-bicyclo[2.2.2]octane]-2-ylamino)benzo[d]thiazol-6-ol

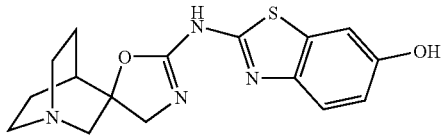

Step A: N-(6-(tert-Butyldimethylsilyloxy)benzo[d]thiazol-2-yl)-1H-imidazole-1-carbothioamide

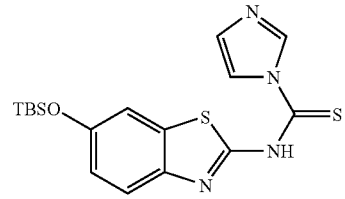

To 6-(tert-butyldimethylsilyloxy)benzo[d]thiazol-2-amine (prepared as described in WO 2007/086800 p.102) (3.1 g, 11.05 mmol) in acetonitrile (30 mL) was added thiocarbonyl diimidazole (2.56 g, 14.37 mmol). The reaction was heated to 70° C. overnight. The reaction was cooled to room temperature and the precipitate was filtered and washed with acetonitrile to afford a yellow solid. The product, N-(6-(tert-butyldimethylsilyloxy)benzo[d]thiazol-2-yl)-1H-imidazole-1-carbothioamide (3.85 g, 9.86 mmol, 89% yield), was taken directly to the next step without any further purification. MS (LC/MS) R.T.=2.56; [M+H]$^+$=388.9.

Step B: (3-((3-(6-(tert-Butyldimethylsilyloxy)benzo[d]thiazol-2-yl)thioureido)methyl)-3-hydroxy-1-ammoniobicyclo[2.2.2]octan-1-yl)trihydroborate

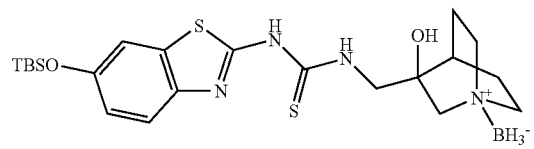

To N-(6-(tert-butyldimethylsilyloxy)benzo[d]thiazol-2-yl)-1H-imidazole-1-carbothioamide (3.85 g, 9.86 mmol) in N,N-dimethylformamide (40 mL) was added (3-(aminomethyl)-3-hydroxy-1-ammoniobicyclo[2.2.2]octan-1-yl)trihydroborate (1.68 g, 9.86 mmol). The reaction was heated at 80° C. for 2 hours. The reaction was cooled and then poured into a mixture of chloroform and water. The organic layer was collected and concentrated in vacuo to afford (3-((3-(6-(tert-butyldimethylsilyloxy)benzo[d]thiazol-2-yl)thioureido)methyl)-3-hydroxy-1-ammoniobicyclo[2.2.2]octan-1-yl)trihydroborate (6.2 g) as a yellow oil.

Step C: (2-(6-(tert-Butyldimethylsilyloxy)benzo[d]thiazol-2-ylamino)-4H-1'-ammoniospiro[oxazole-5,3'-bicyclo[2.2.2]octane]-1'-yl)trihydroborate

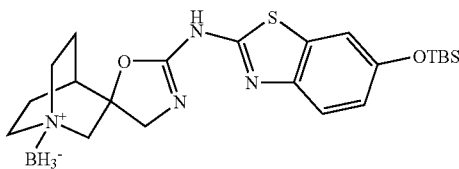

To (3-((3-(6-(tert-butyldimethylsilyloxy)benzo[d]thiazol-2-yl)thioureido)methyl)-3-hydroxy-1-ammoniobicyclo[2.2.2]octan-1-yl)trihydroborate (4.9 g, 9.9 mmol) in N,N-dimethylformamide (10 mL) was added 1,3-diisopropylcarbodiimide (5.4 mL, 34.5 mmol). The reaction was heated to 80° C. and monitored by LC/MS. The reaction was cooled and then poured into a mixture of chloroform and water. The organic layer was collected and concentrated in vacuo. The remaining residue was triturated in ether. The precipitate was collected to afford (2-(6-(tert-butyldimethylsilyloxy)benzo[d]thiazol-2-ylamino)-4H-1'-ammoniospiro[oxazole-5,3'-bicyclo[2.2.2]octane]-1'-yl)trihydroborate (3.28 g, 7.15 mmol, 72.6% yield). MS (LC/MS) R.T.=3.60; [M+H—BH$_3$]$^+$=445.2.

Step D: 2-(4H-1'-Azaspiro[oxazole-5,3'-bicyclo[2.2.2]octane]-2-ylamino)benzo[d]thiazol-6-ol

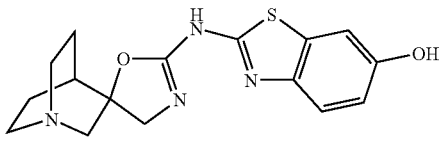

To (2-(6-(tert-butyldimethylsilyloxy)benzo[d]thiazol-2-ylamino)-4H-1'-ammoniospiro[oxazole-5,3'-bicyclo[2.2.2]octane]-1'-yl)trihydroborate (3.2 g, 6.98 mmol) in acetone (10 mL) was added HCl (8.14 mL, 24.43 mmol). The reaction was stirred at room temperature for 3 hours. The mixture was poured into water and neutralized with saturated sodium bicarbonate. The aqueous layer was then extracted with chloroform. The organic layer was collected and concentrated in vacuo. The remaining residue was triturated in ether to afford racemic 2-(4H-1'-azaspiro[oxazole-5,3'-bicyclo[2.2.2]octane]-2-ylamino)benzo[d]thiazol-6-ol (958 mg, 2.90 mmol, 41.5% yield) as a white powder. $^1$H NMR (500 MHz, DMSO-d$_6$) δ ppm 9.36 (1 H, br. s.), 8.85 (1 H, br. s.), 7.41 (1 H, d, J=8.85 Hz), 7.12 (1 H, d, J=2.44 Hz), 6.78 (1 H, dd, J=8.85, 2.44 Hz), 3.86 (1 H, d, J=10.07 Hz), 3.61 (1 H, d, J=10.07 Hz), 2.96-3.06 (2 H, m), 2.71-2.85 (2 H, m), 2.66 (2 H, t, J=7.78 Hz), 2.04 (1 H, br. s.), 1.90 (1 H, br. s.), 1.43-1.64 (3 H, m). MS (LC/MS) R.T.=1.03; [M+H]$^+$=331.29.

The enantiomers were separated using a Chiralpak AD-H (30×250mm, 5 μm) column with a mobile phase consisting of 30% methanol (0.1% DEA) in CO$_2$. The wavelength was set at 300 nM. The separated peaks were concentrated in vacuo to yield white powders. The first peak off the column was (S)-2-(4H-1'-azaspiro[oxazole-5,3'-bicyclo[2.2.2]octane]-2-ylamino)benzo[d]thiazol-6-ol (395.2 mg, 1.19 mmol, 41.4% yield). (13a, S-isomer): $^1$H NMR (500 MHz, DMSO-d$_6$) δ ppm 9.36 (1 H, br. s.), 8.84 (1 H, br. s.), 7.41 (1 H, d, J=8.55 Hz), 7.12 (1 H, d, J=2.44 Hz), 6.78 (1 H, dd, J=8.55, 2.44 Hz), 3.86 (1 H, d, J=9.77 Hz), 3.61 (1 H, d, J=10.07 Hz), 2.96-3.05 (2 H, m), 2.72-2.84 (2 H, m), 2.65 (2 H, t, J=7.63 Hz), 2.04 (1 H, br. s.), 1.90 (1 H, br. s.), 1.52-1.64 (2 H, m), 1.43-1.52 (1H, m). MS (LC/MS) R.T.=1.30; [M+H]$^+$=331.4. The second peak was (R)-2-(4H-1'-azaspiro[oxazole-5,3'-bicyclo[2.2.2]octane]-2-ylamino)benzo[d]thiazol-6-ol (375 mg, 1.14 mmol, 39.3% yield). (13b, R-isomer): $^1$H NMR (500 MHz, DMSO-d$_6$) δ ppm 7.40 (1 H, d, J=8.55 Hz), 7.11 (1 H, d, J=2.44 Hz), 6.77 (1 H, dd, J=8.55, 2.44 Hz), 3.86 (1 H, d, J=10.07 Hz), 3.60 (1 H, d, J=10.07 Hz), 3.01 (2 H, s), 2.73-2.84 (2 H, m), 2.65 (2 H, t, J=7.78 Hz), 2.04 (1 H, br. s.), 1.90 (1 H, br. s.), 1.54-1.62 (2 H, m), 1.43-1.52 (1 H, m). MS (LC/MS) R.T.=1.43; [M+H]$^+$=331.4.

EXAMPLE 14

N-(4,5,6,7-Tetrahydrobenzo[d]thiazol-2-yl)-4H-1'-azaspiro[oxazole-5,3'-bicyclo[2.2.2]octan]-2-amine

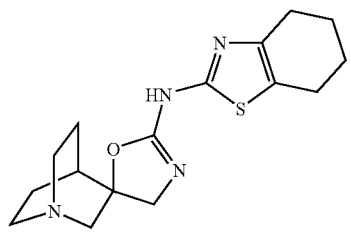

Step A: N-(4,5,6,7-Tetrahydrobenzo[d]thiazol-2-yl)-1H-imidazole-1-carbothioamide

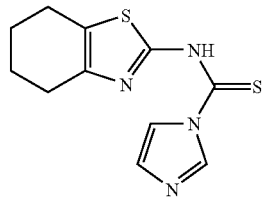

To 4,5,6,7-tetrahydrobenzo[d]thiazol-2-amine (0.5 g, 3.24 mmol) in acetonitrile (20 mL) was added di(1H-imidazol-1-yl)methanethione (0.58 g, 3.24 mmol). The reaction was stirred at 50° C. for 4 hours. The reaction was cooled and concentrated to yield crude product. The crude material was purified via flash chromatography (50-100% ethyl acetate-hexane) to yield N-(4,5,6,7-tetrahydrobenzo[d]thiazol-2-yl)-1H-imidazole-1-carbothioamide (0.60 g, 2.27 mmol, 70.0% yield) as a white powder.

Step B: (3-Hydroxy-3-((3-(4,5,6,7-tetrahydrobenzo[d]thiazol-2-yl)thioureido)methyl)-1-ammoniobicyclo[2.2.2]octan-1-yl)trihydroborate

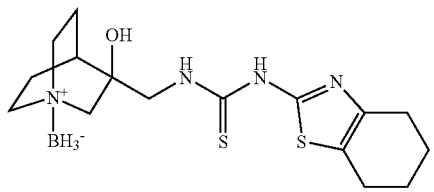

To N-(4,5,6,7-tetrahydrobenzo[d]thiazol-2-yl)-1H-imidazole-1-carbothioamide (0.54 g, 2 mmol) in N,N-dimethylformamide (20 mL) was added (3-(aminomethyl)-3-hydroxy-1-ammoniobicyclo[2.2.2]octan-1-yl)trihydroborate (0.35 g, 2 mmol). The reaction was stirred at 50° C. for 3 hours. The reaction was cooled and concentrated to yield crude product. The crude material was purified via flash chromatography (50-100% ethyl acetate-hexane) yielding the first spot/fractions (TLC) as the product. The fractions were combined and concentrated to yield (3-hydroxy-3-((3-(4,5,6,7-tetrahydrobenzo[d]thiazol-2-yl)thioureido)methyl)-1-ammoniobicyclo[2.2.2]octan-1-yl)trihydroborate (0.51 g, 1.39 mmol, 68.2% yield) as a white powder. $^1$H NMR (500 MHz, DMSO-D6) δ ppm 11.46 (s, 1 H), 5.26 (s, 1 H), 3.89 (dd, J=13.58, 5.34 Hz, 1 H), 3.68 (dd, J=13.73, 4.88 Hz, 1 H), 2.55-2.94 (m, 8 H), 2.06 (dd, J=9.31, 3.20 Hz, 1 H), 1.66-1.90 (m, 6 H), 1.21-1.59 (m, 4 H); [M+H]$^+$=365.1.

Step C: (2-(4,5,6,7-Tetrahydrobenzo[d]thiazol-2-ylamino)-4H-1'-ammoniospiro[oxazole-5,3'-bicyclo[2.2.2]octane]-1'-yl)trihydroborate

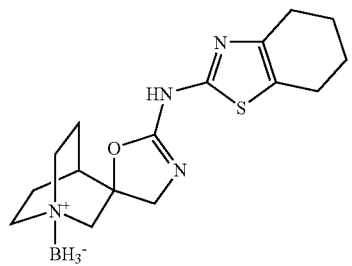

To (3-hydroxy-3-((3-(4,5,6,7-tetrahydrobenzo[d]thiazol-2-yl)thioureido)methyl)-1-ammoniobicyclo[2.2.2]octan-1-yl)trihydroborate (0.5 g, 1.37 mmol) in N,N-dimethylformamide (20 mL) was added N,N-diisopropylcarbodiimide (0.74 mL, 4.78 mmol). The reaction was stirred at 70° C. for 4 hours. The reaction was concentrated to yield a crude residue. The crude material was purified via flash chromatography (50-100% ethyl acetate-hexanes) yielding the second spot/fractions (TLC) as the product. The fractions were combined and concentrated to yield (2-(4,5,6,7-tetrahydrobenzo[d]thiazol-2-ylamino)-4H-1'-ammoniospiro[oxazole-5,3'-bicyclo[2.2.2]octane]-1'-yl)trihydroborate (0.38 g, 1.14 mmol, 84% yield) as a white powder. $^1$H NMR (500 MHz, DMSO-D6) δ ppm 8.26-8.86 (m, 1 H), 3.78 (d, J=9.46 Hz, 1 H), 3.66 (d, J=9.77 Hz, 1 H), 3.19-3.30 (m, J=14.95, 2.14 Hz, 1 H), 2.96-3.12 (m, 2 H), 2.78-2.94 (m, 3 H), 2.54-2.65 (m, 4 H), 2.19 (s, 1 H), 2.00 (s, 1 H), 1.66-1.85 (m, 7 H), 1.43 (m, 3 H). MS (LC/MS) R.T.=2.50; [M+H—BH$_3$]$^+$=319.1.

Step D: N-(4,5,6,7-Tetrahydrobenzo[d]thiazol-2-yl)-4H-1'-azaspiro[oxazole-5,3'-bicyclo[2.2.2]octan]-2-amine

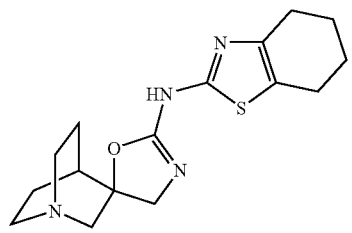

To (2-(4,5,6,7-tetrahydrobenzo[d]thiazol-2-ylamino)-4H-1'-ammoniospiro[oxazole-5,3'-bicyclo[2.2.2]octane]-1'-yl)trihydroborate (0.36 g, 1.08 mmol) in acetone (9 mL) was added 3M HCl (0.36 mL, 1.08 mmol). The reaction was stirred at room temperature for 4 hours. The reaction was complete by TLC (lower spot). Ethyl acetate was added and the aqueous layer was then separated. The aqueous layer was neutralized with 1N sodium hydroxide. The product was extracted with ethyl acetate (2×40 mL). The organics were combined, dried with magnesium sulfate, filtered, and concentrated in vacuo to afford racemic N-(4,5,6,7-tetrahydrobenzo[d]thiazol-2-yl)-4H-1'-azaspiro[oxazole-5,3'-bicyclo[2.2.2]octan]-2-amine (0.28 g, 0.84 mmol, 78% yield) as a white powder. $^1$H NMR (500 MHz, DMSO-D6) δ ppm 8.30-8.75 (br.s, 1 H), 3.79 (d, J=9.44 Hz, 1 H), 3.55 (d, J=9.76 Hz, 1 H), 2.90-3.03 (m, 2 H), 2.54-2.84 (m, 8 H), 2.00 (s, 1 H), 1.81-1.93 (m, 1 H), 1.75 (d, J=2.44 Hz, 4 H), 1.36-1.67 (m, 3 H). MS (LC/MS) R.T.=1.39; [M+H]$^+$=319.1.

The enantiomers were separated using a Chiralpak AD-H (30×250 mm, 5 μm) column with a mobile phase consisting of 23% methanol (0.1% DEA) in CO$_2$. The wavelength was set at 300 nM. The separated peaks were concentrated in vacuo to yield white powders. The first peak off the column was (S)—N-(4,5,6,7-tetrahydrobenzo[d]thiazol-2-yl)-4H-1'-azaspiro[oxazole-5,3'-bicyclo[2.2.2]octan]-2-amine (0.1 g, 0.29 mmol, 36.8% yield). (14a, S-isomer): $^1$H NMR (500 MHz, DMSO-D6) δ ppm 8.29-8.89 (br.s, 1 H), 3.80 (d, J=9.46 Hz, 1 H), 3.54 (d, J=9.77 Hz, 1 H), 2.94-3.04 (m, 2 H), 2.55-2.85 (m, 8 H), 2.00 (s, 1 H), 1.85-1.94 (m, 1 H), 1.70-1.81 (m, J=2.43 Hz, 4 H), 1.39-1.65 (m, 3 H). MS (LC/MS) R.T.=1.54; [M+H]$^+$=319.1. The second peak was (R)—N-(4,5,6,7-tetrahydrobenzo[d]thiazol-2-yl)-4H-1'-azaspiro[oxazole-5,3'-bicyclo[2.2.2]octan]-2-amine (0.11 g, 0.30 mmol, 38.2% yield). (14b, R-isomer): $^1$H NMR (500 MHz, DMSO-D6) δ ppm 8.24-8.96 (br.s, 1 H), 3.79 (d, J=9.46 Hz, 1 H), 3.52 (d, J=9.76 Hz, 1 H), 2.95-3.08 (m, 2 H), 2.55-2.80 (m, 8 H), 2.00 (s, 1 H), 1.85-1.90 (m, 1 H), 1.70-1.79 (m, J=2.42 Hz, 4H), 1.39-1.63 (m, 3 H); [M+H]$^+$=319.1.

EXAMPLE 15

N-(4-Isopropylthiazol-2-yl)-4H-1'-azaspiro[oxazole-5,3'-bicyclo[2.2.2]octan]-2-amine

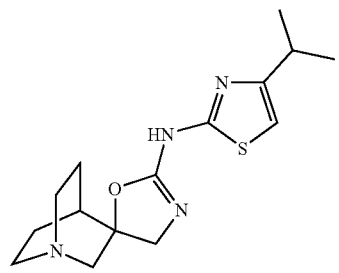

Step A: N-(4-Isopropylthiazol-2-yl)-1H-imidazole-1-carbothioamide

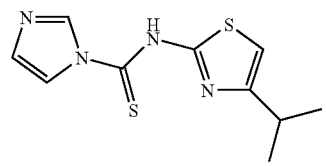

To 4-isopropylthiazol-2-amine (1.04 g, 7.31 mmol) in acetonitrile (30 mL) was added 1,1-thiocarbonyldiimidazole (1.7 g, 9.5 mmol). The reaction was stirred at 50° C. for 18 hours. The reaction was cooled to room temperature and the precipitate was filtered and washed with acetonitrile (2×50 mL). The yellow powder was dried in a vacuum oven (40° C.) for 2 hours. The product, N-(4-isopropylthiazol-2-yl)-1H-imidazole-1-carbothioamide (1.02 g, 4.04 mmol, 55.3% yield), was taken directly to the next step without any further purification.

Step B: (3-Hydroxy-3-((3-(4-isopropylthiazol-2-yl)thioureido)methyl)-1-ammoniobicyclo[2.2.2]octan-1-yl)trihydroborate

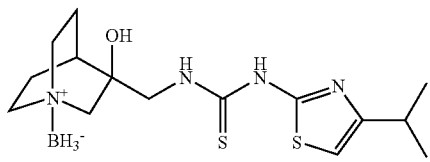

To N-(4-isopropylthiazol-2-yl)-1H-imidazole-1-carbothioamide (0.57 g, 2.26 mmol) in N,N-dimethylformamide (20 mL) was added (3-(aminomethyl)-3-hydroxy-1-ammoniobicyclo[2.2.2]octan-1-yl)trihydroborate (0.38 g, 2.26 mmol). The reaction was stirred at 70° C. for 24 hours. The reaction was cooled and concentrated to yield crude product. The crude material was purified via flash chromatography (50-100% ethyl acetate-hexane) to yield (3-hydroxy-3-((3-(4-isopropylthiazol-2-yl)thioureido)methyl)-1-ammoniobicyclo[2.2.2]octan-1-yl)trihydroborate (0.56 g, 1.58 mmol, 70.0% yield) as a white powder. $^1$H NMR (500 MHz, DMSO-$d_6$) δ ppm 11.62 (s, 1 H), 6.70 (s, 1 H), 5.31 (s, 1 H), 3.58-3.96 (m, 2 H), 2.63-3.11 (m, 7H), 2.00-2.22 (m, 1 H), 1.65-1.97 (m, 3 H), 1.16-1.61 (m, 10 H). MS (LC/MS) R.T.=3.43; [M+H]$^+$=353.2.

Step C: (2-(5-Isopropylthiazol-2-ylamino)-4H-1'-ammoniospiro[oxazole-5,3'-bicyclo[2.2.2]octane]-1'-yl)trihydroborate

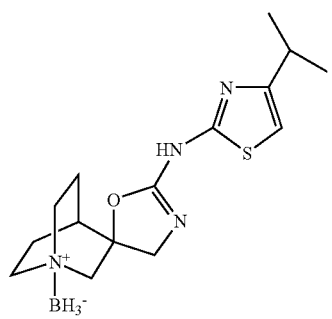

To (3-hydroxy-3-((3-(5-isopropylthiazol-2-yl)thioureido)methyl)-1-ammoniobicyclo[2.2.2]octan-1-yl)trihydroborate (0.54 g, 1.52 mmol) in N,N-dimethylformamide (20 mL) was added N,N'-diisopropylcarbodiimide (0.83 mL, 5.33 mmol). The reaction was stirred at 50° C. for 24 hours. The reaction was concentrated to yield a crude residue. The crude material was purified via flash chromatography (50-100% ethyl acetate-hexanes) yielding the second spot/fractions (TLC) as the product. The fractions were combined and concentrated to yield (2-(5-isopropylthiazol-2-ylamino)-4H-1'-ammoniospiro[oxazole-5,3'-bicyclo[2.2.2]octane]-1'-yl)trihydroborate (0.39 g, 1.22 mmol, 80% yield) as a white powder. $^1$H NMR (500 MHz, DMSO-$d_6$) δ ppm 6.55 (s, 1 H), 3.75 (m, 2 H), 3.20-3.31 (m, 1 H), 2.96-3.15 (m, 2 H), 2.77-2.97 (m, 4 H), 2.22 (s, 1 H), 2.01 (s, 1 H), 1.68-1.90 (m, 3 H), 1.43 (s, 3 H), 1.21 (d, J=7.02 Hz, 6 H). MS (LC/MS) R.T.=2.36; [M+H—BH$_3$]$^+$=307.2.

Step D: N-(4-Isopropylthiazol-2-yl)-4H-1'-azaspiro[oxazole-5,3'-bicyclo[2.2.2]octan]-2-amine

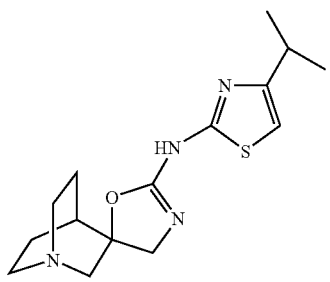

To (2-(4-isopropylthiazol-2-ylamino)-4H-1'-ammoniospiro[oxazole-5,3'-bicyclo[2.2.2]octane]-1'-yl)trihydroborate (0.42 g, 1.31 mmol) in acetone (9 mL) was added 3M HCl (0.44 mL, 1.31 mmol). The reaction was stirred at room temperature for 4 hours. The reaction was complete by TLC (lower spot). Ethyl acetate was added and the aqueous layer was then separated. The aqueous layer was neutralized with 1N sodium hydroxide. The product was extracted with ethyl acetate (2×40 mL). The organics were combined, dried with magnesium sulfate, filtered, and concentrated in vacuo to afford racemic N-(4-isopropylthiazol-2-yl)-4H-1'-azaspiro[oxazole-5,3'-bicyclo[2.2.2]octan]-2-amine (0.34 g, 1.05 mmol, 80% yield) as a white powder. $^1$H NMR (500 MHz, DMSO-D6) δ ppm 8.20-8.91 (m, 1 H), 6.52 (s, 1 H), 3.83 (d, J=9.46 Hz, 1 H), 3.57 (d, J=9.46 Hz, 1 H), 2.99 (s, 2 H), 2.58-2.92 (m, 5 H), 2.02 (s, 1 H), 1.82-1.96 (m, 1 H), 1.38-1.66 (m, 3 H), 1.20 (d, J=7.02 Hz, 6 H). MS (LC/MS) R.T.=1.27; [M+H]$^+$=307.1.

The enantiomers were separated using a Chiralcel OJ-H (30×250 mm, 5 µm) column with a mobile phase consisting of 23% methanol (0.1% DEA) in CO$_2$. The wavelength was set at 300 nM. The separated peaks were concentrated in vacuo to yield white powders. The first peak off the column was (S)—N-(4-isopropylthiazol-2-yl)-4H-1'-azaspiro[oxazole-5,3'-bicyclo[2.2.2]octan]-2-amine (0.01 g, 0.03 mmol, 2.95% yield). (15a, S-isomer): $^1$H NMR (500 MHz, DMSO-D6) δ ppm 8.35-8.95 (m, 1 H), 6.52 (s, 1 H), 3.82 (d, J=9.41 Hz, 1 H), 3.57 (d, J=9.46 Hz, 1 H), 2.99 (s, 2 H), 2.60-2.88 (m, 5 H), 2.02 (s, 2 H), 1.82-1.96 (m, 1 H), 1.38-1.65 (m, 3 H), 1.20 (d, J=6.71 Hz, 6 H). MS (LC/MS) R.T.=1.38; [M+H]$^+$=307.1. The second peak was (R)—N-(4-isopropylthiazol-2-yl)-4H-1'-azaspiro[oxazole-5,3'-bicyclo[2.2.2]octan]-2-amine (0.02 g, 0.05 mmol, 4.83% yield). (15b, R-isomer): $^1$H NMR (500 MHz, DMSO-D6) δ ppm 8.35-8.91 (m, 1 H), 6.52 (s, 1 H), 3.82 (d, J=9.44 Hz, 1 H), 3.57 (d, J=9.46 Hz, 1 H), 2.99 (s, 2 H), 2.60-2.90 (m, 5 H), 2.02 (s, 2 H), 1.82-1.96 (m, 1 H), 1.38-1.62 (m, 3 H), 1.20 (d, J=6.78 Hz, 6 H). MS (LC/MS) R.T.=1.49; [M+H]$^+$=307.3.

EXAMPLE 16

N-(Thiazol-2-yl)-4H-1'-azaspiro[oxazole-5,3'-bicyclo[2.2.2]octan]-2-amine

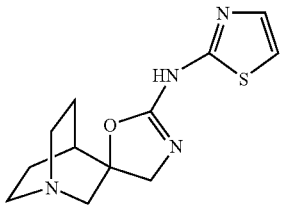

Step A:
N-(Thiazol-2-yl)-1H-imidazole-1-carbothioamide

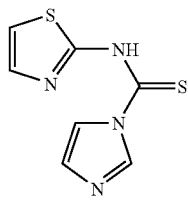

To thiazol-2-amine (2.12 g, 21.17 mmol) in acetonitrile (30 mL) and tetrahydrofuran (5 mL) was added di(1H-imidazol-1-yl)methanethione (4.90 g, 27.5 mmol). The reaction was stirred at 60° C. for 5 hours. The reaction was cooled to room temperature and the precipitate was filtered and washed with cold acetonitrile (2×15 mL) to afford an orange-brown powder. The product, N-(thiazol-2-yl)-1H-imidazole-1-carbothioamide (3.70 g, 17.60 mmol, 83% yield), was taken directly to the next step without any further characterization.

Step B: (3-Hydroxy-3-((3-thiazol-2-ylthioureido)methyl)-1-ammoniobicyclo[2.2.2]octan-1-yl)trihydroborate

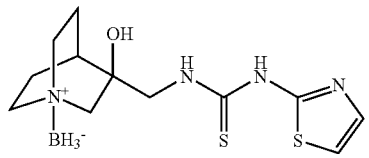

To N-(thiazol-2-yl)-1H-imidazole-1-carbothioamide (1.7 g, 8 mmol) in N,N-dimethylformamide (30 mL) was added (3-(aminomethyl)-3-hydroxy-1-ammoniobicyclo[2.2.2]octan-1-yl)trihydroborate (1.37 g, 8 mmol). The reaction was stirred at 50° C. for 4 hours. The reaction was cooled and concentrated to yield crude product. The crude material was purified via flash chromatography (50-100% ethyl acetate-hexane) yielding the first spot/fractions (TLC) as the product. The fractions were combined and concentrated to yield (3-hydroxy-3-((3-thiazol-2-ylthioureido)methyl)-1-ammoniobicyclo[2.2.2]octan-1-yl)trihydroborate (1.5 g, 4.80 mmol, 59.8% yield) as a white powder. $^1$H NMR (500 MHz, DMSO-d$_6$) δ ppm 11.64 (s, 1 H), 7.42 (d, J=3.36 Hz, 1 H), 7.14 (m, 1 H), 5.32 (s, 1 H), 3.78 (dd, 2 H), 2.59-3.02 (m, 6 H), 1.99-2.18 (m, 1 H), 1.79-1.92 (m, 2 H), 1.64-1.80 (m, 1 H), 1.19-1.65 (m, 4 H). MS (LC/MS) R.T.=2.73; [M+H]$^+$=311.1.

Step C: (2-(Thiazol-2-ylamino)-4H-1'-ammoniospiro[oxazole-5,3'-bicyclo[2.2.2]octane]-1'-yl)trihydroborate

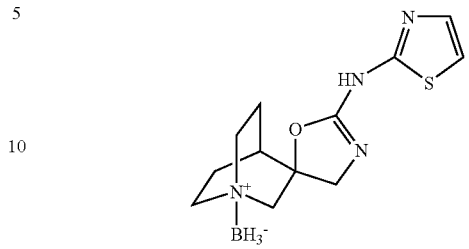

To (3-hydroxy-3-((3-thiazol-2-ylthioureido)methyl)-1-ammoniobicyclo[2.2.2]octan-1-yl)trihydroborate (1.2 g, 3.84 mmol) in N,N-dimethylformamide (20 mL) was added N,N'-diisopropylcarbodiimide (2.09 mL, 13.45 mmol). The reaction was stirred at 50° C. for 24 hours. The reaction was concentrated to yield a crude residue. The crude material was purified via flash chromatography (50-100% ethyl acetate-hexane) yielding the first spot/fractions (TLC) as the product. The fractions were combined and concentrated to yield (2-(thiazol-2-ylamino)-4H-1'-ammoniospiro[oxazole-5,3'-bicyclo[2.2.2]octane]-1'-yl)trihydroborate (0.84 g, 3.02 mmol, 79% yield) as a white powder. $^1$H NMR (500 MHz, DMSO-D6) δ ppm 8.37-9.14 (m, 1 H), 7.32 (d, J=3.66 Hz, 1 H), 7.04 (d, J=3.66 Hz, 2 H), 3.79 (d, J=10.07 Hz, 1 H), 3.67 (d, J=10.07 Hz, 1 H), 3.20-3.29 (m, J=14.95, 2.14 Hz, 1 H), 2.97-3.15 (m, 2 H), 2.78-2.94 (m, 3 H), 2.22 (s, 1 H), 1.95-2.08 (m, 1 H), 1.66-1.85 (m, 3 H), 1.43 (s, 3 H). MS (LC/MS) R.T.=1.57; [M+H—BH$_3$]$^+$=265.1.

Step D: N-(Thiazol-2-yl)-4H-1'-azaspiro[oxazole-5,3'-bicyclo[2.2.2]octan]-2-amine

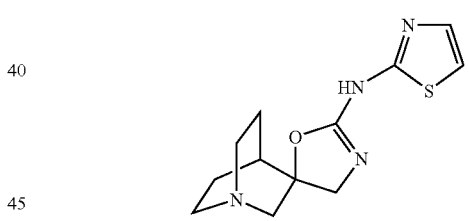

To (2-(thiazol-2-ylamino)-4H-1'-ammoniospiro[oxazole-5,3'-bicyclo[2.2.2]octane]-1'-yl)trihydroborate (0.57 g, 2.05 mmol) in acetone (9 mL) was added 3M HCl (0.68 mL, 2.05 mmol). The reaction was stirred at room temperature for 4 hours. The reaction was complete by TLC (lower spot). Ethyl acetate was added and the aqueous layer was then separated. The aqueous layer was neutralized with 1N sodium hydroxide. The product was extracted with ethyl acetate (2×40 mL). The organics were combined, dried with magnesium sulfate, filtered, and concentrated in vacuo to afford racemic N-(thiazol-2-yl)-4H-1'-azaspiro[oxazole-5,3'-bicyclo[2.2.2]octan]-2-amine (0.4 g, 1.44 mmol, 70.2% yield) as a white powder. $^1$H NMR (400 MHz, DMSO-d$_6$) δ ppm 8.64 (s, 1 H), 7.24 (d, J=3.74 Hz, 2 H), 7.01 (d, J=3.75 Hz, 2 H), 3.78 (d, J=9.80 Hz, 2 H), 3.53 (d, J=9.80 Hz, 2 H), 2.97-3.05 (m, 4 H), 2.74-2.86 (m, 4 H), 2.65 (t, J=7.84 Hz, 4 H), 2.01 (s, 2 H), 1.88 (s, 2 H), 1.53-1.64 (m, 4 H), 1.45-1.56 (m, 2 H). MS (LC/MS) R.T.=0.28; [M+H]$^+$=265.1.

The enantiomers were separated using a Chiralcel OJ-H (30×250 mm, 5 µm) column with a mobile phase consisting of 23% methanol (0.1% DEA) in $CO_2$. The wavelength was set at 300 nM. The separated peaks were concentrated in vacuo to yield white powders. The first peak off the column was (S)—N-(thiazol-2-yl)-4H-1'-azaspiro[oxazole-5,3'-bicyclo[2.2.2]octan]-2-amine (0.12 g, 0.43 mmol, 18.80% yield). (16a, S-isomer): $^1$H NMR (400 MHz, DMSO-$d_6$) δ ppm 8.64 (s, 1 H), 7.26 (d, J=3.75 Hz, 2 H), 7.00 (d, J=3.77 Hz, 2 H), 3.78 (d, J=9.81 Hz, 2 H), 3.54 (d, J=9.82 Hz, 2 H), 2.95-3.10 (m, 4 H), 2.75-2.82 (m, 4 H), 2.65 (t, J=7.80 Hz, 4 H), 2.01 (s, 2 H), 1.88 (s, 2 H), 1.53-1.60 (m, 4 H), 1.42-1.51 (m, 2 H). MS (LC/MS) R.T.=0.32; [M+H]$^+$=265.1. The second peak was (R)—N-(thiazol-2-yl)-4H-1'-azaspiro[oxazole-5,3'-bicyclo[2.2.2]octan]-2-amine (0.15 g, 0.52 mmol, 22.96% yield). (16b, R-isomer): $^1$H NMR (400 MHz, DMSO-$d_6$) δ ppm 8.64 (s, 1 H), 7.25 (d, J=3.74 Hz, 2 H), 7.00 (d, J=3.76 Hz, 2 H), 3.78 (d, J=9.80 Hz, 2 H), 3.53 (d, J=9.80 Hz, 2 H), 2.95-3.08 (m, 4 H), 2.75-2.84 (m, 4 H), 2.65 (t, J=7.80 Hz, 4 H), 2.01 (s, 2 H), 1.88 (s, 2 H), 1.54-1.62 (m, 4 H), 1.43-1.53 (m, 2 H). MS (LC/MS) R.T.=0.28; [M+H]$^+$=265.3.

EXAMPLE 17

N-(4-(4-Methoxyphenyl)-5-methylthiazol-2-yl)-4H-1'-azaspiro[oxazole-5,3'-bicyclo[2.2.2]octan]-2-amine

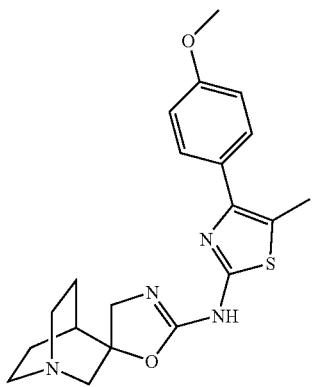

Step A: N-(4-(4-Methoxyphenyl)-5-methylthiazol-2-yl)-1H-imidazole-1-carbothioamide

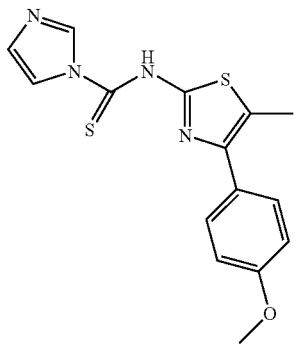

To 4-(4-methoxyphenyl)-5-methylthiazol-2-amine (0.98 g, 4.45 mmol) in acetonitrile (25 mL) was added di(1H-imidazol-1-yl)methanethione (1.03 g, 5.78 mmol). The reaction was stirred at 50° C. for 3 hours. The reaction was cooled to room temperature and the precipate was filtered. The powder was washed with acetonitrile (2×10 mL) and dried to yield racemic N-(4-(4-methoxyphenyl)-5-methylthiazol-2-yl)-1H-imidazole-1-carbothioamide (1.28 g, 3.87 mmol, 87% yield) as a yellow powder. The product was taken directly to the next step.

Step B: (2-(4-(4-Methoxyphenyl)-5-methylthiazol-2-ylamino)-4H-1'-ammoniospiro[oxazole-5,3'-bicyclo[2.2.2]octane]-1'-yl)trihydroborate

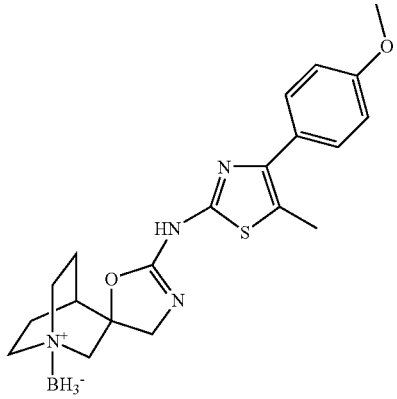

To N-(4-(4-methoxyphenyl)-5-methylthiazol-2-yl)-1H-imidazole-1-carboxamide (0.44 g, 1.39 mmol) in N,N-dimethylformamide (25 mL) was added (3-(aminomethyl)-3-hydroxy-1-ammoniobicyclo[2.2.2]octan-1-yl)trihydroborate (0.24 g, 1.39 mmol). The reaction was stirred at 70° C. for 2 hours. N,N'-Diisopropylcarbodiimide (0.65 mL, 4.16 mmol) was added and the reaction heated to 75° C. for 2 hours. The reaction was cooled and concentrated to afford the crude product. The crude material was purified via column chromatography (60-100% ethyl acetate/hexanes) to yield (2-(4-(4-methoxyphenyl)-5-methylthiazol-2-ylamino)-4H-1'-ammoniospiro[oxazole-5,3'-bicyclo[2.2.2]octane]-1'-yl) trihydroborate (0.41 g, 1.029 mmol, 74.2% yield) as a yellow powder. $^1$H NMR (500 MHz, DMSO-D6) δ ppm 7.59 (d, J=7.63 Hz, 2 H), 6.98 (d, J=8.55 Hz, 2 H), 3.80 (s, 4 H), 3.67 (s, 1 H), 3.24-3.31 (m, 1 H), 3.13 (s, 1 H), 3.03 (s, 1 H), 2.83-2.92 (m, 3 H), 2.39 (s, 3 H), 2.23 (s, 1 H), 2.07 (s, 1 H), 1.73-1.82 (m, 2 H), 1.44 (s, 1 H). MS (LC/MS) R.T.=2.88; [M+H]$^+$=399.34.

Step C: N-(4-(4-Methoxyphenyl)-5-methylthiazol-2-yl)-4H-1'-azaspiro[oxazole-5,3'-bicyclo[2.2.2]octan]-2-amine

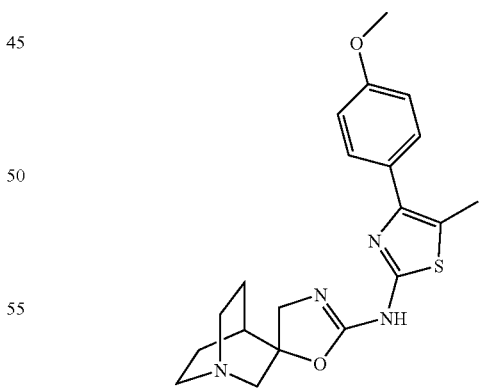

To (3-hydroxy-3-((3-(4-(4-methoxyphenyl)-5-methylthiazol-2-yl)thioureido)methyl)-1-ammoniobicyclo[2.2.2]octan-1-yl)trihydroborate (0.08 g, 0.19 mmol) in acetone (9 mL) was added 2M HCl (0.09 mL, 0.19 mmol). The reaction was stirred at room temperature for 1 hour. The reaction was complete by TLC (lower spot). Ethyl acetate was added and the aqueous layer was collected and neutralized with 1N sodium hydroxide. The product was extracted with ethyl acetate (2×40 mL). The organics were combined, dried with magnesium sulfate, filtered, and concentrated in vacuo to afford racemic N-(4-(4-methoxyphenyl)-5-methylthiazol-2-yl)-4H-1'-azaspiro[oxazole-5,3'-bicyclo[2.2.2]octan]-2-amine (0.05 g, 0.12 mmol, 66.8% yield) as a white powder. $^1$H NMR (500 MHz, DMSO-D6) δ ppm 7.58 (d, J=8.24 Hz, 2 H), 6.98 (d, J=8.55 Hz, 2 H), 3.83 (d, J=9.16 Hz, 1 H), 3.80 (s, 3 H), 3.56 (d, J=9.46 Hz, 1 H), 3.00 (s, 2 H), 2.74-2.83 (m, 2 H), 2.66 (t, J=7.63 Hz, 2 H), 2.38 (s, 3 H), 2.03 (s, 1 H), 1.91 (s, 1 H), 1.54-1.62 (m, 2 H), 1.48 (d, J=7.02 Hz, 1 H). MS (LC/MS) R.T.=2.04; [M+H]$^+$=385.28.

EXAMPLE 18

(E)-N-(1'-Azaspiro[oxazolidine-5,3'-bicyclo[2.2.2]octane]-2-ylidene)pyridin-3-amine

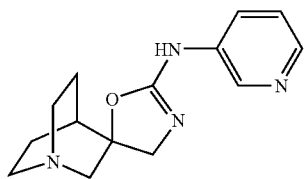

Step A: (3-Hydroxy-3-((3-pyridin-3-ylthioureido)methyl)-1-ammoniobicyclo[2.2.2]octan-1-yl)trihydroborate

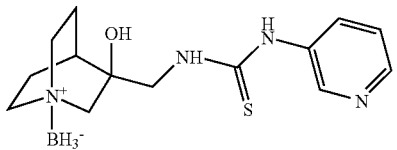

To a stirring suspension of (3-(aminomethyl)-3-hydroxy-1-ammoniobicyclo[2.2.2]octan-1-yl)trihydroborate (247 mg, 1.45 mmol) in tetrahydrofuran (3 mL) was added a solution of 3-isothiocyanatopyridine (298 mg, 2.19 mmol) in tetrahydrofuran (1.5 mL) and the reaction mixture was stirred at room temperature overnight. The reaction mixture was evaporated in vacuo and the residue (white waxy solid) purified via column chromatography (3% methanol/ethyl acetate) to yield (3-hydroxy-3-((3-pyridin-3-ylthioureido)methyl)-1-ammoniobicyclo[2.2.2]octan-1-yl)trihydroborate (294.6 mg, 0.96 mmol, 66.2% yield) as a white foam. $^1$H NMR (500 MHz, MeOD-d$_4$) δ ppm 8.56-8.70 (m, 1 H), 8.24-8.36 (m, 1 H), 8.08-8.16 (m, 1 H), 7.32-7.48 (m, 1 H), 4.02-4.18 (m, 1 H), 3.67-3.77 (m, 1 H), 3.53-3.62 (m, 1 H), 2.88-3.11 (m, 3 H), 2.70-2.88 (m, 1), 2.15-2.29 (m, 1 H), 1.92-2.12 (m,2 H), 1.73-1.89 (m, 1 H), 1.54-1.69 (m, 2 H). MS (LC/MS) R.T.=1.00; [MH$^+$—BH$_3$]=293.10.

Step B: (E)-(2-(Pyridin-3-ylimino)-1'-ammoniospiro[oxazolidine-5,3'-bicyclo[2.2.2]octane]-1'-yl)trihydroborate

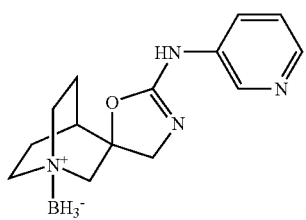

To a solution of (3-hydroxy-3-((3-pyridin-3-ylthioureido)methyl)-1-ammoniobicyclo[2.2.2]octan-1-yl)trihydroborate (294.6 mg, 0.96 mmol) in N,N-dimethylformamide (5 mL) was added a solution of N,N'-methanediylidenedipropan-2-amine (121 mg, 0.96 mmol) in N,N-dimethylformamide (1 mL) and the reaction mixture was allowed to stand at room temperature for 7 days. An additional 133 mg N,N'-methanediylidenedipropan-2-amine in 0.5 mL N,N-dimethylformamide was added and the reaction was left to continue for another 7 days. The reaction was purified via column chromatography (5-10% methanol/ethyl acetate) to afford (E)-(2-(pyridin-3-ylimino)-1'-ammoniospiro[oxazolidine-5,3'-bicyclo[2.2.2]octane]-1'-yl)trihydroborate (134.3 mg, 0.49 mmol, 51.3% yield). $^1$H NMR (500 MHz, MeOD) δ ppm 8.34-8.60 (m, 1 H), 8.16 (d, J=4.27 Hz, 1 H), 7.59-7.96 (m, 1 H), 7.35 (dd, J=8.24, 4.88 Hz, 1 H), 3.89 (br. s., 1 H), 3.65 (d, J=9.46 Hz, 1 H), 3.16-3.23 (m, 1H), 3.04-3.16 (m, 1 H), 2.85-3.04 (m, 2 H), 2.23 (br. s., 1 H), 1.74-1.97 (m, 4H), 1.36-1.70 (m, 2 H). MS (LC/MS) R.T.=0.65; [M+H—BH$_3$]$^+$=259.21.

Step C: (E)-N-(1'-Azaspiro[oxazolidine-5,3'-bicyclo[2.2.2]octane]-2-ylidene)pyridin-3-amine

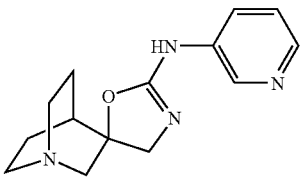

To a suspension of (E)-(2-(pyridin-3-ylimino)-1'-ammoniospiro[oxazolidine-5,3'-bicyclo[2.2.2]octane]-1'-yl)trihydroborate (127 mg, 0.47 mmol) in acetone (5 mL) was added 3M hydrochloric acid (2 mL, 6.00 mmol) and the mixture was allowed to stand at room temperature for 2 hrs. It was then added it to a separatory funnel containing water and chloroform. The layers were separated, then the aqueous layer was made basic with sodium carbonate solution and the mixture was re-extracted with chloroform. Finally, the aqueous phase was washed with ethyl acetate. The organics were combined, dried with magnesium sulfate, filtered, and concentrated in vacuo. The residue was purified by column chromatography (1% ammonium hydroxide/9% methanol/90% dichloromethane) to afford racemic (E)-N-(1'-azaspiro[oxazolidine-5,3'-bicyclo[2.2.2]octane]-2-ylidene)pyridin-3-amine (19 mg, 0.074 mmol, 15.8% yield) as a white solid. $^1$H NMR (500 MHz, MeOD-d$_4$) δ ppm 8.39 (br. s., 1 H), 8.14 (d, J=4.27 Hz, 1 H), 7.72 (br. s., 1 H), 7.34 (dd, J=8.24, 4.88 Hz, 1 H), 3.89 (d, J=9.77 Hz, 1 H), 3.57 (d, J=10.38 Hz, 1 H), 3.14-3.27 (m, 1H), 3.00-3.13 (m, 1 H), 2.70-3.00 (m, 4 H), 1.97-2.22 (m, 2 H), 1.54-1.84 (m, 3H). MS (LC/MS) R.T.=0.26; [M+H]$^+$=259.16.

EXAMPLE 19

N-(Pyridin-2-yl)-4H-1'-azaspiro[oxazole-5,3'-bicyclo[2.2.2]octan]-2-amine

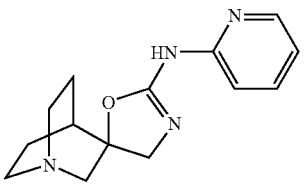

147

Step A: 2-Bromo-6-isothiocyanatopyridine

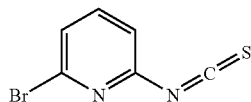

A mixture of 6-bromopyridin-2-amine (253 mg, 1.46 mmol), chloroform (2 mL), sodium bicarbonate (850 mg, 10.12 mmol) and water (3 mL) was assembled, and to this was added a solution of thiophosgene (190 mg, 1.65 mmol) in chloroform (1 mL). The reaction mixture was stirred at room temperature for 4 hours. The reaction mixture was transferred to a separatory funnel and partitioned between ethyl acetate and water. The organic layer was washed with brine, dried over magnesium sulfate, filtered and the solvent evaporated to give a yellow solid. The solid was purified by column chromatography (5% ethyl acetate/hexanes) to afford 2-bromo-6-isothiocyanatopyridine (281 mg, 1.31 mmol, 89% yield) as a white solid. $^1$H NMR (500 MHz, CDCl$_3$) δ ppm 7.50-7.62 (m, 1 H), 7.34-7.43 (m, 1 H), 6.91-7.11 (m, 1H). MS (LC/MS) R.T.=1.92; [M+H]$^+$=216.86.

Step B: N-(6-Bromopyridin-2-yl)-4H-1'-azaspiro [oxazole-5,3'-bicyclo[2.2.2]octan]-2-amine

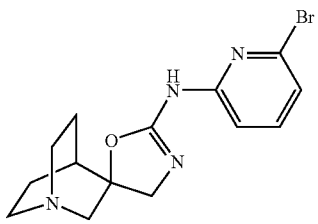

To a solution of 2-bromo-6-isothiocyanatopyridine (281 mg, 1.31 mmol) in N,N-dimethylformamide (8 mL) and Hunig's base (0.6 mL, 3.44 mmol) was added (±)3-(aminomethyl)quinuclidin-3-ol dihydrochloride (300 mg, 1.31 mmol) and the resulting mixture was heated to 75° C. for 2.5 hrs. MS (LC/MS) R.T.=1.04; [M+H]$^+$=373.01. To this reaction mixture was added di-isopropyl-carbodiimide (523 mg, 4.14 mmol) and the heating at 75° C. was continued for 2.25 hours. The mixture was allowed to cool to room temperature over the weekend. The reaction mixture was concentrated in vacuo. The material was purified by column chromatography then preparative HPLC to afford N-(6-bromopyridin-2-yl)-4H-1'-azaspiro[oxazole-5,3'-bicyclo[2.2.2]octan]-2-amine (291.5 mg, 0.86 mmol, 66.2 5 yield) as a yellow solid (containing 2-amino-6-bromopyridine impurity). MS (LC/MS) R.T.=0.65; [M+H]$^+$=337.0.

Step C: N-(Pyridin-2-yl)-4H-1'-azaspiro[oxazole-5, 3'-bicyclo[2.2.2]octan]-2-amine

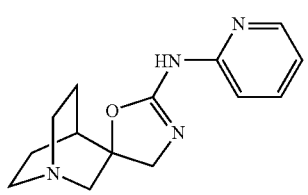

To N-(6-bromopyridin-2-yl)-4H-1'-azaspiro[oxazole-5,3'-bicyclo[2.2.2]octan]-2-amine (291 mg, 0.86 mmol) in methanol (20 mL) was hydrogenated over 10% palladium on carbon

148

(23 mg) in the Parr apparatus for 2 hours. The catalyst was removed by filtration and the filtrated concentrated in vacuo. The residue was purified by column chromatography (0.7% ammonium hydroxide/6.3% methanol/93% chloroform) to give racemic N-(pyridin-2-yl)-4H-1'-azaspiro[oxazole-5,3'-bicyclo[2.2.2]octan]-2-amine (41.3 mg, 0.16 mmol, 18.6 5 yield). $^1$H NMR (500 MHz, MeOD) δ ppm 8.13-8.33 (m, 1 H), 7.57-7.72 (m, 1 H), 6.83-7.04 (m, 2 H), 3.97 (d, J=10.07 Hz, 1 H), 3.66 (d, J=10.07 Hz, 1 H), 3.18-3.27 (m, 1 H), 3.03-3.14 (m, 1 H), 2.94 (t, J=7.63 Hz, 2 H), 2.70-2.90 (m, 2 H), 2.06-2.24 (m, 2 H), 1.57-1.87 (m, 3 H). MS (LC/MS) R.T.=1.76; [M+H]$^+$=259.25.

EXAMPLE 20

N-(4-(4-Methoxyphenyl)thiazol-2-yl)-4H-1'-azaspiro [oxazole-5,3'-bicyclo[2.2.2]octan]-2-amine

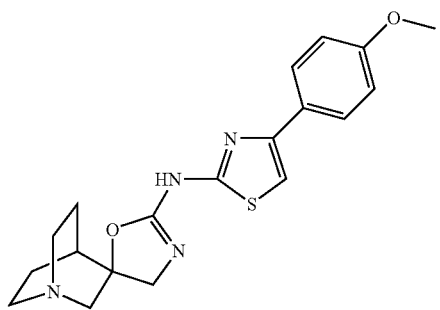

Step A: N-(5-(4-Methoxyphenyl)thiazol-2-yl)-1H-imidazole-1-carbothioamide

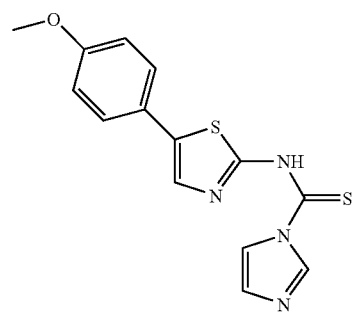

To 5-(4-methoxyphenyl)thiazol-2-amine (1.07 g, 5.19 mmol) in acetonitrile (30 mL) and tetrahydrofuran (5 mL) was added di(1H-imidazol-1-yl)methanethione (1.20 g, 6.74 mmol). The reaction was stirred at 60° C. for 18 hours. The reaction was cooled to room temperature and the precipitate was filtered. The powder was washed with cold acetonitrile (2×15 mL) and dried to yield N-(5-(4-methoxyphenyl)thiazol-2-yl)-1H-imidazole-1-carbothioamide (0.59 g, 1.86 mmol, 35.9% yield) as a orange-brown powder. The product was taken directly to the next step without any further characterization.

Step B: (3-Hydroxy-3-((3-(4-(4-methoxyphenyl) thiazol-2-yl)thioureido)methyl)-1-ammoniobicyclo[2.2.2]octan-1-yl)trihydroborate

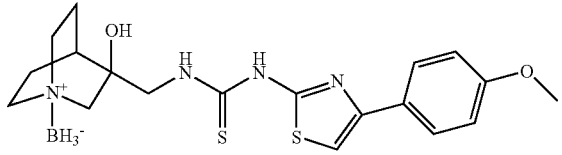

To N-(4-(4-methoxyphenyl)thiazol-2-yl)-1H-imidazole-1-carbothioamide (0.57 g, 1.82 mmol) in N,N-dimethylformamide (20 mL) was added (3-(aminomethyl)-3-hydroxy-1-ammoniobicyclo[2.2.2]octan-1-yl)trihydroborate (0.31 g, 1.82 mmol). The reaction was stirred at 60° C. for 4 hours. The reaction was cooled and concentrated to yield crude product. The crude material was purified via flash chromatography (60-100% ethyl acetate-hexane) yielding the first spot/fractions (TLC) as the product. The fractions were combined and concentrated in vacuo to yield (3-hydroxy-3-((3-(4-(4-methoxyphenyl)thiazol-2-yl)thioureido)methyl)-1-ammoniobicyclo[2.2.2]octan-1-yl)trihydroborate (0.6 g, 1.43 mmol, 79% yield) as a white powder. $^1$H NMR (500 MHz, DMSO-$d_6$) δ ppm 11.74 (s, 1 H), 7.91 (d, J=8.55 Hz, 2 H), 7.43 (s, 1 H), 6.97 (d, J=8.85 Hz, 2 H), 5.50 (s, 1 H), 3.62-3.98 (m, 5H), 2.70-3.10 (m, 6H), 2.13 (s, 1 H), 1.94 (s, 1 H), 1.66-1.91 (m, 2 H), 1.11-1.62 (m, 4 H). MS (LC/MS) R.T.=3.54; [M+H]$^+$=417.1.

Step C: (2-(4-(4-Methoxyphenyl)thiazol-2-ylamino)-4H-1'-ammoniospiro[oxazole-5,3'-bicyclo[2.2.2]octane]-1'-yl) trihydroborate

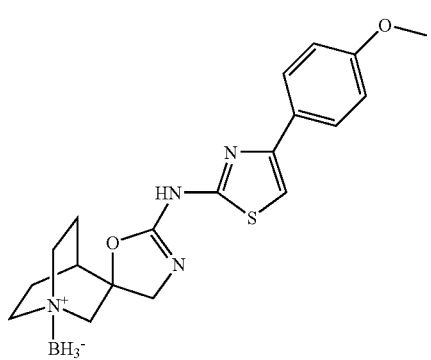

To (3-hydroxy-3-((3-(4-(4-methoxyphenyl)thiazol-2-yl)thioureido)methyl)-1-ammoniobicyclo[2.2.2]octan-1-yl)trihydroborate (0.59 g, 1.41 mmol) in N,N-dimethylformamide (20 mL) was added N,N'-diisopropylcarbodiimide (0.66 mL, 4.23 mmol). The reaction was stirred at 70° C. for 24 hours. The solvent was removed in vacuo and the residue was purified by flash chromatography (50-100% ethyl acetate-hexanes), collecting the first component as the product, to yield (2-(4-(4-methoxyphenyl)thiazol-2-ylamino)-4H-1'-ammoniospiro[oxazole-5,3'-bicyclo[2.2.2]octane]-1'-yl)trihydroborate (0.45 g, 1.17 mmol, 83% yield) as a white powder. $^1$H NMR (500 MHz, DMSO-$d_6$) δ ppm 8.65 (s, 1 H), 7.89 (d, J=7.32 Hz, 2H), 7.15-7.43 (m, 1 H), 6.95 (d, J=8.85 Hz, 2 H), 3.64-3.93 (m, 5 H), 3.23-3.31 (m, J=1.53 Hz, 1 H), 3.09-3.21 (m, 1 H), 2.99-3.09 (m, 1 H), 2.79-2.97 (m, 3H), 2.25 (s, 1 H), 1.96-2.16 (m, 1 H), 1.68-1.91 (m, 3 H), 1.45 (s, 3 H). MS (LC/MS R.T.=2.80; [M+H—BH$_3$]$^+$=371.1.

Step D: N-(4-(4-Methoxyphenyl)thiazol-2-yl)-4H-1'-azaspiro[oxazole-5,3'-bicyclo[2.2.2]octan]-2-amine

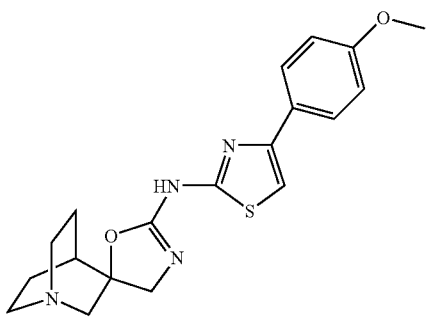

To (2-(4-(4-methoxyphenyl)thiazol-2-ylamino)-4H-1'-ammoniospiro[oxazole-5,3'-bicyclo[2.2.2]octane]-1'-yl)trihydroborate (0.41 g, 1.07 mmol) in acetone (9 mL) was added 3M HCl (0.36 mL, 1.07 mmol). The reaction was stirred at room temperature for 4 hours. The reaction was complete by TLC (lower spot). Ethyl acetate was added and the aqueous layer was then separated. The aqueous layer was neutralized with 1N sodium hydroxide. The product was extracted with ethyl acetate (2×40 mL). The organics were combined, dried with magnesium sulfate, filtered, and concentrated in vacuo to afford racemic N-(4-(4-methoxyphenyl)thiazol-2-yl)-4H-1'-azaspiro[oxazole-5,3'-bicyclo[2.2.2]octan]-2-amine (0.3 g, 0.77 mmol, 72.1% yield) as a white powder. $^1$H NMR (500 MHz, DMSO-$d_6$) δ ppm 8.56 (s, 1 H), 7.77-8.00 (m, J=8.55 Hz, 2 H), 7.27 (s, 1 H), 6.80-7.08 (m, 2 H), 3.87 (d, J=9.77 Hz, 1H), 3.79 (s, 3 H), 3.61 (d, J=9.77 Hz, 1 H), 3.02 (s, 3 H), 2.60-2.92 (m, 4 H), 2.06 (s, 2 H), 1.82-2.00 (m, 1 H), 1.39-1.70 (m, 3 H). MS (LC/MS) R.T.=1.95; [M+H]$^+$=371.2.

The enantiomers were separated using a Chiralpak AD-H (30×250 mm, 5 μm) column with a mobile phase consisting of 30% methanol (0.1% DEA) in CO$_2$. The wavelength was set at 220 nM. The separated peaks were concentrated in vacuo to yield white powders. The first peak off the column was (S)—N-(4-(4-methoxyphenyl)thiazol-2-yl)-4H-1'-azaspiro[oxazole-5,3'-bicyclo[2.2.2]octan]-2-amine (0.035 g, 0.09 mmol, 22.87% yield). $^1$H NMR (500 MHz, DMSO-$d_6$) δ ppm 8.56 (1 H, br. s.), 7.86 (2 H, d, J=8.55 Hz), 7.25 (1 H, s), 6.93-6.96 (2 H, m), 3.86 (1H, d, J=9.77 Hz), 3.78 (3 H, s), 3.60 (1 H, d, J=9.46 Hz), 3.01 (2 H, s), 2.72-2.84 (2H, m), 2.62-2.71 (2 H, m), 2.05 (1 H, br. s.), 1.91 (1 H, br. s.), 1.55-1.64 (2 H, m), 1.44-1.52 (1 H, m). MS (LC/MS) R.T.=2.03; [M+H]$^+$=371.3. The second peak was (R)—N-(4-(4-methoxyphenyl)thiazol-2-yl)-4H-1'-azaspiro[oxazole-5,3'-bicyclo[2.2.2]octan]-2-amine (0.055 g, 0.15 mmol, 35.9% yield). (21b, R-isomer): $^1$H NMR (500 MHz, DMSO-$d_6$) δ ppm 8.58 (1 H, br. s.), 7.87 (2 H, d, J=8.55 Hz), 7.26 (1 H, s), 6.92-6.97 (2 H, m), 3.86 (1 H, d, J=9.77 Hz), 3.78 (3 H, s), 3.60 (1 H, d, J=9.77 Hz), 3.01 (2 H, s), 2.73-2.85 (2 H, m), 2.63-2.71 (2 H, m), 2.05 (1H, br. s.), 1.91 (1 H, br. s.), 1.54-1.64 (2 H, m), 1.43-1.53 (1 H, m). MS (LC/MS) R.T.=2.03; [M+H]$^+$=371.3.

EXAMPLE 21

(R)—N-(2-(4H-1'-Azaspiro[oxazole-5,3'-bicyclo[2.2.2]octane]-2-ylamino)benzo[d]thiazol-6-yl)acetamide

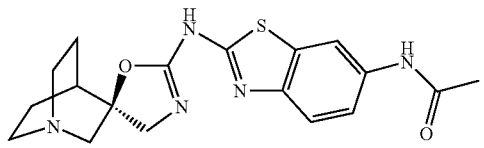

Step A: (3-((Benzyloxycarbonylamino)methyl)-3-hydroxy-1-ammoniobicyclo[2.2.2]octan-1-yl)trihydroborate

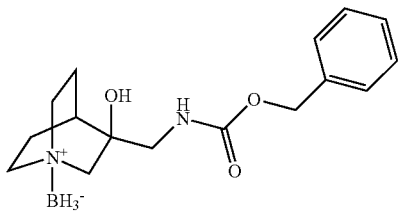

To (3-(aminomethyl)-3-hydroxy-1-ammoniobicyclo[2.2.2]octan-1-yl)trihydroborate (10 g, 47.0 mmol) in dichloromethane (150 mL) was added sodium carbonate (200 mL, 200 mmol) and benzyl chloroformate (9.5 mL, 66.5 mmol). The reaction mixture was stirred at room temperature for 40 minutes. Dichloromethane and water were added and the aqueous layer was then separated and extracted again with dichloromethane (2×). The organic layers were combined, dried over sodium sulfate, filtered and concentrated. The residue was purified via flash chromatography (12-100% ethyl acetate-hexanes). The product fractions were combined and concentrated to yield racemic (3-((benzyloxycarbonylamino)methyl)-3-hydroxy-1-ammoniobicyclo[2.2.2]octan-1-yl)trihydroborate (3 g, 9.86 mmol, 20.96% yield) as a clear oil. $^1$H NMR (400 MHz, CDCl$_3$) δ ppm 7.30-7.43 (5 H, m), 5.27 (1 H, br. s.), 5.12 (2 H, s), 3.36 (2 H, d, J=6.04 Hz), 2.76-3.21 (6H, m), 2.21 (1H, br. s.), 1.97 (1 H, br. s.), 1.71-1.86 (2 H, m).

The enantiomers were separated using a Chiralpak OJ-H (5×25) column with a mobile phase consisting of 20% acetonitrile/methanol (1: 1) in CO$_2$. The wavelength was set at 210 nM. The first peak off the column was (R)-(3-(aminomethyl)-3-hydroxy-1-ammoniobicyclo[2.2.2]octan-1-yl)trihydroborate (37.67 g, 123 mmol) as a colorless oil. Optical rotation: +28.2, c=2.9 in chloroform. The second peak off the column was (S)-(3-((benzyloxycarbonylamino)methyl)-3-hydroxy-1-ammoniobicyclo[2.2.2]octan-1-yl)trihydroborate (46.82 g, 153 mmol) as a light amber oil. Optical rotation: −27.4, c=2.5 in chloroform.

Step B: (S)-3-(Aminomethyl)quinuclidin-3-ol, 2HCl

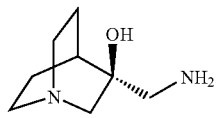

A solution of (S)-(3-((benzyloxycarbonylamino)methyl)-3-hydroxy-1-ammoniobicyclo[2.2.2]octan-1-yl)trihydroborate (20.5 g, 67 mmol) in acetone (120 mL) was cooled on an ice bath. 3M Aqueous HCl (120 mL, 360 mmol) was added over 2 minutes. Vigorous bubbling was observed. After 10 minutes, the cold ice bath was removed and the mixture was allowed to warm to room temperature. After 20 minutes, it was diluted with methanol (800 mL) and flushed with nitrogen. Palladium on carbon (2 g, 1.88 mmol) was added and the reaction was flushed with nitrogen and fitted with balloon of hydrogen. The reaction mixture was stirred at room temperature overnight. It was then flushed with nitrogen and filtered through a pad of Celite using methanol. The solvent was evaporated to yield a crude yellow solid. The solids were dissolved in water (25 mL), then ethanol (400 mL) was added. White crystals formed immediately. They were collected by filtration and washed with ethanol, followed by ether. A white crystalline solid was obtained, (S)-3-(aminomethyl)quinuclidin-3-ol, 2HCl (10.7 g, 46.7 mmol, 69.3% yield). $^1$H NMR (500 MHz, DMSO-d$_6$) δ ppm 10.93 (1 H, br. s.), 8.24 (3 H, br. s.), 6.02 (1 H, s), 3.26 (1 H, d, J=13.43 Hz), 2.99-3.22 (5 H, m), 2.10-2.19 (2 H, m), 1.81-1.90 (1H, m), 1.72-1.81 (1 H, m), 1.60-1.72 (1 H, m). Optical rotation: $[α]^{20}_D$=−50.9° (c=6.4 water).

Step C: N-(2-(1H-Imidazole-1-carbothioamido)benzo[d]thiazol-6-yl)acetamide

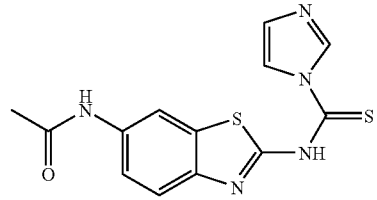

To N-(2-aminobenzo[d]thiazol-6-yl)acetamide (4 g, 19.3 mmol) in acetonitrile (100 mL) was added di(1H-imidazol-1-yl)methanethione (3.44 g, 19.30 mmol). The reaction was allowed to stir at 80° C. overnight. The reaction was cooled to room temperature and the precipitate was filtered. The product, N-(2-(1H-imidazole-1-carbothioamido)benzo[d]thiazol-6-yl)acetamide (3.6 g, 11.34 mmol, 58.8 5 yield), was taken directly to the next step without any further purification.

Step D: (R)—N-(2-(4H-1'-Azaspiro[oxazole-5,3'-bicyclo[2.2.2]octane]-2-ylamino)benzo[d]thiazol-6-yl)acetamide

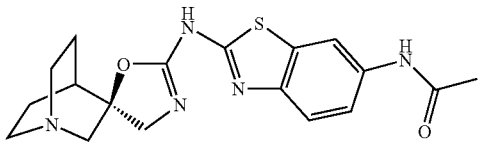

To N-(2-(1H-imidazole-1-carbothioamido)benzo[d]thiazol-6-yl)acetamide (300 mg, 0.95 mmol) in N,N-dimethylformamide (10 mL) was added (S)-3-(aminomethyl)quinuclidin-3-ol, 2HCl (238 mg, 1 mmol) and triethylamine (0.39 mL, 2.84 mmol). The reaction was heated to 80° C. for 3 hours. N,N'-diisopropylcarbodiimide (0.59 mL, 3.78 mmol) was then added to the reaction mixture. The mixture was heated at 80° C. for another 2 hours. The reaction was cooled, then chloroform and water were added to the mixture. The organic layer concentrated in vacuo to yield crude product. The crude material was purified via flash chromatography (2-20% [10% ammonium hydroxide/methanol-chloroform). The product fractions were then triturated with ether to yield (R)—N-(2-(4H-1'-azaspiro[oxazole-5,3'-bicyclo[2.2.2]oc-tane]-2-ylamino)benzo[d]thiazol-6-yl)acetamide (144.5 mg, 0.39 mmol, 41.2% yield) as a white solid. $^1$H NMR (300 MHz, DMSO-$d_6$) δ ppm 9.98 (1 H, s), 8.93 (1 H, br. s.), 8.12 (1 H, d, J=1.83 Hz), 7.52 (1 H, d, J=8.42 Hz), 7.38 (1 H, dd, J=8.60, 2.01 Hz), 3.88 (1 H, d, J=9.88 Hz), 3.62 (1 H, d, J=9.88 Hz), 3.02 (2 H, s), 2.74-2.85 (2 H, m), 2.66 (2 H, t, J=7.68 Hz), 2.05 (4 H, s), 1.91 (1 H, br. s.), 1.41-1.64 (3 H, m). MS (LC/MS) R.T.=1.55; [M+H]$^+$=372.2.

EXAMPLE 22

(R)—N-(6-(Difluoromethoxy)benzo[d]thiazol-2-yl)-4H-1'-azaspiro[oxazole-5,3-bicyclo[2.2.2]octan]-2-amine

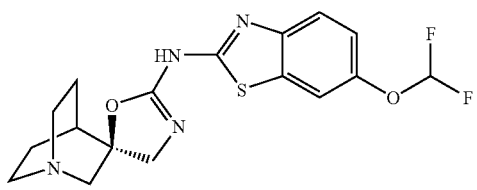

Step A:
6-(Difluoromethoxy)benzo[d]thiazol-2-amine

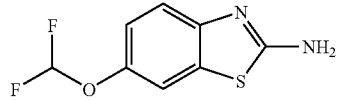

To 4-(difluoromethoxy)aniline (9.55 g, 60 mmol) in acetic acid (90 mL) was added potassium thiocyanate (KSCN) (12.41 mL, 240 mmol). The mixture was stirred for 20 minutes (KSCN dissolved into solution). To this mixture bromine (3.08 mL, 60.0 mmol) in acetic acid (40 mL) was added dropwise over 20 minutes. The reaction was stirred at room temperature overnight. It was poured into a mixture of 800 ml ice water and 200 ml saturated ammonium hydroxide. The product was extracted with ethyl acetate (5×). The organics were combined, washed with brine, dried over sodium sulfate, filtered and concentrated in vacuo to afford 6-(difluoromethoxy)benzo[d]thiazol-2-amine (12.6 g, 52.4 mmol, 87% yield) as a yellow solid.

Step B: N-(6-(Difluoromethoxy)benzo[d]thiazol-2-yl)-1H-imidazole-1-carbothioamide

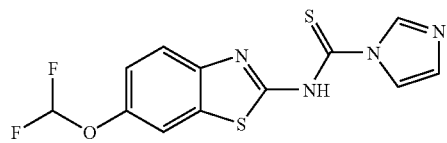

To 6-(difluoromethoxy)benzo[d]thiazol-2-amine (0.5 g, 2.3 mmol) in acetonitrile (15 mL) was added 1,1'-thiocarbonyldiimidazole (0.49 g, 2.8 mmol). The reaction was stirred at 70° C. overnight. The reaction was cooled to room temperature and the precipitate was filtered to yield N-(6-(difluoromethoxy)benzo[d]thiazol-2-yl)-1H-imidazole-1-carbothioamide (500 mg, 1.53 mmol, 66.3% yield) as a yellow solid.

Step C: (R)—N-(6-(Difluoromethoxy)benzo[d]thiazol-2-yl)-4H-1'-azaspiro[oxazole-5,3'-bicyclo[2.2.2]octan]-2-amine

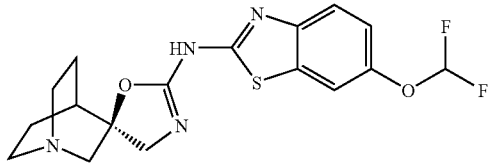

To a solution of N-(6-(difluoromethoxy)benzo[d]thiazol-2-yl)-1H-imidazole-1-carbothioamide (285 mg, 0.87 mmol) in N,N-dimethylformamide (5 mL) was added (S)-3-(aminomethyl)quinuclidin-3-ol, 2HCl (200 mg, 0.87 mmol) and triethylamine (0.4 mL, 2.87 mmol). The reaction was heated to 70° C. for 2 hours. N,N'-diisopropylcarbodiimide (0.4 mL, 2.57 mmol) was then added to the reaction mixture. The mixture was heated at 70° C. for another 3 hours. It was cooled and then poured into toluene/0.3M sodium hydroxide. The product was extracted with toluene (4×) and chloroform (3×). The organics were combined, washed with water (3×), dried over sodium sulfate, filtered and concentrated in vacuo to yield crude product. The crude material was purified via flash chromatography (2-20% [10% ammonium hydroxide/methanol]-chloroform) to afford (R)—N-(6-(difluoromethoxy)benzo[d]thiazol-2-yl)-4H-1'-azaspiro[oxazole-5,3'-bicyclo[2.2.2]octan]-2-amine (186.2mg, 0.49 mmol, 55.5% yield) as a white powder. M.P. 223-5° C. $^1$H NMR (500 MHz, DMSO-$d_6$) δ ppm 8.99 (1 H, br. s.), 7.69 (1 H, d, J=2.75 Hz), 7.61 (1 H, d, J=8.55 Hz), 7.02-7.34 (2 H, m), 3.89 (1 H, d, J=10.07 Hz), 3.64 (1 H, d, J=9.77 Hz), 3.03 (2 H, d, J=2.44 Hz), 2.73-2.86 (2 H, m), 2.62-2.70 (2 H, m), 2.07 (1 H, br. s.), 1.92 (1 H, br. s.), 1.54-1.65 (2 H, m), 1.44-1.53 (1H, m). MS (LC/MS) R.T.=1.43; [M+H]$^+$=381.1.

EXAMPLE 23

(R)—N-(6-Methoxypyrimidin-4-yl)-4H-1'-azaspiro[oxazole-5,3'-bicyclo[2.2.2]octan]-2-amine

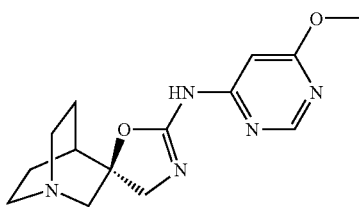

Step A: 4-Isothiocyanato-6-methoxypyrimidine

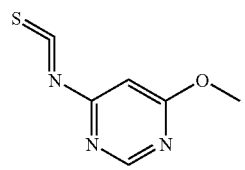

To a bright orange solution of 1,1'-thiocarbonyldipyridin-2(1H)-one (1.86 g, 7.99 mmol) in dichloromethane at room temperature was added 6-methoxypyrimidin-4-amine (1 g, 8 mmol). The orange solution was stirred at room temperature for 18 hours. The LC/MS showed the desired product as one of the major peaks. The deep orange solution was concentrated and the remaining residue was filtered. The filtrate was purified by silica gel chromatography (10-50% ethyl acetate/hexanes) to afford 4-isothiocyanato-6-methoxypyrimidine (0.72 g, 4.3 mmol, 54% yield) as a yellow oil. $^1$H NMR (400 MHz, DMSO-d$_6$) δ ppm 8.49 (1 H, d, J=5.79 Hz), 6.95 (1 H, d, J=5.79 Hz), 3.92 (3 H, s). MS (LC/MS) R.T.=3.15; [M+H]$^+$=168.1.

Step B: (R)—N-(6-Methoxypyrimidin-4-yl)-4H-1'-azaspiro[oxazole-5,3'-bicyclo[2.2.2]octan]-2-amine

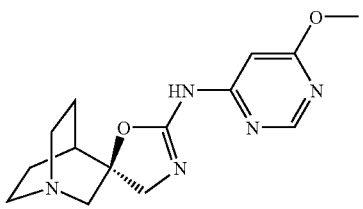

To (S)-3-(aminomethyl)quinuclidin-3-ol dihydrochloride (from Step B of Example 21) (0.34 g, 1.49 mmol) in N,N-dimethylformamide (15 mL) was added Cs$_2$CO$_3$ (1.22 g, 3.74 mmol) and 4-isothiocyanato-6-methoxypyrimidine (0.25 g, 1.5 mmol). The suspension was stirred at room temperature for 30 minutes. N,N'-diisopropylcarbodiimide (0.7 mL, 4.5 mmol) was then added and the mixture was stirred at room temperature for 18 hours. The mixture was concentrated and purified by silica gel chromatography (5-15% [9:1 methanol:ammonium hydroxide]/chloroform) to afford (R)—N-(6-methoxypyrimidin-4-yl)-4H-1'-azaspiro[oxazole-5,3'-bicyclo[2.2.2]octan]-2-amine (0.21 g, 0.72 mmol, 48.2% yield) as a white solid. M.P. 186-8° C. $^1$H NMR (400 MHz, MeOD) δ ppm 8.40 (1 H, s), 6.17 (1 H, br. s.), 3.92-4.04 (1 H, m), 3.89 (3 H, s), 3.68 (1 H, d, J=10.32Hz), 3.12-3.23 (1 H, m), 2.98-3.12 (1 H, m), 2.67-2.97 (4 H, m), 2.11 (2 H, br. s.), 148-1.82 (3 H, m). MS (LC/MS) R.T.=0.82; [M+H]$^+$=290.3.

EXAMPLE 24

(R)—N-(6-Methoxy-[1,2,4]triazolo[1,5-a]pyridin-2-yl)-4H-1'-azaspiro[oxazole-5,3'-bicyclo[2.2.2]octan]-2-amine

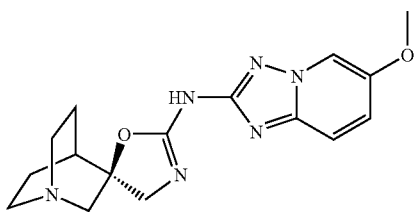

Step A: 5-Methoxypyridin-2-amine ethoxycarbonyl thiourea

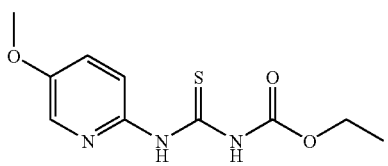

To 5-methoxypyridin-2-amine (5 g, 40 mmol) in dioxane (40 mL) was added ethoxycarbonyl isothiocyanate (5.23 mL, 44.3 mmol). The reaction mixture was stirred at room temperature overnight. The mixture was concentrated in vacuo to afford 5-methoxypyridin-2-amine ethoxycarbonyl thiourea (10.28 g, 40.3 mmol, 100% yield). $^1$H NMR (300 MHz, DMSO-d$_6$) δ ppm 12.03 (1 H, br. s.), 11.37 (1 H, br. s.), 8.53 (1 H, br. s.), 8.11 (1 H, d, J=2.93 Hz), 7.50 (1 H, dd, J=8.97, 3.11 Hz), 4.22 (2 H, q, J=7.07 Hz), 3.84 (3 H, s), 1.26 (3 H, t, J=7.14 Hz). MS (LC/MS) R.T.=2.40; [M+H]$^+$=256.1.

Step B:
6-Methoxy-[1,2,4]triazolo[1,5-a]pyridin-2-amine

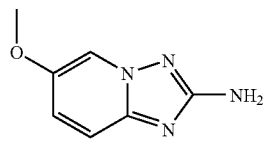

To 5-methoxypyridin-2-amine ethoxycarbonyl thiourea (10.21 g, 40 mmol) in ethanol (57 mL) and methanol (57 mL) was added hydroxylamine hydrochloride (14 g, 200 mmol) and Hunig's Base (21 mL, 120 mmol). The mixture was stirred at room temperature for 2 hours, and then heated at 60° C. for 4 hours. The reaction was cooled to room temperature and filtered to remove solids. It was concentrated in vacuo and then suspended in chloroform. The solids were filtered off to yield 6-methoxy-[1,2,4]triazolo[1,5-a]pyridin-2-amine (6.05 g, 33.2 mmol, 83% yield). $^1$H NMR (300 MHz, DMSO-d$_6$) δ ppm 8.30 (1 H, d, J=1.83 Hz), 7.24-7.32 (1 H, m), 7.16-7.23 (1 H, m), 5.82 (2 H, br. s.), 3.78 (3 H, s). MS (LC/MS) R.T.=0.53; [M+H]$^+$=165.2.

Two grams of 6-methoxy-[1,2,4]triazolo[1,5-a]pyridin-2-amine were purified via flash chromatography (2-20% [10% ammonium hydroxide/methanol]/chloroform) to afford 6-methoxy-[1,2,4]triazolo[1,5-a]pyridin-2-amine (1.35 g, 8.22 mmol, 67.5% yield). $^1$H NMR (300 MHz, DMSO-d$_6$) δ ppm 8.29 (1 H, d, J=2.20 Hz), 7.24-7.30 (1 H, m), 7.15-7.22 (1 H, m), 5.79 (2 H, s), 3.78 (3 H, s).

Step C: 2-Isothiocyanato-6-methoxy-[1,2,4]triazolo[1,5-a]pyridine

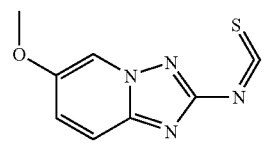

To 6-methoxy-[1,2,4]triazolo[1,5-a]pyridin-2-amine (0.3 g, 1.8 mmol) in dichloromethane (15 mL) was added 1,1'-thiocarbonyldi-2(1H)-pyridone (0.51 g, 2.2 mmol). The reaction was stirred at room temperature overnight, concentrated in vacuo and purified via flash chromatography yielding 2-isothiocyanato-6-methoxy-[1,2,4]triazolo[1,5-a]pyridine (166 mg, 0.8 mmol, 44% yield) as a white solid. $^1$H NMR (300 MHz, CDCl$_3$) δ ppm 8.03 (1 H, d, J=2.20 Hz), 7.54 (1 H, d, J=9.88 Hz), 7.34 (1 H, dd, J=9.51, 2.56 Hz), 3.88 (3 H, s).

Step D: (R)—N-(6-Methoxy-[1,2,4]triazolo[1,5-a]pyridin-2-yl)-4H-1'-azaspiro[oxazole-5,3'-bicyclo[2.2.2]octan]-2-amine

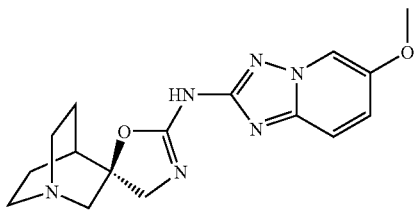

To 2-isothiocyanato-6-methoxy-[1,2,4]triazolo[1,5-a]pyridine (160 mg, 0.78 mmol) in N,N-dimethylformamide (5 ml) was added (S)-3-(aminomethyl)quinuclidin-3-ol, 2HCl (178 mg, 0.78 mmol) and triethylamine (0.32 ml, 2.33 mmol). The reaction was stirred at 70° C. for 1 hour. N,N'-Diisopropylcarbodiimide (0.36 ml, 2.33 mmol) was then added to the reaction mixture. The mixture was heated at 70° C. for 4 hours, then cooled and poured into aqueous sodium bicarbonate/chloroform. The product was extracted (3×) with chloroform. The combined organics were washed with water (3×), dried over sodium sulfate, filtered, and concentrated in vacuo, then purified via flash chromatography (2-20% [10% ammonium hydroxide:methanol]/chloroform) to yield (R)—N-(6-methoxy-[1,2,4]triazolo[1,5-a]pyridin-2-yl)-4H-1'-azaspiro-[oxazole-5,3'-bicyclo[2.2.2]octan]-2-amine (114.5 mg, 0.33 mmol, 42% yield) as a white powder. $^1$H NMR (500 MHz, CDCl$_3$) δ ppm 8.51 (1 H, br. s.), 8.08 (1 H, d, J=2.44 Hz), 7.35 (1 H, d, J=9.77 Hz), 7.18 (1 H, dd, J=9.46, 2.44 Hz), 3.92 (1 H, d, J=8.85 Hz), 3.84 (3 H, s), 3.58 (1 H, d, J=8.85 Hz), 3.36-3.41 (1 H, m), 2.72-3.05 (4 H, m), 2.18-2.26 (1 H, m, J=13.26, 9.98, 3.66, 3.49, 3.49 Hz), 2.13 (1 H, br. s.), 1.79 (1 H, br. s.), 1.67-1.76 (1 H, m, J=13.96, 9.84, 4.27, 4.27 Hz), 1.45-1.63 (2 H, m). MS (LC/MS) R.T.=0.86; [M+H]$^+$=329.2.

EXAMPLE 25

(R)—N-(5-(Trifluoromethyl)pyrazin-2-yl)-4H-1'-azaspiro[oxazole-5,3'-bicyclo[2.2.2]octan]-2-amine

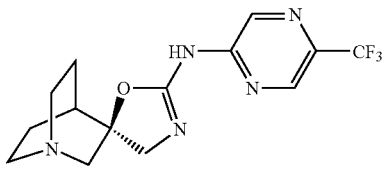

Step A: 5-(Trifluoromethyl)pyrazin-2-amine

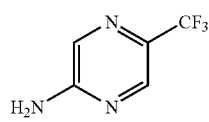

To an ice bath-cooled solution of 5,6-diaminopyrimidin-4-ol (18 g, 143 mmol) in 3M sodium hydroxide (180 mL, 540 mmol), was added 3,3-dibromo-1,1,1-trifluoropropan-2-one (25.2 g, 93 mmol). The reaction was stirred for 3 days at ambient temperature. The solids were filtered, dissolved in 60% sulfuric acid (140 mL), and stirred at 135° C. for 8 h. The reaction was cooled, poured over ice and allowed to sit for 16 hours. The solution was neutralized to pH 8 with conc. ammonium hydroxide and extracted with ethyl acetate (5×100 mL), dried over sodium sulfate, filtered and concentrated. The solid residue was recrystallized from benzene/hexane to afford 5-(trifluoromethyl)pyrazin-2-amine (2.28 g, 14 mmol, 15% yield). $^1$H NMR (400 MHz, CDCl$_3$) δ ppm 8.32 (1 H, s), 7.99 (1 H, d, J=1.26 Hz), 5.02 (2 H, br. s.). MS (LC/MS) R.T.=1.56; [M+H]$^+$=164.03.

Step B: (R)—N-(5-(Trifluoromethyl)pyrazin-2-yl)-4H-1'-azaspiro[oxazole-5,3'-bicyclo[2.2.2]octan]-2-amine

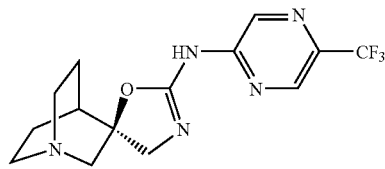

(R)—N-(5-(trifluoromethyl)pyrazin-2-yl)-4H-1'-azaspiro[oxazole-5,3'-bicyclo[2.2.2]octan]-2-amine was prepared by following the general procedures of Example 23, Steps A-B and using 5-(trifluoromethyl)pyrazin-2-amine (from Step A above) as the starting material. $^1$H NMR (400 MHz, CDCl$_3$) δ ppm 9.08 (1 H, br. s.), 8.35 (1 H, s), 8.32 (1 H, s), 3.95 (1 H, d, J=9.57 Hz), 3.61 (1 H, d, J=9.57 Hz), 3.30 (1 H, dd, J=14.86, 1.76 Hz), 2.65-2.99 (5 H, m), 2.05-2.16 (2 H, m), 1.64-1.74 (1H, m), 1.42-1.57 (2 H, m). MS (LC/MS) R.T.=1.06; [M+H]$^+$=328.30.

EXAMPLE 26

(R)—N-(6-Fluoro-1H-indazol-3-yl)-4H-1'-azaspiro[oxazole-5,3'-bicyclo[2.2.2]octan]-2-amine

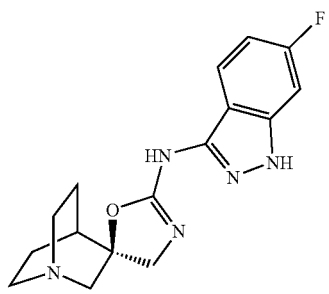

Step A: 6-Fluoro-1H-indazol-3-amine

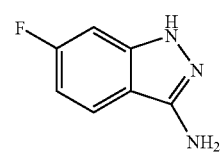

To 2,4-difluorobenzonitrile (1.21 g, 8.70 mmol) was added hydrazine monohydrate (8.46 mL, 174 mmol). The mixture was heated to reflux for 5 hours and then poured onto ice. The solution was extracted with ethyl acetate, dried with magnesium sulfate, filtered and concentrated. The residue was purified by column chromatography (25-100% ethyl acetate/hexane) to afford 6-fluoro-1H-indazol-3-amine (0.5 g, 3.3 mmol, 38% yield) as light yellow powder. $^1$H NMR (500 MHz, DMSO-D6) δ ppm 11.42 (s, 1 H), 7.70 (dd, J=8.55, 5.49 Hz, 1 H), 6.97 (dd, J=10.07, 1.83 Hz, 1 H), 6.72-6.79 (m, 1 H), 5.40 (s, 2 H). MS (LC/MS) R.T.=0.61; [M+H]$^+$=152.11.

Step B: 6-Fluoro-3-isothiocyanato-1H-indazole

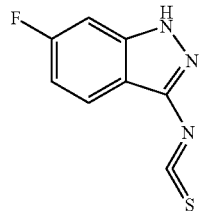

To 6-fluoro-1H-indazol-3-amine (0.32 g, 2.1 mmol) in dichloromethane (15 mL) was added 1,1'-thiocarbonyldipyridin-2(1H)-one (0.53 g, 2.30 mmol). The reaction was stirred at 50° C. for 3 hours. The reaction was cooled to room temperature and the crude product was purified by column chromatography (25% ethyl acetate/hexanes) to afford 6-fluoro-3-isothiocyanato-1H-indazole (0.30 g, 1.53 mmol, 73.0% yield) as a light yellow powder. $^1$H NMR (500 MHz, DMSO-D6) δ ppm 13.39 (s, 1 H), 7.78 (dd, J=8.85, 4.88 Hz, 1 H), 7.41 (dd, J=9.31, 1.68 Hz, 1 H), 7.14 (td, J=9.16, 1.83 Hz, 1 H). MS (LC/MS) R.T.=3.69; [M+H]$^+$=194.07.

Step C: (R)—N-(6-Fluoro-1H-indazol-3-yl)-4H-1'-azaspiro[oxazole-5,3'-bicyclo[2.2.2]octan]-2-amine

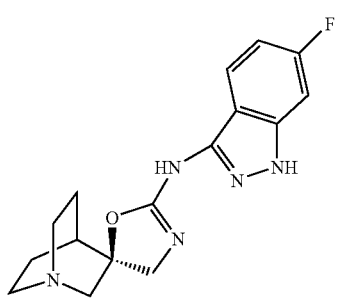

To 6-fluoro-3-isothiocyanato-1H-indazole (0.20 g, 1.04 mmol) in DMF (15 mL) was added triethylamine (0.43 mL, 3.11 mmol) and (S)-3-(aminomethyl)quinuclidin-3-ol dihydrochloride (0.26 g, 1.14 mmol) at room temperature. The reaction was stirred at 70° C. for 2 hours. The reaction was cooled to room temperature and treated with N,N'-diisopropylcarbodiimide (0.48 mL, 3.11 mmol). The reaction was then heated to 70° C. for 2 hours. The reaction was cooled to ambient temperature and concentrated. The crude product was purified by column chromatography (85% chloroform, 14% methanol, 1% ammonium hydroxide) to afford (R)—N-(6-fluoro-1H-indazol-3-yl)-4H-1'-azaspiro[oxazole-5,3'-bicyclo[2.2.2]octan]-2-amine (0.22 g, 0.66 mmol, 64% yield) as a white powder. $^1$H NMR (500 MHz, DMSO-D6) δ ppm 12.16 (s, 1 H), 8.00 (s, 1 H), 7.59-7.67 (m, 1H), 7.09 (dd, J=9.77, 2.14 Hz, 1 H), 6.81-6.88 (m, 1 H), 3.81 (d, J=9.16 Hz, 1 H), 3.56 (d, J=8.85 Hz, 1 H), 3.00 (s, 2 H), 2.78 (s, 2 H), 2.67 (t, J=7.32 Hz, 2 H), 2.01 (d, J=2.44 Hz, 1 H), 1.92 (s, 1 H), 1.59 (d, J=5.80 Hz, 2 H), 1.46 (s, 1 H). MS (LC/MS) R.T.=1.44; [M+H]$^+$=316.16.

EXAMPLE 27

(R)—N-(Furo[3,2-c]pyridin-4-yl)-4H-1'-azaspiro[oxazole-5,3'-bicyclo[2.2.2]octan]-2-amine

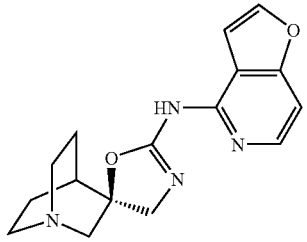

Step A: Furo[3,2-c]pyridin-4-amine

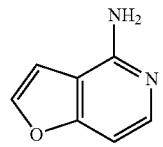

To 4-chlorofuro[3,2-c]pyridine (1 g, 6.5 mmol) in toluene under nitrogen was added racemic BINAP (0.243 g, 0.4 mmol), Pd$_2$(dba)$_3$ (0.12 g, 0.13 mmol) and sodium tert-butoxide (0.88 g, 9.1 mmol). Benzophenoneimine (1.3 mL, 7.81 mmol) was added and the mixture was heated to 80° C. for 3 h and cooled to room temperature. The reaction mixture was diluted with ether, filtered through Celite, and washed with ether. The filtrate was concentrated and the deep orange residue was taken up in methanol (90 ml) and treated with hydroxylamine (1.2 mL, 19.5 mmol). The mixture was stirred at ambient temperature for 18 h and concentrated. The residue was purified by column chromatography (95-100% ethyl acetate/hexanes) to afford furo[3,2-c]pyridin-4-amine (776 mg, 5.79 mmol, 89% yield) as a deep orange solid. MS (LC/MS) R.T.=0.51; [M+H]$^+$=135.02.

Step B: (R)—N-(Furo[3, 2-c]pyridin-4-yl)-4H-1'-azaspiro[oxazole-5,3'-bicyclo[2.2.2]octan]-2-amine

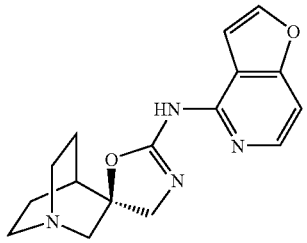

(R)—N-(Furo[3,2-c]pyridin-4-yl)-4H-1'-azaspiro[oxazole-5,3'-bicyclo[2.2.2]octan]-2-amine was prepared by following the general procedures of Example 23, Steps A-B using furo[3,2-c]pyridin-4-amine (Step A above) as the starting material. $^1$H NMR (400 MHz, MeOD) δ ppm 8.08 (1 H, d, J=5.79 Hz), 7.69 (1 H, d, J=2.01 Hz), 6.99-7.13 (2 H, m), 4.00 (1 H, d, J=10.07 Hz), 3.69 (1 H, d J=10.07 Hz), 3.19-3.26 (1 H, m), 3.05-3.13 (1 H, m), 2.93 (2 H, t, J=7.43 Hz), 2.73-2.87 (2 H, m), 2.08-2.24 (2 H, m), 1.52-1.82 (3 H, m). MS (LC/MS) R.T.=0.68; [M+H]$^+$=299.19.

EXAMPLE 28

(R)—N-(5-Phenylpyridin-3-yl)-4H-1'-azaspiro[oxazole-5,3'-bicyclo[2.2.2]octan]-2-amine

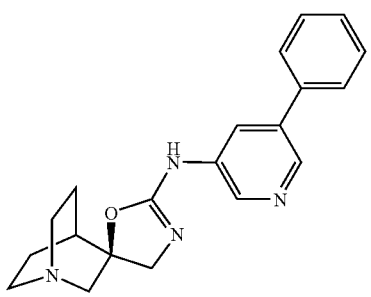

Step A: 5-Phenylpyridin-3-amine

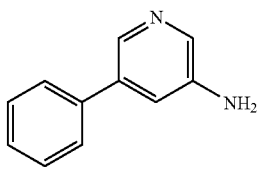

A mixture of 5-bromopyridin-3-amine (248 mg, 1.43 mmol), Pd(PPh$_3$)$_4$ (50.4 mg, 0.04 mmol), toluene (3 mL), sodium carbonate (2 M, 3 mL, 6 mmol), and phenylboronic acid (195 mg, 1.60 mmol) dissolved in ethanol (3 mL) was heated for 4 hours in an oil bath at 90° C. and allowed to cool to room temperature for 16 hours. The reaction mixture was transferred to a separatory funnel and partitioned between ethyl acetate and water. The aqueous phase was washed once more with ethyl acetate, and the combined organic phases were washed with brine and dried over magnesium sulfate, filtered and concentrated in vacuo. The residue was purified by column chromatography (80% ethyl acetate/hexanes) to afford 5-phenylpyridin-3-amine (31.9 mg, 0.19 mmol, 13% yield) as a white solid. $^1$H NMR (500 MHz, CDCl$_3$) δ ppm 8.17-8.42 (m, 1 H), 8.02-8.20 (m, 1 H), 7.32-7.62 (m, 4 H), 7.25 (s, 1 H), 7.06-7.20 (m, 1 H). MS (LC/MS) R.T.=0.91; [M+H]$^+$=171.09.

Step B: (R)—N-(5-Phenylpyridin-3-yl)-4H-1'-azaspiro[oxazole-5,3'-bicyclo[2.2.2]octan]-2-amine

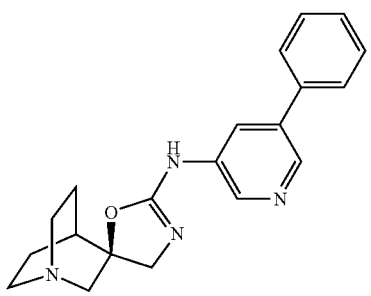

(R)—N-(5-Phenylpyridin-3-yl)-4H-1'-azaspiro[oxazole-5,3'-bicyclo[2.2.2]octan]-2-amine was prepared by following the general procedures of Example 23, Steps A-B using 5-phenylpyridin-3-amine (from Step A above) as the starting material. $^1$H NMR (500 MHz, MeOD-d$_4$) δ ppm 8.40 (br. s., 2 H), 7.66 (d, J=7.32 Hz, 2 H), 7.46-7.56 (m, 3 H), 7.43 (d, J=7.32 Hz, 1 H), 3.79-4.02 (m, 1 H), 3.51-3.68 (m, 1 H), 3.22 (d, J=14.95 Hz, 1 H), 3.02-3.15 (m, 1 H), 2.72-2.99 (m, 3 H), 2.14 (br. s., 2 H), 1.76 (dd, J=9.31, 4.12 Hz, 3 H), 1.12-1.35 (m, 1 H). MS (LC/MS) R.T.=0.90; [M+H]$^+$=335.17.

EXAMPLE 29

(R)—N-(2-Phenylpyridin-4-yl)-4H-1'-azaspiro[oxazole-5,3'-bicyclo[2.2.2]octan]-2-amine

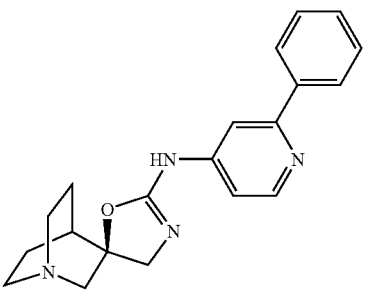

(R)—N-(2-Phenylpyridin-4-yl)-4H-1'-azaspiro[oxazole-5,3'-bicyclo[2.2.2]octan]-2-amine was prepared from 2-bromopyridin-4-amine by following the general procedures of Example 28, Steps A-B. $^1$H NMR (500 MHz, MeOD) δ ppm 8.38 (d, J=5.49 Hz, 1 H), 7.88 (d, J=7.93 Hz, 2 H), 7.71-7.84 (m, 1H), 7.48 (d, J=7.63 Hz, 3 H), 7.19-7.36 (m, 1 H), 3.94-4.09 (m, 1 H), 3.61-3.79 (m, 1 H), 3.17-3.27 (m, 1 H), 3.00-3.14 (m, 1 H), 2.74-3.00 (m, 4 H), 2.05-2.23 (m, 2 H), 1.55-1.86 (m, 3 H). MS (LC/MS) R.T.=0.86; [M+H]$^+$=335.23.

EXAMPLE 30

(R)—N-(6-Phenylpyridin-2-yl)-4H-1'-azaspiro[oxazole-5,3'-bicyclo[2.2.2]octan]-2-amine

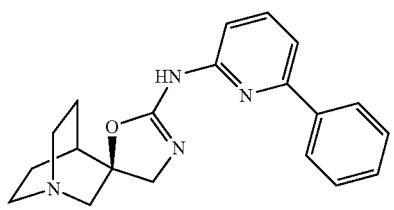

(R)—N-(6-Phenylpyridin-2-yl)-4H-1'-azaspiro[oxazole-5,3'-bicyclo[2.2.2]octan]-2-amine was prepared from 6-bromopyridin-2-amine by following the general procedures of Example 28, Steps A-B. $^1$H NMR (500 MHz, MeOD-d$_4$) δ ppm 7.91 (d, J=7.63 Hz, 2 H), 7.71 (t, J=7.78 Hz, 1 H), 7.32-7.55 (m, 5H), 4.04 (d, J=10.07 Hz, 1 H), 3.72 (d, J=9.77 Hz, 1 H), 3.23 (d, J=1.22 Hz, 1 H), 3.12 (s, 1 H), 2.95 (s, 2 H), 2.84 (s, 2 H), 2.16 (br. s., 2 H), 1.58-1.85 (m, 3H), MS (LC/MS) R.T.=0.75; [M+H]$^+$=335.23.

EXAMPLE 31

(R)—N-(6-(Difluoromethoxy)-1-methyl-1H-indazol-3-yl)-4H-1'-azaspiro[oxazole-5,3'-bicyclo[2.2.2]octan]-2-amine

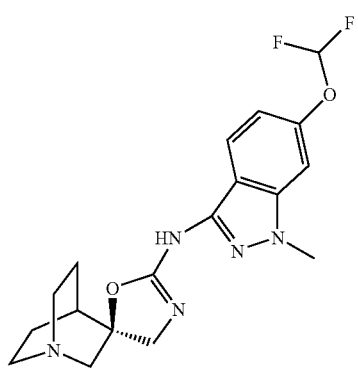

Step A:
6-(Difluoromethoxy)-1-methyl-1H-indazol-3-amine

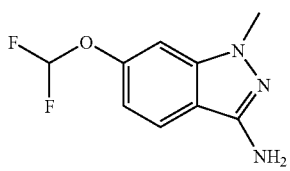

To 4-(difluoromethoxy)-2-fluorobenzonitrile (1 g, 5.3 mmol) was added methylhydrazine (4.92 g, 107 mmol). The mixture was heated to 50° C. for 5 hours and then cooled to room temperature. The crude product was purified by column chromatography (40-100% ethyl acetate/hexanes) to afford 6-(difluoromethoxy)-1-methyl-1H-indazol-3-amine (0.5 g, 2.35 mmol, 44% yield) as a white powder. $^1$H NMR (500 MHz, DMSO-d$_6$) δ ppm 7.70 (d, J=8.55 Hz, 1 H), 7.14 (s, 1 H), 6.73 (d, J=8.55 Hz, 1 H), 5.49 (s, 1 H), 3.70 (s, 3 H).

Step B: (R)—N-(6-(Difluoromethoxy)-1-methyl-1H-indazol-3-yl)-4H-1'-azaspiro[oxazole-5,3'-bicyclo[2.2.2]octan]-2-amine

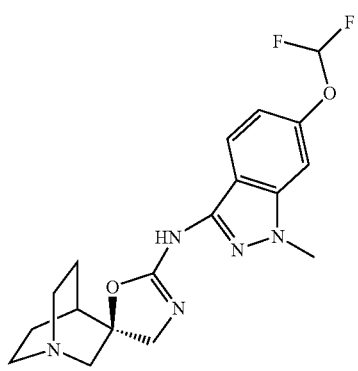

(R)—N-(6-(difluoromethoxy)-1-methyl-1H-indazol-3-yl)-4H-1'-azaspiro[oxazole-5,3'-bicyclo[2.2.2]octan]-2-amine was prepared by following the general procedures of Example 23, Steps A-B using 6-(difluoromethoxy)-1-methyl-1H-indazol-3-amine (Step A) as the starting material. $^1$H NMR (500 MHz, DMSO-d$_6$) δ ppm 7.64 (d, J=8.55 Hz, 1 H), 7.28 (d, J=5.19 Hz, 1 H), 6.83 (dd, J=8.55, 1.83 Hz, 1 H), 3.88 (s, 3 H), 3.77-3.84 (m, 1 H), 3.51-3.64 (m, 1 H), 3.00 (s, 2 H), 2.72-2.84 (m, 2 H), 2.67 (t, J=7.48 Hz, 2 H), 2.02 (br. s., 1 H), 1.85-1.98 (m, 1 H), 1.59 (d, J=5.80 Hz, 2 H), 1.36-1.53 (m, 1 H), 1.09 (d, J=6.41 Hz, 1 H). MS (LC/MS) R.T.=1.04; [M+H]$^+$=378.19.

EXAMPLE 32

(R)—N-(5-(Difluoromethoxy)thiazolo[5,4-b]pyridin-2-yl)-4H-1'-azaspiro[oxazole-5,3'-bicyclo[2.2.2]octan]-2-amine

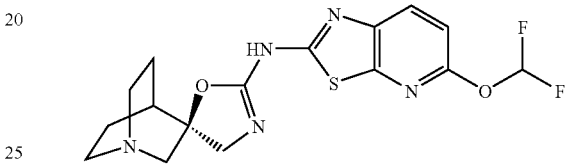

Step A: 2-(Difluoromethoxy)-5-nitropyridine

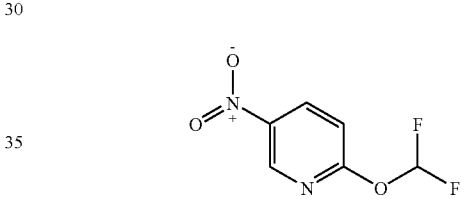

To 2-hydroxy-5-nitropyridine (7 g, 50 mmol) in acetonitrile (500 mL) was added sodium sulfate (1.5 g, 10.6 mmol), and 2,2-difluoro-2-(fluorosulfonyl)acetic acid (6.2 mL, 60 mmol) and the reaction was allowed to stir at room temperature for 16 hours. The reaction was quenched with saturated aqueous sodium bicarbonate and the acetonitrile was removed in vacuo. The remaining aqueous component was extracted with ethyl acetate, washed with brine, dried over sodium sulfate, filtered and concentrated in vacuo. The pale brown oily solid was triturated with ether/hexanes, filtered and the filtrate concentrated to afford 2-(difluoromethoxy)-5-nitropyridine (4.7 g, 24.7 mmol, 49% yield) as a yellow oil. $^1$H NMR (400 MHz, DMSO-d$_6$) δ ppm 9.14 (d, J=2.76 Hz, 1 H), 8.68 (dd, J=9.03, 2.76 Hz, 1 H), 7.98 (s, 0.5 H), 7.62 (s, 0.5 H), 7.34 (d, J=9.03 Hz, 1 H).

Step B: 6-(Difluoromethoxy)pyridin-3-amine

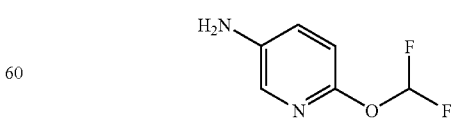

To 2-(difluoromethoxy)-5-nitropyridine (4.7 g, 24.7 mmol) in degassed methanol (100 mL) was added 10% palladium on carbon (500 mg, 0.47 mmol) and the reaction was hydrogenated at atmospheric pressure for 1 hour. To this was added acetic acid (2.83 mL, 49.4 mmol) and the reaction was filtered through Celite and concentrated in vacuo to afford 6-(difluoromethoxy)pyridin-3-amine (6.33 g, 25.9 mmol, 105% yield) as an olive green liquid. $^1$H NMR (400 MHz, MeOD-d$_4$) δ ppm 7.60 (d, J=2.76 Hz, 1 H), 7.37 (s, 0.5 H), 7.15 (dd, J=8.66, 2.89 Hz, 1 H), 7.00 (s, 0.5H), 6.71 (d, J=8.78 Hz, 1 H).

Step C:
5-(Difluoromethoxy)thiazolo[5,4-b]pyridin-2-amine

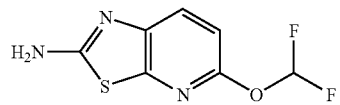

To acetic acid (10 mL) cooled in an ice bath was added potassium thiocyanate (3.18 g, 32.8 mmol) and 6-(difluoromethoxy)pyridin-3-amine (1 g, 4.1 mmol). The reaction was cooled in an ice-salt bath until the reaction temperature reached <0° C. A solution of bromine (0.65 mL, 12.7 mmol) in acetic acid (3 mL) was added dropwise over 2 hours at a rate that maintained the reaction temperature <0° C. This gave a very thick mixture. After the addition was complete, the mixture was left to stir and allowed to slowly warm to room temperature overnight. After stirring overnight, water (5 mL) was added and the mixture was heated to 85° C. in an oil bath. This mixture was then filtered while still hot. The yellow filter cake was returned to the reaction flask, and an additional 5 mL acetic acid was added. The mixture was heated again to 85° C., and then filtered while still hot. The combined filtrates were cooled in an ice bath and neutralized to pH 8 with concentrated ammonium hydroxide. A yellow precipitate formed which was then collected by filtration. This crude material was purified by column chromatography (12-100% ethyl acetate/hexanes) to afford 5-(difluoromethoxy)thiazolo[5,4-b]pyridin-2-amine (321 mg, 1.48 mmol, 36.1% yield) as a yellow solid. $^1$H NMR (400 MHz, DMSO-d$_6$) δ ppm 7.64-7.81 (m, 2 H), 6.92 (d, J=8.53 Hz, 1 H). MS (LC/MS) R.T.=1.66; [M+H]$^+$=218.10.

Step D: N-(5-(Difluoromethoxy)thiazolo[5,4-b]pyridin-2-yl)-1H-imidazole-1-carbothioamide

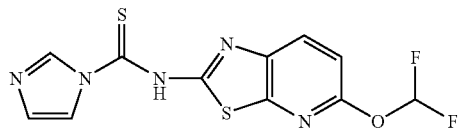

5-(Difluoromethoxy)thiazolo[5,4-b]pyridin-2-amine (310 mg, 1.43 mmol) and di(1H-imidazol-1-yl)methanethione (311 mg, 1.75 mmol) were dissolved in acetonitrile (5 mL) and heated to 70° C. in a sealed vial for 10 hours. The vial was then stored in the freezer for 16 hours. The solids were collected by filtration and washed with acetonitrile to afford N-(5-(difluoromethoxy)thiazolo[5,4-b]pyridin-2-yl)-1H-imidazole-1-carbothioamide (296 mg, 0.72 mmol, 51% yield). $^1$H NMR (400 MHz, DMSO-d$_6$) δ ppm 8.77 (d, J=4.77 Hz, 1 H), 8.06 (d, J=8.53 Hz, 1 H), 8.01 (s, 1H), 7.72 (s, 1 H), 7.54 (s, 1 H), 6.94-7.13 (m, 1 H).

Step E: (R)—N-(5-(Difluoromethoxy)thiazolo[5,4-b]pyridin-2-yl)-4H-1'-azaspiro[oxazole-5,3'-bicyclo[2.2.2]octan]-2-amine

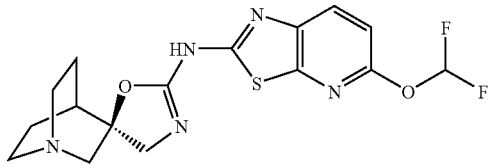

To N-(5-(difluoromethoxy)thiazolo[5,4-b]pyridin-2-yl)-1H-imidazole-1-carbothioamide (296 mg, 0.72 mmol) in N,N-dimethylformamide (4 mL) in a sealed vial was added (S)-3-(aminomethyl)quinuclidin-3-ol, 2HCl (175 mg, 0.76 mmol) and triethylamine (0.3 ml, 2.2 mmol) and the mixture was heated to 70° C. overnight.

To this was added N,N'-diisopropylcarbodiimide (350 μl, 2.25 mmol) and the reaction was heated to 70° C. for 6 hours. It was cooled to ambient temperature and poured into water/chloroform, extracted with additional chloroform and concentrated in vacuo. The residue was then taken up in toluene and washed with water to remove the residual N,N-dimethylformamide. The residue was purified by column chromatography (2%-20% (10% ammonium hydroxide/methanol)/chloroform) to afford (R)—N-(5-(difluoromethoxy)thiazolo[5,4-b]pyridin-2-yl)-4H-1'-azaspiro[oxazole-5,3'-bicyclo[2.2.2]octan]-2-amine (104 mg, 0.27 mmol, 37% yield) as a pale cream colored solid. $^1$H NMR (400 MHz, DMSO-d$_6$) δ ppm 7.99 (d, J=8.78 Hz, 1 H), 7.68 (s, 1 H), 7.03 (d, J=8.53 Hz, 1 H), 3.87 (d, J=10.04 Hz, 1 H), 3.62 (d, J=10.04 Hz, 1 H), 3.03 (d, J=5.02 Hz, 2 H), 2.80 (d, J=9.03 Hz, 2 H), 2.65 (t, J=7.65 Hz, 2 H), 2.08 (br. s., 1 H), 1.83-1.99 (m, 1 H), 1.43-1.68 (m, 3 H). MS (LC/MS) R.T.=1.73; [M+H]$^+$=382.20.

EXAMPLE 33

(R)—N-(6-Isopropoxybenzo[d]thiazol-2-yl)-4H-1'-azaspiro[oxazole-5,3'-bicyclo[2.2.2]octan]-2-amine

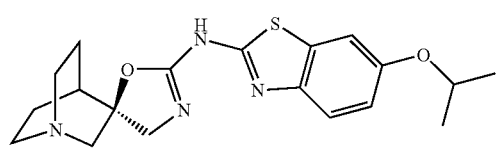

(R)—N-(6-Isopropoxybenzo[d]thiazol-2-yl)-4H-1'-azaspiro[oxazole-5,3'-bicyclo[2.2.2]octan]-2-amine was prepared from 4-isopropoxyaniline by following the general procedures of Example 32, Steps C-E. $^1$H NMR (400 MHz, DMSO-d$_6$) δ ppm 7.49 (d, J=8.78 Hz, 1 H), 7.38 (d, J=2.51 Hz, 1 H), 6.90 (dd, J=8.78, 2.51 Hz, 1 H), 4.50-4.68 (m, 1 H), 3.87 (d, J=10.04 Hz, 1 H), 3.62 (d, J=9.79 Hz, 1H), 2.79 (d, J=9.03 Hz, 2 H), 2.66 (t, J=7.78 Hz, 2 H), 2.06 (br. s., 1 H), 1.85-1.96 (m, 1 H), 1.42-1.67 (m, 3 H), 1.17-1.34 (m, 6H), 0.96-1.19 (m, 2 H).

EXAMPLE 34

(R)—N-(5-(Pyrrolidin-1-yl)pyrazin-2-yl)-4H-1'-azaspiro[oxazole-5,3'-bicyclo[2.2.2]octan]-2-amine

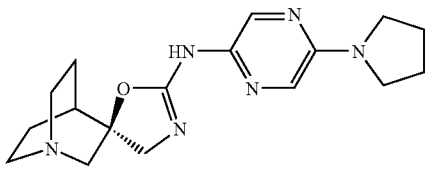

Step A: 5-(Pyrrolidin-1-yl)pyrazin-2-amine

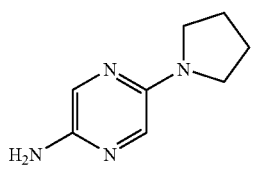

A mixture of 5-bromopyrazin-2-amine (1.2 g, 6.9 mmol) and pyrrolidine (4 mL, 48 mmol) was microwaved at 180° C., 200 W for 2 h. The reaction was diluted into 125 mL ethyl acetate and extracted with water (3×50 mL) and brine (50 mL). It was dried over sodium sulfate, filtered and concentrated. The crude product was purified by column chromatography (0 to 3% methanol/methylene chloride) to afford 5-(pyrrolidin-1-yl)pyrazin-2-amine (495 mg, 3. mmol, 43.7% yield). $^1$H NMR (400 MHz, DMSO-$d_6$) δ ppm 7.52 (1 H, d, J=1.51 Hz), 7.36 (1 H, d, J=1.76 Hz), 5.21 (2H, s), 3.24-3.29 (4 H, m), 1.90 (4 H, ddd, J=6.48, 3.53, 3.34 Hz). MS (LC/MS) R.T.=0.52; [M+H]$^+$=165.29.

Step B: (R)—N-(5-(Pyrrolidin-1-yl)pyrazin-2-yl)-4H-1'-azaspiro[oxazole-5,3'-bicyclo[2.2.2]octan]-2-amine

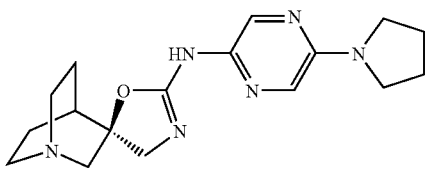

(R)—N-(5-(Pyrrolidin-1-yl)pyrazin-2-yl)-4H-1'-azaspiro[oxazole-5,3'-bicyclo[2.2.2]octan]-2-amine was prepared from 5-(pyrrolidin-1-yl)pyrazin-2-amine by following the general procedures of Example 23, Steps A-B. $^1$H NMR (500 MHz, CDCl$_3$) δ ppm 8.51 (1 H, br. s.), 8.02 (1 H, s), 7.44 (1 H, d, J=0.92 Hz), 3.84 (1H, d, J=9.16 Hz), 3.51 (1 H, d, J=8.85 Hz), 3.39-3.45 (4 H, m), 3.31 (1 H, dd, J=14.80, 1.07 Hz), 2.69-3.04 (5 H, m), 2.15-2.25 (1 H, m), 2.09 (1 H, br. s.), 1.98-2.02 (4H+HOD, m), 1.64-1.74 (1 H, m), 1.42-1.61 (2 H, m). MS (LC/MS) R.T.=0.76; [M+H]$^+$=329.40.

EXAMPLE 35

(R)-1-(5-(4H-1'-Azaspiro[oxazole-5,3'-bicyclo[2.2.2]octane]-2-ylamino)pyrazin-2-yl)pyrrolidin-2-one

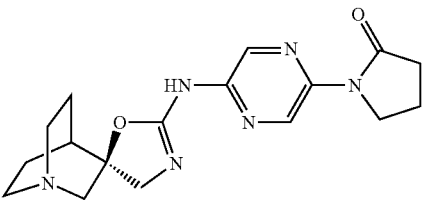

Step A: 1-(5-Aminopyrazin-2-yl)pyrrolidin-2-one

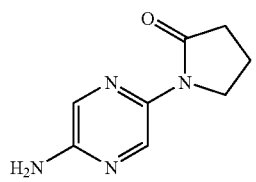

A mixture of 5-bromopyrazin-2-amine (5 g, 29 mmol), pyrrolidin-2-one (11 mL, 144 mmol), copper (I) iodide (1.1 g, 5.75 mmol), potassium carbonate (7.94 g, 57.5 mmol), and (1R,2R)-cyclohexane-1,2-diamine (1.38 mL, 11.49 mmol) was refluxed under nitrogen in dioxane (100 mL) for 18 h. After cooling, 200 mL ethyl acetate and 20 mL methanol were added to the reaction. This was filtered through celite, concentrated, and absorbed onto sodium sulfate for purification by column chromatography (0-5% methanol/methylene chloride). The purified product was recrystallized from ether/ethyl acetate to afford 1-(5-aminopyrazin-2-yl)pyrrolidin-2-one (1.57 g, 8.81 mmol, 30.7% yield). $^1$H NMR (400 MHz, DMSO-$d_6$) δ ppm 8.74 (1 H, d, J=1.51 Hz), 7.69 (1 H, d, J=1.51 Hz), 6.20 (2 H, s), 3.84 (2 H, t, J=7.05 Hz), 2.49 (2 H, t, J=7.93 Hz), 2.04 (2 H, dq, J=7.68, 7.51 Hz). MS (LC/MS) R.T.=0.48; [M+H]$^+$=179.27.

Step B: (R)-1-(5-(4H-1'-Azaspiro[oxazole-5,3'-bicyclo[2.2.2]octane]-2-ylamino)pyrazin-2-yl)pyrrolidin-2-one

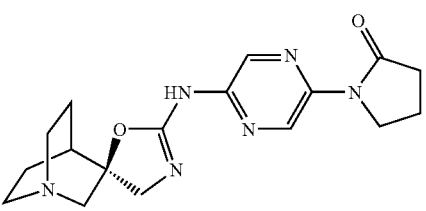

(R)-1-(5-(4H-1'-Azaspiro[oxazole-5,3'-bicyclo[2.2.2]octane]-2-ylamino)pyrazin-2-yl)pyrrolidin-2-one was prepared from 1-(5-aminopyrazin-2-yl)pyrrolidin-2-one by following the general procedures of Example 23, Steps A-B. $^1$H NMR (500 MHz, CDCl$_3$) δ ppm 9.20 (1 H, d, J=1.22 Hz), 8.91 (1 H, br. s.), 8.13 (1 H, s), 4.02 (2 H, t, J=7.02 Hz), 3.92 (1 H, d, J=9.46 Hz), 3.58 (1 H, d, J=9.16 Hz), 3.33 (1 H, dd, J=14.95, 1.53 Hz), 2.71-3.01 (5 H, m), 2.63 (2 H, t, J=8.09 Hz), 2.08-2.23 (4 H, m), 1.66-1.76 (1 H, m), 1.42-1.61 (2 H, m). MS (LC/MS) R.T.=0.67; [M+H]+=343.30.

EXAMPLE 36

(R)—N-(5-(Pyridin-3-yl)pyrazin-2-yl)-4H-1'-azaspiro[oxazole-5,3'-bicyclo[2.2.2]octan]-2-amine

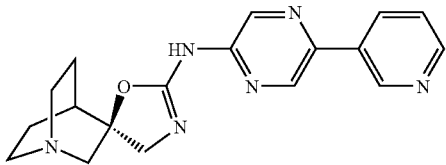

Step A: 5-(Pyridin-3-yl)pyrazin-2-amine

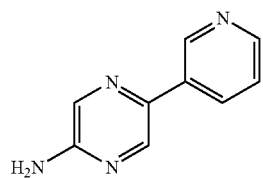

Pyridin-3-ylboronic acid (307 mg, 2.50 mmol), 5-bromopyrazin-2-amine (391 mg, 2.25 mmol) and dichlorobis(triphenylphosphine)-palladium(II) (88 mg, 0.13 mmol) were added to degassed dioxane (12 mL) and the mixture was stirred for 30 min. Then sodium carbonate (795 mg, 7.50 mmol) and degassed water (8 mL) were added and the reaction was heated in a closed reaction vial at 100° C. for 8 h. The reaction was allowed to stand at ambient temperature over the weekend. It was diluted into ethyl acetate (100 mL) and extracted with brine (3×25 mL). The organic layers were dried over sodium sulfate and concentrated in vacuo. The crude product was purified by column chromatography (0 to 5% methanol/ethyl acetate) to afford 5-(pyridin-3-yl)pyrazin-2-amine (235 mg, 1.37 mmol, 54.6% yield). $^1$H NMR (400 MHz, Acetone) δ ppm 9.13 (1 H, d, J=1.51 Hz), 8.54 (1 H, d, J=1.26 Hz), 8.50 (1 H, dd, J=4.78, 1.51 Hz), 8.22-8.28 (1 H, m), 8.07 (1 H, d, J=1.26 Hz), 7.39 (1 H, ddd, J=7.87, 4.72, 0.76 Hz), 6.05 (2 H, br. s.). MS (LC/MS) R.T.=0.58; [M+H]+=173.20.

Step B: (R)—N-(5-(Pyridin-3-yl)pyrazin-2-yl)-4H-1'-azaspiro[oxazole-5,3'-bicyclo[2.2.2]octan]-2-amine

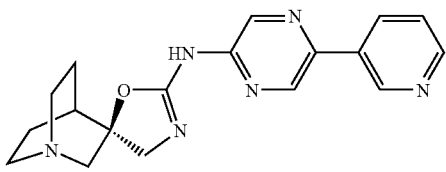

(R)—N-(5-(Pyridin-3-yl)pyrazin-2-yl)-4H-1'-azaspiro[oxazole-5,3'-bicyclo[2.2.2]octan]-2-amine was prepared from 5-(pyridin-3-yl)pyrazin-2-amine by following the general procedures of Example 23, Steps A-B. $^1$H NMR (400 MHz, CDCl$_3$) δ ppm 9.12 (1 H, dd, J=2.27, 0.76 Hz), 9.08 (1 H, br. s.), 8.59 (1 H, dd, J=4.78, 1.76 Hz), 8.55 (1 H, d, J=1.51 Hz), 8.45 (1 H, d, J=1.26 Hz), 8.25 (1H, dt, J=7.99, 1.92 Hz), 7.38 (1 H, ddd, J=8.06, 4.78, 0.76 Hz), 3.97 (1 H, d, J=9.57 Hz), 3.63 (1 H, d, J=9.32 Hz), 3.36 (1 H, dd, J=14.86, 1.76 Hz), 2.69-3.06 (5 H, m), 2.14-2.24 (1 H, m), 2.12 (1 H, br. s.), 1.66-1.77 (1 H, m, J=13.94, 9.66, 4.31, 4.31 Hz), 1.44-1.62 (2 H, m). MS (LC/MS) R.T.=0.65; [M+H]+=337.30.

EXAMPLE 37

(R)—N-(5-(6-Methoxypyridin-3-yl)pyrazin-2-yl)-4H-1'-azaspiro[oxazole-5,3'-bicyclo[2.2.2]octan]-2-amine

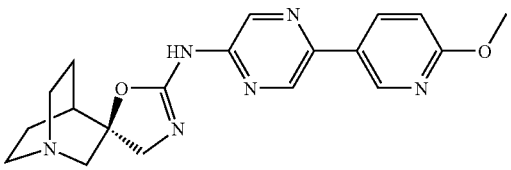

(R)—N-(5-(6-Methoxypyridin-3-yl)pyrazin-2-yl)-4H-1'-azaspiro[oxazole-5,3'-bicyclo[2.2.2]octan]-2-amine was prepared from 5-bromopyrazin-2-amine by following the general procedures of Example 36, Steps A-B. $^1$H NMR (400 MHz, CDCl$_3$) δ ppm 9.04 (1 H, br. s.), 8.66 (1 H, d, J=2.01 Hz), 8.46 (1 H, d, J=1.51 Hz), 8.41 (1 H, d, J=1.01 Hz), 8.15 (1 H, dd, J=8.81, 2.52 Hz), 6.82 (1 H, d, J=8.31 Hz), 3.97 (3 H, s), 3.95 (1 H, d, J=9.57 Hz), 3.61 (1 H, d, J=9.32 Hz), 3.35 (1 H, dd, J=14.86, 1.51 Hz), 2.68-3.07 (5 H, m), 2.14-2.24 (1 H, m, J=13.27, 9.93, 3.53, 3.38, 3.38 Hz), 2.11 (1 H, br. s.), 1.67-1.77 (1 H, m), 1.45-1.61 (2 H, m). MS (LC/MS) R.T.=0.81; [M+H]+=367.40.

EXAMPLE 38

(R)—N-(6-Methoxyquinoxalin-2-yl)-4H-1'-azaspiro[oxazole-5,3'-bicyclo[2.2.2]octan]-2-amine

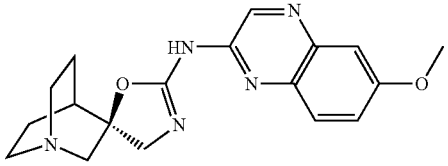

Step A: 7-Methoxyquinoxalin-2(1H)-one and 6-methoxyquinoxalin-2(1H)-one

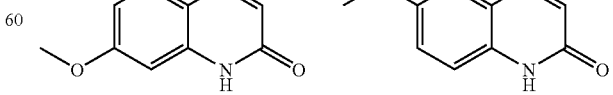

A 50% solution of ethyl 2-oxoacetate (18.47 mL, 93 mmol) in toluene was added to a solution of 4-methoxybenzene-1,2-diamine (10.73 g, 78 mmol) in ethanol (100 mL) at ambient temperature and the reaction was refluxed for 2 h. The reaction was concentrated in vacuo and crystallized from ethanol to afford a mixture of 6-methoxyquinoxalin-2(1H)-one and 7-methoxyquinoxalin-2(1H)-one (5.73 g, 32.50 mmol, 42% yield). MS (LC/MS) R.T.=0.68; [M+H]⁺=177.10.

Step B: 2-Chloro-6-methoxyquinoxaline

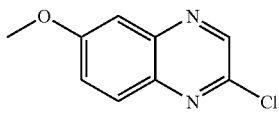

A mixture of 6-methoxyquinoxalin-2(1H)-one and 7-methoxyquinoxalin-2(1H)-one (5.67 g, 32.20 mmol) was refluxed in phosphorus oxychloride (120 mL) for 1 h. The reaction was concentrated and quenched by addition of ice, then basified with sodium carbonate, and extracted with ethyl acetate (3×200 mL). The organic layers were combined and concentrated in vacuo. The crude product was absorbed onto sodium sulfate and purified by column chromatography (0 to 5% ethyl acetate/hexanes) to afford 2-chloro-6-methoxyquinoxaline (2.21 g, 11.36 mmol, 35% yield). ¹H NMR (400 MHz, CDCl₃) δ ppm 8.69 (s, 1 H), 7.88 (d, J=9.32 Hz, 1 H), 7.43 (dd, J=9.32, 2.77 Hz, 1 H), 7.37 (d, J=2.77 Hz, 1 H), 3.95 (s, 3 H).

Step C: N-(2,4-Dimethoxybenzyl)-6-methoxyquinoxalin-2-amine

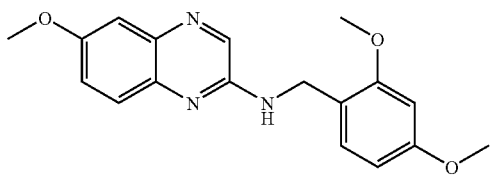

2-Chloro-6-methoxyquinoxaline (0.93 g, 4.77 mmol) and (2,4-dimethoxyphenyl)methanamine (2.2 ml, 14.64 mmol) were microwaved in dimethylsulfoxide (5 mL) for 30 min at 150° C. The reaction was diluted into ethyl acetate (250 mL) and extracted with brine (3×100 mL). The crude product was purified by column chromatography (20 to 80% ethyl acetate/hexanes) to afford N-(2,4-dimethoxybenzyl)-6-methoxyquinoxalin-2-amine (1.46 g, 87% yield). ¹H NMR (400 MHz, CDCl₃) δ ppm 8.13 (1 H, s), 7.59-7.63 (1 H, m), 7.30 (1 H, d, J=8.31 Hz), 7.21-7.24 (2 H, m), 6.47 (1 H, d, J=2.27 Hz), 6.42 (1 H, dd, J=8.31, 2.27 Hz), 5.10 (1 H, t, J=5.92 Hz), 4.61 (2 H, d, J=5.79 Hz), 3.88 (3 H, s), 3.84 (3 H, s), 3.78 (3H, s). MS (LC/MS) R.T.=1.95; [M+H]⁺=326.23.

Step D: 6-Methoxyquinoxalin-2-amine

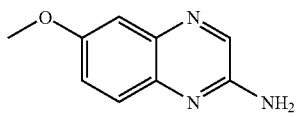

N-(2,4-Dimethoxybenzyl)-6-methoxyquinoxalin-2-amine (2.8 g, 8.61 mmol) was stirred in TFA (10 mL, 130 mmol) and dichloromethane (10 mL) at ambient temperature for 30 min. The solvents were removed in vacuo. Saturated aq. sodium hydrogen carbonate (200 mL) was added to the red residue, which then precipitated a yellow solid. The mixture was extracted extensively with dichloromethane. The organic layer was dried over sodium sulfate, filtered and concentrated in vacuo to afford 6-methoxyquinoxalin-2-amine (1.50 g, 8.56 mmol, 99% yield). ¹H NMR (400 MHz, CDCl₃) δ ppm 8.27 (1 H, s), 7.54-7.58 (1 H, m), 7.25-7.29 (2 H, m), 4.71 (2 H, br. s.), 3.90 (3 H, s). MS (LC/MS) R.T.=0.86; [M+H]⁺=176.23.

Step E: (R)—N-(6-Methoxyquinoxalin-2-yl)-4H-1'-azaspiro[oxazole-5,3'-bicyclo[2.2.2]octan]-2-amine

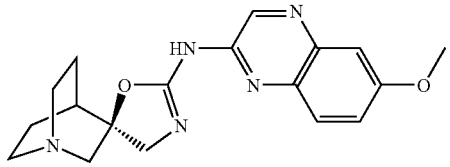

(R)—N-(6-Methoxyquinoxalin-2-yl)-4H-1'-azaspiro[oxazole-5,3'-bicyclo[2.2.2]octan]-2-amine was prepared from 6-methoxyquinoxalin-2-amine by following the general procedures of Example 23, Steps A-B. ¹H NMR (400 MHz, CDCl₃) δ ppm 9.61 (1 H, br. s.), 8.57 (1 H, s), 7.62 (1 H, d, J=9.06 Hz), 7.23-7.32 (2 H, m), 4.01 (1 H, d, J=9.32 Hz), 3.90 (3 H, s), 3.66 (1 H, d, J=9.32 Hz), 3.37 (1 H, dd, J=14.86, 1.51 Hz), 2.68-3.08 (5 H, m), 2.15-2.25 (1 H, m), 2.10-2.14 (1 H, m), 1.67-1.77 (1 H, m), 1.42-1.63 (2 H, m). MS (LC/MS) R.T.=0.81; [M+H]⁺=340.30.

EXAMPLE 39

(R)—N-(5-(Difluoromethoxy)pyrimidin-2-yl)-4H-1'-azaspiro[oxazole-5,3'-bicyclo[2.2.2]octan]-2-amine

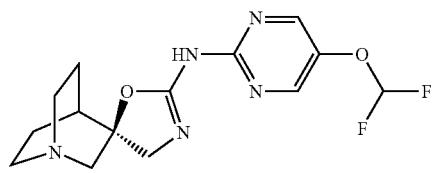

Step A: 2-Chloro-5-(Difluoromethoxy)pyrimidine

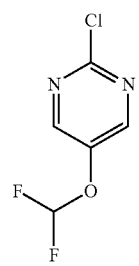

2-Chloropyrimidin-5-ol (1 g, 7.66 mmol) and sodium 2-chloro-2,2-difluoroacetate (3.50 g, 22.98 mmol) in N,N-dimethylformamide (20 mL) and water (0.2 mL) were heated to 90° C. for 24 hours and concentrated in vacuo. The residue was purified by column chromatography (5-30% ethyl acetate/hexanes) to afford 2-chloro-5-(difluoromethoxy)pyrimidine (549 mg, 3.04 mmol, 39.7% yield) as a pale yellow oil. MS (LC/MS) R.T.=1.32; [M+H]⁺=181.14.

Step B: (R)—N-(5-(Difluoromethoxy)pyrimidin-2-yl)-4H-1'-azaspiro[oxazole-5,3'-bicyclo[2.2.2]octan]-2-amine

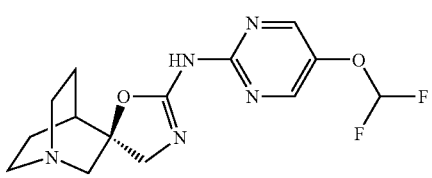

(R)—N-(5-(Difluoromethoxy)pyrimidin-2-yl)-4H-1'-azaspiro[oxazole-5,3'-bicyclo[2.2.2]octan]-2-amine was prepared from 2-chloro-5-(difluoromethoxy)pyrimidine by following the general procedures of Example 23, Steps A-B. ¹H NMR (400 MHz, MeO-d₄) δ ppm 8.46 (2 H, s), 6.85 (1 H, t), 4.02 (1H, d, J=10.07 Hz), 3.73 (1 H, d, J=10.32 Hz), 3.28 (1 H, d, J=1.01 Hz), 3.16 (1 H, d), 2.81-3.05 (4 H, m), 2.08-2.25 (2 H, m), 1.46-1.89 (3 H, m). MS (LC/MS) R.T.=0.53; [M+H]⁺=326.30.

EXAMPLE 40

(R)—N-(4,5-Dimethylpyrimidin-2-yl)-4H-1'-azaspiro[oxazole-5,3'-bicyclo[2.2.2]octan]-2-amine

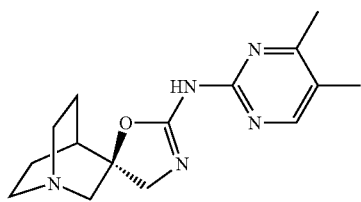

Step A: 4,5-Dimethylpyrimidin-2-amine

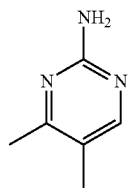

A solution of 4-chloro-5,6-dimethylpyrimidin-2-amine (0.35 g, 2.22 mmol) in 2M ammonia in methanol (100 ml) was flushed with nitrogen and palladium on carbon (0.035 g, 0.33 mmol) was added, flushed with nitrogen and the reaction was hydrogenated at 1 atm, ambient temperature for 18 h. The reaction mixture was flushed with nitrogen and filtered through celite and the celite pad washed with methanol. The filtrate was evaporated to dryness in vacuo to afford 4,5-dimethylpyrimidin-2-amine (0.35 g, 2.56 mmol, 90% yield) which was used without further purification. ¹H NMR (400 MHz, DMSO-d₆) δ ppm 7.89 (1 H, s), 6.19 (2 H, s), 2.18 (3 H, s), 1.99 (3 H, s). MS (LC/MS) R.T.=0.56; [M+H]⁺=124.20.

Step B: (R)—N-(4,5-Dimethylpyrimidin-2-yl)-4H-1'-azaspiro[oxazole-5,3'-bicyclo[2.2.2]octan]-2-amine

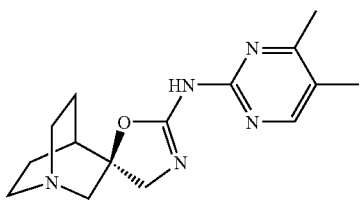

(R)—N-(4,5-Dimethylpyrimidin-2-yl)-4H-1'-azaspiro[oxazole-5,3'-bicyclo[2.2.2]octan]-2-amine was prepared from 4,5-dimethylpyrimidin-2-amine by following the general procedures of Example 23, Steps A-B. ¹H NMR (400 MHz, MeOD-d₄) δ ppm 8.22 (1 H, s), 4.01 (1 H, d, J=10.07 Hz), 3.73 (1 H, d, J=10.32 Hz), 3.40 (1 H, d), 3.25 (1 H, d), 2.91-3.12 (4 H, m), 2.41 (3 H, s), 2.09-2.28 (5 H, m), 1.62-1.97 (3 H, m). MS (LC/MS) R.T.=0.47; [M+H]⁺=288.31.

EXAMPLE 41

(R)—N-(6-Phenylpyrimidin-4-yl)-4H-1'-azaspiro[oxazole-5,3'-bicyclo[2.2.2]octan]-2-amine

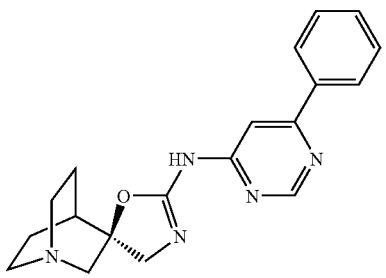

Step A: 6-Phenylpyrimidin-4-amine

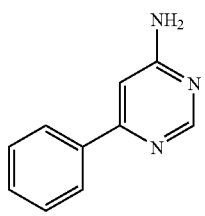

A mixture of 6-chloropyrimidin-4-amine (0.32 g, 2.5 mmol), phenylboronic acid (0.38 g, 3.13 mmol), saturated aqueous sodium carbonate (0.80 g, 7.50 mmol) and bis(triphenylphosphine)palladium(II) chloride (0.035 g, 0.05 mmol) were suspended in a mixture of dimethoxyethane (15 mL)/ ethanol (2 mL)/water (2 mL). The mixture was heated in the microwave at 125° C. for 20 min then concentrated in vacuo. The residue was purified by column chromatography (10-60% ethyl acetate/hexanes) to afford 6-phenylpyrimidin-4-amine (167 mg, 0.98 mmol, 39% yield) as an off-white solid. MS (LC/MS) R.T.=0.99; [M+H]$^+$=172.23.

Step B: (R)—N-(6-Phenylpyrimidin-4-yl)-4H-1'-azaspiro[oxazole-5,3'-bicyclo[2.2.2]octan]-2-amine

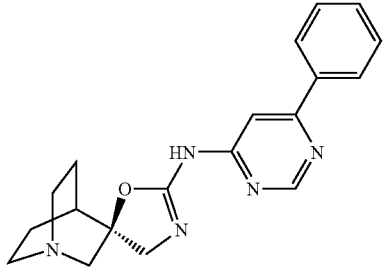

(R)—N-(6-Phenylpyrimidin-4-yl)-4H-1'-azaspiro[oxazole-5,3'-bicyclo[2.2.2]octan]-2-amine was prepared from 6-phenylpyrimidin-4-amine by following the general procedures of Example 23, Steps A-B. $^1$H NMR (400 MHz, MeOD-d$_4$) δ ppm 9.54 (1 H, d, J=1.01 Hz), 8.75-8.86 (2 H, m), 8.18-8.28 (3 H, m), 8.00 (1 H, br. s.), 4.70 (1 H, d, J=10.32 Hz), 4.43 (1 H, d, J=10.58 Hz), 3.72-3.88 (2H, m), 3.41-3.63 (4 H, m), 2.63-2.87 (2 H, m), 2.18-2.48 (3 H, m). MS (LC/MS) R.T.=1.36; [M+H]$^+$=336.24.

EXAMPLE 42

(R)—N-(6-(4-Methoxyphenyl)pyrimidin-4-yl)-4H-1'-azaspiro[oxazole-5,3-bicyclo[2.2.2]octan]-2-amine

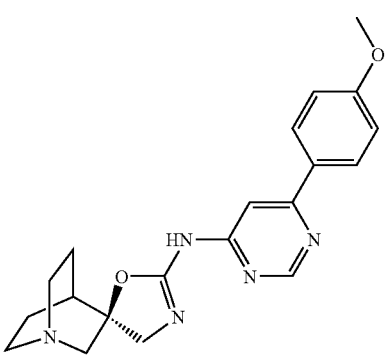

(R)—N-(6-(4-Methoxyphenyl)pyrimidin-4-yl)-4H-1'-azaspiro[oxazole-5,3-bicyclo[2.2.2]octan]-2-amine was prepared from 6-chloropyrimidin-4-amine by following the general procedures of Example 41, Steps A-B. $^1$H NMR (400 MHz, MeOD-d$_4$) δ ppm 8.72 (1 H, d, J=1.26 Hz), 7.90-8.00 (2 H, m), 7.16 (1 H, br. s.), 6.96-7.05 (2 H, m), 4.04 (1 H, d, J=10.07 Hz), 3.84 (3 H, s), 3.73 (1 H, d, J=10.07 Hz), 3.22 (1 H, d), 3.09 (1 H, d), 2.73-2.98 (4 H, m), 2.02-2.21 (2 H, m), 1.51-1.85 (3 H, m). MS (LC/MS) R.T.=1.44; [M+H]$^+$=366.28.

EXAMPLE 43

(R)—N-(6-(6-Methoxypyridin-3-yl)pyrimidin-4-yl)-4H-1'-azaspiro[oxazole-5,3-bicyclo[2.2.2]octan]-2-amine

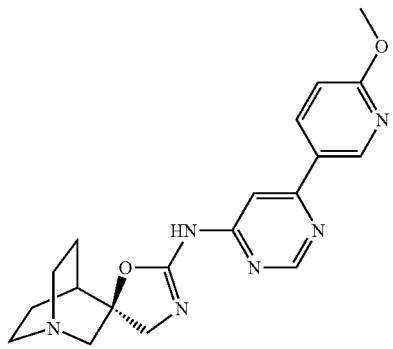

(R)—N-(6-(6-Methoxypyridin-3-yl)pyrimidin-4-yl)-4H-1'-azaspiro[oxazole-5,3'-bicyclo[2.2.2]octan]-2-amine was prepared from 6-chloropyrimidin-4-amine by following the general procedures of Example 41, Steps A-B. $^1$H NMR (400 MHz, MeOD-d$_4$) δ ppm 8.79 (2 H, dd, J=19.01, 1.89 Hz), 8.27 (1 H, dd, J=8.56, 2.52 Hz), 7.18 (1 H, br. s.), 6.89 (1 H, d, J=8.81 Hz), 4.05 (1 H, d, J=10.32 Hz), 3.96 (3 H, s), 3.74 (1 H, d, J=10.32 Hz), 3.23 (1 H, d), 3.10 (1 H, d), 2.73-2.99 (4 H, m), 2.02-2.21 (2 H, m), 1.53-1.84 (3 H, m). MS (LC/MS) R.T.=1.34; [M+H]$^+$=367.25.

EXAMPLE 44

(R)—N-(6-(Naphthalen-2-yl)pyrimidin-4-yl)-4H-1'-azaspiro[oxazole-5,3'-bicyclo[2.2.2]octan]-2-amine

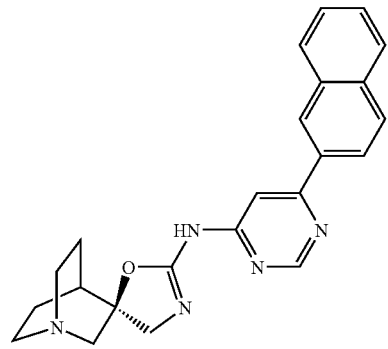

(R)—N-(6-(Naphthalen-2-yl)pyrimidin-4-yl)-4H-1'-azaspiro[oxazole-5,3'-bicyclo[2.2.2]octan]-2-amine was prepared from 6-chloropyrimidin-4-amine by following the general procedures of Example 41, Steps A-B. $^1$H NMR (400 MHz, MeOD-d$_4$) δ ppm 8.83 (1 H, s), 8.56 (1 H, s), 7.83-8.13 (4 H, m), 7.49-7.58 (2 H, m), 7.37 (1 H, br. s.), 4.06 (1 H, d, J=10.32 Hz), 3.76 (1 H, d, J=10.32 Hz), 3.23 (1H, s), 3.12 (1 H, d), 2.75-3.00 (4 H, m), 2.02-2.24 (2 H, m), 1.56-1.84 (3 H, m). MS (LC/MS) R.T.=1.93; [M+H]$^+$=386.31.

The compounds in Table 2 were synthesized according to the method of Example 1 using the appropriate commercially available isothiocyanate or amine. Amide-containing intermediates were obtained by the procedures described in Example 3.

TABLE 2

| Example Number | R₁ | LCMS RT (min) | LCMS Ion [M + H]⁺ | ¹HNMR |
|---|---|---|---|---|
| 45 | thiazole-phenyl | 1.48 | 341.3 | ¹H NMR (500 MHz, DMSO-d₆) δ ppm 8.60 (1H, br. s.), 7.94 (2H, d, J = 7.63 Hz), 7.43 (1H, s), 7.39 (2H, t, J = 7.78 Hz), 7.28 (1H, t, J = 7.32 Hz), 3.86 (1H, d, J = 9.77 Hz), 3.60 (1H, d, J = 9.77 Hz), 2.98-3.06 (2H, m), 2.71-2.85 (2H, m), 2.66 (2H, t, J = 7.78 Hz), 2.05 (1H, br. s.), 1.91 (1H, br. s.), 1.53-1.64 (2H, m), 1.48 (1H, td, J = 9.99, 7.78 Hz) |
| 46 | morpholino-benzothiazole | 1.41 | 400.4 | ¹H NMR (500 MHz, DMSO-d₆) δ ppm 8.86 (1H, br. s.), 7.47 (1H, d, J = 8.85 Hz), 7.33 (1H, d, J = 2.44 Hz), 7.01 (1H, dd, J = 8.85, 2.75 Hz), 3.87 (1H, d, J = 10.07 Hz), 3.71-3.77 (4H, m), 3.61 (1H, d, J = 9.77 Hz), 3.06-3.12 (4H, m), 3.01 (2H, s), 2.72-2.86 (2H, m), 2.66 (2H, t, J = 7.63 Hz), 2.05 (1H, br. s.), 1.91 (1H, br. s.), 1.53-1.64 (2H, m), 1.43-1.52 (1H, m) |
| 47 | F-benzothiazole | 1.31 | 333.3 | ¹H NMR (500 MHz, DMSO-d₆) δ ppm 9.03 (1H, br. s.), 7.80 (1H, dd, J = 8.70, 5.65 Hz), 7.37 (1H, dd, J = 10.38, 2.44 Hz), 7.04 (1H, td, J = 9.08, 2.59 Hz), 3.89 (1H, d, J = 10.07 Hz), 3.64 (1H, d, J = 10.07 Hz), 3.03 (2H, d, J = 2.75 Hz), 2.74-2.85 (2H, m), 2.62-2.70 (2H, m), 2.07 (1H, d, J = 2.44 Hz), 1.90 (1H, d, J = 8.85 Hz), 1.54-1.64 (2H, m), 1.43-1.53 (1H, m) |
| 48 | CF₃-benzothiazole | 2.07 | 383.3 | ¹H NMR (500 MHz, DMSO-d₆) δ ppm 8.00 (1H, s), 7.41-7.54 (2H, m), 3.89 (1H, d, J = 11.29 Hz), 3.57 (1H, d, J = 11.60 Hz), 2.96-3.03 (1H, m), 2.88-2.93 (1H, m), 2.73-2.81 (2H, m), 2.64 (2H, dd, J = 8.85, 5.19 Hz), 1.93 (2H, br. s.), 1.56 (2H, br. s.), 1.38-1.50 (1H, m) |
| 49 | OCF₃-benzothiazole | 2.15 | 399.4 | ¹H NMR (500 MHz, DMSO-d₆) δ ppm 9.03 (1H, br. s.), 7.91 (1H, br. s.), 7.65 (1H, d, J = 8.85 Hz), 7.30 (1H, d, J = 7.63 Hz), 3.89 (1H, d, J = 10.07 Hz), 3.64 (10H, d, J = 10.07 Hz), 2.97-3.09 (2H, m), 2.80 (2H, d, J = 8.55 Hz), 2.66 (2H, t, J = 7.48 Hz), 2.08 (1H, br. s.), 1.93 (1H, br. s.), 1.54-1.66 (2H, m), 1.44-1.54 (1H, m) |

TABLE 2-continued

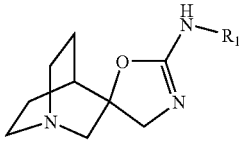

| Example Number | R₁ | LCMS RT (min) | LCMS Ion [M + H]⁺ | ¹HNMR |
|---|---|---|---|---|
| 50 | 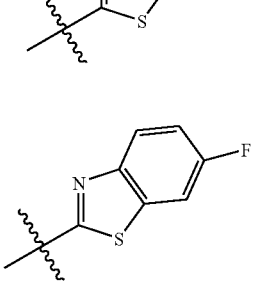 | 1.89 | 333.1 | ¹H NMR (500 MHz, MeOD) δ ppm 7.51-7.58 (1H, m), 7.17-7.25 (1H, m), 7.08-7.16 (1H, m), 4.04-4.13 (1H, m), 3.72-3.82 (1H, m), 3.30 (1H, br. s.), 3.17 (1H, d, J = 14.95 Hz), 3.01 (2H, t, J = 7.48 Hz), 2.80-2.92 (2H, m), 2.12-2.27 (2H, m), 1.66-1.88 (3H, m) |
| 51 | 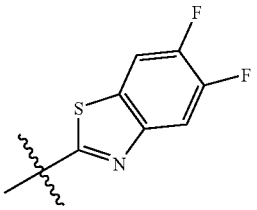 | 1.24 | 333.4 | ¹H NMR (500 MHz, DMSO-d₆) δ ppm 8.95 (1H, br. s.), 7.66-7.77 (1H, m), 7.52-7.63 (1H, m), 7.08-7.24 (1H, m), 3.88 (1H, d, J = 9.77 Hz), 3.63 (1H, d, J = 9.77 Hz), 3.03 (2H, br. s.), 2.78 (2H, br. s.), 2.66 (2H, t, J = 7.17 Hz), 2.06 (1H, br. s.), 1.91 (1H, br. s.), 1.39-1.67 (3H, m) |
| 52 | 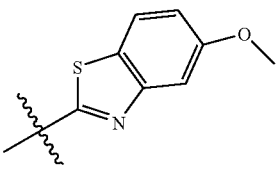 | 2.05 | 351.2 | ¹H NMR (500 MHz, DMSO-d₆) δ ppm 9.01 (1H, br. s.), 7.88-8.00 (1H, m), 7.53-7.64 (1H, m), 3.88 (1H, d, J = 10.07 Hz), 3.63 (1H, d, J = 10.07 Hz), 2.98-3.08 (2H, m), 2.72-2.87 (2H, m), 2.66 (2H, t, J = 7.17 Hz), 2.07 (1H, br. s.), 1.92 (1H, br. s.), 1.42-1.65 (3H, m) |
| 53 | 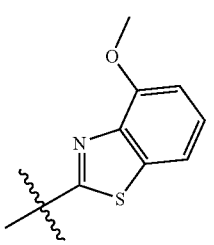 | 1.80 | 345.3 | ¹H NMR (500 MHz, DMSO-d₆) δ ppm 9.03 (s, 1H), 7.65 (d, J = 8.55 Hz, 1H), 7.19 (d, J = 2.44 Hz, 1H), 6.82 (dd, J = 8.70, 2.59 Hz, 1H), 3.90 (d, J = 10.07 Hz, 1H), 3.79 (s, 3H), 3.64 (d, J = 10.07 Hz, 1H), 3.04 (d, J = 2.44 Hz, 2H), 2.75-2.84 (m, 2H), 2.67 (t, J = 7.78 Hz, 2H), 2.07 (s, 1H), 1.92 (s, 1H), 1.55-1.63 (m, 2H), 1.49 (dd, J = 9.77, 2.75 Hz, 1H) |
| 54 | | 1.23 | 345.2 | ¹H NMR (500 MHz, DMSO-d₆) δ ppm 8.83 (s, 1H), 7.37 (d, J = 7.94 Hz, 1H), 7.14 (t, J = 7.93 Hz, 1H), 6.92 (d, J = 7.93 Hz, 1H), 3.89-3.95 (m, 4H), 3.66 (d, J = 10.07 Hz, 1H), 3.00-3.08 (m, 2H), 2.76-2.85 (m, 2H), 2.67 (t, J = 7.78 Hz, 2H), 2.08 (s, 1H), 1.93 (d, J = 3.66 Hz, 1H), 1.60 (ddd, J = 15.26, 6.87, 3.20 Hz, 2H), 1.50 (ddd, J = 7.48, 5.19, 2.59 Hz, 1H) |

TABLE 2-continued

| Example Number | R₁ | LCMS RT (min) | LCMS Ion [M + H]⁺ | ¹HNMR |
|---|---|---|---|---|
| 55 | 5,6-dimethoxy-benzothiazol-2-yl | 1.72 | 375.2 | ¹H NMR (500 MHz, DMSO-d₆) δ ppm 8.89 (s, 1H), 7.40 (s, 1H), 7.22 (s, 1H), 3.87 (d, J = 10.07 Hz, 1H), 3.79 (d, J = 8.55 Hz, 6H), 3.62 (d, J = 10.07 Hz, 1H), 2.99-3.07 (m, 2H), 2.75-2.84 (m, 2H), 2.67 (t, J = 7.63 Hz, 2H), 2.06 (s, 1H), 1.93 (s, 1H), 1.56-1.64 (m, 2H), 1.46-1.55 (m, 1H) |
| 56 | 5-phenyl-1,3,4-thiadiazol-2-yl | 2.14 | 342.1 | ¹H NMR (500 MHz, DMSO-d₆) δ ppm 8.75 (s, 1H), 7.84 (dd, J = 7.93, 1.53 Hz, 3H), 7.46-7.53 (m, 5H), 3.85 (d, J = 9.77 Hz, 2H), 3.60 (d, J = 10.07 Hz, 2H), 3.01-3.09 (m, 3H), 2.84 (t, J = 7.78 Hz, 3H), 2.67 (t, J = 7.78 Hz, 3H), 2.09 (s, 2H), 1.91-1.99 (m, 2H), 1.53-1.62 (m, 3H) |
| 57 | 6-(N,N-dimethylcarbamoyl)-benzothiazol-2-yl | 1.04 | 386.2 | ¹H NMR (400 MHz, DMSO-d₆) δ ppm 9.05 (1H, br. s.), 7.86 (1H, d, J = 1.51 Hz), 7.60 (1H, d, J = 8.06 Hz), 7.36 (1H, dd, J = 8.31, 1.76 Hz), 3.90 (1H, d, J = 10.07 Hz), 3.65 (1H, d, J = 10.07 Hz), 3.03 (2H, s), 2.97 (6H, s), 2.72-2.87 (2H, m), 2.66 (2H, t, J = 7.68 Hz), 2.07 (1H, br. s.), 1.92 (1H, br. s.), 1.55-1.64 (2H, m), 1.44-1.54 (1H, m) |
| 58 | 6-(piperidin-1-ylcarbonyl)-benzothiazol-2-yl | 1.57 | 426.2 | ¹H NMR (400 MHz, DMSO-d₆) δ ppm 9.06 (1H, br. s.), 7.83 (1H, d, J = 1.51 Hz), 7.61 (1H, d, J = 8.31 Hz), 7.32 (1H, dd, J = 8.31, 1.76 Hz), 3.90 (1H, d, J = 10.07 Hz), 3.65 (1H, d, J = 10.07 Hz), 3.37-3.57 (4H, m), 3.04 (2H, d, J = 1.76 Hz), 2.73-2.86 (2H, m), 2.66 (2H, t, J = 7.68 Hz), 2.07 (1H, d, J = 2.52 Hz), 1.92 (1H, dd, J = 8.18, 5.67 Hz), 1.43-1.67 (9H, m) |
| 59 | 5-(4-fluorophenyl)-1,3,4-thiadiazol-2-yl | 2.17 | 360.1 | ¹H NMR (500 MHz, DMSO-D6) δ ppm 8.74 (s, 1H), 7.86-7.92 (m, 2H), 7.31-7.37 (m, 2H), 3.85 (d, J = 9.77 Hz, 1H), 3.60 (d, J = 9.77 Hz, 1H), 3.00-3.09 (m, 2H), 2.84 (t, J = 7.48 Hz, 2H), 2.67 (t, J = 7.32 Hz, 2H), 2.09 (d, J = 1.83 Hz, 1H), 1.89-1.98 (m, 1H), 1.55-1.61 (m, 2H), 1.51-1.54 (m, J = 11.29 Hz, 1H) |

TABLE 2-continued

| Example Number | R₁ | LCMS RT (min) | LCMS Ion [M + H]⁺ | ¹HNMR |
|---|---|---|---|---|
| 60 | (5-(furan-2-yl)-1,3,4-thiadiazol-2-yl) | 1.67 | 332.2 | ¹H NMR (500 MHz, DMSO-D6) δ ppm 7.87 (s, 1H), 7.01 (d, J = 3.05 Hz, 1H), 6.68 (dd, J = 3.51, 1.68 Hz, 1H), 3.84 (d, J = 10.38 Hz, 1H), 3.58 (d, J = 10.07 Hz, 1H), 3.03 (d, J = 11.29 Hz, 2H), 2.78-2.86 (m, 2H), 2.66 (t, J = 7.48 Hz, 2H), 2.06 (s, 1H), 1.87-1.96 (m, 1H), 1.55-1.61 (m, 2H), 1.51-1.54 (m, 1H) |
| 61 | 6-bromobenzo[d]thiazol-2-yl | 1.83 | 393.0 | ¹H NMR (400 MHz, DMSO-d₆) δ ppm 9.02 (1H, br. s.), 8.04 (1H, d, J = 2.01 Hz), 7.49-7.53 (1H, m), 7.43-7.47 (1H, m), 3.88 (1H, d, J = 10.07 Hz), 3.63 (1H, d, J = 10.07 Hz), 3.02 (2H, s), 2.74-2.84 (2H, m), 2.65 (2H, t, J = 7.68 Hz), 2.06 (1H, d, J = 2.52 Hz), 1.89 (1H, br. s.), 1.42-1.64 (3H, m) |
| 62 | 6-(methylsulfonyl)benzo[d]thiazol-2-yl | 1.16 | 391.1 | ¹H NMR (400 MHz, DMSO-d₆) δ ppm 9.21 (1H, br. s.), 8.40 (1H, d, J = 1.51 Hz), 7.80-7.85 (1H, m), 7.72-7.77 (1H, m), 3.92 (1H, d, J = 10.32 Hz), 3.67 (1H, d, J = 10.07 Hz), 3.21 (3H, s), 3.05 (2H, d, J = 4.03 Hz), 2.82 (2H, d, J = 6.80 Hz), 2.67 (2H, t, J = 7.43 Hz), 2.10 (1H, br. s.), 1.94 (1H, d, J = 3.27 Hz), 1.45-1.66 (3H, m) |
| 63 | benzo[d]thiazol-5-yl | 1.35 | 329.1 | ¹H NMR (500 MHz, DMSO-D6) δ ppm 8.54 (s, 1H), 7.32 (s, 1H), 3.79 (d, J = 10.07 Hz, 1H), 3.54 (d, J = 10.07 Hz, 1H), 2.98-3.05 (m, 2H), 2.76-2.85 (m, 2H), 2.66 (t, J = 7.63 Hz, 2H), 2.05 (s, 1H), 1.87-1.95 (m, 1H), 1.41-1.68 (m, 3H) |
| 64 | 5-bromothiazol-2-yl | 1.02 | 349.9 | ¹H NMR (500 MHz, DMSO-d₆) δ ppm 8.54 (s, 1H), 7.32 (s, 1H), 3.67 (dd, J = 126.04, 10.07 Hz, 2H), 2.92-3.09 (m, 2H), 2.72-2.91 (m, 2H), 2.60-2.73 (m, J = 7.63, 7.63 Hz, 2H), 2.00-2.12 (m, 1H), 1.81-1.99 (m, 1H), 1.35-1.69 (m, 3H) |
| 65 | 6-chloro-5-methoxybenzo[d]thiazol-2-yl | 2.14 | 380 | ¹H NMR (500 MHz, DMSO-d₆) δ ppm 8.93 (s, 1H), 7.54-7.76 (m, J = 10.53, 3.81 Hz, 2H), 3.79-4.04 (m, 1H), 3.56-3.72 (m, J = 9.92, 3.20 Hz, 1H), 3.26-3.45 (m, 2H), 2.98-3.12 (m, 2H), 2.75-2.90 (m, 2H), 2.61-2.74 (m, J = 1.22 Hz, 2H), 2.09 (s, 1H), 1.87-2.04 (m, 1H), 1.42-1.76 (m, 3H) |

TABLE 2-continued

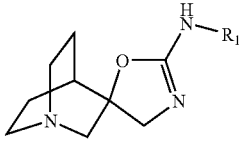

| Example Number | R₁ | LCMS RT (min) | LCMS Ion [M + H]⁺ | ¹HNMR |
|---|---|---|---|---|
| 66 | 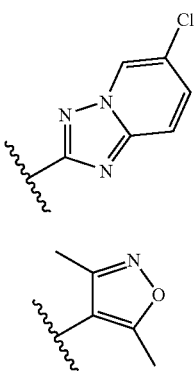 | 1.26 | 333.1 | ¹H NMR (500 MHz, DMSO-d₆) δ ppm 9.04 (1H, d, J = 1.22 Hz), 8.44 (1H, br. s.), 7.52-7.69 (2H, m), 3.77-3.82 (1H, m), 3.68 (1H, d, J = 10.07 Hz), 3.05-3.12 (2H, m), 2.94-3.04 (2H, m), 2.80-2.91 (2H, m), 2.19 (1H, d, J = 1.83 Hz), 2.01 (1H, br. s.), 1.67-1.85 (3H, m) |
| 67 | 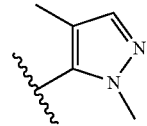 | 0.28 | 277.1 | ¹H NMR (500 MHz, DMSO-d₆) δ ppm 6.72-7.61 (m, 1H), 3.49-3.70 (m, 1H), 3.31-3.46 (m, 1H), 2.86-3.06 (m, J = 9.46 Hz, 2H), 2.56-2.84 (m, 4H), 2.10-2.31 (m, 3H), 1.91-2.10 (m, 4H), 1.70 (s, 1H), 1.49-1.61 (m, 2H), 1.36-1.49 (m, 1H) |
| 68 | 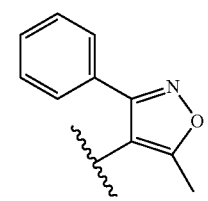 | 0.44 | 276.2 | ¹H NMR (500 MHz, DMSO-d₆) δ ppm 7.55 (s, 1H), 5.63 (s, 1H), 3.57-3.74 (m, J = 8.55 Hz, 1H), 3.48 (s, 3H), 2.96 (s, 2H), 2.72-2.88 (m, 2H), 2.65 (s, 2H), 1.93-2.17 (m, 4H), 1.86 (s, 1H), 1.57 (s, 3H) |
| 69 | 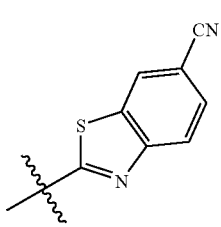 | 1.35 | 339.1 | ¹H NMR (500 MHz, DMSO-d6) δ ppm 7.87 (d, J = 6.71 Hz, 1H), 7.80 (d, J = 7.02 Hz, 2H), 7.42-7.48 (m, 4H), 3.49-3.57 (m, 1H), 3.25-3.33 (m, 4H), 2.77 (t, J = 15.41 Hz, 2H), 2.59-2.68 (m, 1H), 2.49-2.57 (m, 15H), 2.24-2.31 (m, 2H), 2.21 (s, 1H), 1.94 (s, 1H), 1.47 (s, 2H) |
| 70 | 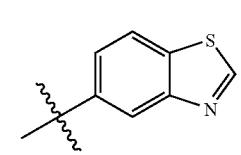 | 0.73 | 340.1 | ¹H NMR (300 MHz, DMSO-d₆) δ ppm 9.20 (1H, br. s.), 8.29-8.42 (1H, m), 7.63-7.76 (2H, m), 3.91 (1H, d, J = 10.25 Hz), 3.66 (1H, d, J = 10.25 Hz), 3.05 (2H, s), 2.74-2.90 (2H, m), 2.66 (2H, t, J = 7.68 Hz), 2.09 (1H, br. s.), 1.92 (1H, d, J = 4.03 Hz), 1.42-1.66 (3H, m) |
| 71 | | 1.00 | 315.1 | ¹H NMR (400 MHz, CDCl₃) δ ppm 8.92 (1H, s), 8.00 (1H, br. s.), 7.78 (1H, d, J = 8.56 Hz), 7.42 (1H, d, J = 8.06 Hz), 3.92 (1H, d, J = 11.08 Hz), 3.55 (1H, d, J = 10.83 Hz), 3.23 (1H, d, J = 14.86 Hz), 2.83-2.90 (2H, m), 2.65-2.83 (2H, m), 1.89-2.17 (3H, m), 1.41-1.75 (3H, m) |

TABLE 2-continued

| Example Number | R₁ | LCMS RT (min) | LCMS Ion [M + H]⁺ | ¹HNMR |
|---|---|---|---|---|
| 72 | benzothiazol-6-yl | 0.75 | 315.1 | ¹H NMR (400 MHz, CDCl₃) δ ppm 8.82 (1H, s), 8.22 (1H, s), 7.98 (1H, d, J = 8.56 Hz), 7.21-7.25 (1H, m), 6.37 (1H, br. s.), 3.99 (1H, d, J = 11.58 Hz), 3.61 (1H, d, J = 11.58 Hz), 3.23 (1H, d, J = 14.86 Hz), 2.89 (2H, t, J = 7.68 Hz), 2.69-2.84 (2H, m), 1.91-2.09 (2H, m), 1.45-1.73 (4H, m) |
| 73 | quinolin-3-yl | 0.85 | 309.2 | ¹H NMR (400 MHz, CDCl₃) δ ppm 8.70 (1H, d, J = 1.76 Hz), 8.09 (1H, br. s.), 8.00 (1H, d, J = 8.31 Hz), 7.43-7.58 (2H, m), 3.90 (1H, d, J = 10.58 Hz), 3.54 (1H, d, J = 10.32 Hz), 3.26 (1H, d, J = 14.60 Hz), 2.65-3.06 (5H, m), 2.13 (1H, br. s.), 2.00 (1H, br. s.), 1.34-1.79 (5H, m) |
| 74 | 6-methyl-[1,2,4]triazolo[1,5-a]pyridin-2-yl | 0.65 | 313.2 | ¹H NMR (500 MHz, MeOD) δ ppm 8.55 (1H, s), 7.66-7.70 (1H, m), 7.59-7.63 (1H, m), 4.25 (1H, d, J = 10.99 Hz), 4.04 (1H, d, J = 10.68 Hz), 3.91 (1H, d, J = 14.95 Hz), 3.76 (1H, dd, J = 14.95, 2.44 Hz), 3.45-3.53 (1H, m), 3.29-3.40 (3H, m), 2.61 (1H, d, J = 2.14 Hz), 2.40 (3H, s), 2.31 (1H, tt, J = 10.26, 3.47 Hz), 2.06-2.16 (1H, m, J = 14.23, 9.35, 4.54, 4.54 Hz), 1.92-2.06 (2H, m) |
| 75 | quinoxalin-6-yl | 1.24 | 310.1 | ¹H NMR (400 MHz, CDCl₃) δ ppm 8.73 (1H, d, J = 1.76 Hz), 8.66 (1H, d, J = 2.01 Hz), 7.96 (1H, d, J = 9.07 Hz), 7.90 (1H, br. s.), 7.68 (1H, br. s.), 7.50 (1H, br. s.), 3.93 (1H, d, J = 10.32 Hz), 3.56 (1H, d, J = 9.32 Hz), 3.29 (1H, d, J = 14.86 Hz), 2.97 (1H, d, J = 14.86 Hz), 2.88-2.94 (2H, m), 2.69-2.87 (2H, m), 2.12 (1H, br. s.), 2.06 (1H, br. s.), 1.64-1.73 (1H, m), 1.46-1.64 (2H, m) |
| 76 | 6-methoxy-1H-benzimidazol-2-yl | 1.58 | 328.2 | ¹H NMR (500 MHz, DMSO-d₆) δ ppm 11.30 (s, 1H), 9.16 (s, 1H), 7.04-7.43 (m, 1H), 6.70-7.03 (m, 1H), 6.54-6.69 (m, 1H), 3.89 (d, J = 9.77 Hz, 1H), 3.53-3.81 (m, 4H), 3.01 (s, 2H), 2.58-2.91 (m, 4H), 2.03 (s, 1H), 1.78-1.96 (m, 1H), 1.32-1.73 (m, 3H) |

TABLE 2-continued

| Example Number | R₁ | LCMS RT (min) | LCMS Ion [M + H]⁺ | ¹HNMR |
|---|---|---|---|---|
| 77 | (6-fluoro-1H-benzimidazol-2-yl) | 1.40 | 316.1 | ¹H NMR (500 MHz, DMSO-D6) δ ppm 11.53 (s, 1H), 9.12 (s, 1H), 6.94-7.46 (m, 2H), 6.83 (s, 2H), 3.90 (d, J = 9.77 Hz, 1H), 3.64 (d, J = 9.77 Hz, 1H), 2.90-3.09 (m, 2H), 2.61-2.87 (m, 4H), 1.95-2.10 (m, 1H), 1.88 (d, J = 3.05 Hz, 1H), 1.33-1.70 (m, 3H) |
| 78 | (1H-indazol-6-yl) | 0.35 | 298.1 | ¹H NMR (400 MHz, CDCl₃) δ ppm 7.94 (1H, s), 7.80 (1H, br. s.), 7.26-7.36 (1H, m), 7.17-7.25 (1H, m), 3.97 (1H, d, J = 11.33 Hz), 3.59 (1H, d, J = 11.58 Hz), 3.23 (1H, d, J = 14.60 Hz), 2.65-3.01 (5H, m), 1.86-2.16 (2H, m), 1.35-1.73 (3H, m) |
| 79 | (2-(pyridin-4-yl)benzoxazol-6-yl) | 1.10 | 376.1 | ¹H NMR (400 MHz, CDCl₃) δ ppm 8.78 (2H, d, J = 5.79 Hz), 8.03 (2H, d, J = 6.04 Hz), 7.73 (1H, br. s.), 7.48 (1H, d, J = 8.56 Hz), 7.36 (1H, br. s.), 3.92 (1H, d, J = 8.81 Hz), 3.55 (1H, d, J = 9.06 Hz), 3.24 (1H, d, J = 14.10 Hz), 2.57-3.06 (5H, m), 1.86-2.20 (2H, m), 1.30-1.80 (3H, m) |
| 80 | (2-(3-fluorophenyl)benzoxazol-6-yl) | 2.36 | 393.1 | ¹H NMR (400 MHz, CDCl₃) δ ppm 8.00 (1H, d, J = 7.81 Hz), 7.83-7.97 (1H, m), 7.68 (1H, br. s.), 7.39-7.55 (2H, m), 7.35 (1H, br. s.), 7.20 (2H, td, J = 8.31, 2.27 Hz), 3.93 (1H, d, J = 10.83 Hz), 3.56 (1H, d, J = 10.58 Hz), 3.24 (1H, d, J = 15.11 Hz), 2.62-3.05 (5H, m), 1.88-2.22 (2H, m), 1.34-1.79 (3H, m) |
| 81 | (2-(4-ethylphenyl)benzoxazol-6-yl) | 2.81 | 403.1 | ¹H NMR (400 MHz, CDCl₃) δ ppm 8.12 (2H, d, J = 8.06 Hz), 7.64 (1H, br. s.), 7.43 (1H, d, J = 8.56 Hz), 7.32 (3H, d, J = 8.06 Hz), 3.94 (1H, d, J = 10.07 Hz), 3.56 (1H, d, J = 9.57 Hz), 3.24 (1H, d, J = 13.60 Hz), 2.57-3.03 (7H, m), 1.88-2.22 (2H, m), 1.39-1.74 (3H, m), 1.27 (3H, t, J = 7.68 Hz) |
| 82 | (2-(4-(dimethylamino)phenyl)benzoxazol-6-yl) | 2.62 | 418.1 | ¹H NMR (400 MHz, CDCl₃) δ ppm 8.06 (2H, d, J = 9.07 Hz), 7.56 (1H, br. s.), 7.30-7.43 (2H, m), 6.74 (2H, d, J = 9.07 Hz), 3.95 (1H, d, J = 11.58 Hz), 3.58 (1H, d, J = 11.83 Hz), 3.24 (1H, d, J = 14.10 Hz), 3.05 (6H, s), 2.61-2.99 (5H, m), 1.88-2.13 (2H, m), 1.35-1.81 (4H, m) |

TABLE 2-continued

| Example Number | R₁ | LCMS RT (min) | LCMS Ion [M + H]⁺ | ¹HNMR |
|---|---|---|---|---|
| 83 | [6-(trifluoromethyl)-[1,2,4]triazolo[1,5-a]pyridin-2-yl] | 1.15 | 367.1 | ¹H NMR (500 MHz, MeOD) δ ppm 9.12 (1H, s), 7.78-7.82 (1H, m), 7.70-7.74 (1H, m), 4.05 (1H, d, J = 9.77 Hz), 3.75 (1H, d, J = 9.77 Hz), 3.29 (1H, d, J = 14.65 Hz), 3.11-3.18 (1H, m), 2.98 (2H, t, J = 7.93 Hz), 2.80-2.91 (2H, m), 2.13-2.22 (2H, m), 1.71-1.87 (2H, m), 1.62-1.71 (1H, m) |
| 84 | [2-(4-fluorophenyl)-1,3-benzoxazol-6-yl] | 1.96 | 393.1 | ¹H NMR (400 MHz, CDCl₃) δ ppm 8.18-8.26 (2H, m), 7.66 (1H, s), 7.44 (1H, d, J = 8.56 Hz), 7.32 (1H, d, J = 8.56 Hz), 7.16-7.23 (2H, m), 3.95 (1H, d, J = 11.33 Hz), 3.57 (1H, d, J = 11.33 Hz), 3.25 (1H, d, J = 14.60 Hz), 2.69-3.04 (6H, m), 2.09 (1H, br. s.), 1.45-1.74 (4H, m) |
| 85 | [quinolin-6-yl] | 1.34 | 309.1 | ¹H NMR (400 MHz, CDCl₃) δ ppm 8.75 (1H, dd, J = 4.15, 1.64 Hz), 8.04 (1H, d, J = 8.06 Hz), 7.98 (2H, d, J = 8.81 Hz), 7.49 (1H, d, J = 8.81 Hz), 7.31 (1H, dd, J = 8.31, 4.28 Hz), 6.71 (1H, br. s.), 4.03 (1H, d, J = 11.83 Hz), 3.65 (1H, d, J = 12.09 Hz), 3.25 (1H, d, J = 14.86 Hz), 2.96 (1H, d, J = 14.86 Hz), 2.89 (2H, t, J = 7.55 Hz), 2.69-2.84 (2H, m), 2.07 (1H, br. s.) 1.98 (1H, br. s.), 1.57-1.73 (2H, m), 1.44-1.55 (1H, m) |
| 86 | [2-oxo-2,3-dihydro-1H-indol-5-yl] | 1.16 | 313.1 | ¹H NMR (400 MHz, CDCl₃) δ ppm 9.78 (1H, br. s.), 7.19 (1H, br. s.), 6.99 (1H, d, J = 6.80 Hz), 6.67 (1H, d, J = 8.31 Hz), 3.87 (1H, d, J = 10.32 Hz), 3.50 (1H, d, J = 11.08 Hz), 3.46 (2H, s), 3.21 (1H, d, J = 14.60 Hz), 2.93 (1H, d, J = 15.11 Hz), 2.87 (2H, t, J = 7.68 Hz), 2.65-2.81 (2H, m), 2.04 (1H, br. s.), 1.96 (1H, br. s.), 1.40-1.75 (3H, m) |
| 87 | [[1,2,4]triazolo[1,5-a]pyridin-2-yl] | 1.13 | 299.2 | ¹H NMR (500 MHz, MeOD) δ ppm 8.57-8.63 (1H, m), 7.55-7.64 (2H, m), 7.06-7.12 (1H, m), 4.04 (1H, dd, J = 9.92, 1.98 Hz), 3.81 (1H, dd, J = 10.07, 2.14 Hz), 3.46-3.57 (1H, m), 3.23 (2H, d, J = 10.68 Hz), 3.09-3.18 (2H, m), 2.82-3.02 (1H, m), 2.41 (1H, br. s.), 2.28-2.37 (1H, m), 1.99-2.07 (1H, m), 1.86-1.97 (2H, m) |

TABLE 2-continued

| Example Number | R₁ | LCMS RT (min) | LCMS Ion [M + H]⁺ | ¹HNMR |
|---|---|---|---|---|
| 88 | pyridin-2-yl-thiazol-2-yl | 1.26 | 342.1 | ¹H NMR (500 MHz, DMSO-d₆) δ ppm 9.20 (s, 1H), 8.64 (s, 1H), 8.45-8.56 (m, J = 4.58, 1.53 Hz, 1H), 8.21-8.38 (m, J = 7.63 Hz, 1H), 7.62 (s, 1H), 7.33-7.50 (m, J = 7.93, 4.88 Hz, 1H), 3.75 (dd, J = 128.64, 9.92 Hz, 2H), 2.95-3.14 (m, 2H), 2.62-2.91 (m, 4H), 2.06 (s, 1H), 1.92 (s, 1H), 1.42-1.70 (m, 3H) |
| 89 | 4,6-dimethylbenzothiazol-2-yl | 2.13 | 343.1 | ¹H NMR (500 MHz, DMSO-d₆) δ ppm 8.81 (s, 1H), 7.39 (s, 1H), 6.97 (s, 1H), 3.78 (dd, J = 130.16, 9.92 Hz, 2H), 2.95-3.15 (m, 2H), 2.74-2.90 (m, 2H), 2.61-2.72 (m, J = 7.78, 7.78 Hz, 2H), 2.47-2.55 (m, J = 3.66, 1.83 Hz, 3H), 2.33 (s, 3H), 2.07 (s, 1H), 1.85-2.01 (m, 1H), 1.41-1.70 (m, 3H) |
| 90 | 6-acetamidobenzothiazol-2-yl | 0.55 | 372.0 | ¹H NMR (300 MHz, DMSO-d₆) δ ppm 9.98 (1H, s), 8.92 (1H, br. s.), 8.11 (1H, d, J = 1.83 Hz), 7.48-7.53 (1H, m), 7.34-7.40 (1H, m), 3.88 (1H, d, J = 10.25 Hz), 3.62 (1H, d, J = 10.25 Hz), 3.02 (2H, s), 2.74-2.83 (2H, m), 2.66 (2H, t, J = 7.50 Hz), 2.04 (4H, s), 1.90 (1H, br. s.), 1.58 (3H, br. s.) |
| 91 | 6-ethylbenzothiazol-2-yl | 1.60 | 343.3 | ¹H NMR (300 MHz, DMSO-d₆) δ ppm 7.61 (1H, s), 7.47-7.53 (1H, m), 7.16 (1H, d, J = 8.05 Hz), 3.84-3.92 (1H, m), 3.62 (1H, d, J = 10.25 Hz), 3.26-3.46 (3H, m), 3.02 (1H, s), 2.79 (1H, d, J = 6.95 Hz), 2.65 (2H, q, J = 7.32 Hz), 2.01-2.20 (1H, m), 1.93 (2H, d, J = 9.88 Hz), 1.40-1.64 (2H, m), 1.15-1.28 (3H, m), 1.00 (1H, d, J = 6.59 Hz) |
| 92 | 5-methylthiazol-2-yl | 0.45 | 279.1 | ¹H NMR (500 MHz, DMSO-D6) δ ppm 8.34-8.83 (m, 1H), 6.96 (s, 1H), 3.79 (d, J = 9.77 Hz, 2H), 3.53 (d, J = 9.77 Hz, 2H), 2.89-3.06 (m, 2H), 2.71-2.86 (m, 2H), 2.60-2.70 (m, J = 7.78, 7.78 Hz, 2H), 2.29 (s, 3H), 2.01 (s, 1H), 1.90 (d, J = 13.43 Hz, 2H), 1.35-1.65 (m, 3H) |

TABLE 2-continued

| Example Number | R₁ | LCMS RT (min) | LCMS Ion [M + H]⁺ | ¹HNMR |
|---|---|---|---|---|
| 93 | thiazole-pyrrolidine carbonyl | 1.79 | 355.1 | ¹H NMR (500 MHz, DMSO-d₆) δ ppm 8.74 (s, 1H), 7.62-7.88 (m, 1H), 3.83 (d, J = 10.07 Hz, 1H), 3.63-3.76 (m, 2H), 3.58 (d, J = 10.07 Hz, 1H), 3.40-3.53 (m, 2H), 2.96-3.10 (m, 2H), 2.73-2.90 (m, 2H), 2.58-2.72 (m, J = 7.63, 7.63 Hz, 2H), 2.06 (s, 1H), 1.75-1.99 (m, 5H), 1.43-1.69 (m, 3H) |
| 94 | 6-methyl-[1,2,4]triazolo[1,5-a]pyridine | 1.53 | 313.1 | ¹H NMR (500 MHz, MeOD) δ ppm 8.63 (1H, d, J = 7.02 Hz), 7.55 (1H, s), 7.19-7.23 (1H, m), 4.27 (1H, d, J = 10.68 Hz), 4.06 (1H, d, J = 10.68 Hz), 3.94 (1H, d, J = 14.95 Hz), 3.76-3.83 (1H, m), 3.54 (1H, t, J = 11.90 Hz), 3.36-3.48 (3H, m), 2.64 (1H, d, J = 1.83 Hz), 2.56 (3H, s), 2.34-2.42 (1H, m, J = 10.15, 10.15, 3.66, 3.51 Hz), 2.17 (1H, dddd, J = 14.19, 9.46, 4.58, 4.43 Hz), 1.97-2.11 (2H, m) |
| 95 | pyrazinyl | 0.63 | 260.2 | ¹H NMR (400 MHz, CDCl₃) δ ppm 9.05 (1H, br. s.), 8.34 (1H, s), 8.04 (1H, dd, J = 2.77, 1.26 Hz), 8.00 (1H, d, J = 2.77 Hz), 3.91 (1H, d, J = 9.32 Hz), 3.57 (1H, d, J = 9.57 Hz), 3.31 (1H, dd, J = 14.98, 1.64 Hz), 2.65-3.02 (5H, m), 2.10-2.20 (1H, m), 2.05-2.09 (1H, m), 1.63-1.75 (1H, m), 1.40-1.60 (2H, m) |
| 96 | 1-methyl-5-phenyl-imidazole | 1.88 | 338.1 | ¹H NMR (500 MHz, DMSO-D6) δ ppm 8.85 (s, 1H), 7.41-7.47 (m, 4H), 7.28-7.35 (m, 1H), 6.85 (s, 1H), 3.83 (d, J = 9.77 Hz, 1H), 3.57 (d, J = 9.77 Hz, 1H), 3.46-3.51 (m, 3H), 3.00 (s, 2H), 2.78 (t, J = 7.78 Hz, 2H), 2.67 (t, J = 7.78 Hz, 2H), 1.98-2.03 (m, 1H), 1.85-1.93 (m, 1H), 1.54-1.63 (m, J = 8.16, 7.82, 7.82, 3.05 Hz, 2H), 1.43-1.51 (m, 1H) |
| 97 | 8-methyl-[1,2,4]triazolo[1,5-a]pyridine | 1.57 | 313.1 | ¹H NMR (500 MHz, MeOD) δ ppm 8.61 (1H, d, J = 6.71 Hz), 7.65 (1H, d, J = 7.32 Hz), 7.25 (1H, t, J = 7.02 Hz), 4.32 (1H, d, J = 10.99 Hz), 4.11 (1H, d, J = 10.68 Hz), 3.98 (1H, dd, J = 14.80, 1.68 Hz), 3.82 (1H, dd, J = 14.95, 2.14 Hz), 3.52-3.61 (1H, m), 3.35-3.47 (3H, m), 2.66-2.71 (1H, m), 2.62 (3H, s), 2.34-2.44 (1H, m), 2.14-2.24 (1H, m), 1.99-2.13 (2H, m) |

TABLE 2-continued

| Example Number | R₁ | LCMS RT (min) | LCMS Ion [M + H]⁺ | ¹HNMR |
|---|---|---|---|---|
| 98 | (4-methyl-2-yl thiazole-5-carboxamide, N,N-dimethyl) | 0.57 | 350.1 | ¹H NMR (500 MHz, DMSO-D6) δ ppm 8.64 (s, 1H), 3.82 (d, J = 10.07 Hz, 1H), 3.57 (d, J = 9.77 Hz, 1H), 3.02 (s, 2H), 2.97 (s, 6H), 2.79 (s, 2H), 2.67 (t, J = 7.63 Hz, 2H), 2.19 (s, 3H), 2.04 (s, 1H), 1.85-1.94 (m, 1H), 1.58 (s, 2H), 1.49 (d, J = 6.71 Hz, 1H) |
| 99 | (4-methoxypyrimidin-2-yl) | 0.87 | 290.1 | ¹H NMR (400 MHz, MeOD) δ ppm 8.20 (1H, d, J = 5.79 Hz), 6.34 (1H, d, J = 5.79 Hz), 3.94-4.04 (1H, m), 3.91 (3H, s), 3.55-3.76 (1H, m), 3.00-3.28 (2H, m), 2.63-2.97 (4H, m), 1.99-2.21 (2H, m), 1.44-1.85 (3H, m) |
| 100 | (6-methoxypyrimidin-4-yl) | 0.91 | 290.1 | ¹H NMR (400 MHz, MeOD) δ ppm 8.39 (1H, s), 6.21 (1H, d, J = 6.04 Hz), 3.98 (1H, d, J = 10.32 Hz), 3.89 (3H, s), 3.67 (1H, d, J = 10.32 Hz), 3.01-3.24 (2H, m), 2.65-2.97 (4H, m), 1.96-2.17 (2H, m), 1.43-1.81 (3H, m) |
| 101 | (pyrimidin-2-yl) | 1.18 | 260.1 | ¹H NMR (400 MHz, MeOD) δ ppm 8.56 (2H, d, J = 4.78 Hz), 6.94-6.99 (1H, m), 3.98-4.04 (1H, m), 3.78 (1H, d, J = 10.32 Hz), 3.45-3.52 (1H, m), 3.35 (1H, s), 3.15-3.22 (2H, m), 3.05-3.12 (2H, m), 2.22-2.38 (2H, m), 1.95-2.03 (1H, m), 1.80-1.92 (2H, m) |
| 102 | (4,7-dimethylbenzothiazol-2-yl) | 2.19 | 343.4 | ¹H NMR (500 MHz, DMSO-d₆) δ ppm 8.87 (1H, br. s.), 7.06 (1H, d, J = 7.63 Hz), 6.91 (1H, d, J = 7.63 Hz), 3.92 (1H, d, J = 10.07 Hz), 3.66 (1H, d, J = 10.07 Hz), 3.03 (2H, s), 2.72-2.85 (2H, m), 2.64-2.70 (2H, m), 2.51 (3H, s), 2.35 (3H, s), 2.07 (1H, br. s.), 1.91 (1H, br. s.), 1.55-1.65 (2H, m), 1.44-1.53 (1H, m) |
| 103 | (4-chloro-6-methylbenzothiazol-2-yl) | 2.48 | 363.3 | ¹H NMR (500 MHz, DMSO-d₆) δ ppm 8.84 (1H, br. s.), 7.71 (1H, d, J = 1.83 Hz), 7.18 (1H, s), 3.90 (1H, d, J = 10.07 Hz), 3.64 (1H, d, J = 10.07 Hz), 3.03 (2H, s), 2.72-2.85 (2H, m), 2.66 (2H, t, J = 7.63 Hz), 2.53 (3H, s), 2.07 (1H, br. s.), 1.88-1.96 (1H, m), 1.55-1.63 (2H, m), 1.44-1.53 (1H, m) |

TABLE 2-continued

| Example Number | R₁ | LCMS RT (min) | LCMS Ion [M + H]⁺ | ¹HNMR |
|---|---|---|---|---|
| 104 | benzothiazole with OCHF₂ substituent | 1.45 | 381.0 | ¹H NMR (500 MHz, DMSO-d₆) δ ppm 8.99 (1H, br. s.), 7.69 (1H, d, J = 2.44 Hz), 7.61 (1H, d, J = 8.55 Hz), 7.01-7.34 (2H, m), 3.89 (1H, d, J = 10.07 Hz), 3.64 (1H, d, J = 10.07 Hz), 3.03 (2H, d, J = 2.44 Hz), 2.72-2.86 (2H, m), 2.66 (2H, t, J = 7.78 Hz), 2.07 (1H, br. s.), 1.88-1.96 (1H, m), 1.55-1.64 (2H, m), 1.45-1.53 (1H, m) |
| 105 | 5-benzylthiazole | 1.83 | 355.1 | ¹H NMR (500 MHz, DMSO-D6) δ ppm 8.57 (s, 1H), 7.31 (t, J = 7.32 Hz, 2H), 7.20-7.26 (m, 3H), 7.08 (s, 1H), 4.01 (s, 2H), 3.78 (d, J = 9.77 Hz, 1H), 3.53 (d, J = 10.07 Hz, 1H), 2.97 (s, 2H), 2.70-2.78 (m, 2H), 2.64 (t, J = 7.78 Hz, 2H), 1.99 (s, 1H), 1.81-1.90 (m, 1H), 1.52-1.60 (m, 2H), 1.41-1.49 (m, J = 6.90, 2.90, 2.67, 2.48 Hz, 1H) |
| 106 | 5-methylpyrazine | 0.71 | 274.2 | ¹H NMR (400 MHz, CDCl₃) δ ppm 8.87 (1H, br. s.), 8.23 (1H, s), 7.88 (1H, s), 3.85 (1H, d, J = 9.32 Hz), 3.51 (1H, d, J = 9.32 Hz), 3.27 (1H, dd, J = 14.98, 1.64 Hz), 2.60-2.97 (5H, m), 2.37 (3H, s), 2.06-2.16 (1H, m, J = 13.25, 9.85, 3.46, 3.46, 3.46 Hz), 1.99-2.05 (1H, m), 1.57-1.70 (1H, m), 1.36-1.54 (2H, m) |
| 107 | 5-bromopyrazine | 0.93 | 338.1 | ¹H NMR (400 MHz, CDCl₃) δ ppm 8.71 (1H, br. s.), 8.14 (1H, d, J = 1.26 Hz), 8.11 (1H, d, J = 1.26 Hz), 3.92 (1H, d, J = 9.32 Hz), 3.58 (1H, d, J = 9.57 Hz), 3.32 (1H, dd, J = 14.98, 1.89 Hz), 2.68-3.03 (5H, m), 2.04-2.19 (2H, m), 1.63-1.75 (1H, m, J = 14.01, 9.85, 4.31, 4.31 Hz), 1.42-1.59 (2H, m) |
| 108 | 4-(4-chlorophenyl)thiazole | 2.34 | 375.0 | ¹H NMR (500 MHz, DMSO-D6) δ ppm 8.58 (s, 1H), 7.98 (d, J = 8.24 Hz, 2H), 7.51 (s, 1H), 7.45 (d, J = 8.54 Hz, 2H), 3.87 (d, J = 10.07 Hz, 1H), 3.62 (d, J = 9.77 Hz, 1H), 3.04 (s, 2H), 2.75-2.87 (m, 2H), 2.68 (t, J = 7.63 Hz, 2H), 2.07 (s, 1H), 1.92 (s, 1H), 1.40-1.68 (m, 3H) |

TABLE 2-continued

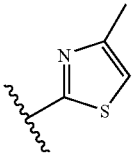

| Example Number | R₁ | LCMS RT (min) | LCMS Ion [M + H]⁺ | ¹HNMR |
|---|---|---|---|---|
| 109 | 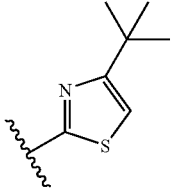 | 0.73 | 279.3 | ¹H NMR (400 MHz, DMSO-D6) δ ppm 8.61 (s, 1H), 6.54 (d, J = 1.01 Hz, 1H), 3.80 (d, J = 10.07 Hz, 1H), 3.54 (d, J = 9.82 Hz, 1H), 2.98 (s, 2H), 2.70-2.81 (m, 2H), 2.65 (t, J = 7.81 Hz, 2H), 2.20 (s, 3H), 1.95-2.05 (m, 1H), 1.88 (s, 1H), 1.50-1.61 (m, 2H), 1.41-1.50 (m, 1H) |
| 110 | 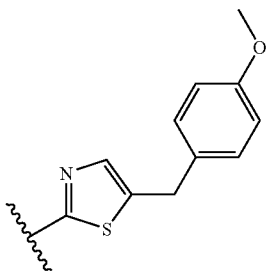 | 1.76 | 321.4 | ¹H NMR (400 MHz, DMSO-D6) δ ppm 8.24-8.82 (m, 1H), 6.51 (s, 1H), 3.83 (d, J = 9.57 Hz, 1H), 3.57 (d, J = 9.32 Hz, 1H), 2.98 (s, 2H), 2.70-2.82 (m, 2H), 2.65 (t, J = 7.68 Hz, 2H), 1.97-2.04 (m, 1H), 1.88 (s, 1H), 1.52-1.61 (m, 2H), 1.46 (dd, J = 9.69, 2.90 Hz, 1H), 1.24 (s, 9H) |
| 111 | 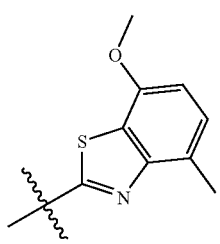 | 1.64 | 312.3 | ¹H NMR (400 MHz, DMSO-$d_6$) δ ppm 8.55 (s, 1H), 7.13 (d, J = 8.56 Hz, 2H), 7.04 (s, 1H), 6.86 (d, J = 8.56 Hz, 2H), 3.92 (s, 2H), 3.66-3.85 (m, 4H), 3.45-3.60 (m, J = 10.07 Hz, 1H), 2.95 (s, 2H), 2.57-2.86 (m, 4H), 1.98 (s, 1 H), 1.84 (s, 1H), 1.31-1.66 (m, 2H) |
| 112 | 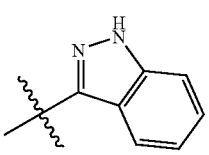 | 1.70 | 359.1 | ¹H NMR (300 MHz, DMSO-$d_6$) δ ppm 8.83 (1H, d, J = 1.83 Hz), 7.08 (1H, d, J = 8.42 Hz), 6.71 (1H, d, J = 8.05 Hz), 3.87-3.94 (1H, m), 3.85 (3H, s), 3.65 (1H, d, J = 9.88 Hz), 3.04 (2H, s), 2.61-2.85 (4H, m), 2.47 (3H, s), 2.08 (1H, d, J = 2.20 Hz), 1.82-1.99 (1H, m), 1.41-1.66 (3H, m) |
| 113 |  | 1.48 | 298.3 | ¹H NMR (500 MHz, DMSO-$d_6$) δ ppm 12.09 (s, 1H), 8.02 (s, 1H), 7.63 (d, J = 7.32 Hz, 1H), 7.33-7.36 (m, 1H), 7.30 (d, J = 5.80 Hz, 1H), 6.99 (t, J = 7.02 Hz, 1H), 3.82 (d, J = 8.24 Hz, 1H), 3.57 (s, 1H), 3.00 (s, 2H), 2.79 (s, 2H), 2.67 (s, 2H), 1.99-2.04 (m, 1H), 1.93 (s, 1H), 1.58 (s, 2H), 1.47 (s, 1H) |

The compounds in Table 3 were synthesized according to the method of Example 21, steps C-D using the appropriate isothiocyanate or amine and racemic 3-(aminomethyl)quinuclidin-3-ol, 2HCl.

TABLE 3

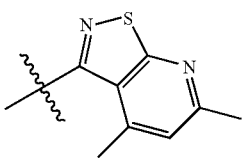

| Example Number | R₁ | LCMS RT (min) | LCMS Ion [M + H]⁺ | ¹H NMR |
|---|---|---|---|---|
| 114 | 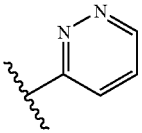 | 2.06 | 344.3 | ¹H NMR (400 MHz, DMSO-d₆) δ ppm 9.02 (1H, s), 7.10 (1H, s), 3.67-3.88 (2H, m), 3.07-3.30 (2H, m), 2.80-3.05 (4H, m), 2.78 (3H, s), 2.55 (3H, s), 2.22 (1H, br. s.), 2.00 (1H, d, J = 12.09 Hz), 1.55-1.88 (3H, m) |
| 115 | 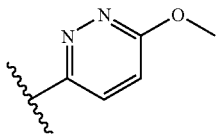 | 1.19 | 260.3 | ¹H NMR (400 MHz, MeOD) δ ppm 8.70 (1H, dd, J = 4.41, 1.39 Hz), 7.51 (1H, dd, J = 8.81, 4.53 Hz), 7.15 (1H, d, J = 7.81 Hz), 4.03 (1H, d, J = 10.07 Hz), 3.72 (1H, d, J = 10.07 Hz), 3.14-3.26 (1H, m), 3.03-3.14 (1H, m), 2.85-2.99 (2H, m), 2.69-2.84 (2H, m), 2.00-2.26 (2H, m), 1.51-1.87 (3H, m) |
| 116 | 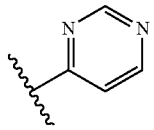 | 0.73 | 290.3 | ¹H NMR (400 MHz, MeOD) δ ppm 6.99-7.12 (2H, m), 3.95-4.02 (4H, m), 3.68 (1H, d, J = 10.07 Hz), 3.20 (1H, dd), 3.08 (1H, dd), 2.84-2.95 (2H, m), 2.69-2.84 (2H, m), 1.99-2.21 (2H, m), 1.47-1.87 (3H, m) |
| 117 | 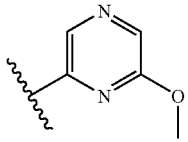 | | | ¹H NMR (400 MHz, MeOD) δ ppm 8.71 (1H, s), 8.33 (1H, d, J = 5.54 Hz), 6.84 (1H, br. s.), 4.04 (1H, d, J = 10.32 Hz), 3.73 (1H, d, J = 10.32 Hz), 3.17-3.25 (1H, m), 3.04-3.13 (1H, m), 2.70-3.00 (4H, m), 2.02-2.18 (2H, m), 1.51-1.81 (3H, m) |
| 118 | 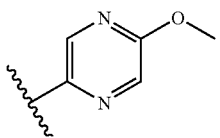 | 0.83 | 290.3 | ¹H NMR (400 MHz, CDCl₃) δ ppm 8.48 (1H, br. s.), 7.96 (1H, br. s.), 7.71 (1H, s), 3.91 (1H, d, J = 9.32 Hz), 3.87 (3H, s), 3.57 (1H, d, J = 9.32 Hz), 3.30 (1H, d, J = 14.86 Hz), 2.62-3.03 (5H, m), 2.09-2.21 (1H, m), 2.08 (1H, br. s.), 1.61-1.78 (1H, m), 1.39-1.60 (2H, m) |
| 119 | | 0.84 | 290.3 | ¹H NMR (400 MHz, CDCl₃) δ ppm 8.56 (1H, br. s.), 7.96 (1H, d, J = 1.26 Hz), 7.79 (1H, d, J = 1.51 Hz), 3.89 (3H, s), 3.85 (1H, s), 3.53 (1H, d, J = 9.06 Hz), 3.31 (1H, d, J = 14.86 Hz), 2.65-3.04 (5H, m), 2.11-2.23 (1H, m, J = 9.85, 9.85, 6.74, 3.53 Hz), 2.08 (1H, br. s.), 1.62-1.75 (1H, m), 1.40-1.61 (2H, m) |

TABLE 3-continued

| Example Number | R₁ | LCMS RT (min) | LCMS Ion [M + H]⁺ | ¹H NMR |
|---|---|---|---|---|
| 120 | methoxypyrazinyl | 0.75 | 290.3 | ¹H NMR (400 MHz, CDCl₃) δ ppm 9.30 (1H, br. s.), 7.58 (1H, d, J = 3.02 Hz), 7.52 (1H, d, J = 3.02 Hz), 3.92 (3H, s), 3.88 (1H, d, J = 9.32 Hz), 3.54 (1H, d, J = 9.32 Hz), 3.28 (1H, dd, J = 14.86, 1.51 Hz), 2.63-2.96 (5H, m), 2.07-2.22 (1H, m), 2.02 (1H, br. s.), 1.57-1.71 (1H, m), 1.33-1.55 (2H, m) |
| 121 | tert-butylpyrimidinyl | 1.15 | 316.4 | ¹H NMR (400 MHz, MeOD) δ ppm 8.65 (1H, d, J = 3.02 Hz), 6.82 (1H, br. s.), 4.02 (1H, dd, J = 10.32, 3.02 Hz), 3.71 (1H, dd, J = 10.32, 3.02 Hz), 2.98-3.26 (2H, m), 2.66-2.96 (4H, m), 1.97-2.18 (2H, m), 1.48-1.86 (3H, m), 1.29 (9H, s) |
| 122 | isoquinolinyl | 1.73 | 309.3 | ¹H NMR (400 MHz, MeOD) δ ppm 8.99 (1H, s), 7.90 (1H, d, J = 8.31 Hz), 7.70 (1H, d, J = 8.31 Hz), 7.57 (1H, t, J = 7.55 Hz), 7.39 (1H, t, J = 7.55 Hz), 7.30 (1H, br. s.), 3.94 (1H, d, J = 9.82 Hz), 3.63 (1H, d, J = 10.07 Hz), 3.14-3.24 (1H, m), 3.00-3.10 (1H, m), 2.68-2.98 (4H, m), 2.01-2.24 (2H, m), 1.45-1.87 (3H, m) |
| 123 | dimethylpyrimidinyl | 0.79 | 288.30 | ¹H NMR (400 MHz, MeOD-d₄) δ ppm 6.51 (1H, br. s.), 4.03 (1H, d, J = 10.32 Hz), 3.71 (1H, d, J = 10.32 Hz), 3.12-3.24 (1H, m), 3.01-3.12 (1H, m), 2.72-3.00 (4H, m), 2.52 (3H, s), 2.33 (3H, s), 1.98-2.20 (2H, m), 1.51-1.87 (3H, m) |
| 124 | methylpyridazinyl | 0.72 | 274.30 | ¹H NMR (400 MHz, MeOD-d₄) δ ppm 7.42 (1H, d, J = 9.07 Hz), 7.07 (1H, d, J = 8.06 Hz), 4.02 (1H, d, J = 10.07 Hz), 3.71 (1H, d, J = 10.07 Hz), 3.15-3.25 (1H, m), 3.04-3.14 (1H, m), 2.69-2.98 (4H, m), 2.55 (3H, s), 1.99-2.21 (2H, m), 1.47-1.89 (3H, m) |

The compounds in Table 3 were synthesized according to the method of Example 21, steps C-D using the appropriate isothiocyanate or amine and (S)-3-(aminomethyl)quinuclidin-3-ol, 2HCl.

TABLE 3

| Example Number | R₁ | LCMS RT (min) | LCMS Ion [M + H]⁺ | ¹H NMR |
|---|---|---|---|---|
| 125 | [1,2,4]triazolo[1,5-a]pyridine with OMe | 2.06 | 329.11 | ¹H NMR (500 MHz, MeOD-d₄) δ ppm 8.37 (d, J = 7.32 Hz, 1H), 6.92 (d, J = 2.75 Hz, 1H), 6.65-6.75 (m, 1H), 4.01 (d, J = 9.77 Hz, 1H), 3.86-3.95 (m, 3H), 3.70 (d, J = 9.77 Hz, 1H), 3.26 (d, J = 14.95 Hz, 2H), 3.12 (d, J = 14.95 Hz, 1H), 2.96 (t, J = 7.32 Hz, 2H), 2.76-2.89 (m, 2H), 2.06-2.26 (m, 2H), 1.58-1.86 (m, 3H) |
| 126 | pyrimidin-2-yl | 0.56 | 260.30 | ¹H NMR (400 MHz, CDCl₃) δ ppm 8.52 (2H, d, J = 4.78 Hz), 6.83 (1H, t, J = 4.78 Hz), 3.94-4.10 (2H, m), 3.87 (1H, d, J = 14.60 Hz), 3.62 (1H, dd, J = 14.48, 1.89 Hz), 3.41-3.56 (1H, m), 3.29 (2H, t, J = 8.44 Hz), 3.04-3.18 (1H, m), 2.27-2.50 (2H, m), 1.88-2.06 (2H, m), 1.71-1.87 (1H, m) |
| 127 | 6-chloropyrazin-2-yl | 0.88 | 294.20 | ¹H NMR (400 MHz, CDCl₃) δ ppm 8.58 (1H, br. s.), 8.18 (1H, s), 7.97 (1H, s), 3.93 (1H, d, J = 9.32 Hz), 3.58 (1H, d, J = 9.57 Hz), 3.28 (1H, dd, J = 14.86, 1.51 Hz), 2.64-2.98 (5H, m), 2.02-2.15 (2H, m), 1.60-1.73 (1H, m), 1.38-1.56 (2H, m) |
| 128 | 5-chloropyrazin-2-yl | 0.86 | 294.20 | ¹H NMR (400 MHz, CDCl₃) δ ppm 8.72 (1H, br. s.), 8.12 (1H, d, J = 0.76 Hz), 8.06 (1H, d, J = 1.26 Hz), 3.93 (1H, d, J = 9.32 Hz), 3.59 (1H, d, J = 9.32 Hz), 3.32 (1H, dd, J = 14.98, 1.38 Hz), 2.68-3.02 (5H, m), 2.05-2.21 (2H, m), 1.64-1.76 (1H, m), 1.42-1.59 (2H, m). M.P.. 185-8° C. |
| 129 | 4-methyl-5-(4-methoxyphenyl)thiazol-2-yl | 2.04 | 385.28 | ¹H NMR (500 MHz, DMSO-D₆) δ ppm 8.48 (s, 1H), 7.58 (d, J = 8.24 Hz, 2H), 6.98 (d, J = 8.55 Hz, 2H), 3.73-3.87 (m, 4H), 3.56 (d, J = 9.16 Hz, 1H), 3.00 (s, 2H), 2.72-2.87 (m, 2H), 2.61-2.72 (m, J = 7.63, 7.63 Hz, 2H), 2.38 (s, 3H), 2.03 (s, 1H), 1.91 (s, 1H), 1.37-1.70 (m, 3H) |
| 130 | 5-bromo-3-methoxypyrazin-2-yl | 1.10 | 368.20 | ¹H NMR (400 MHz, CDCl₃) δ ppm 8.97 (1H, br. s.), 7.67 (1H, s), 3.94 (3H, s), 3.89 (1H, d, J = 9.57 Hz), 3.55 (1H, d, J = 9.57 Hz), 3.28 (1H, dd, J = 14.86, 1.76 Hz), 2.63-2.95 (5H, m), 2.08-2.19 (1H, m), 1.99-2.06 (1H, m), 1.60-1.70 (1H, m, J = 14.01, 9.85, 4.31, 4.31 Hz), 1.35-1.55 (2H, m) |

TABLE 3-continued

| Example Number | R₁ | LCMS RT (min) | LCMS Ion [M + H]⁺ | ¹H NMR |
|---|---|---|---|---|
| 131 | | 1.19 | 336.30 | ¹H NMR (400 MHz, CDCl₃) δ ppm 9.06 (1H, br. s.), 8.52 (1H, d, J = 1.51 Hz), 8.44 (1H, d, J = 1.26 Hz), 7.89-7.93 (2H, m), 7.40-7.47 (2H, m), 7.33-7.39 (1H, m), 3.94 (1H, d, J = 9.32 Hz), 3.60 (1H, d, J = 9.32 Hz), 3.34 (1H, dd, J = 14.86, 1.76 Hz), 2.69-3.05 (5H, m), 2.13-2.23 (1H, m), 2.07-2.12 (1H, m), 1.65-1.76 (1H, m), 1.44-1.60 (2H, m) |
| 132 | | 1.35 | 332.23 | ¹H NMR (500 MHz, DMSO-D6) δ ppm 12.40 (s, 1H), 7.95 (s, 1H), 7.30 (d, J = 8.24 Hz, 1H), 7.22 (t, J = 7.78 Hz, 2H), 6.97 (d, J = 7.02 Hz, 1H), 3.79 (d, J = 6.71 Hz, 1H), 3.53 (s, 1H), 3.18 (d, J = 4.58 Hz, 3H), 3.00 (s, 2H), 2.79 (d, J = 2.14 Hz, 2H), 2.74 (s, 1H), 2.66 (d, J = 7.93 Hz, 3H), 1.96-2.04 (m, 2H), 1.91 (s, 1H), 1.59 (s, 3H), 1.46 (s, 1H) |
| 133 | | 1.94 | 378.16 | ¹H NMR (500 MHz, DMSO-D6) δ ppm 12.22 (s, 1H), 8.32 (s, 1H), 8.01 (s, 1H), 7.58 (d, J = 8.24 Hz, 1H), 7.55 (s, 1H), 7.08-7.14 (m, 1H), 3.82 (d, J = 9.77 Hz, 1H), 3.56 (d, J = 9.16 Hz, 1H), 2.96-3.04 (m, 2H), 2.73-2.82 (m, 2H), 2.67 (t, J = 7.48 Hz, 2H), 2.00-2.05 (m, 1H), 1.91 (s, 1H), 1.54-1.63 (m, 2H), 1.45 (s, 1H) |
| 134 | | 1.86 | 332.16 | ¹H NMR (500 MHz, DMSO-D6) δ ppm 12.22 (s, 1H), 8.00 (s, 1H), 7.63 (d, J = 8.55 Hz, 1H), 7.40 (s, 1H), 7.00 (d, J = 7.93 Hz, 1H), 3.82 (d, J = 9.46 Hz, 1H), 3.56 (d, J = 9.16 Hz, 1H), 3.00 (s, 2H), 2.78 (s, 2H), 2.67 (t, J = 7.32 Hz, 2H), 2.02 (s, 1H), 1.91 (s, 1H), 1.58 (s, 2H), 1.45 (s, 1H) |
| 135 | | 1.51 | 328.28 | ¹H NMR (500 MHz, DMSO-D6) δ ppm 11.88 (s, 2H), 8.01 (s, 1H), 7.48 (d, J = 8.55 Hz, 2H), 6.73 (s, 2H), 6.62 (dd, J = 8.70, 1.68 Hz, 2H), 3.77-3.83 (m, 7H), 3.55 (d, J = 8.85 Hz, 2H), 2.97-3.05 (m, 4H), 2.80 (s, 3H), 2.65-2.72 (m, 4H), 1.98-2.04 (m, 3H), 1.92 (s, 2H), 1.60 (d, J = 2.14 Hz, 2H), 1.59 (s, 2H), 1.47 (s, 2H) |

TABLE 3-continued

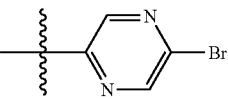

| Example Number | R$_1$ | LCMS RT (min) | LCMS Ion [M + H]$^+$ | $^1$H NMR |
|---|---|---|---|---|
| 136 | 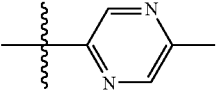 | 0.91 | 338.20 | $^1$H NMR (400 MHz, CDCl$_3$) δ ppm 8.69 (1H, br. s.), 8.12 (1H, d, J = 1.51 Hz), 8.08 (1H, d, J = 1.26 Hz), 3.91 (1H, d, J = 9.57 Hz), 3.57 (1H, d, J = 9.32 Hz), 3.29 (1H, dd, J = 14.86, 1.51 Hz), 2.62-3.01 (5H, m), 2.01-2.18 (2H, m), 1.61-1.76 (1H, m), 1.39-1.59 (2H, m) |
| 137 | | 0.77 | 274.30 | $^1$H NMR (400 MHz, CDCl$_3$) δ ppm 8.92 (1H, br. s.), 8.27 (1H, s), 7.92 (1H, s), 3.90 (1H, d, J = 9.32 Hz), 3.56 (1H, d, J = 9.32 Hz), 3.32 (1H, dd, J = 14.86, 1.76 Hz), 2.67-3.02 (5H, m), 2.42 (3H, s), 2.10-2.21 (1H, m, J = 13.17, 9.84, 3.49, 3.49, 3.49 Hz), 2.04-2.10 (1H, m), 1.64-1.74 (1H, m), 1.39-1.59 (2H, m) |
| 138 | 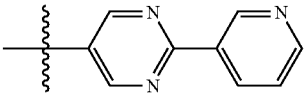 | 0.84 | 337.40 | $^1$H NMR (400 MHz, MeOD-d$_4$) d ppm 9.39 (1H, s), 8.57-8.73 (2H, m), 8.52 (1H, d, J = 5.79 Hz), 7.56 (1H, dd, J = 8.06, 5.04 Hz), 6.54-7.00 (1H, m), 4.11 (1H, d, J = 10.32 Hz), 3.79 (1H, d, J = 10.58 Hz), 3.02-3.29 (2H, m), 2.72-3.02 (4H, m), 2.01-2.25 (2H, m), 1.47-1.89 (3H, m) |
| 139 | 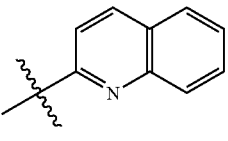 | 1.15 | 309.30 | $^1$H NMR (500 MHz, MeOD-d$_4$) δ ppm 8.07 (1H, d, J = 8.85 Hz), 7.88 (1H, d, J = 8.24 Hz), 7.75 (1H, d, J = 7.93 Hz), 7.56-7.66 (1H, m), 7.39 (1H, t, J = 7.48 Hz), 7.06 (1H, d, J = 8.85 Hz), 4.09 (1H, d, J = 10.07 Hz), 3.78 (1H, d, J = 10.07 Hz), 3.27 (1H, d, J = 14.95 Hz), 3.06-3.18 (1H, m), 2.93-3.01 (2H, m), 2.75-2.93 (2H, m), 2.07-2.29 (2H, m), 1.57-1.88 (3H, m) |
| 140 | 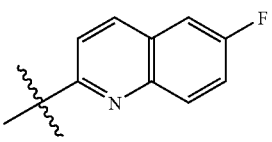 | 1.26 | 327.30 | $^1$H NMR (500 MHz, MeOD-d$_4$) δ ppm 8.05 (1H, d, J = 8.85 Hz), 7.92 (1H, dd, J = 9.00, 5.34 Hz), 7.35-7.49 (2H, m), 7.08 (1H, d, J = 8.24 Hz), 4.09 (1H, d, J = 10.07 Hz), 3.78 (1H, d, J = 10.07 Hz), 3.22-3.30 (1H, m), 3.09-3.18 (1H, m), 2.91-3.04 (2H, m), 2.71-2.91 (2H, m), 2.06-2.30 (2H, m), 1.56-1.90 (3H, m) |

TABLE 3-continued

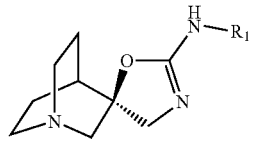

| Example Number | R₁ | LCMS RT (min) | LCMS Ion [M + H]⁺ | ¹H NMR |
|---|---|---|---|---|
| 141 | (2-pyrimidinyl, 5-Br) | 0.80 | 339.40 | ¹H NMR (400 MHz, MeOD-d₄) δ ppm 8.58 (2H, s), 3.99 (1H, d, J = 10.07 Hz), 3.69 (1H, d, J = 10.07 Hz), 3.16-3.24 (1H, m), 3.03-3.12 (1H, m), 2.85-2.95 (2H, m), 2.70-2.85 (2H, m), 1.96-2.21 (2H, m), 1.42-1.87 (3H, m) |
| 142 | (6-chloropyrimidin-4-yl) | 0.80 | 294.40 | ¹H NMR (400 MHz, MeOD-d₄) δ ppm 8.54 (1H, d, J = 1.01 Hz), 6.83 (1H, br. s.), 4.04 (1H, d, J = 10.32 Hz), 3.73 (1H, d, J = 10.32 Hz), 3.04-3.25 (2H, m), 2.69-2.97 (4H, m), 1.96-2.18 (2H, m), 1.43-1.84 (3H, m) |
| 143 | (5-(thiophen-2-yl)-1H-pyrazol-3-yl) | 1.60 | 330.28 | ¹H NMR (500 MHz, DMSO-D6) δ ppm 11.95 (s, 1H), 7.54 (s, 1H), 7.35 (s, 1H), 7.22 (s, 1H), 7.04 (s, 1H), 6.09 (s, 1H), 3.66 (s, 1H), 3.39 (d, J = 7.02 Hz, 1H), 3.04 (s, 1H), 2.99 (s, 1H), 2.84 (s, 2H), 2.67 (s, 3H), 2.02 (s, 1H), 1.92 (s, 1H), 1.59 (s, 2H), 1.51 (s, 1H) |
| 144 | (6-(difluoromethoxy)pyrimidin-4-yl) | 1.00 | 326.30 | ¹H NMR (400 MHz, MeOD-d₄) +Z,944 ppm 8.47 (1H, s), 7.30-7.79 (1H, m), 6.28 (1H, br. s.), 4.02 (1H, d, J = 10.32 Hz), 3.71 (1H, d, J = 10.32 Hz), 3.16-3.25 (1H, m), 3.04-3.13 (1H, m), 2.85-2.99 (2H, m), 2.70-2.86 (2H, m), 1.94-2.20 (2H, m), 1.49-1.84 (3H, m). M.P. 185-90° C. |
| 145 | (4,6-dimethylisothiazolo[5,4-b]pyridin-3-yl) | 1.16 | 344.30 | ¹H NMR (400 MHz, MeOD-d₄) δ ppm 7.06 (1H, s), 3.96 (1H, d, J = 9.82 Hz), 3.65 (1H, d, J = 10.07 Hz), 3.18-3.26 (1H, m), 3.05-3.13 (1H, m), 2.87-2.98 (2H, m), 2.70-2.86 (5H, m), 2.57 (3H, s), 2.03-2.20 (2H, m), 1.51-1.85 (3H, m) |
| 146 | (isoquinolin-1-yl) | 1.20 | 309.30 | ¹H NMR (400 MHz, MeOD-d₄) δ ppm 8.46 (1H, d, J = 8.31 Hz), 8.06 (1H, d, J = 6.04 Hz), 7.58-7.78 (2H, m), 7.51 (1H, td, J = 7.68, 1.26 Hz), 7.25 (1H, d, J = 6.04 Hz), 3.99 (1H, d, J = 9.82 Hz), 3.67 (1H, d, J = 9.82 Hz), 3.23 (1H, s), 3.04-3.13 (1H, m), 2.89-2.99 (2H, m), 2.71-2.88 (2H, m), 2.04-2.27 (2H, m), 1.46-1.85 (3H, m) |

TABLE 3-continued

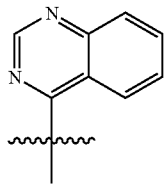

| Example Number | R₁ | LCMS RT (min) | LCMS Ion [M + H]⁺ | ¹H NMR |
|---|---|---|---|---|
| 147 | 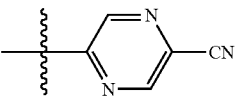 | 0.98 | 310.30 | ¹H NMR (400 MHz, MeOD-d₄) δ ppm 8.72 (1H, s), 8.46 (1H, d, J = 7.81 Hz), 7.72-7.88 (2H, m), 7.56 (1H, ddd, J = 8.25, 6.86, 1.26 Hz), 4.11 (1H, d, J = 10.32 Hz), 3.80 (1H, d, J = 10.32 Hz), 3.09-3.17 (1H, m), 2.97 (2H, t, J = 7.43 Hz), 2.76-2.89 (2H, m), 2.04-2.26 (2H, m), 1.50-1.87 (3H, m) |
| 148 | 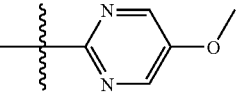 | 0.81 | 285.30 | ¹H NMR (400 MHz, MeOD-d₄) δ ppm 8.64 (1H, d, J = 1.26 Hz), 8.28 (1H, d, J = 1.26 Hz), 4.19 (1H, d, J = 10.83 Hz), 3.97 (1H, d, J = 11.08 Hz), 3.86 (1H, dd, J = 14.60, 1.51 Hz), 3.72 (1H, dd, J = 14.86, 2.52 Hz), 3.44-3.56 (1H, m), 3.31-3.43 (3H, m), 2.49-2.58 (1H, m), 2.28-2.42 (1H, m, J = 13.53, 10.07, 3.56, 3.56, 3.27 Hz), 1.91-2.18 (3H, m) |
| 149 | 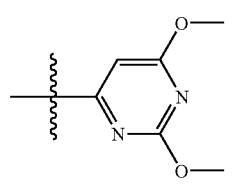 | 0.73 | 290.30 | ¹H NMR (400 MHz, MeOD-d₄) δ ppm 8.28 (2H, s), 3.95 (1H, d, J = 9.82 Hz), 3.86 (3H, s), 3.65 (1H, d, J = 9.82 Hz), 3.15-3.24 (1H, m), 3.03-3.11 (1H, m), 2.68-2.96 (4H, m), 1.97-2.19 (2H, m), 1.49-1.85 (3H, m) |
| 150 | 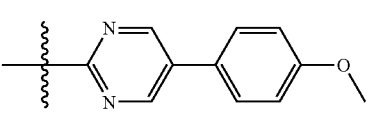 | 0.90 | 320.40 | ¹H NMR (400 MHz, MeOD-d₄) δ ppm 5.87 (1H, br. s.), 3.99 (1H, d, J = 10.32 Hz), 3.92 (3H, s), 3.88 (3H, s), 3.67 (1H, d, J = 10.32 Hz), 3.14-3.22 (1H, m), 3.01-3.10 (1H, m), 2.70-2.94 (4H, m), 1.98-2.16 (2H, m), 1.51-1.82 (3H, m) |
| 151 | 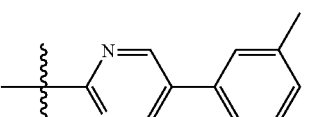 | 1.15 | 366.30 | ¹H NMR (400 MHz, MeOD-d₄) δ ppm 8.74 (2H, s), 7.53 (2H, d, J = 8.81 Hz), 7.02 (2H, d, J = 8.81 Hz), 4.01 (1H, d, J = 10.07 Hz), 3.81 (3H, s), 3.71 (1H, d, J = 10.07 Hz), 3.26 (1H, s), 3.08-3.18 (1H, m), 2.73-3.03 (4H, m), 2.16 (2H, br. s.), 1.51-1.90 (3H, m) |
| 152 | | 1.27 | 350.40 | ¹H NMR (400 MHz, MeOD-d₄) δ ppm 8.78 (2H, s), 7.27-7.47 (3H, m), 7.20 (1H, d, J = 7.30 Hz), 4.02 (1H, d, J = 10.07 Hz), 3.71 (1H, d, J = 10.07 Hz), 3.24 (1H, d, J = 15.11 Hz), 3.03-3.14 (1H, m), 2.70-3.00 (4H, m), 2.40 (3H, s), 2.03-2.22 (2H, m), 1.53-1.84 (3H, m) |

TABLE 3-continued

| Example Number | R₁ | LCMS RT (min) | LCMS Ion [M + H]⁺ | ¹H NMR |
|---|---|---|---|---|
| 153 | (5,6-dihydrobenzo[h]quinazolin-2-yl) | 2.13 | 362.28 | ¹H NMR (400 MHz, MeOD-d₄) δ ppm 8.37 (1H, s), 8.24 (1H, dd, J = 7.55, 1.51 Hz), 7.88 (1H, s), 7.19-7.44 (3H, m), 4.02 (1H, d, J = 10.07 Hz), 3.71 (1H, d, J =10.07 Hz), 3.24 (1H, d, J = 16.87 Hz), 3.05-3.12 (1H, m), 2.70-2.99 (8H, m), 2.05-2.21 (2H, m), 1.48-1.84 (3H, m) |
| 154 | 2-bromopyridin-4-yl | 0.57 | 339.10 | ¹H NMR (500 MHz, MeOD-d₄) δ ppm 8.07 (d, J = 5.49 Hz, 1H), 7.47-7.71 (m, 1H), 7.13-7.34 (m, 1H), 3.91-4.06 (m, 1H), 3.56-3.73 (m, 1H), 3.14-3.24 (m, 1H), 3.02-3.14 (m, 1H), 2.73-3.01 (m, 4H), 1.98-2.21 (m, 2H), 1.58-1.85 (m, 3H) |
| 155 | 6-bromopyridin-2-yl | 0.64 | 339.04 | ¹H NMR (500 MHz, MeOD-d₄) δ ppm 7.45-7.58 (m, 1H), 7.04-7.16 (m, 1H), 6.90 (d, J = 7.32 Hz, 1H), 3.95-4.09 (m, 1H), 3.67-3.77 (m, 1H), 3.18-3.28 (m, 1H), 3.07-3.17 (m, 1H), 2.76-3.05 (m, 4H), 2.04-2.22 (m, 2H), 1.50-1.89 (m, 3H) |
| 156 | 6-bromoquinolin-2-yl | 1.47 | 388.40 | ¹H NMR (500 MHz, MeOD-d₄) δ ppm 7.96-8.03 (1H, m), 7.88-7.95 (1H, m), 7.75-7.84 (1H, m), 7.61-7.73 (1H, m), 7.06 (1H, d, J = 8.55 Hz), 4.01-4.11 (1H, m), 3.69-3.82 (1H, m), 3.20-3.29 (1H, m), 3.09-3.19 (1H, m), 2.76-3.02 (4H, m), 2.09-2.23 (2H, m), 1.58-1.87 (3H, m) |
| 157 | 6-methylquinolin-2-yl | 1.33 | 323.50 | ¹H NMR (500 MHz, MeOD-d₄) δ ppm 7.99 (1H, d, J = 8.55 Hz), 7.77 (1H, d, J = 8.55 Hz), 7.41-7.57 (2H, m), 7.02 (1H, d, J = 8.55 Hz), 4.08 (1H, d, J = 9.77 Hz), 3.76 (1H, d, J = 9.77 Hz), 3.26 (1H, d, J = 14.95 Hz), 3.08-3.17 (1H, m), 2.78-3.02 (4H, m), 2.49 (3H, s), 2.08-2.31 (2H, m), 1.54-1.89 (3H, m) |
| 158 | 4-fluoro-1H-indazol-3-yl | 1.19 | 316.16 | ¹H NMR (500 MHz, DMSO-D6) δ ppm 12.36 (s, 1H), 7.98 (s, 1H), 7.19-7.27 (m, 1H), 7.15 (d, J = 8.24 Hz, 1H), 6.64-6.71 (m, 1H), 3.80 (d, J = 7.63 Hz, 1H), 3.54 (s, 1H), 2.95-3.04 (m, 2H), 2.78 (s, 2H), 2.66 (s, 2H), 2.01 (s, 1H), 1.93 (s, 1 H), 1.58 (s, 2H), 1.46 (s, 1H) |

TABLE 3-continued

| Example Number | R₁ | LCMS RT (min) | LCMS Ion [M + H]⁺ | ¹H NMR |
|---|---|---|---|---|
| 159 | 5-fluoro-1H-indazol-3-yl | 1.40 | 316.16 | ¹H NMR (500 MHz, DMSO-D6) δ ppm 12.20 (s, 1H), 7.98 (s, 1H), 7.38 (dd, J = 8.55, 3.36 Hz, 1H), 7.32 (d, J = 8.55 Hz, 1H), 7.18 (t, J = 8.85 Hz, 1H), 3.81 (d, J = 8.85 Hz, 1H), 3.55 (d, J = 8.55 Hz, 1H), 2.97-3.05 (m, 2H), 2.79 (s, 2H), 2.68 (t, J = 7.32 Hz, 3H), 2.02 (s, 1H), 1.92 (s, 1H), 1.59 (d, J = 6.41 Hz, 2H), 1.47 (d, J = 8.85 Hz, 1H) |
| 160 | pyridazin-4-yl | 0.83 | 260.27 | ¹H NMR (400 MHz, MeOD) δ ppm 8.89 (1H, br. s.), 8.80 (1H, d, J = 5.79 Hz), 7.53 (1H, br. s.), 3.91 (1H, d, J = 10.83 Hz), 3.60 (1H, d, J = 10.83 Hz), 3.16-3.25 (1H, m), 3.02-3.12 (1H, m), 2.68-2.99 (4H, m), 1.94-2.17 (2H, m), 1.53-1.83 (3H, m) |
| 161 | 5,6-dimethylfuro[2,3-d]pyrimidin-4-yl | 1.55 | 328.21 | ¹H NMR (400 MHz, MeOD-d₄) δ ppm 8.35 (1H, s), 4.01 (1H, d, J = 10.07 Hz), 3.70 (1H, d, J = 10.07 Hz), 3.20-3.27 (1H, m), 3.05-3.13 (1H, m), 2.69-2.99 (4H, m), 2.34 (3H, s), 2.29 (3H, s), 2.01-2.22 (2H, m), 1.51-1.83 (3H, m) |
| 162 | 5-(4-methoxyphenyl)-1H-pyrazol-3-yl | 1.85 | 354.25 | ¹H NMR (500 MHz, DMSO-D6) δ ppm 11.75-12.09 (m, J = 14.95 Hz, 1H), 7.62 (d, J = 7.93 Hz, 2H), 7.38-7.54 (m, J = 10.99 Hz, 1H), 6.95 (d, J = 6.71 Hz, 2H), 6.13 (s, 1H), 3.76-3.83 (m, 4H), 3.74 (s, 1H), 3.38 (d, J = 2.75 Hz, 1H), 2.98 (s, 1H), 2.82 (s, 2H), 2.62-2.71 (m, 2H), 2.00 (s, 1H), 1.92 (s, 1H), 1.58 (s, 2H), 1.50 (s, 1H) |
| 163 | 5-(trifluoromethyl)-1H-indazol-3-yl | 2.09 | 366.17 | ¹H NMR (500 MHz, DMSO-D6) δ ppm 12.54 (s, 1H), 8.05 (s, 1H), 7.97 (s, 1H), 7.52-7.60 (m, 2H), 3.82 (s, 1H), 3.58 (s, 1H), 3.01 (s, 2H), 2.78 (s, 2H), 2.64-2.70 (m, 2H), 1.99-2.05 (m, 1H), 1.92 (s, 1H), 1.58 (s, 2H), 1.47 (s, 1H) |

TABLE 3-continued

| Example Number | R₁ | LCMS RT (min) | LCMS Ion [M + H]⁺ | ¹H NMR |
|---|---|---|---|---|
| 164 | | 2.12 | 366.17 | ¹H NMR (500 MHz, DMSO-D6) δ ppm 12.54 (s, 1H), 8.03 (s, 1H), 7.85 (d, J = 8.24 Hz, 1H), 7.70 (s, 1H), 7.26 (d, J = 8.24 Hz, 1H), 3.83 (d, J = 9.46 Hz, 1H), 3.57 (d, J = 8.85 Hz, 1H), 2.97-3.05 (m, 2H), 2.79 (s, 2H), 2.67 (t, J = 7.48 Hz, 2H), 2.03 (d, J = 2.44 Hz, 1H), 1.92 (s, 1H), 1.59 (d, J = 5.80 Hz, 2H), 1.46 (s, 1H) |
| 165 | | 1.24 | 298.16 | ¹H NMR (500 MHz, DMSO-D6) δ ppm 12.07 (s, 1H), 8.02 (s, 1H), 7.63 (d, J = 7.63 Hz, 1H), 7.27-7.36 (m, 2H), 6.99 (t, J = 7.32 Hz, 1H), 3.82 (d, J = 9.46 Hz, 1H), 3.56 (d, J = 8.85 Hz, 1H), 3.00 (s, 2H), 2.79 (s, 2H), 2.67 (t, J = 6.87 Hz, 2H), 2.02 (d, J = 2.75 Hz, 1H), 1.93 (s, 1H), 1.58 (s, 2H), 1.47 (s, 1H) |
| 166 | | 1.16 | 366.30 | ¹H NMR (500 MHz, MeOD-d₄) δ ppm 8.53 (1H, d, J = 5.19 Hz), 8.02-8.15 (2H, m), 7.39 (1H, d, J = 5.19 Hz), 7.01-7.11 (2H, m), 4.06 (1H, d, J = 10.07 Hz), 3.89 (3H, s), 3.74 (1H, d, J = 10.07 Hz), 3.28 (1H, d, J = 14.95 Hz), 3.13 (1H, d, J = 14.95 Hz), 2.73-3.02 (4H, m), 2.07-2.25 (2H, m), 1.54-1.86 (3H, m) |
| 167 | | 1.25 | 344.40 | ¹H NMR (500 MHz, MeOD-d₄) δ ppm 8.48 (1H, s), 4.05 (1H, d, J = 10.07 Hz), 3.74 (1H, d, J = 10.07 Hz), 3.26 (1H, s), 3.14 (1H, d, J = 14.65 Hz), 2.76-3.02 (4H, m), 2.59 (3H, s), 2.46 (3H, s), 2.09-2.23 (2H, m), 1.57-1.89 (3H, m) |
| 168 | | 1.73 | 390.20 | ¹H NMR (500 MHz, MeOD-d₄) δ ppm 9.27 (1H, s), 8.14 (1H, d, J = 2.14 Hz), 7.93 (1H, dd, J = 8.85, 1.83 Hz), 7.78 (1H, d, J = 8.85 Hz), 4.11 (1H, d, J = 10.07 Hz), 3.80 (1H, d, J = 10.07 Hz), 3.28 (1H, s), 3.15 (1H, d, J = 14.95 Hz), 2.78-3.02 (4H, m), 2.05-2.25 (2H, m), 1.52-1.88 (3H, m) |

TABLE 3-continued

| Example Number | R₁ | LCMS RT (min) | LCMS Ion [M + H]⁺ | ¹H NMR |
|---|---|---|---|---|
| 169 | pyrimidine | 0.71 | 260.40 | ¹H NMR (500 MHz, MeOD-d₄) δ ppm 8.73 (1H, s), 8.59 (2H, br. s.), 3.86 (1H, d, J = 9.77 Hz), 3.56 (1H, d, J = 9.77 Hz), 3.18-3.26 (1H, m), 3.05-3.12 (1H, m), 2.72-2.99 (4H, m), 2.17 (1H, br. s.), 2.01 (1H, br. s.), 1.54-1.86 (3H, m) |
| 170 | methoxypyrazine | 0.78 | 290.30 | ¹H NMR (400 MHz, CDCl₃) δ ppm 8.57 (1H, br. s.), 7.97 (1H, d, J = 1.51 Hz), 7.80 (1H, d, J = 1.26 Hz), 3.90 (3H, s), 3.87 (1H, d, J = 9.06 Hz), 3.54 (1H, d, J = 9.06 Hz), 3.32 (1H, dd, J = 14.86, 1.76 Hz), 2.69-3.04 (5H, m), 2.13-2.23 (1H, m), 2.06-2.11 (1H, m), 1.63-1.76 (1H, m), 1.41-1.61 (2H, m) |
| 171 | bromo-dimethylpyrimidine | 1.06 | 368.40 | ¹H NMR (400 MHz, MeOD-d₄) δ ppm 3.99 (1H, d, J = 10.07 Hz), 3.68 (1H, d, J = 10.07 Hz), 3.15-3.24 (1H, m), 3.02-3.10 (1H, m), 2.68-2.96 (4H, m), 2.53 (6H, s), 2.02-2.19 (2H, m), 1.46-1.83 (3H, m) |
| 172 | methoxy-methylpyrimidine | 0.89 | 304.25 | ¹H NMR (400 MHz, MeOD-d₄) δ ppm 6.22 (1H, s), 3.99 (1H, d, J = 10.07 Hz), 3.89 (3H, s), 3.67 (1H, d, J = 10.07 Hz), 3.15-3.25 (1H, m), 3.00-3.11 (1H, m), 2.67-2.97 (4H, m), 2.32 (3H, s), 2.00-2.19 (2H, m), 1.42-1.83 (3H, m) |
| 173 | methoxyphenyl-thiazole | 1.07 | 371.17 | ¹H NMR (500 MHz, DMSO-D6) δ ppm 8.57 (s, 1H), 7.46-7.54 (m, 6H), 7.31 (t, J = 7.93 Hz, 2H), 6.87 (dd, J = 8.24, 2.44 Hz, 2H), 3.87 (d, J = 9.77 Hz, 2H), 3.82 (s, 6H), 3.61 (d, J = 9.77 Hz, 2H), 3.03 (s, 4H, 2.75-2.84 (m, 4H), 2.68 (t, J = 7.63 Hz, 4H), 2.06 (s, 2H), 1.93 (s, 2H), 1.56-1.64 (m, 4H), 1.50 (dd, J = 9.46, 2.44 Hz, 2H) |
| 174 | chloro-methyl-benzothiazole | 1.32 | 363.44 | ¹H NMR (500 MHz, DMSO-d₆) δ ppm 8.73-8.93 (m, 1H), 7.73 (s, 1H), 7.20 (s, 1H), 3.91 (d, J = 9.77 Hz, 1H), 3.66 (d, J = 10.07 Hz, 1H), 3.05 (s, 2H, 2.74-2.89 (m, 1H), 2.68 (t, J = 7.63 Hz, 1H), 2.54 (s, 3H), 2.09 (br. s., 2H), 1.83-1.98 (m, 1H), 1.42-1.69 (m, 2 H) |

TABLE 3-continued

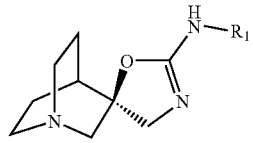

| Example Number | R₁ | LCMS RT (min) | LCMS Ion [M + H]⁺ | ¹H NMR |
|---|---|---|---|---|
| 175 | | 0.40 | 274.26 | ¹H NMR (400 MHz, MeOD-d₄) δ ppm 8.36 (1H, d, J = 5.04 Hz), 6.82 (1H, d, J = 5.04 Hz), 3.98 (1H, d, J = 10.07 Hz), 3.67 (1H, d, J = 10.07 Hz), 3.17-3.25 (1H, m), 3.03-3.10 (1H, m), 2.70-2.96 (4H, m), 2.41 (3H, s), 1.98-2.22 (2H, m), 1.44-1.87 (3H, m) |
| 176 | | 0.72 | 288.25 | ¹H NMR (400 MHz, MeOD-d₄) δ ppm 6.72 (1H, s), 3.98 (1H, d, J = 10.07 Hz), 3.67 (1H, d, J = 9.82 Hz), 3.18-3.24 (1H, m), 3.02-3.12 (1H, m), 2.65-2.96 (4H, m), 2.36 (6H, s), 2.02-2.21 (2H, m), 1.45-1.83 (3H, m) |
| 177 | | 2.13 | 362.28 | ¹H NMR (400 MHz, MeOD-d₄) δ ppm 8.37 (1H, s), 8.24 (1H, dd, J = 7.55, 1.51 Hz), 7.88 (1H, s), 7.19-7.44 (3H, m), 4.02 (1H, d, J = 10.07 Hz), 3.71 (1H, d, J = 10.07 Hz), 3.24 (1H, d, J = 16.87 Hz), 3.05-3.12 (1H, m), 2.70-2.99 (8H, m), 2.05-2.21 (2H, m), 1.48-1.84 (3H, m) |
| 178 | | 1.31 | 370.18 | ¹H NMR (400 MHz, MeOD-d₄) δ ppm 8.32 (1H, s), 3.94-4.03 (4H, m), 3.68 (1H, d, J = 10.07 Hz), 3.15-3.26 (1H, m), 3.01-3.12 (1H, m), 2.68-2.96 (4H, m), 2.01-2.16 (2H, m), 1.51-1.84 (3H, m) |
| 179 | | 1.87 | 353.28 | ¹H NMR (500 MHz, MeOD-d₄) δ ppm 7.83 (1H, s), 7.63-7.76 (1H, m), 7.19 (1H, dd, J = 9.00, 2.90 Hz), 7.09 (1H, d, J = 2.75 Hz), 3.93-4.02 (1H, m), 3.84-3.93 (3H, m), 3.69 (1H, d, J = 9.77 Hz), 3.26 (1H, d, J = 14.65 Hz), 3.11 (1H, d, J = 14.95 Hz), 2.70-3.01 (4H, m), 2.39 (3H, s), 2.06-2.27 (2H, m), 1.57-1.85 (3H, m) |
| 180 | | 1.94 | 350.30 | ¹H NMR (400 MHz, MeOD-d₄) δ ppm 7.91-8.15 (2H, m), 7.38-7.53 (3H, m), 7.31 (1H, s), 4.02 (1H, d, J = 10.07 Hz), 3.70 (1H, d, J = 10.07 Hz), 3.17-3.26 (1H, m), 3.02-3.14 (1H, m), 2.66-2.98 (4H, m), 2.48 (3H, s), 2.03-2.20 (2H, m), 1.49-1.83 (3H, m) |

TABLE 3-continued

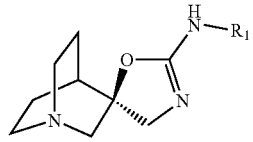

| Example Number | R₁ | LCMS RT (min) | LCMS Ion [M + H]⁺ | ¹H NMR |
|---|---|---|---|---|
| 181 | 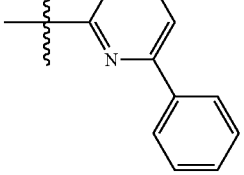 | 1.17 | 336.40 | ¹H NMR (400 MHz, MeOD-d₄) δ ppm 8.55 (1H, d, J = 5.29 Hz), 8.08 (2H, dd, J = 6.67, 2.90 Hz), 7.44-7.53 (3H, m), 7.40 (1H, d, J = 5.29 Hz), 4.01 (1H, d, J = 10.07 Hz), 3.70 (1H, d, J = 10.07 Hz), 3.20-3.28 (1H, m), 3.04-3.14 (1H, m), 2.67-2.99 (4H, m), 2.05-2.24 (2H, m), 1.49-1.85 (3H, m) |
| 182 | 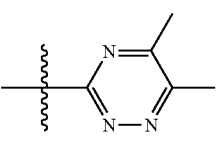 | 0.42 | 289.22 | ¹H NMR (400 MHz, MeOD-d₄) δ ppm 4.02 (1H, d, J = 10.32 Hz), 3.71 (1H, d, J = 10.32 Hz), 3.23 (1H, d, J = 15.36 Hz), 3.03-3.13 (1H, m), 2.69-2.98 (4H, m), 2.54 (3H, s), 2.48 (3H, s), 2.01-2.21 (2H, m), 1.41-1.85 (3H, m) |
| 183 | 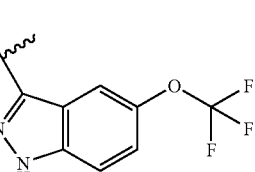 | 1.19 | 382.19 | ¹H NMR (500 MHz, DMSO-D6) δ ppm 12.37 (s, 1H), 8.01 (s, 1H), 7.53 (s, 1H), 7.45 (d, J = 9.16 Hz, 1H), 7.28 (d, J = 8.85 Hz, 1H), 3.82 (d, J = 9.16 Hz, 1H), 3.57 (d, J = 9.46 Hz, 1H), 3.00 (s, 2H), 2.78 (s, 2H), 2.67 (t, J = 7.48 Hz, 2H), 1.96-2.04 (m, 1H), 1.91 (d, J = 8.85 Hz, 1H), 1.55-1.63 (m, 2H), 1.47 (d, J = 7.02 Hz, 1H) |
| 184 | 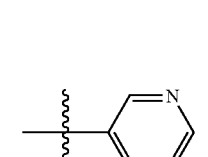 | 0.75 | 274.30 | ¹H NMR (400 MHz, CDCl₃) δ ppm 9.08 (1H, br. s.), 8.12 (1H, s), 7.85 (1H, s), 3.89 (1H, d, J = 9.32 Hz), 3.55 (1H, d, J = 9.32 Hz), 3.28 (1H, dd, J = 14.86, 1.26 Hz), 2.62-2.97 (5H, m), 2.35 (3H, s), 2.06-2.17 (1H, m, J = 13.13, 9.82, 3.53, 3.38, 3.38 Hz), 2.04 (1H, br. s.), 1.59-1.73 (1H, m), 1.37-1.57 (2H, m) |
| 185 |  | 0.75 | 274.30 | ¹H NMR (400 MHz, CDCl₃) δ ppm 9.29 (1H, br. s.), 7.90 (2H, br. s.), 3.90 (1H, d, J = 9.32 Hz), 3.55 (1H, d, J = 9.06 Hz), 3.35 (1H, d, J = 14.86 Hz), 2.65-3.08 (5H, m), 2.56 (3H, s), 2.12-2.27 (1H, m), 2.08 (1H, br. s.), 1.62-1.77 (1H, m), 1.38-1.61 (2H, m) |

TABLE 3-continued

| Example Number | R₁ | LCMS RT (min) | LCMS Ion [M + H]⁺ | ¹H NMR |
|---|---|---|---|---|
| 186 | 3,6-dimethylpyrazin-2-yl | 0.79 | 288.30 | ¹H NMR (400 MHz, CDCl₃) δ ppm 9.16 (1H, br. s.), 7.78 (1H, s), 3.88 (1H, d, J = 9.06 Hz), 3.53 (1H, d, J = 9.32 Hz), 3.34 (1H, dd, J = 14.86, 2.01 Hz), 2.64-3.07 (5H, m), 2.55 (3H, s), 2.38 (3H, s), 2.14-2.25 (1H, m), 2.04-2.11 (1H, m), 1.68 (1H, dddd, J = 13.94, 9.66, 4.53, 4.34 Hz), 1.41-1.61 (2H, m) |
| 187 | 4,5-dimethylthiazol-2-yl | 0.58 | 293.06 | ¹H NMR (500 MHz, DMSO-d₆) d ppm 3.73-3.87 (m, 1H), 3.47-3.58 (m, 1H), 2.98 (s, 2H), 2.71-2.85 (m, 2H), 2.65 (t, J = 7.78 Hz, 2H), 2.18 (s, 3H), 2.11 (s, 3H), 2.00 (br. s., 1H), 1.80-1.96 (m, 1H), 1.57 (dd, J = 8.24, 2.75 Hz, 3H) |
| 188 | 3-phenyl-1H-1,2,4-triazol-5-yl | 0.86 | 325.20 | ¹H NMR (500 MHz, DMSO-d₆) δ ppm 8.07 (d, J = 7.32 Hz, 2H), 7.42 (d, J = 7.63 Hz, 3H), 3.87 (s, 1H), 3.55-3.70 (m, 1H), 3.02 (s, 2H), 2.72-2.88 (m, 2H), 2.68 (s, 2H), 1.98-2.10 (m, 1H), 1.81-1.97 (m, 1H), 1.40-1.68 (m, 3H) |
| 189 | 4-methyl-5-phenylthiazol-2-yl | 1.04 | 355.24 | ¹H NMR (500 MHz, DMSO-d₆) δ ppm 7.36-7.47 (m, 3H), 7.24-7.34 (m, 2H), 3.84 (d, J = 10.07 Hz, 1H), 3.58 (d, J = 9.77 Hz, 1H), 3.01 (s, 2H), 2.71-2.87 (m, 2H), 2.66 (t, J = 7.63 Hz, 2H), 2.32 (s, 3H), 2.04 (br. s., 1H), 1.83-1.98 (m, 1H), 1.43-1.64 (m, 3H) |
| 190 | 1-methyl-1H-pyrazol-3-yl | 0.26 | 262.11 | ¹H NMR (500 MHz, DMSO-d₆) d ppm 7.43 (br. s., 1H), 5.56-5.76 (m, 1H), 3.58-3.83 (m, 4H), 3.37-3.52 (m, 1H), 2.94 (s, 2H), 2.68-2.88 (m, 2H), 2.60-2.68 (m, 2H), 1.94 (br. s., 2H), 1.37-1.65 (m, 3H) |
| 191 | 5-methyl-4-phenylpyrimidin-2-yl | 1.65 | 350.30 | ¹H NMR (400 MHz, MeOD) δ ppm 8.43 (1H, s), 7.58 (2H, dd, J = 7.55, 1.76 Hz), 7.39-7.52 (3H, m), 3.96 (1H, d, J = 10.07 Hz), 3.66 (1H, d, J = 9.82 Hz), 3.25 (1H, d, J = 16.12 Hz), 3.05-3.14 (1H, m), 2.88-2.98 (2H, m), 2.68-2.87 (2H, m), 2.24 (3H, s), 2.03-2.17 (2H, m), 1.45-1.84 (3H, m) |

TABLE 3-continued

| Example Number | R₁ | LCMS RT (min) | LCMS Ion [M + H]⁺ | ¹H NMR |
|---|---|---|---|---|
| 192 | | 1.02 | 337.28 | ¹H NMR (400 MHz, MeOD) δ ppm 8.64 (2H, d, J = 5.29 Hz), 8.40 (1H, d, J = 7.81 Hz), 7.86-7.97 (1H, m), 7.80 (1H, d, J = 5.04 Hz), 7.47 (1H, dd, J = 6.55, 5.04 Hz), 4.03 (1H, d, J = 10.07 Hz), 3.74 (1H, d, J = 10.07 Hz), 3.29 (1H, d, J = 1.51 Hz), 3.12-3.22 (1H, m), 2.99 (2H, t, J = 7.68 Hz), 2.78-2.92 (2H, m), 2.03-2.26 (2H, m), 1.45-1.88 (3H, m) |
| 193 | | NA | NA | ¹H NMR (400 MHz, MeOD) δ ppm 8.69 (1H, s), 7.61-7.78 (2H, m), 7.34-7.56 (3H, m), 3.99 (1H, d, J = 10.07 Hz), 3.68 (1H, d, J = 10.32 Hz), 3.15-3.25 (1H, m), 3.02-3.11 (1H, m), 2.92 (2H, t, J = 7.55 Hz), 2.69-2.86 (2H, m), 2.01-2.20 (2H, m), 1.47-1.81 (3H, m) |
| 194 | | NA | NA | ¹H NMR (400 MHz, MeOD) δ ppm 9.24 (1H, d, J = 1.51 Hz), 8.60-8.68 (2H, m), 8.53 (1H, dt, J = 7.99, 1.92 Hz), 7.40-7.64 (2H, m), 4.05 (1H, d, J = 10.32 Hz), 3.76 (1H, d, J = 10.07 Hz), 3.33-3.40 (1H, m), 3.17-3.26 (1H, m), 2.82-3.09 (4H, m), 2.09-2.31 (2H, m), 1.55-1.91 (3H, m) |
| 195 | | 1.41 | 403.36 | ¹H NMR (400 MHz, MeOD) δ ppm 8.65 (1H, s), 8.40 (1H, s), 8.17 (1H, s), 7.25-7.47 (5H, m), 4.04 (1H, d, J = 10.32 Hz), 3.73 (1H, d, J = 10.32 Hz), 3.17-3.27 (1H, m), 3.04-3.13 (1H, m), 2.63-3.00 (4H, m), 2.00-2.22 (2H, m), 1.48-1.87 (3H, m) |
| 196 | | 1.69 | 364.36 | ¹H NMR (400 MHz, MeOD) δ ppm 8.33 (1H, s), 8.16 (1H, dd, J = 7.81, 1.51 Hz), 7.30-7.44 (1H, m), 7.08 (1H, t, J = 7.55 Hz), 6.95 (1H, d, J = 8.31 Hz), 5.16 (2H, s), 4.02 (1H, d, J = 9.82 Hz), 3.71 (1H, d, J = 10.07 Hz), 3.18-3.26 (1H, m), 3.04-3.13 (1H, m), 2.93 (2H, t, J = 7.68 Hz), 2.71-2.86 (2H, m), 2.01-2.23 (2H, m), 1.50-1.83 (3H, m) |

TABLE 3-continued

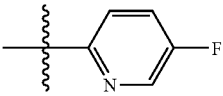

| Example Number | R₁ | LCMS RT (min) | LCMS Ion [M + H]⁺ | ¹H NMR |
|---|---|---|---|---|
| 197 | 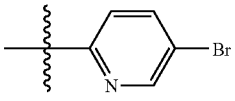 | 0.53 | 277.13 | ¹H NMR (500 MHz, DMSO-D6) δ ppm 8.76 (s, 1H), 8.15 (d, J = 2.44 Hz, 1H), 7.55 (s, 1H), 6.83 (s, 1H), 3.79 (s, 1H), 3.54 (d, J = 10.07 Hz, 1H), 2.92-3.00 (m, 3H), 2.70-2.80 (m, 3H), 2.66 (t, J = 7.78 Hz, 3H), 1.97 (s, 1H), 1.88 (s, 1H), 1.53-1.61 (m, 3H), 1.41-1.49 (m, 1 H) |
| 198 | 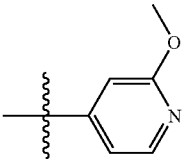 | 0.77 | 377.07 | ¹H NMR (500 MHz, DMSO-d₆) δ ppm 8.26 (br. s., 1H), 7.76 (br. s., 1H), 6.75 (br. s., 1H), 3.81 (br. s., 1H), 3.56 (d, J = 9.46 Hz, 1H), 2.85-3.10 (m, 2H), 2.56-2.85 (m, 4H), 1.97 (br. s., 2H), 1.36-1.67 (m, 3H) |
| 199 | 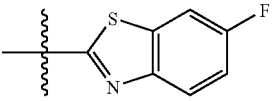 | 0.16 | 289.19 | ¹H NMR (500 MHz, MeOD) δ ppm 7.90 (d, J = 6.10 Hz, 1H), 6.74-7.00 (m, 2H), 3.93-4.09 (m, 1H), 3.88 (s, 3H), 3.61-3.71 (m, 1H), 3.14-3.25 (m, 1H), 3.06 (d, J = 1.83 Hz, 1H), 2.69-2.99 (m, 3H), 2.07 (br. s., 2H), 1.74 (d, J = 8.24 Hz, 3H), 1.18 (d, J = 6.41 Hz, 1H) |
| 200 | 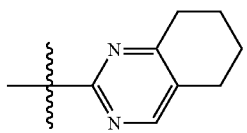 | 0.82 | 332.97 | ¹H NMR (400 MHz, DMSO-d₆) δ ppm 7.71 (dd, J = 8.78, 2.76 Hz, 1H), 7.59 (dd, J = 8.91, 4.89 Hz, 1H), 7.17 (td, J = 9.03, 2.76 Hz, 1H), 3.89 (d, J = 10.04 Hz, 1H), 3.64 (d, J = 10.04 Hz, 1H), 2.97-3.13 (m, 2H), 2.75-2.88 (m, 2H), 2.67 (t, J = 7.65 Hz, 2H), 2.02-2.12 (m, 1H), 1.81-1.98 (m, 1H), 1.36-1.69 (m, 3H) |
| 201 | 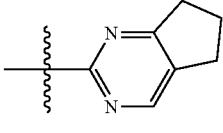 | 1.16 | 314.35 | ¹H NMR (400 MHz, MeOD) δ ppm 8.20 (1H, s), 3.96 (1H, d, J = 10.07 Hz), 3.65 (1H, d, J = 9.82 Hz), 3.20 (1H, d), 3.06 (1H, d), 2.91 (2H, t, J = 7.43 Hz), 2.71-2.84 (4H, m), 2.66 (2H, t, J = 6.04 Hz), 1.98-2.21 (2H, m), 1.43-1.94 (7H, m) |
| 202 |  | 0.69 | 300.29 | ¹H NMR (400 MHz, MeOD) δ ppm 8.30 (1H, s), 3.97 (1H, d, J = 9.82 Hz), 3.66 (1H, d, J = 10.07 Hz), 3.21 (1H, d), 3.06 (1H, d), 2.74-2.97 (8H, m), 2.11 (4H, dq, J = 7.68, 7.51 Hz), 1.39-1.85 (3H, m) |

TABLE 3-continued

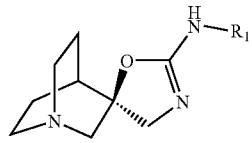

| Example Number | R₁ | LCMS RT (min) | LCMS Ion [M + H]⁺ | ¹H NMR |
|---|---|---|---|---|
| 203 | | 1.19 | 322.25 | ¹H NMR (400 MHz, MeOD) δ ppm 4.00 (1H, d, J = 10.07 Hz), 3.69 (1H, d, J = 10.07 Hz), 3.22 (1H, d, J = 14.60 Hz), 3.03-3.14 (1H, m), 2.69-2.97 (4H, m), 2.46 (3H, s), 2.26 (3H, s), 2.03-2.17 (2H, m), 1.51-1.84 (3H, m) |
| 204 | | 0.67 | 328.28 | ¹H NMR (400 MHz, MeOD) δ ppm 8.92 (1H, s), 4.05 (1H, d, J = 10.32 Hz), 3.75 (1H, d, J = 10.32 Hz), 3.24 (1H, d, J = 1.26 Hz), 3.06-3.17 (1H, m), 2.75-3.03 (6H, m), 2.56-2.68 (2H, m), 2.13 (4H, ddd, J = 12.72, 6.30, 6.17 Hz), 1.54-1.84 (3H, m) |
| 205 | | 0.15 | 284.10 | ¹H NMR (500 MHz, DMSO-D6) δ ppm 9.01 (s, 1H), 8.40 (d, J = 4.88 Hz, 1H), 7.21 (s, 1H), 7.16 (s, 1H), 3.84 (s, 1H), 3.59 (d, J = 10.07 Hz, 1H), 2.94-3.02 (m, 3H), 2.70-2.79 (m, 3H), 2.62-2.68 (m, 3H), 1.99 (s, 1H), 1.87 (s, 1H), 1.57 (d, J = 3.05 Hz, 2H), 1.56 (s, 1H), 1.41-1.49 (m, 1H) |
| 206 | | 0.78 | 366.10 | ¹H NMR (500 MHz, DMSO-D6) δ ppm 12.63 (s, 1H), 7.95 (d, J = 7.63 Hz, 2H), 7.68 (d, J = 6.71 Hz, 1H), 7.16 (t, J = 7.32 Hz, 1H), 3.84 (s, 1H), 3.60 (s, 1H), 3.03 (s, 2H), 2.80 (s, 2H), 2.64-2.72 (m, 2H), 2.05 (s, 1H), 1.92 (s, 1H), 1.60 (d, J = 8.24 Hz, 2H), 1.48 (s, 1H) |
| 207 | | 0.77 | 335.17 | ¹H NMR (500 MHz, DMSO-D6) δ ppm 9.05 (s, 1H), 8.52 (d, J = 2.44 Hz, 1H), 7.91 (s, 1H), 7.66 (d, J = 7.63 Hz, 2H), 7.47 (t, J = 7.63 Hz, 2H), 7.36 (t, J = 7.32 Hz, 1H), 6.87 (s, 1H), 3.84 (s, 1H), 3.59 (d, J = 10.07 Hz, 1H), 2.99 (s, 2H), 2.72-2.81 (m, 2H), 2.63-2.71 (m, 3H), 1.99 (s, 1H), 1.90 (s, 1H), 1.59 (s, 2H), 1.42-1.50 (m, 1H) |

TABLE 3-continued

| Example Number | R₁ | LCMS RT (min) | LCMS Ion [M + H]⁺ | ¹H NMR |
|---|---|---|---|---|
| 208 | 1-methyl-5-methoxy-benzimidazol-2-yl | 0.63 | 342.25 | ¹H NMR (500 MHz, DMSO-D6) δ ppm 9.30 (s, 1H), 7.19 (d, J = 8.55 Hz, 1H), 6.94 (d, J = 2.44 Hz, 1H), 6.69 (dd, J = 8.55, 2.14 Hz, 1H), 3.92 (d, J = 10.07 Hz, 1H), 3.75 (s, 3H), 3.66 (d, J = 9.77 Hz, 1H), 3.54 (s, 3H), 2.99-3.07 (m, 2H), 2.79 (t, J = 7.78 Hz, 2H), 2.68 (t, J = 7.78 Hz, 2H), 2.02-2.07 (m, 1H), 1.89 (dd, J = 6.41, 3.36 Hz, 1H), 1.56-1.64 (m, 2H), 1.44-1.52 (m, 1H) |
| 209 | 4-cyclopropyl-pyrimidin-2-yl | 0.96 | 300.34 | ¹H NMR (400 MHz, MeOD) d ppm 8.27 (1H, d, J = 5.04 Hz), 6.78 (1H, d, J = 5.29 Hz), 3.98 (1H, d, J = 10.07 Hz), 3.66 (1H, d, J = 10.07 Hz), 3.21 (1H, d), 3.06 (1H, d), 2.64-2.99 (4H, m), 2.02-2.17 (2H, m), 1.92-2.05 (1H, m), 1.54-1.82 (3H, m), 0.92-1.11 (4H, m) |
| 210 | 4-cyclopropyl-5-bromo-pyrimidin-2-yl | 1.64 | 378.23 | ¹H NMR (400 MHz, MeOD) d ppm 8.42 (1H, s), 3.97 (1H, d, J = 10.07 Hz), 3.66 (1H, d, J = 10.07 Hz), 3.20 (1H, d), 3.06 (1H, d), 2.63-2.97 (4H, m), 2.35-2.50 (1H, m), 1.99-2.16 (2H, m), 1.50-1.83 (3H, m), 0.98-1.24 (4H, m) |
| 211 | 1-methyl-6-methoxy-indazol-3-yl | 0.64 | 342.18 | ¹H NMR (500 MHz, DMSO-D6) δ ppm 7.98 (s, 1H), 7.46 (t, J = 7.93 Hz, 1H), 6.91 (d, J = 5.49 Hz, 1H), 6.59-6.65 (m, 1H), 3.82-3.88 (m, 6H), 3.82 (s, 2H), 3.55 (s, 1H), 3.00 (s, 2H), 2.78 (s, 2H), 2.67 (d, J = 6.71 Hz, 2H), 2.01 (s, 1H), 1.91 (s, 1H), 1.59 (s, 2H), 1.46 (s, 1H) |
| 212 | 1-methyl-5-methoxy-indazol-3-yl | 0.63 | 342.25 | ¹H NMR (500 MHz, DMSO-D6) δ ppm 7.94 (s, 1H), 7.37 (d, J = 9.16 Hz, 1H), 7.02 (d, J = 9.46 Hz, 1H), 6.99 (d, J = 1.83 Hz, 1H), 3.87 (s, 3H), 3.82 (d, J = 9.46 Hz, 1H), 3.78 (s, 3H), 3.56 (d, J = 9.16 Hz, 1H), 3.00 (s, 2H), 2.78 (s, 2H), 2.63-2.70 (m, 2H), 2.01 (s, 1H), 1.91 (s, 1H), 1.58 (s, 2H), 1.46 (s, 1H) |
| 213 | 5-chloro-pyrimidin-2-yl | 0.35 | 294.25 | ¹H NMR (400 MHz, MeOD) d ppm 8.51 (2H, s), 4.00 (1H, d, J = 10.32 Hz), 3.69 (1H, d, J = 10.32 Hz), 3.22 (1H, d), 3.08 (1H, d), 2.70-2.98 (4H, m), 2.01-2.21 (2H, m), 1.50-1.84 (3H, m) |

TABLE 3-continued

| Example Number | R₁ | LCMS RT (min) | LCMS Ion [M + H]⁺ | ¹H NMR |
|---|---|---|---|---|
| 214 | | 0.36 | 293.14 | ¹H NMR (500 MHz, DMSO-D6) δ ppm 8.80 (s, 1H), 8.19 (s, 1H), 7.66 (s, 1H), 6.80 (s, 1H), 3.81 (s, 1H), 3.56 (d, J = 10.07 Hz, 1H), 2.92-3.01 (m, 2H), 2.70-2.79 (m, 2H), 2.62-2.68 (m, 2H), 1.97 (s, 1H), 1.87 (s, 1H), 1.57 (d, J = 7.32 Hz, 2H), 1.40-1.49 (m, 1H) |
| 215 | | 0.35 | 293.14 | ¹H NMR (500 MHz, DMSO-D6) δ ppm 9.01 (s, 1H), 8.17 (d, J = 5.49 Hz, 2H), 6.97 (s, 2H), 6.83 (s, 1H), 3.83 (s, 2H), 3.57 (d, J = 10.38 Hz, 2H), 2.93-3.01 (m, 3H), 2.74-2.82 (m, 3H), 2.73 (s, 1H), 2.66 (t, J = 7.63 Hz, 3H), 1.98 (s, 2H), 1.87 (s, 2H), 1.53-1.62 (m, 3H), 1.41-1.49 (m, 2H) |
| 216 | | 0.82 | 318.30 | ¹H NMR (400 MHz, CDCl₃) δ ppm 8.56 (1H, br. s.), 7.94 (1H, d, J = 1.26 Hz), 7.72 (1H, d, J = 1.26 Hz), 5.14 (1H, spt, J = 6.13 Hz), 3.85 (1H, d, J = 9.06 Hz), 3.52 (1H, d, J = 9.06 Hz), 3.30 (1H, dd, J = 14.86, 1.51 Hz), 2.67-3.03 (5H, m), 2.11-2.26 (1H, m, J = 13.17, 9.84, 3.65, 3.42, 3.42 Hz), 2.07 (1H, br. s.), 1.62-1.75 (1H, m), 1.41-1.59 (2H, m), 1.30 (6H, d, J = 6.30 Hz) |
| 217 | | 0.18 | 342.19 | ¹H NMR (400 MHz, DMSO-D6) δ ppm 8.09 (s, 1H), 7.53 (s, 1H), 3.80 (s, 1H), 3.54 (d, J = 10.32 Hz, 1H), 3.07-3.18 (m, 1H), 2.91-3.01 (m, 3H), 2.75 (d, J = 8.31 Hz, 2H), 2.60-2.71 (m, 2H), 2.19 (q, J = 8.90 Hz, 1H), 2.01-2.12 (m, 4H), 1.94 (s, 1H), 1.83 (d, J = 15.11 Hz, 2H), 1.56 (s, 3H), 1.43 (s, 1H) |

EXAMPLE 218

(R)—N-(6-(methoxymethyl)pyrimidin-4-yl)-4H-1'-azaspiro[oxazole-5,3'-bicyclo[2.2.2]octan]-2-amine

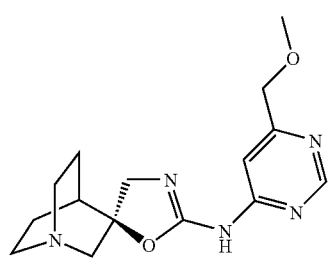

Step A: 6-(Methoxymethyl)pyrimidin-4-ol

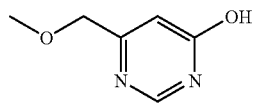

To a solution of methyl 4-methoxy-3-oxobutanoate (3.54 mL, 26.5 mmol) in methanol (30 ml) was added formamidine acetate (3.07 g, 29.2 mmol) and sodium methoxide (13 mL, 58.4 mmol). The mixture was then heated to reflux for 18 hours and cooled to ambient temperature, then concentrated. The residue was taken up in water and the pH adjusted to 7 with 1N HCl. The aqueous mixture was extracted with chloroform. The combined organic layers were dried over magnesium sulfate, filtered and concentrated to afford 6-(methoxymethyl)pyrimidin-4-ol (1.38 g, 9.85 mmol, 37.1% yield). MS (LC/MS) R.T.=0.19; [M+H]⁺=141.20.

Step B: 4-Chloro-6-(methoxymethyl)pyrimidine

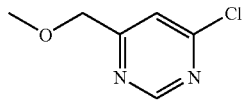

6-(Methoxymethyl)pyrimidin-4-ol (1.38 g, 9.85 mmol) was taken up in dichloromethane (14 ml) and phosphorous oxychloride (9 mL, 97 mmol) was added at ambient temperature. The mixture was stirred at ambient for 18 h and concentrated. The residue was taken up in ice-water and the pH was adjusted to 7 with 1N sodium hydroxide. The mixture was extracted with chloroform and dried over sodium sulfate, filtered and concentrated in vacuo. The residue was purified by column chromatography (5-10% ethyl acetate/chloroform) to afford 4-chloro-6-(methoxymethyl)pyrimidine (1.2 g, 7.57 mmol, 77% yield) as a pale yellow oil, which solidified on standing. 1H NMR (400 MHz, CDCl₃) δ ppm 8.88 (1 H, d, J=1.01 Hz), 7.52 (1 H, d, J=1.01 Hz), 4.53 (2 H, s), 3.50 (3 H, s). MS (LC/MS) R.T.=0.98; [M+H]⁺=159.10.

Step C: 6-(Methoxymethyl)pyrimidin-4-amine

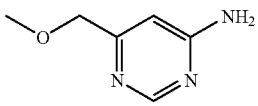

A mixture of 4-chloro-6-(methoxymethyl)pyrimidine (1.2 g, 7.57 mmol) and ammonium hydroxide (20 ml) was heated in a sealed tube for 3 hours. The mixture was cooled to ambient temperature and concentrated. The residue was triturated with ether to afford 6-(methoxymethyl)pyrimidin-4-amine (0.50 g, 3.59 mmol, 48% yield) as a pale yellow solid. ¹H NMR (400 MHz, CDCl₃) δ ppm 8.47 (1 H, s), 6.55 (1 H, s), 5.12 (2 H, br. s.), 4.38 (2 H, s), 3.45 (3 H, s). MS (LC/MS) R.T.=0.42; [M+H]⁺=140.20.

Step D: 4-Isothiocyanato-6-(methoxymethyl)pyrimidine

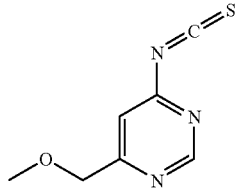

To a bright orange solution of 1,1'-thiocarbonyldipyridin-2(1H)-one (0.84 g, 3.59 mmol) was in dichloromethane at ambient temperature was added 6-(methoxymethyl)pyrimidin-4-amine (0.5 g, 3.59 mmol). The orange solution was stirred at ambient temperature for 18 h. The solution was purified by column chromatography (0-40% ethyl acetate/hexanes) to afford 4-isothiocyanato-6-(methoxymethyl)pyrimidine (0.32 g, 1.77 mmol, 49% yield) as a yellow solid. ¹H NMR (400 MHz, CDCl₃) δ ppm 8.91 (1 H, d, J=1.26 Hz), 7.19 (1 H, d, J=1.01 Hz), 4.52 (2 H, s), 3.49 (3 H, s). MS (LC/MS) R.T.=1.39; [M+H]⁺=182.10.

Step E: (R)—N-(6-(Methoxymethyl)pyrimidin-4-yl)-4 H-1'-azaspiro[oxazole-5,3'-bicyclo[2.2.2]octan]-2-amine

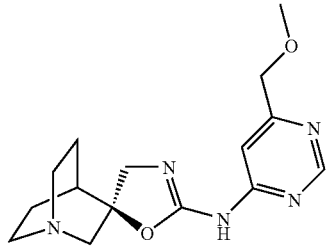

To (S)-3-(aminomethyl)quinuclidin-3-ol dihydrochloride (0.39 g, 1.71 mmol) in dimethylformamide was added cesium carbonate (1.39 g, 4.28 mmol) and 4-isothiocyanato-6-(methoxymethyl)pyrimidine (0.31 g, 1.71 mmol). The suspension was stirred at ambient temperature for 15 min. To the reaction mixture was added N,N'-diisopropylcarbodiimide (0.80 mL, 5.13 mmol) and the mixture was stirred overnight then concentrated. The residue was purified by column chromatography (5-25% 9:1 methanol/ammonium hydroxide in ethyl acetate) to afford (R)—N-(6-(methoxymethyl)pyrimidin-4-yl)-4 H-1'-azaspiro[oxazole-5,3'-bicyclo[2.2.2]octan]-2-amine (0.18 g, 0.58 mmol, 34% yield) as a yellow solid. ¹H NMR (400 MHz, MeOD-d₄) δ ppm 8.65 (1 H, d, J=1.01 Hz), 6.92 (1 H, br. s.), 4.40 (3 H, s), 4.03 (1 H, d, J=10.32 Hz), 3.72 (1 H, d, J=10.32 Hz), 3.44 (2 H, s), 3.18-3.26 (1 H, m), 3.06-3.13 (1 H, m), 2.69-2.96 (4 H, m), 1.94-2.19 (2 H, m), 1.45-1.86 (3 H, m). MS (LC/MS) R.T.=0.76; [M+H]⁺=304.30.

EXAMPLE 219

(R)—N-(5-(Cyclopentyloxy)pyrimidin-2-yl)-4 H-1'-azaspiro[oxazole-5,3'-bicyclo[2.2.2]octan]-2-amine

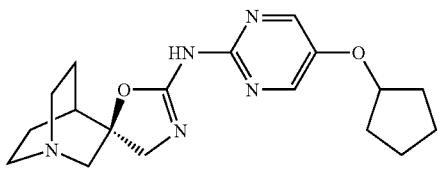

Step A: 2-Chloro-5-(cyclopentyloxy)pyrimidine

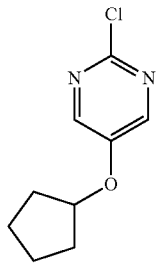

A mixture of 2-chloropyrimidin-5-ol (1 g, 7.66 mmol), chlorocyclopentane (2.39 mL, 22.98 mmol) and potassium carbonate (3.18 g, 22.98 mmol) in N,N-dimethylformamide were heated at 65° C. for 16 h at ambient temperature. Water was added and the mixture was extracted with ethyl acetate. The organic layer was washed with water and brine, dried over sodium sulfate and concentrated in vacuo. The residue was purified by column chromatography (0-25% ethyl acetate/hexanes) to afford 2-chloro-5-(cyclopentyloxy)pyrimidine (831 mg, 4.18 mmol, 54.6% yield) as a white solid. MS (LC/MS) R.T.=2.32; [M+H]⁺=199.23.

Step B: 5-(Cyclopentyloxy)pyrimidin-2-amine

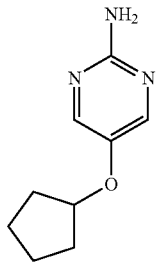

5-(Cyclopentyloxy)pyrimidin-2-amine was prepared from 2-chloro-5-(cyclopentyloxy)pyrimidine by following the general procedures of Example 218, Step C. ¹H NMR (400 MHz, DMSO-d₆) δ ppm 7.99 (2 H, s), 6.18 (2 H, s), 4.54-4.75 (1 H, m), 1.30-1.91 (8 H, m). MS (LC/MS) R.T.=1.47; [M+H]⁺=180.24.

Step C: (R)—N-(5-(Cyclopentyloxy)pyrimidin-2-yl)-4H-1'-azaspiro[oxazole-5,3'-bicyclo[2.2.2]octan]-2-amine

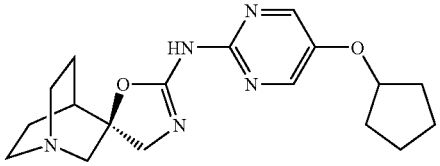

(R)—N-(5-(Cyclopentyloxy)pyrimidin-2-yl)-4H-1'-azaspiro[oxazole-5,3'-bicyclo[2.2.2]octan]-2-amine was prepared from 5-(cyclopentyloxy)pyrimidin-2-amine by following the general procedures of Example 23, Steps A-B. ¹H NMR (400 MHz, MeOD-d₄) δ ppm 8.24 (2 H, s), 4.76-4.86 (1 H, m), 3.98 (1 H, d, J=10.07 Hz), 3.69 (1 H, d, J=10.07 Hz), 3.33 (1 H, d), 3.20 (1 H, d), 2.77-3.08 (4 H, m), 2.04-2.26 (2 H, m), 1.49-2.03 (11 H, m). MS (LC/MS) R.T.=1.56; [M+H]⁺=344.32.

The compounds in Table 5 were synthesized according to the method of Example 218 using the appropriate commercially available chlorides as in Example 218, Step C.

TABLE 4

| Example Number | R₁ | LCMS RT (min) | LCMS Ion [M + H]⁺ | ¹H NMR |
|---|---|---|---|---|
| 220 | quinoxalin-2-yl | 0.99 | 310.30 | ¹H NMR (400 MHz, CDCl₃) δ ppm 9.82 (1H, br. s.), 8.62 (1H, s), 7.95 (1H, dd, J = 8.18, 1.13 Hz), 7.72 (1H, dd, J = 8.18, 1.13 Hz), 7.58-7.64 (1H, m, J = 7.62, 7.62, 7.05, 1.39 Hz), 7.51 (1H, ddd, J = 7.68, 7.05, 1.26 Hz), 4.05 (1H, d, J = 9.32 Hz), 3.70 (1H, d, J = 9.57 Hz), 3.39 (1H, dd, J = 14.86, 1.51 Hz), 2.72-3.06 (5H, m), 2.12-2.26 (2H, m), 1.69-1.80 (1H, m), 1.45-1.64 (2H, m). M.P. 212-5° C. |
| 221 | 6-chloroquinoxalin-2-yl | 1.32 | 180.99 | ¹H NMR (400 MHz, DMSO-d₆) δ ppm 8.31 (1H, s), 7.80 (1H, d, J = 2.52 Hz), 7.55 (1H, dd, J = 8.81, 2.52 Hz), 7.50 (1H, d, J = 9.06 Hz), 7.13 (2H, s) |
| 222 | thieno[2,3-d]pyrimidin-4-yl | 0.90 | 316.30 | ¹H NMR (400 MHz, MeOD-d₄) δ ppm 8.60 (s, 1H), 7.60 (d, J = 6.04 Hz, 1H), 7.52 (s, 1H), 4.04-4.17 (m, 1H), 3.73-3.87 (m, 1H), 3.23-3.26 (m, 1H), 3.07-3.19 (m, 1H), 2.88-3.01 (m, 2H), 2.75-2.88 (m, 2H), 2.08-2.27 (m, 2H), 1.56-1.86 (m, 3H) |

TABLE 4-continued

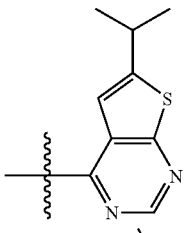

| Example Number | R₁ | LCMS RT (min) | LCMS Ion [M + H]⁺ | ¹H NMR |
|---|---|---|---|---|
| 223 | 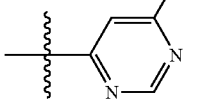 | 2.28 | 358.20 | ¹H NMR (400 MHz, MeOD-d₄) δ ppm 8.52 (1H, s), 7.30 (1H, d, J = 1.01 Hz), 4.03-4.09 (1H, m), 3.76 (1H, d, J = 10.07 Hz), 3.16-3.27 (2H, m), 3.06-3.14 (1H, m), 2.68-3.01 (4H, m), 2.01-2.23 (2H, m), 1.54-1.82 (3H, m), 1.37 (6H, d, J = 6.80 Hz) |
| 224 | 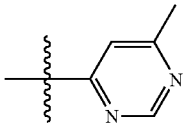 | 0.86 | 302.24 | ¹H NMR (400 MHz, MeOD-d₄) δ ppm 8.63 (1H, s), 6.73 (1H, br. s.), 4.02 (1H, d, J = 10.32 Hz), 3.72 (1H, d, J = 10.32 Hz), 3.17-3.25 (1H, m), 3.01-3.13 (1H, m), 2.68-2.97 (5H, m), 1.98-2.16 (2H, m), 1.51-1.82 (3H, m), 1.24 (6H, d, J = 7.05 Hz) |
| 225 | 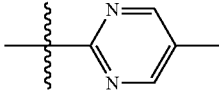 | 0.25 | 274.19 | ¹H NMR (400 MHz, MeOD-d₄) δ ppm 8.60 (1H, s), 6.71 (1H, br. s.), 4.02 (1H, d, J = 10.32 Hz), 3.71 (1H, d, J = 10.32 Hz), 3.17-3.24 (1H, m), 3.04-3.13 (1H, m), 2.65-3.02 (4H, m), 2.37 (3H, s), 1.99-2.20 (2H, m), 1.32-1.88 (3H, m) |
| 226 | 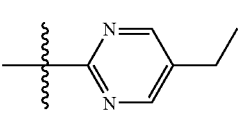 | 0.37 | 274.26 | ¹H NMR (400 MHz, MeOD-d₄) δ ppm 8.38 (2H, s), 3.97 (1H, d, J = 10.07 Hz), 3.66 (1H, d, J = 10.07 Hz), 3.16-3.25 (1H, m), 3.02-3.13 (1H, m), 2.92 (2H, t, J = 7.55 Hz), 2.73-2.86 (2H, m), 2.21 (3H, s), 2.03-2.16 (2H, m), 1.45-1.86 (3H, m) |
| 227 | 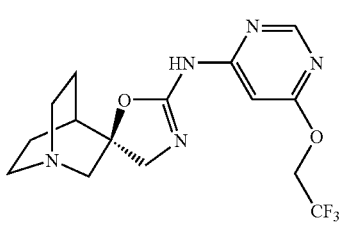 | 0.96 | 288.31 | ¹H NMR (400 MHz, MeOD-d₄) δ ppm 8.41 (2H, s), 3.98 (1H, d, J = 10.07 Hz), 3.67 (1H, d, J = 10.07 Hz), 3.17-3.25 (1H, m), 3.02-3.13 (1H, m), 2.92 (2H, t, J = 7.43 Hz), 2.72-2.87 (2H, m), 2.57 (2H, q, J = 7.55 Hz), 2.01-2.23 (2H, m), 1.48-1.84 (3H, m), 1.22 (3H, t, J = 7.68 Hz) |

EXAMPLE 228

(R)—N-(6-(2,2,2-Trifluoroethoxy)pyrimidin-4-yl)-4H-1'-azaspiro[oxazole-5,3-bicyclo[2.2.2]octan]-2-amine

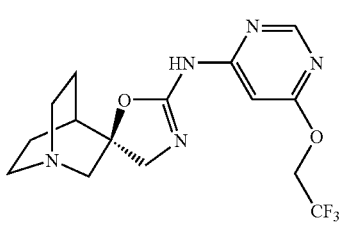

Step A:
4-Chloro-6-(2,2,2-trifluoroethoxy)pyrimidine

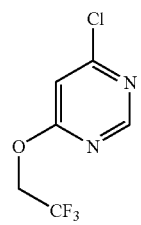

A solution of 2,2,2-trifluoroethanol (2.61 g, 26.10 mmol) in tetrahydrofuran (12 ml) was added dropwise to a suspension of sodium hydride (1.31 g, 32.60 mmol) in tetrahydrofuran (48 ml) at 0° C. The mixture was stirred at 0° C. for 30 min and a solution of 4,6-dichloropyrimidine (3.6 g, 24.16 mmol) in tetrahydrofuran (12 ml) was added at 0° C. The reaction mixture was stirred at ambient temperature for 3 h and poured into sat. aqueous ammonium chloride and extracted with ethyl acetate. The ethyl acetate extract was washed with water, dried over magnesium sulfate and concentrated in vacuo. The orange residue was purified by column chromatography (10-40% ethyl acetate/hexanes) to afford 4-chloro-6-(2,2,2-trifluoroethoxy)pyrimidine (2.0 g, 2.41 mmol, 38.9% yield) as a pale yellow oil. MS (LC/MS) R.T.=2.78; [M+H]$^+$=213.12.

Step B: 6-(2,2,2-Trifluoroethoxy)pyrimidin-4-amine

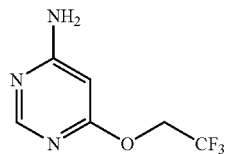

6-(2,2,2-trifluoroethoxy)pyrimidin-4-amine was prepared from 4-chloro-6-(2,2,2-trifluoroethoxy)pyrimidine by following the general procedure of Example 218, Step C. MS (LC/MS) R.T.=1.16; [M+H]$^+$=194.07.

Step C: (R)—N-(6-(2,2,2-Trifluoroethoxy)pyrimidin-4-yl)-4H-1'-azaspiro[oxazole-5,3'-bicyclo[2.2.2]octan]-2-amine

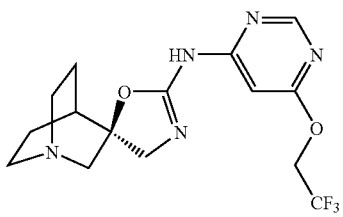

(R)—N-(6-(2,2,2-trifluoroethoxy)pyrimidin-4-yl)-4H-1'-azaspiro[oxazole-5,3'-bicyclo[2.2.2]octan]-2-amine was prepared from 6-(2,2,2-trifluoroethoxy)pyrimidin-4-amine by following the general procedures of Example 23, Steps A-B. $^1$H NMR (400 MHz, CDCl$_3$) δ ppm 9.30 (1 H, br. s.), 8.39 (1 H, s), 6.38 (1 H, br. s.), 4.59-4.84 (2 H, m), 3.94 (1 H, d, J=9.32 Hz), 3.59 (1 H, d, J=9.57 Hz), 3.33 (1 H, d, J=16.62 Hz), 2.61-3.01 (5 H, m), 1.97-2.25 (2 H, m), 1.37-1.81 (3 H, m). MS (LC/MS) R.T.=1.42; [M+H]$^+$=358.33.

EXAMPLE 229

(R)—N-(5-Bromo-4-isopropylpyrimidin-2-yl)-4H-1'-azaspiro[oxazole-5,3'-bicyclo[2.2.2]octan]-2-amine

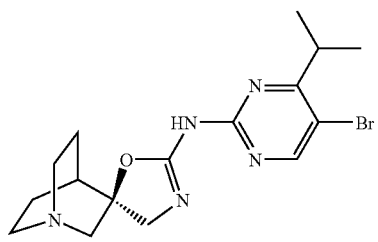

Step A: 4-Isopropylpyrimidin-2-amine

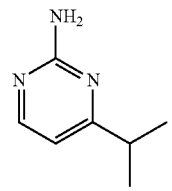

4-Isopropylpyrimidin-2-amine was prepared from 2-chloro-4-isopropylpyrimidine by following the general procedure for Example 218, Step C. $^1$H NMR (400 MHz, DMSO-d$_6$) d ppm 8.10 (1 H, d, J=5.04 Hz), 6.45 (3 H, d, J=5.04 Hz), 2.59-2.80 (1 H, m), 1.15 (6 H, d, J=7.05 Hz). MS (LC/MS) R.T.=0.76;
[M+H]$^+$=138.12.

Step B: 5-Bromo-4-isopropylpyrimidin-2-amine

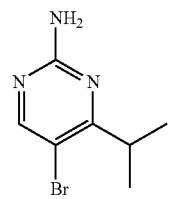

N-Bromosuccinimide (0.5 g, 2.8 mmol) was added to a solution of 4-isopropylpyrimidin-2-amine (0.39 g, 2.81 mmol) in chloroform. The resultant yellow solution was stirred at ambient temperature for 1 h and concentrated in vacuo. The residue was purified by column chromatography (3-10% 9:1 methanol:ammonium hydroxide in chloroform) to afford 5-bromo-4-isopropylpyrimidin-2-amine (0.69 g, 3.18 mmol, 113%) as a pale yellow solid. $^1$H NMR (400 MHz, DMSO-d$_6$) δ ppm 8.21 (1 H, s), 6.75 (2 H, s), 3.10-3.23 (1 H, m), 1.14 (6 H, d, J=6.80 Hz). MS (LC/MS) R.T.=2.58; [M]$^+$=216.09.

Step C: (R)—N-(5-Bromo-4-isopropylpyrimidin-2-yl)-4H-1'-azaspiro[oxazole-5,3'-bicyclo[2.2.2]octan]-2-amine

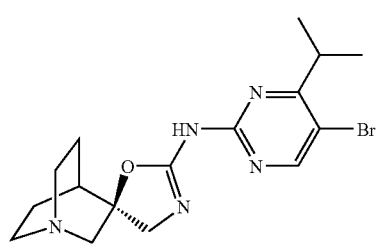

(R)—N-(5-Bromo-4-isopropylpyrimidin-2-yl)-4H-1'-azaspiro[oxazole-5,3'-bicyclo[2.2.2]octan]-2-amine was prepared from 5-bromo-4-isopropylpyrimidin-2-amine by following the general procedures of Example 23, Steps A-B. $^1$H NMR (400 MHz, MeOD-d$_4$) δ ppm 8.49 (1 H, s), 4.02 (1 H, d, J=10.07 Hz), 3.72 (1 H, d, J=10.07 Hz), 3.34-3.44 (1 H, m), 3.23 (1 H, s), 3.06-3.15 (1 H, m), 2.95 (2H, t, J=7.55 Hz), 2.75-2.89 (2 H, m), 2.00-2.21 (2 H, m), 1.52-1.83 (3 H, m), 1.24 (6H, d, J=6.80 Hz). MS (LC/MS) R.T.=1.84; [M+H]$^+$=382.24.

EXAMPLE 230

(R)—N-(5-Bromo-4-(pyridin-3-yl)pyrimidin-2-yl)-4H-1'-azaspiro[oxazole-5,3'-bicyclo[2.2.2]octan]-2-amine

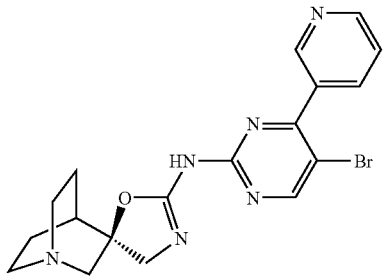

(R)—N-(5-Bromo-4-(pyridin-3-yl)pyrimidin-2-yl)-4H-1'-azaspiro[oxazole-5,3'-bicyclo[2.2.2]octan]-2-amine was prepared from 4-(pyridin-3-yl)pyrimidin-2-amine by following the general procedures of Example 229, Steps B-C. $^1$H NMR (400 MHz, MeOD-d$_4$) δ ppm 8.92 (1 H, d, J=1.51 Hz), 8.73 (1 H, s), 8.64 (1 H, dd, J=4.91, 1.64 Hz), 8.23 (1 H, dt, J=8.06, 1.89 Hz), 7.56 (1 H, dd, J=7.93, 4.91 Hz), 4.00 (1 H, d, J=10.07 Hz), 3.69 (1 H, d, J=10.07 Hz), 3.22 (1 H, d), 3.07 (1 H, d), 2.60-2.99 (4 H, m), 2.00-2.21 (2 H, m), 1.50-1.83 (3 H, m). MS (LC/MS) R.T.=0.76; [M+H]$^+$=416.30.

EXAMPLE 231

(R)—N-(6-(Cyclopentyloxy)pyrimidin-4-yl)-4H-1'-azaspiro[oxazole-5,3'-bicyclo[2.2.2]octan]-2-amine

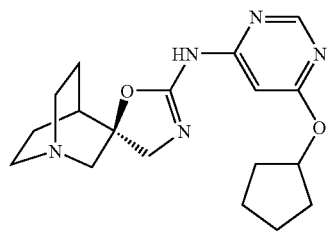

Step A: 4-Chloro-6-(cyclopentyloxy)pyrimidine

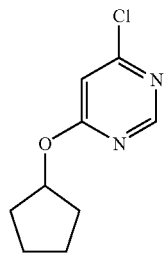

A solution of cyclopentanol (2.25 g, 26.1 mmol) in tetrahydrofuran (12 ml) was added dropwise to a suspension of sodium hydride (1.31 g, 32.6 mmol) in tetrahydrofuran (48 ml) at 0° C. The mixture was stirred at 0° C. for 30 min and a solution of 4,6-dichloropyrimidine (3.6 g, 24.16 mmol) in tetrahydrofuran (12 ml) was added at 0° C. The reaction mixture was stirred at ambient temperature for 3 h and poured into sat. aqueous ammonium chloride and extracted with ethyl acetate. The organic layers were washed with water, dried over magnesium sulfate and concentrated in vacuo. The orange residue was purified by column chromatography (10-40% ethyl acetate/hexanes). To afford 4-chloro-6-(cyclopentyloxy)pyrimidine as a pale yellow oil. This material was used directly for the next reaction.

Step B: 6-(Cyclopentyloxy)pyrimidin-4-amine

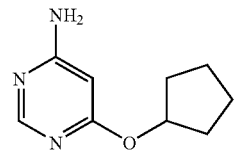

6-(Cyclopentyloxy)pyrimidin-4-amine was prepared from 4-chloro-6-(cyclopentyloxy)pyrimidine by following the general procedure of Example 218, Step C. MS (LC/MS) R.T.=1.64; [M+H]$^+$=180.22.

Step C: (R)—N-(6-(Cyclopentyloxy)pyrimidin-4-yl)-4H-1'-azaspiro[oxazole-5,3'-bicyclo[2.2.2]octan]-2-amine

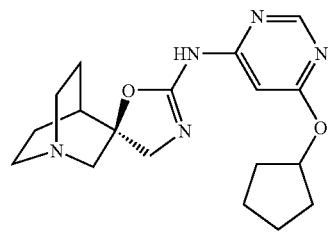

(R)—N-(6-(cyclopentyloxy)pyrimidin-4-yl)-4H-1'-azaspiro[oxazole-5,3'-bicyclo[2.2.2]octan]-2-amine was prepared from 6-(cyclopentyloxy)pyrimidin-4-amine by following the general procedures of Example 23, Steps A-B. $^1$H NMR (400 MHz, MeOD-d$_4$) δ ppm 8.37 (1 H, s), 6.16 (1 H, br. s.), 5.27 (1 H, br. s.), 3.98 (1 H, d, J=10.32 Hz), 3.67 (1 H, d, J=10.32 Hz), 3.15-3.24 (1 H, m), 3.02-3.12 (1 H, m), 2.71-2.97 (4 H, m), 2.01-2.14 (2 H, m), 1.87-2.00 (3 H, m), 1.49-1.84 (8 H, m). MS (LC/MS) R.T.=1.96; [M+H]$^+$=344.34.

EXAMPLE 232

(R)—N-(6-Isopropoxypyrimidin-4-yl)-4H-1'-azaspiro[oxazole-5,3'-bicyclo[2.2.2]octan]-2-amine

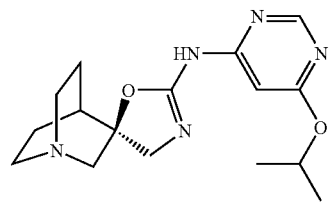

(R)—N-(6-Isopropoxypyrimidin-4-yl)-4H-1'-azaspiro[oxazole-5,3'-bicyclo[2.2.2]octan]-2-amine was prepared from 4,6-dichloropyrimidine by following the general procedures of Example 231, Steps A-C. $^1$H NMR (400 MHz, MeOD-d$_4$) δ ppm 8.37 (1 H, s), 6.13 (1 H, br. s.), 5.09-5.30 (1 H, m), 3.98 (1 H, d, J=10.32 Hz), 3.67 (1 H, d, J=10.32 Hz), 3.13-3.24 (1 H, m), 3.01-3.09 (1 H, m), 2.68-2.98 (4 H, m), 1.98-2.17 (2 H, m), 1.49-1.83 (3 H, m), 1.30(6 H, d, J=6.04 Hz). MS (LC/MS) R.T.=1.36; [M+H]$^+$=318.24.

EXAMPLE 233

(R)—N-(6-(2,2-Difluoroethoxy)pyrimidin-4-yl)-4H-1'-azaspiro[oxazole-5,3-bicyclo[2.2.2]octan]-2-amine

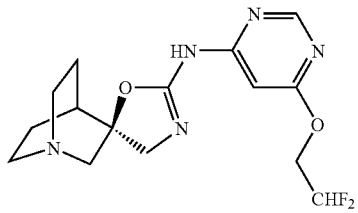

(R)—N-(6-(2,2-Difluoroethoxy)pyrimidin-4-yl)-4H-1'-azaspiro[oxazole-5,3'-bicyclo[2.2.2]octan]-2-amine was prepared from 4,6-dichloropyrimidine by following the general procedures of Example 231, Steps A-C. M.P. 83-8° C. 1H NMR (400 MHz, MeOD-$d_4$) δ ppm 8.42 (1 H, s), 5.93-6.37 (2 H, m), 4.52 (2 H, td, J=13.98, 3.78 Hz), 3.99 (1 H, d, J=10.32 Hz), 3.68 (1 H, d, J=10.32 Hz), 3.19 (1 H, d), 3.07 (1 H, d), 2.67-2.97 (4 H, m), 1.99-2.19 (2 H, m), 1.51-1.82 (3 H, m). MS (LC/MS) R.T.=0.99; [M+H]$^+$=340.26.

EXAMPLE 234

(R)—N-(Pyridin-2-yl)-4H-1'-azaspiro[oxazole-5,3'-bicyclo[2.2.2]octan]-2-amine

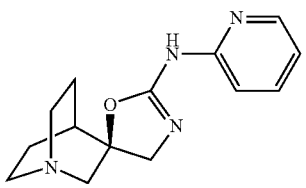

(R)—N-(Pyridin-2-yl)-4H-1'-azaspiro[oxazole-5,3'-bicyclo[2.2.2]octan]-2-amine was prepared from (R)—N-(6-bromopyridin-2-yl)-4H-1'-azaspiro[oxazole-5,3'-bicyclo[2.2.2]octan]-2-amine (from Example 155) according to the general procedure of Example 19, Step C. $^1$H NMR (500 MHz, MeOD-$d_4$) δ ppm 8.26 (d, J=4.88 Hz, 1 H), 7.58-7.74 (m, 1 H), 6.85-7.02 (m, 2 H), 4.00 (d, J=10.07 Hz, 1H), 3.70 (d, J=10.07 Hz, 1 H), 3.26-3.35 (m, 1 H), 3.14-3.21 (m, 1 H), 3.02 (d, J=8.24 Hz, 2 H), 2.84-2.97 (m, 2 H), 2.11-2.25 (m, 2 H), 1.58-1.92 (m, 3 H). MS (LC/MS) R.T.=0.30; [M+H]$^+$=259.16.

EXAMPLE 235

(R)—N-(Pyridin-4-yl)-4H-1'-azaspiro[oxazole-5,3'-bicyclo[2.2.2]octan]-2-amine

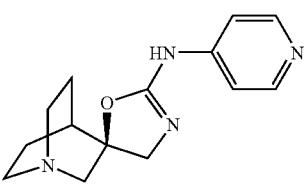

(R)—N-(Pyridin-4-yl)-4H-1'-azaspiro[oxazole-5,3'-bicyclo[2.2.2]octan]-2-amine was prepared from (R)—N-(2-bromopyridin-4-yl)-4H-1'-azaspiro[oxazole-5,3'-bicyclo[2.2.2]octan]-2-amine (from Example 154) according to the procedure of Example 19, Step C. $^1$H NMR (500 MHz, MeOD-$d_4$) δ ppm 8.31 (d, J=6.41 Hz, 2 H), 7.39 (d, J=3.97 Hz, 2 H), 4.01 (d, J=12.21 Hz, 1 H), 3.70 (d, J=11.90 Hz, 1 H), 3.37 (s, 1 H), 3.29 (s, 1 H), 3.18 (d, J=1.83 Hz, 1 H), 3.15 (d, J=2.14 Hz, 1 H), 2.86-3.09 (m, 3 H), 2.02-2.20 (m, 1 H), 1.59-1.88 (m, 3 H). MS (LC/MS) R.T.=0.22; [M+H]$^+$=259.16.

EXAMPLE 236

(R)—N-(5-(Benzyloxy)thiazolo[5,4-b]pyridin-2-yl)-4H-1'-azaspiro[oxazole-5,3'-bicyclo[2.2.2]octan]-2-amine

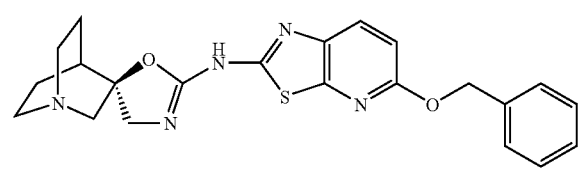

Step A:
5-(Benzyloxy)thiazolo[5,4-b]pyridin-2-amine

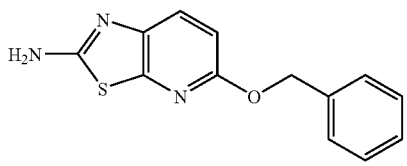

Potassium thiocyanate (12.42 g, 128 mmol) was suspended in acetic acid (45.0 mL) and cooled to 0° C. 6-(Benzyloxy)pyridin-3-amine (3.2 g, 15.98 mmol), prepared according to WO2006/044707 was added. Bromine (2.55 mL, 49.5 mmol) in acetic acid (15 mL) was added dropwise over 30 minutes during which time the reaction mixture became very thick. It was allowed to warm to room temperature slowly and stirred overnight.

Water (20 ml) was added and the reaction mixture was heated to 90° C. and filtered hot. The filtrate was saved and the filter cake returned to the reaction flask, to which was added an additional 40 ml HOAc. The mixture was again heated to 90° C. and filtered hot. The combined filtrates were cooled on ice bath and NH$_4$OH was added dropwise until pH>8. A yellow precipitate formed which was collected by filtration. The solids were dried in vacuo for 1 h to provide 5-(benzyloxy)thiazolo[5,4-b]pyridin-2-amine (1.95 g, 7.58 mmol, 47.4% yield), which was used without further purification. 1H NMR (400 MHz, CDCl$_3$) δ ppm 7.70 (d, J=8.78 Hz, 1 H) 7.48 (d, J=7.28 Hz, 2 H) 7.39 (t, J=7.28 Hz, 2 H) 7.30-7.36 (m, 1 H) 6.78 (d, J=8.78 Hz, 1 H) 5.39 (s, 2 H) 5.14 (br. s., 2 H).

Step B: Dimethyl 5-(benzyloxy)thiazolo[5,4-b]pyridin-2-ylcarbonimidodithioate

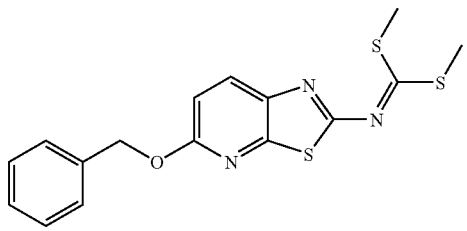

To a suspension of 5-(benzyloxy)thiazolo[5,4-b]pyridin-2-amine (800 mg, 3.11 mmol) in DMF (3.1 mL) was added 20.0M sodium hydroxide (0.3 mL, 6.22 mmol). The mixture was allowed to stir 10 min at room temperature at which time carbon disulfide was added (0.47 mL, 7.77 mmol) and the mixture was stirred for 10 minutes. An additional portion of 20.0M sodium hydroxide (0.3 mL, 6.22 mmol) was added and the mixture was again stirred for 10 minutes. Finally, iodomethane (0.47 mL, 7.46 mmol) was added dropwise. The mixture was stirred for 1 hour, at which time it was poured into water and extracted with EtOAc (3×). The combined organics were washed with brine, dried over sodium sulfate, filtered and concentrated in vacuo. The crude mixture was purified by silica gel chromatography (2-20% EtOAc/CHCl$_3$) to provide dimethyl 5-(benzyloxy)thiazolo[5,4-b]pyridin-2-ylcarbonimidodithioate (1.02 g, 91% yield) as a yellow crystalline solid. 1H NMR (400 MHz, CDCl$_3$) δ ppm 8.02 (d, J=8.78 Hz, 1H) 7.51 (d, J=7.28 Hz, 2H) 7.38-7.45 (m, 2 H) 7.32-7.38 (m, 1 H) 6.89 (d, J=8.53 Hz, 1 H) 5.46 (s, 2 H) 2.65 (s, 6 H).

Step C: (R)—N-(5-(benzyloxy)thiazolo[5,4-b]pyridin-2-yl)-4H-1'-azaspiro[oxazole-5,3'-bicyclo[2.2.2]octan]-2-amine

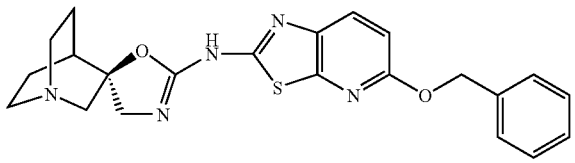

A mixture of dimethyl 5-(benzyloxy)thiazolo[5,4-b]pyridin-2-ylcarbonimidodithioate (500 mg, 1.38 mmol), (S)-3-(aminomethyl)quinuclidin-3-ol dihydrochloride (317 mg, 1.38 mmol) and cesium carbonate (1.0 g, 3.07 mmol) in DMF (7 mL) was heated to 100° C. for 2 hours. The reaction mixture was cooled to ambient temperature, poured into water and extracted with chloroform (4×). The combined organics were washed with brine, dried over sodium sulfate, filtered and concentrated in vacuo. The mixture was purified by silica gel chromatography (2-20% [9:1 methanol:ammonium hydroxide]-chloroform) to afford (R)—N-(5-(benzyloxy)thiazolo[5,4-b]pyridin-2-yl)-4H-1'-azaspiro[oxazole-5,3'-bicyclo[2.2.2]octan]-2-amine (390 mg, 67% yield). 1H NMR (500 MHz, CDCl$_3$) δ ppm 9.18 (br. s., 1 H) 7.76 (d, J=8.85 Hz, 1 H) 7.50 (d, J=7.32 Hz, 2 H) 7.41 (t, J=7.32 Hz, 2 H) 7.32-7.37 (m, 1 H) 5.42 (s, 2 H) 4.02 (d, J=9.46 Hz, 1 H) 3.68 (d, J=9.46 Hz, 1 H) 3.37-3.44 (m, 1 H) 2.75-3.06 (m, 5 H) 2.13-2.25 (m, 2 H) 1.73-1.82 (m, 1 H) 1.49-1.70 (m, 3 H). MS (LC/MS) R.T.=1.69; [M+H]$^+$=421.98.

EXAMPLE 237

(R)-2-(4H-1'-azaspiro[oxazole-5,3'-bicyclo[2.2.2]octane]-2-ylamino)thiazolo[5,4-b]pyridin-5(4H)-one

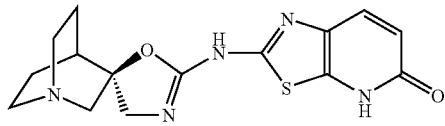

(R)—N-(5-(benzyloxy)thiazolo[5,4-b]pyridin-2-yl)-4H-1'-azaspiro[oxazole-5,3'-bicyclo[2.2.2]octan]-2-amine (390 mg, 0.925 mmol) was dissolved in TFA and allowed to react for 4 hours at ambient temperature, at which time LCMS and TLC showed the starting material to be mostly consumed. The TFA was removed in vacuo and the crude mixture was purified by preparative HPLC. The combined product fractions were concentrated in vacuo and triturated with ether to afford (R)-2-(4H-1'-azaspiro[oxazole-5,3'-bicyclo[2.2.2]octane]-2-ylamino)thiazolo[5,4-b]pyridin-5(4H)-one, TFA (164 mg, 0.368 mmol, 39.8% yield). M.P. 245 (dec). 1H NMR (400 MHz, DMSO-d$_6$) δ ppm 9.99 (br. s., 1 H) 9.05 (br. s., 1 H) 7.81 (d, J=8.53 Hz, 1 H) 6.65 (d, J=8.78 Hz, 1 H) 3.96 (d, J=10.29 Hz, 1 H) 3.82 (d, J=Hz, 1 H) 3.63-3.78 (m, 2 H) 3.36-3.47 (m, 1 H) 3.16-3.34 (m, 3 H) 2.43 (br. s., 1 H) 2.16 (br. s., 1 H) 1.76-2.07 (m, 3 H). MS (LC/MS) R.T.=0.50; [M+H]$^+$=332.15.

EXAMPLE 238

(R)—N-(6-(3-Methoxyphenyl)pyrimidin-4-yl)-4H-1'-azaspiro[oxazole-5,3'-bicyclo[2.2.2]octan]-2-amine

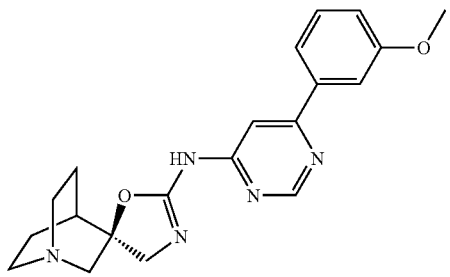

Step A: 6-(3-Methoxyphenyl)pyrimidin-4-amine

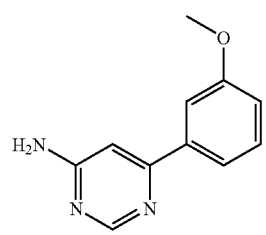

A mixture of 6-chloropyrimidin-4-amine (0.324 g, 2.5 mmol), 3-methoxyphenylboronic acid (0.475 g, 3.13 mmol), Na₂CO₃ (0.795 g, 7.50 mmol) and bis(triphenylphosphine)palladium(II)chloride (0.035 g, 0.050 mmol) was suspended in DME/EtOH/water (15:2:3 mL), heated in the microwave synthesizer at 125° C. for 20 min and concentrated. The residue was purified by silica gel chromatography (10-60% ethyl acetate-hexanes) to afford 6-(3-methoxyphenyl)pyrimidin-4-amine (0.35 g, 1.74 mmol, 70% yield) as an off-white solid. LCMS R.T.=1.28; [M+H]⁺=201.98.

Step B:
4-Isothiocyanato-6-(3-methoxyphenyl)pyrimidine

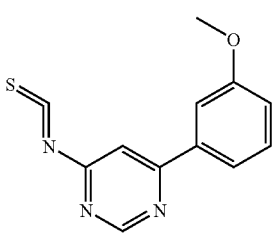

To a solution of 1,1'-thiocarbonyldipyridin-2(1H)-one (0.970 g, 4.17 mmol) in dichloromethane at room temperature was added 6-(3-methoxyphenyl)pyrimidin-4-amine (0.7 g, 3.48 mmol). The reaction was stirred at room temperature for 18 hours. The LC/MS showed the desired product peak as a major peak. The deep orange solution was concentrated and the remaining residue was filtered. The filtrate was purified by silica gel chromatography (0-10% ethyl acetate-hexanes) to afford 4-isothiocyanato-6-(3-methoxyphenyl)pyrimidine (0.39 g, 4.31 mmol, 46% yield) as a yellow oil. LCMS R.T.=2.91; [M+H]⁺=244.03.

Step C: R)—N-(6-(3-Methoxyphenyl)pyrimidin-4-yl)-4H-1'-azaspiro[oxazole-5,3'-bicyclo[2.2.2]octan]-2-amine

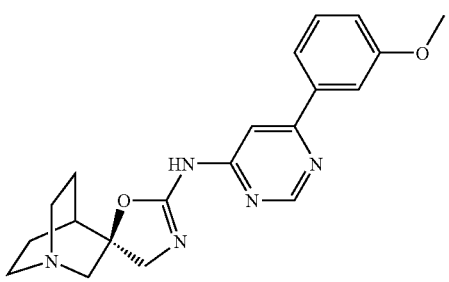

To (S)-3-(aminomethyl)quinuclidin-3-ol dihydrochloride (0.363 g, 1.583 mmol) in N,N-dimethylformamide (20 mL) was added Cs₂CO₃ (1.289 g, 3.96 mmol) and 4-isothiocyanato-6-(3-methoxyphenyl)pyrimidine. The suspension was stirred at room temperature for 30 minutes. N,N'-diisopropylcarbodiimide (0.740 mL, 4.75 mmol) was then added and the mixture was continued to stir at room temperature for 18 hours. The mixture was concentrated and purified by silica gel chromatography (5-25% 9:1 methanol:ammonium hydroxide-ethyl acetate) to afford (R)—N-(6-methoxypyrimidin-4-yl)-4H-1'-azaspiro[oxazole-5,3'-bicyclo[2.2.2]octan]-2-amine (0.294 g, 0.788 mmol, 50% yield) as a a pale yellow solid. M.P 80-5° C. ¹H NMR (400 MHz, MeOD) δ ppm 8.77 (1 H, s), 7.47-7.58 (2 H, m), 7.39 (1 H, t), 7.20 (1 H, br. s.), 7.04 (1 H, dd), 4.05 (1 H, d), 3.85 (3 H, s), 3.74 (1 H, d), 3.23 (1 H, d), 3.10 (1 H, d), 2.71-3.00 (4 H, m), 2.03-2.22 (2 H, m), 1.53-1.85 (3 H, m). MS (LC/MS) R.T.=1.58; [M+H]⁺=366.15.

EXAMPLE 239

(R)—N-(Isoquinolin-3-yl)-4H-1'-azaspiro[oxazole-5,3'-bicyclo[2.2.2]octan]-2-amine

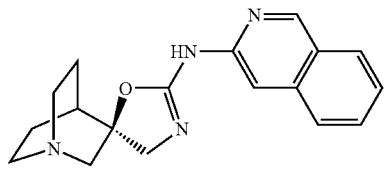

Step A: 3-Isothiocyanatoisoquinoline

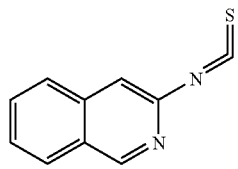

To a solution of 1,1'-thiocarbonyldipyridin-2(1H)-one (0.805 g, 3.47 mmol) in dichloromethane at room temperature was added isoquinolin-3-amine (0.5 g, 3.47 mmol). The reaction was stirred at room temperature for 18 hours. The LC/MS showed the desired product peak a major peak. The deep orange solution was concentrated and filtered. The filtrate was purified by silica gel chromatography (0-40% ethyl acetate-hexanes) to afford 4-isothiocyanato-6-(3-methoxyphenyl)pyrimidine (0.55 g, 2.96 mmol, 85% yield) a white solid. LCMS R.T.=2.47; [M+H]⁺=187.23.

Step B: (R)—N-(Isoquinolin-3-yl)-4H-1'-azaspiro[oxazole-5,3'-bicyclo[2.2.2]octan]-2-amine

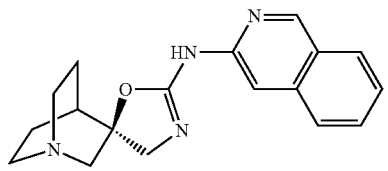

To (S)-3-(aminomethyl)quinuclidin-3-ol dihydrochloride (0.2 g, 0.873 mmol) in N,N-dimethylformamide (20 mL) was added Cs₂CO₃ (0.711 g, 2.182 mmol) and 3-isothiocyanatoisoquinoline (0.163 g, 0.873 mmol). The suspension was stirred at room temperature for 30 minutes. N,N'-Diisopropylcarbodiimide (0.408 mL, 2.62 mmol) was then added and the mixture was stirred at room temperature for 18 hours. The mixture was concentrated and purified by silica gel chromatography (5-25% [9:1 methanol:ammonium hydroxide]-ethyl acetate) to afford (R)—N-(isoquinolin-3-yl)-4H-1'-azaspiro[oxazole-5,3'-bicyclo[2.2.2]octan]-2-amine (0.16 g, 0.508 mmol, 58% yield) as an off-white solid. M.P. 196-200° C. $^1$H NMR (400 MHz, MeOD) δ ppm 9.00 (1 H, s), 7.92 (1 H, d), 7.71 (1 H, d), 7.59 (1 H, t), 7.20-7.45 (2 H, m), 3.96 (1 H, d), 3.65 (1 H, d), 3.22 (1 H, d), 3.08 (1 H, d), 2.66-3.00 (4 H, m), 2.05-2.23 (2 H, m), 1.50-1.86 (3 H, m). R.T.=1.37; [M+H]$^+$=309.31.

EXAMPLE 240

(R)—N-(6-Phenoxypyrimidin-4-yl)-4H-1'-azaspiro[oxazole-5,3'-bicyclo[2.2.2]octan]-2-amine

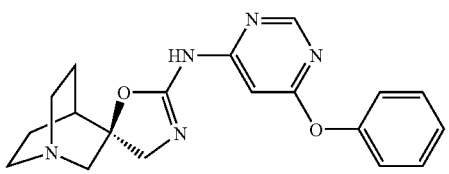

Step A: 6-Phenoxypyrimidin-4-amine

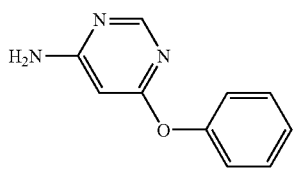

6-Chloropyrimidin-4-amine (3.00 g, 23.14 mmol) was added to a solution of sodium (0.197 g, 8.57 mmol) in phenol (11.29 g, 120 mmol) at 55° C. The mixture was heated at 140° C. for 2 h, then held at room temperature for 20 h. The reaction mixture was poured into 32% aqueous NaOH on ice/water keeping the mixture temperature below 20° C. The mixture was extracted with chloroform and the organic extract dried over calcium chloride and concentrated. The residue was purified by silica gel chromatography (2-20% ethyl acetate in hexanes) to afford 6-phenoxypyrimidin-4-amine (0.6 g, 3.21 mmol, 75% yield) as a white solid. LCMS R.T.=1.37; [M+H]$^+$=197.95.

Step B: 4-Isothiocyanato-6-phenoxypyrimidine

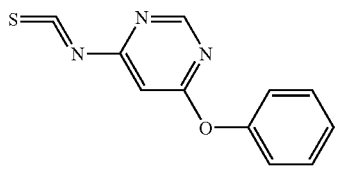

A mixture of 6-phenoxypyrimidin-4-amine (0.288 g, 1.538 mmol) and 1,1'-thiocarbonyldipyridin-2(1H)-one (0.357 g, 1.538 mmol) in DCM was stirred at rt for 18 h. The pale orange mixture was purified by silica gel chromatography (5-35% ethyl acetate-hexanes) to afford 4-isothiocyanato-6-phenoxypyrimidine (0.55 g, 2.96 mmol, 85% yield) a yellow oil. LCMS R.T.=2.78; [M+H]$^+$=229.94.

Step C: (R)—N-(6-Phenoxypyrimidin-4-yl)-4H-1'-azaspiro[oxazole-5,3'-bicyclo[2.2.2]octan]-2-amine

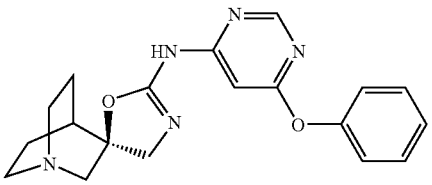

To (S)-3-(aminomethyl)quinuclidin-3-ol dihydrochloride (0.170 g, 0.742 mmol) in N,N-dimethylformamide (20 mL) was added Cs$_2$CO$_3$ (0.604 g, 1.854 mmol) and 4-isothiocyanato-6-phenoxypyrimidine (0.17 g, 0.742 mmol). The suspension was stirred at room temperature for 30 minutes. N,N'-diisopropylcarbodiimide (0.347 mL, 2.225 mmol) was then added and the mixture was continued to stir at room temperature for 18 hours. The mixture was concentrated and purified by silica gel chromatography (5-25% 9:1 methanol:ammonium hydroxide-ethyl acetate) to afford (R)—N-(6-phenoxypyrimidin-4-yl)-4H-1'-azaspiro[oxazole-5,3'-bicyclo[2.2.2]octan]-2-amine (0.21 g, 0.72 mmol, 48.2% yield) as a pale yellow solid. $^1$H NMR (500 MHz, MeOD) δ ppm 8.43 (1 H, s), 7.47 (2 H, t), 7.30 (1 H, t), 7.16 (2 H, d), 6.21 (1 H, br. s.), 4.03 (1 H, d), 3.72 (1 H, d), 3.22 (1 H, d), 3.11 (1 H, d), 2.73-2.99 (4 H, m), 2.00-2.18 (2 H, m), 1.54-1.88 (3 H, m). LCMS R.T.=1.46; [M+H]$^+$=352.19.

EXAMPLE 241

(R)—N-(7-methoxyquinoxalin-2-yl)-4H-1'-azaspiro[oxazole-5,3'-bicyclo[2.2.2]octan]-2-amine

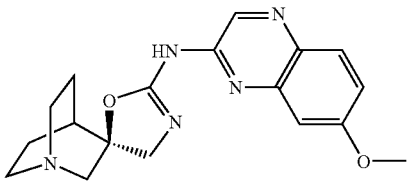

Step A: N-(2,4-Dimethoxybenzyl)-7-methoxyquinoxalin-2-amine

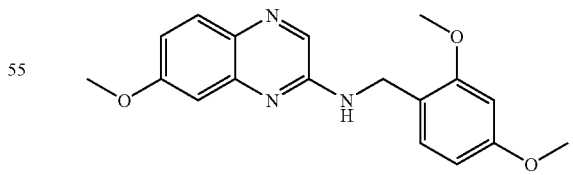

2-Chloro-7-methoxyquinoxaline (0.51 g, 2.62 mmol), prepared according to *J. Chem. Soc. Perk Trans.* 1, 2001, 978-984, and (2,4-dimethoxyphenyl)methanamine (1.181 mL, 7.86 mmol) were microwaved in DMSO (2.5 mL) for 30 min at 150° C. This was diluted into 150 mL EtOAc and extracted three times with 100 mL brine. The crude product was purified by flash chromatography on a 90 g silica gel cartridge with 20 to 80% EtOAc in hexane, 50 min, at 40 mL/min to afford N-(2,4-dimethoxybenzyl)-7-methoxyquinoxalin-2-amine (795 mg, 2.443 mmol, 93% yield).

1H NMR (400 MHz, CDCl₃) δ ppm 8.00 (1 H, s), 7.70 (1 H, d, J=8.81 Hz), 7.29 (1 H, d, J=8.31 Hz), 7.05 (1 H, d, J=2.77 Hz), 6.97 (1 H, dd, J=9.06, 2.77 Hz), 6.47 (1 H, d, J=2.27 Hz), 6.43 (1 H, dd, J=8.18, 2.39 Hz), 5.22 (1 H, t, J=5.29 Hz), 4.63 (2H, d, J=5.54 Hz), 3.91 (3 H, s), 3.83 (3 H, s), 3.78 (3 H, s)

LCMS: RT=1.91 min, MH+=326.15.

Step B: 7-Methoxyquinoxalin-2-amine 2,2,2-trifluoroacetate

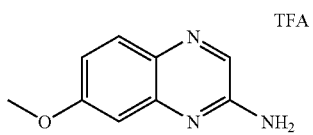

N-(2,4-Dimethoxybenzyl)-7-methoxyquinoxalin-2-amine (0.79 g, 2.428 mmol) was stirred in TFA (10 mL, 130 mmol)/CH₂Cl₂ (10 mL) at room temperature for 30 min. Solvents were removed on the rotary evaporator. Saturated aqueous NaHCO₃ (200 mL) was added to the red residue, which precipitated a yellow solid. The mixture was extracted extensively with DCM. The organic layer was concentrated and dried under vacuum to yield 7-methoxyquinoxalin-2-amine 2,2,2-trifluoroacetate (0.70 g, 2.4 mmol, 99% yield).

1H NMR (400 MHz, DMSO-d₆) δ ppm 8.10 (1 H, s), 7.63 (1 H, d, J=9.07 Hz), 6.95 (1 H, dd, J=9.06, 2.77 Hz), 6.89 (1 H, d, J=2.77 Hz), 6.85 (2 H, br. s.), 3.84 (3 H, s)

LCMS: RT=1.04 min, MH+=176.14.

Step C: 2-Isothiocyanato-7-methoxyquinoxaline

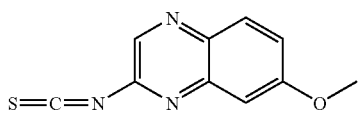

A mixture of 7-methoxyquinoxalin-2-amine 2,2,2-trifluoroacetate (578 mg, 2 mmol), triethylamine (335 µL, 2.400 mmol), and 1,1'-thiocarbonyldipyridin-2(1 H)-one (557 mg, 2.400 mmol) was stirred in 5 mL DCM for 24 h. The reaction was directly eluted on a 120 g silica gel cartridge with 0 to 25% EtOAc in hexane, 25 min, at 35 mL/min to afford 2-isothiocyanato-7-methoxyquinoxaline (84 mg, 0.387 mmol, 19% yield).

LCMS: RT=2.49 min, MH+=218.06.

Step D: (R)—N-(7-Methoxyquinoxalin-2-yl)-4H-1'-azaspiro[oxazole-5,3'-bicyclo[2.2.2]octan]-2-amine

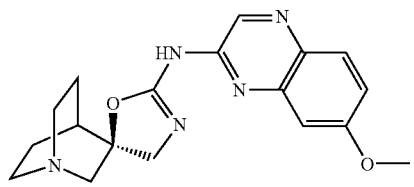

(R)—N-(7-Methoxyquinoxalin-2-yl)-4H-1'-azaspiro[oxazole-5,3'-bicyclo[2.2.2]octan]-2-amine was synthesized by the method of Example 23, Step B. Flash chromatography on a 120 g silica gel cartridge with 1-4% [9:1 MeOH/NH4OH] in CHCl3, 50 min, afforded 24 mg (17% yield).

1H NMR (400 MHz, CDCl₃) δ ppm 9.73 (1 H, br. s.), 8.45 (1 H, s), 7.80 (1 H, d, J=9.07 Hz), 7.12 (1 H, dd, J=9.06, 2.77 Hz), 7.03 (1 H, d, J=2.52 Hz), 4.02 (1 H, d, J=9.32 Hz), 3.90 (3 H, s), 3.67 (1 H, d, J=9.32 Hz), 3.36 (1 H, dd, J=14.86, 1.51 Hz), 2.69-3.06 (5 H, m), 2.10-2.26 (2 H, m), 1.66-1.80 (1 H, m), 1.43-1.63 (2 H, m)

LCMS: RT=0.835 min, MH−=338.2, MH+=340.1.

EXAMPLE 242

(R)—N-(6-Methylquinoxalin-2-yl)-4H-1'-azaspiro[oxazole-5,3'-bicyclo[2.2.2]octan]-2-amine

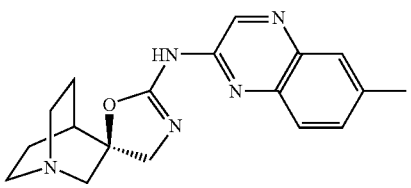

Step A:
N-(2,4-Dimethoxybenzyl)-6-methylquinoxalin-2-amine

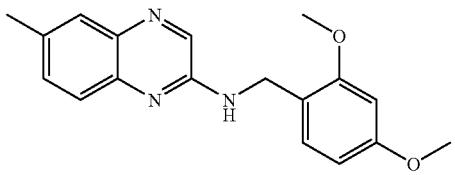

2-Chloro-6-methylquinoxaline (0.51 g, 2.86 mmol), prepared according to J. Chem. Soc. 1948, 1310-1313, and (2,4-dimethoxyphenyl)methanamine (1.29 mL, 8.57 mmol) were microwaved in DMSO (2.5 mL) for 30 min at 150° C. This was diluted into 150 mL EtOAc and extracted three times with 100 mL brine. The crude product was purified by flash chromatography on a 90 g silica gel cartridge with 20 to 60% EtOAc in hexane, 50 min, at 40 mL/min to afford N-(2,4-dimethoxybenzyl)-6-methylquinoxalin-2-amine (848 mg, 2.74 mmol, 96% yield).

1H NMR (400 MHz, CDCl₃) δ ppm 8.12 (1 H, s), 7.60 (1 H, s), 7.59 (1 H, d, J=5.79 Hz), 7.38 (1 H, dd, J=8.56, 1.76 Hz), 7.30 (1 H, d, J=8.31 Hz), 6.46 (1 H, d, J=2.27 Hz), 6.42 (1 H, dd, J=8.18, 2.39 Hz), 5.20 (1 H, t, J=5.41 Hz), 4.62 (2 H, d, J=5.54 Hz), 3.83 (3 H, s), 3.77 (3 H, s), 2.46 (3 H, s)

LCMS: RT=1.93 min, MH+=310.20.

Step B: 6-Methylquinoxalin-2-amine 2,2,2-trifluoroacetate

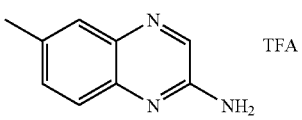

N-(2,4-Dimethoxybenzyl)-6-methylquinoxalin-2-amine (0.84 g, 2.72 mmol) was stirred in TFA (10 mL, 130 mmol)/CH₂Cl₂ (10 mL) at room temperature for 30 min. Solvents were removed on the rotary evaporator. Saturated aqueous Na₂CO₃ (200 mL) was added to the red residue, which then precipitated a tan solid. The mixture was extracted extensively with DCM. The organic layer was dried over sodium sulfate, concentrated, and dried under vacuum to afford 6-methylquinoxalin-2-amine 2,2,2-trifluoroacetate (640 mg, 2.343 mmol, 86% yield).

1H NMR (400 MHz, DMSO-d₆) δ ppm 8.24 (1 H, s), 7.55 (1 H, s), 7.34-7.45 (2 H, m), 6.82 (2 H, s), 2.41 (3 H, s)

LCMS: RT=1.07 min, MH+=160.12.

Step C: 2-Isothiocyanato-6-methylquinoxaline

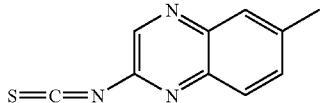

A mixture of 6-methylquinoxalin-2-amine 2,2,2-trifluoroacetate (546 mg, 2 mmol), triethylamine (243 mg, 2.400 mmol), and 1,1'-thiocarbonyldipyridin-2(1H)-one (557 mg, 2.40 mmol) was stirred in 5 mL DCM for 4 h. The reaction was directly eluted on a 120 g silica gel cartridge with 0 to 25% EtOAc in hexane, 25 min, at 35 mL/min to afford 2-isothiocyanato-6-methylquinoxaline (153 mg, 0.760 mmol, 38% yield).

LCMS: RT=2.59 min, MH+=202.04

Step D: (R)—N-(6-Methylquinoxalin-2-yl)-4H-1'-azaspiro[oxazole-5,3'-bicyclo[2.2.2]octan]-2-amine

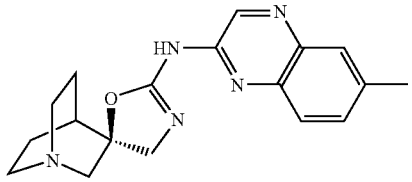

(R)—N-(6-Methylquinoxalin-2-yl)-4H-1'-azaspiro[oxazole-5,3'-bicyclo[2.2.2]octan]-2-amine was synthesized by the method of Example 23, Step B. Flash chromatography on a 120 g silica gel cartridge with 1 to 4% [9:1 MeOH/NH₄OH] in CHCl₃, 50 min, afforded 46 mg (19% yield).

1H NMR (400 MHz, CDCl₃) δ ppm 9.75 (1 H, br. s.), 8.57 (1 H, s), 7.71 (1 H, s), 7.60 (1 H, d, J=8.56 Hz), 7.42 (1 H, dd, J=8.44, 1.89 Hz), 4.01 (1 H, d, J=9.57 Hz), 3.68 (1 H, d, J=9.32 Hz), 3.38 (1 H, dd, J=14.86, 1.01 Hz), 2.73-3.08 (5 H, m), 2.50 (3 H, s), 2.16-2.26 (1 H, m), 2.14 (1 H, br. s.), 1.67-1.79 (1 H, m), 1.45-1.65 (2 H, m).

LCMS: RT=0.838 min, MH-=322.2, MH+=324.2.

EXAMPLE 243

(R)—N-(7-Methylquinoxalin-2-yl)-4H-1'-azaspiro[oxazole-5,3'-bicyclo[2.2.2]octan]-2-amine

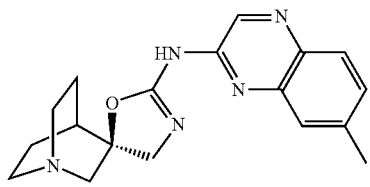

Step A:
N-(2,4-Dimethoxybenzyl)-7-methylquinoxalin-2-amine

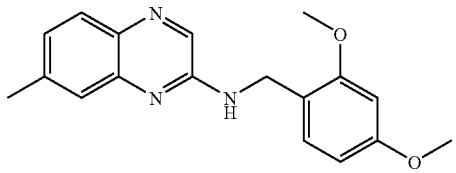

2-Chloro-7-methylquinoxaline (0.51 g, 2.86 mmol), ), prepared according to J. Chem. Soc. 1948 1310-1313, and (2,4-dimethoxyphenyl)methanamine (1.29 mL, 8.57 mmol) were microwaved in DMSO (2.5 mL) for 30 min at 150° C. This was diluted into 150 mL EtOAc and extracted three times with 100 mL brine. The crude product was purified by flash chromatography on a 90 g silica gel cartridge with 20 to 80% EtOAc in hexane, 50 min, at 40 mL/min to afford N-(2,4-dimethoxybenzyl)-7-methylquinoxalin-2-amine (860 mg, 2.78 mmol, 97% yield).

1H NMR (400 MHz, CDCl₃) δ ppm 8.08 (1 H, s), 7.70 (1 H, d, J=8.31 Hz), 7.49 (1 H, s), 7.30 (1 H, d, J=8.06 Hz), 7.17 (1 H, dd, J=8.31, 2.01 Hz), 6.47 (1 H, d, J=2.52 Hz), 6.42 (1 H, dd, J=8.31, 2.52 Hz), 5.23 (1 H, t, J=5.16 Hz), 4.63 (2 H, d, J=5.79 Hz), 3.83 (3 H, s), 3.78 (3 H, s), 2.48 (3 H, s).

LCMS: RT=1.93 min, MH+=310.20.

Step B: 7-Methylquinoxalin-2-amine 2,2,2-trifluoroacetate

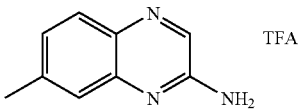

N-(2,4-Dimethoxybenzyl)-7-methylquinoxalin-2-amine (0.85 g, 2.75 mmol) was stirred in TFA (10 mL, 130 mmol)/CH2Cl2 (10 mL) at room temperature for 30 min. Solvents were removed on the rotary evaporator. Saturated aqueous NaHCO₃ (200 mL) was added to the red residue, which then precipitated a pink solid. The mixture was extracted extensively with DCM. The organic layer was dried over sodium sulfate, concentrated, and dried under vacuum to afford 7-methylquinoxalin-2-amine 2,2,2-trifluoroacetate (640 mg, 2.34 mmol, 85% yield).

1H NMR (400 MHz, DMSO-d₆) δ ppm 8.20 (1 H, s), 7.64 (1 H, d, J=8.31 Hz), 7.28 (1 H, s), 7.15 (1 H, dd, J=8.31, 1.76 Hz), 6.89 (2 H, s), 2.42 (3 H, s).

LCMS: RT=1.07 min, MH+=160.12.

Step C: 2-Isothiocyanato-6-methylquinoxaline

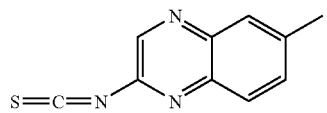

A mixture of 7-methylquinoxalin-2-amine 2,2,2-trifluoroacetate (546 mg, 2 mmol) 78263-058-01, triethylamine (243 mg, 2.40 mmol), and 1,1'-thiocarbonyldipyridin-2(1H)-one (557 mg, 2.40 mmol) was stirred in 5 mL DCM for 2 h. The reaction was directly eluted on a 120 g silica gel cartridge with 0 to 25% EtOAc in hexane, 25 min, at 35 mL/min to afford 2-isothiocyanato-7-methylquinoxaline (185 mg, 0.919 mmol, 46% yield).

LCMS: RT=2.58 min, MH+=202.04

Step D: (R)—N-(7-Methylquinoxalin-2-yl)-4H-1'-azaspiro[oxazole-5,3'-bicyclo[2.2.2]octan]-2-amine

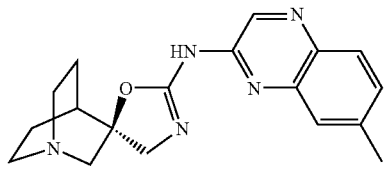

(R)—N-(7-Methylquinoxalin-2-yl)-4H-1'-azaspiro[oxazole-5,3'-bicyclo[2.2.2]octan]-2-amine was synthesized by the method of Example 23, Step B. Flash chromatography on a 120 g silica gel cartridge with 1 to 3% [9:1 MeOH/NH4OH] in CHCl3, 50 min, afforded 22 mg (7% yield).

1H NMR (400 MHz, CDCl$_3$) δ ppm 9.80 (1 H, br. s.), 8.53 (1 H, s), 7.81 (1 H, d, J=8.31 Hz), 7.50 (1 H, s), 7.31 (1 H, dd, J=8.56, 1.76 Hz), 4.01 (1 H, d, J=9.57 Hz), 3.66 (1 H, d, J=9.32 Hz), 3.36 (1 H, d, J=14.86 Hz), 2.70-3.04 (5 H, m), 2.50 (3 H, s), 2.15-2.24 (1 H, m), 2.13 (1 H, br. s.), 1.66-1.79 (1 H, m), 1.44-1.63 (2 H, m)

LCMS: RT=8.67 min, MH−=322.6, MH+=324.1.

EXAMPLE 244

(R)—N-(6-(Pyridin-3-yl)pyrimidin-4-yl)-4H-1'-azaspiro[oxazole-5,3'-bicyclo[2.2.2]octan]-2-amine

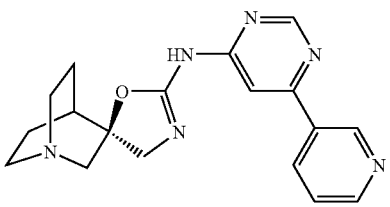

Step A: 6-(Pyridin-3-yl)pyrimidin-4-amine

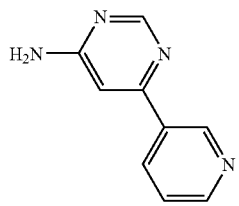

A mixture of 6-chloropyrimidin-4-amine (0.324 g, 2.5 mmol), pyridin-3-ylboronic acid (0.384 g, 3.13 mmol), Na$_2$CO$_3$ (0.795 g, 7.50 mmol) and bis(triphenylphosphine)palladium(II)chloride (0.035 g, 0.050 mmol) was suspended in a mixture of DME/EtOH/water. The mixture was heated in the microwave synthesizer at 125° C. for 20 min and concentrated. The residue was purified by silica gel chromatography (10-60% ethyl acetate in hexanes, then 5-25% 9:1 methanol:ammonium hydroxide-ethyl acetate) to afford 6-(pyridin-3-yl)pyrimidin-4-amine (0.17 g, 0.987 mmol, 40% yield) as an off-white solid. LCMS R.T.=0.31;

[M+H]$^+$=173.11.

Step B: 4-Isothiocyanato-6-(pyridin-3-yl)pyrimidine

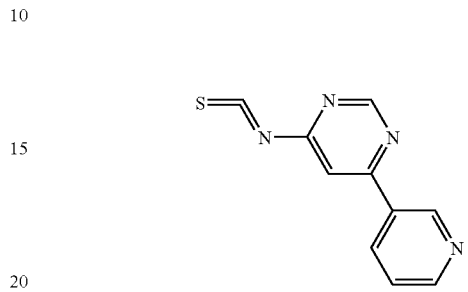

To a solution of 1,1'-thiocarbonyldipyridin-2(1H)-one (0.682 g, 2.94 mmol) in dichloromethane/N,N-dimethylformamide at room temperature was added 6-(pyridin-3-yl)pyrimidin-4-amine (0.337 g, 1.957 mmol). The mixture was heated at 60° C. for 18 hours. LC/MS showed the desired product peak as the major peak. The deep orange mixture was purified by silica gel chromatography (1-40% ethyl acetate-hexanes) to afford 4-isothiocyanato-6-methoxypyrimidine (0.12 g, 0.56 mmol, 28.6% yield) as an orange oil.

Step C: (R)—N-(6-(Pyridin-3-yl)pyrimidin-4-yl)-4H-1'-azaspiro[oxazole-5,3'-bicyclo[2.2.2]octan]-2-amine

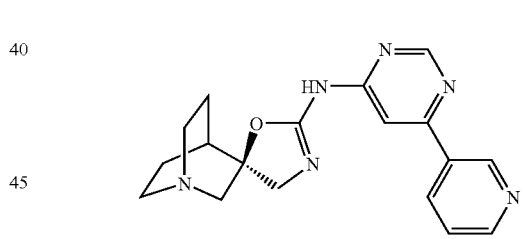

To (S)-3-(aminomethyl)quinuclidin-3-ol dihydrochloride (0.13 g, 0.560 mmol) in N,N-dimethylformamide (20 mL) was added Cs$_2$CO$_3$ (0.46 g, 1.4 mmol) and 4-isothiocyanato-6-(pyridin-3-yl)pyrimidine (0.12 g, 0.56 mmol). The suspension was stirred at room temperature for 30 minutes. N,N'-Diisopropylcarbodiimide (0.26 mL, 1.7 mmol) was then added and the mixture was stirred at room temperature for 18 hours. The mixture was concentrated and purified by silica gel chromatography (0-10% [9:1 methanol:ammonium hydroxide]-ethyl acetate) to afford (S)—N-(5-chloropyrazin-2-yl)-4H-1'-azaspiro[oxazole-5,3'-bicyclo[2.2.2]octan]-2-amine (0.182 g, 0.613 mmol, 35% yield) as an off-white solid. $^1$H NMR (400 MHz, MeOD) δ ppm 9.13-9.21 (1 H, m), 8.82 (1 H, d), 8.63 (1 H, dd), 8.44 (1 H, dt), 7.56 (1 H, dd), 7.31 (1 H, s), 4.06 (1 H, d), 3.76 (1 H, d), 3.20-3.28 (1 H, m), 3.08-3.16 (1 H, m), 2.72-3.01 (4 H, m), 2.00-2.24 (2 H, m), 1.52-1.83 (3 H, m). LCMS R.T.=0.72; [M+H]$^+$=337.2.

EXAMPLE 245

(R)—N-(2'-Methoxy-4,5'-bipyrimidin-6-yl)-4H-1'-azaspiro[oxazole-5,3'-bicyclo[2.2.2]octan]-2-amine

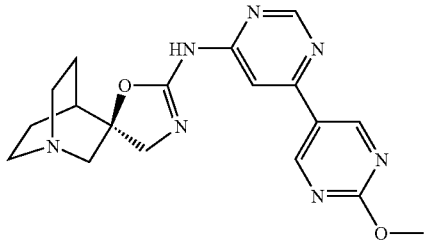

Step A: 2'-Methoxy-4,5'-bipyrimidin-6-amine

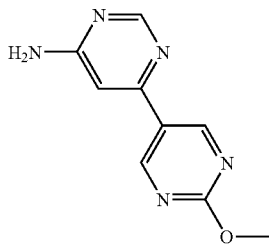

6-Chloropyrimidin-4-amine (0.35 g, 2.70 mmol), 2-methoxypyrimidin-5-ylboronic acid (0.520 g, 3.38 mmol), Na$_2$CO$_3$ (0.859 g, 8.11 mmol) and bis(triphenylphosphine)palladium(II)chloride (0.038 g, 0.054 mmol) were suspended in a mixture of DME/EtOH/water. (15:2:3 mL). The mixture was heated in the microwave synthesizer at 125° C. for 20 min and concentrated. The residue was purified by silica gel chromatography (0-5% 9:1 methanol:ammonium hydroxide-ethyl acetate) to afford 6-(pyridin-3-yl)pyrimidin-4-amine (0.28 g, 1.378 mmol, 51% yield) as an off-white solid. LCMS R.T.=0.53; [M+H]$^+$=204.11.

Step B: 6-Isothiocyanato-2'-methoxy-4,5'-bipyrimidine

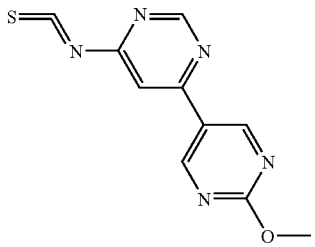

To a solution of 1,1'-thiocarbonyldipyridin-2(1H)-one (0.832 g, 3.58 mmol) in dichloromethane/N,N-dimethylformamide at room temperature was added 2'-methoxy-4,5'-bipyrimidin-6-amine (0.56 g, 2.76 mmol). The orange mixture was heated at 60° C. for 18 hours. The LC/MS showed the desired product peak as the major peak. The deep orange mixture was purified by silica gel chromatography (0-40% ethyl acetate-hexanes) to afford 4-isothiocyanato-6-methoxypyrimidine (0.1 g, 0.408 mmol, 15% yield) as an orange solid. LCMS R.T.=2.29; [M+H]$^+$=246.03.

Step C: (R)—N-(2'-Methoxy-4,5'-bipyrimidin-6-yl)-4H-1'-azaspiro[oxazole-5,3'-bicyclo[2.2.2]octan]-2-amine

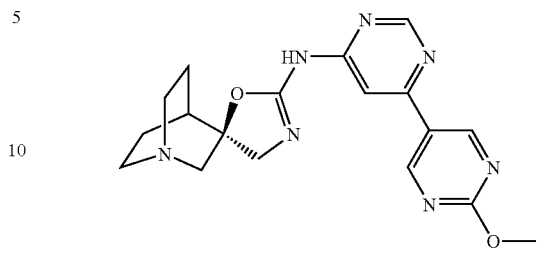

To (S)-3-(aminomethyl)quinuclidin-3-ol dihydrochloride (0.093 g, 0.41 mmol) in N,N-dimethylformamide (20 mL) was added Cs$_2$CO$_3$ (0.33 g, 1 mmol)) and 6-isothiocyanato-2'-methoxy-4,5'-bipyrimidine (0.1 g, 0.41 mmol). The suspension was stirred at room temperature for 30 minutes. N,N'-Diisopropylcarbodiimide (0.19 mL, 1.2 mmol) was then added and the mixture was stirred at room temperature for 18 hours. The mixture was concentrated and purified by silica gel chromatography (5-25% [9:1 methanol:ammonium hydroxide]-ethyl acetate) to afford (R)—N-(2'-methoxy-4,5'-bipyrimidin-6-yl)-4H-1'-azaspiro[oxazole-5,3'-bicyclo[2.2.2]octan]-2-amine (0.072 g, 0.188 mmol, 46% yield) as an off-white solid. $^1$H NMR (400 MHz, MeOD) δ ppm 9.19 (2 H, s), 8.80 (1 H, d), 7.24 (1 H, br. s.), 4.00-4.09 (4 H, m), 3.76 (1 H, d), 3.23 (1 H, s), 3.08-3.15 (1 H, m), 2.72-3.04 (4 H, m), 1.97-2.22 (2 H, m), 1.38-1.85 (3 H, m). R.T.=1.22; [M+H]$^+$=368.22.

EXAMPLE 246

(R)—N-(6-(Pyridin-4-yl)pyrimidin-4-yl)-4H-1'-azaspiro[oxazole-5,3'-bicyclo[2.2.2]octan]-2-amine Step A: 6-(Pyridin-4-yl)pyrimidin-4-amine

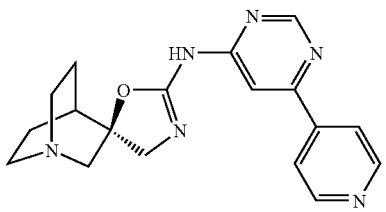

6-Chloropyrimidin-4-amine (0.324 g, 2.5 mmol), pyridin-4-ylboronic acid (0.384 g, 3.13 mmol), Na$_2$CO$_3$ (0.795 g, 7.50 mmol) and bis(triphenylphosphine)palladium(II)chloride (0.035 g, 0.050 mmol) were suspended in a mixture of DME/EtOH/water (15:2:3 mL). The mixture was heated in the microwave synthesizer at 125° C. for 20 min and concentrated. The residue was purified by silica gel chromatography (5-25% [9:1 methanol:ammonium hydroxide]-ethyl acetate) to afford 6-(pyridin-3-yl)pyrimidin-4-amine (0.15 g, 0.871 mmol, 35% yield) as an off-white solid. LCMS R.T.=0.30; [M+H]$^+$=173.11.

Step B: 4-Isothiocyanato-6-(pyridin-4-yl)pyrimidine

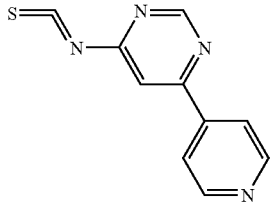

To a solution of 1,1'-thiocarbonyldipyridin-2(1H)-one (0.601 g, 2.59 mmol) in dichloromethane/N,N-dimethylformamide at room temperature was added 6-(pyridin-4-yl)pyrimidin-4-amine (0.297 g, 1.725 mmol). The orange mixture was heated at 60° C. for 18 hours. LC/MS showed the desired product peak as the major peak. The deep orange mixture was purified by silica gel chromatography (0-40% ethyl acetate-hexanes) to afford 4-isothiocyanato-6-(pyridin-4-yl)pyrimidine (0.055 g, 0.257 mmol, 15% yield) as an orange solid. LCMS R.T.=1.46; [M+H]$^+$=215.09.

Step C: (R)—N-(6-(Pyridin-4-yl)pyrimidin-4-yl)-4H-1'-azaspiro[oxazole-5,3'-bicyclo[2.2.2]octan]-2-amine

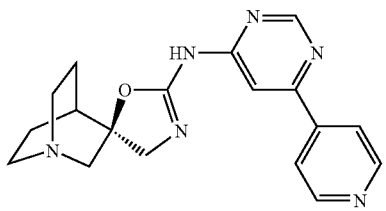

To (S)-3-(aminomethyl)quinuclidin-3-ol dihydrochloride (0.059 g, 0.257 mmol) in N,N-dimethylformamide (15 mL) was added Cs$_2$CO$_3$ (0.209 g, 0.642 mmol) and 4-isothiocyanato-6-(pyridin-4-yl)pyrimidine (0.055 g, 0.257 mmol). The suspension was stirred at room temperature for 30 minutes. N,N'-diisopropylcarbodiimide (0.12 mL, 0.77 mmol) was then added and the mixture was continued to stir at room temperature for 18 hours. The mixture was concentrated and purified by silica gel chromatography (0-10% [9:1 methanol: ammonium hydroxide]-ethyl acetate) to afford (R)—N-(6-(pyridin-4-yl)pyrimidin-4-yl)-4H-1'-azaspiro[oxazole-5,3'-bicyclo[2.2.2]octan]-2-amine (0.014 g, 0.04 mmol, 16% yield) as a yellow film. $^1$H NMR (400 MHz, MeOD) δ ppm 8.85 (1 H, d), 8.67 (2 H, dd), 8.04 (2 H, dd), 7.34 (1 H, br. s.), 4.06 (1 H, d), 3.76 (1 H, d), 3.23 (1 H, d), 3.10 (1 H, d), 2.70-2.99 (4 H, m), 2.01-2.22 (2 H, m), 1.53-1.86 (3 H, m). LCMS R.T.=0.42; [M+H]$^+$=337.14.

EXAMPLE 247

(R)-6-(4H-1'-Azaspiro[oxazole-5,3'-bicyclo[2.2.2] octane]-2-ylamino)-2-methylnicotinonitrile

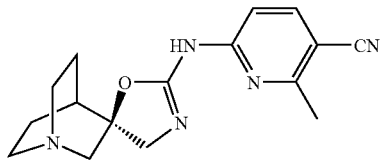

Step A: 6-Isothiocyanato-2-methylnicotinonitrile

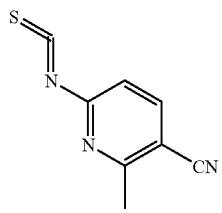

To 6-amino-2-methylnicotinonitrile (0.41 g, 3.08 mmol) in dichloromethane (20 mL) was added 1,1'-thiocarbonyldipyridin-2(1H)-one (0.75 g, 3.23 mmol). The reaction was stirred at 40° C. for 3 hours. The reaction was cooled to room temperature. The crude was purified by chromatography (Biotage: 25-100% ethyl acetate/hexane) to yield 6-isothiocyanato-2-methylnicotinonitrile (0.52 g, 2.97 mmol, 96% yield). 1H NMR (500 MHz, DMSO-D6) δ ppm 8.36 (d, J=8.24 Hz, 1 H), 7.39 (d, J=8.24 Hz, 1 H), 2.65 (s, 3 H). MS (LC/MS) R.T.=2.09; [M+H]$^+$=176.0.

Step B: (R)-6-(4H-1'-Azaspiro[oxazole-5,3'-bicyclo [2.2.2]octane)-2-ylamino)-2-methylnicotinonitrile

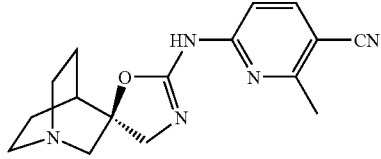

To 6-isothiocyanato-2-methylnicotinonitrile (0.25 g, 1.43 mmol) in N,N-dimethylformamide (20 mL) was added triethylamine (0.5 mL, 3.666 mmol) and 3-(aminomethyl)quinuclidin-3-ol dihydrochloride (0.33 g, 1.46 mmol) at room temperature. The reaction was stirred at 70° C. for 2 hours. The reaction was cooled to room temperature and concentrated in vacuo. The crude urea was purified by chromatography (Biotage: 85% CHCl$_3$, 14% MeOH, 1% NH$_4$OH). The product was then treated with N,N-dimethylformamide (20 mL) and N,N'-diisopropylcarbodiimide (0.67 mL, 4.28 mmol). The reaction was heated to 70° C. for 2 hours. The reaction was cooled to room temperature and concentrated in vacuo to yield the crude product. The crude product was purified by chromatography (Biotage: 85% CHCl$_3$, 14% MeOH, 1% NH$_4$OH) to yield (R)-6-(4H-1'-azaspiro[oxazole- 5,3'-bicyclo[2.2.2]octane]-2-ylamino)-2-methylnicotinonitrile (0.09 g, 0.3 mmol, 21% yield) as a white powder. 1H NMR (500 MHz, DMSO-D6) δ ppm 9.11 (s, 1 H), 7.87 (d, J=7.93 Hz, 2 H), 6.69 (s, 1 H), 3.89 (d, J=10.38 Hz, 2 H), 3.63 (d, J=10.38 Hz, 3 H), 3.00 (s, 5 H), 2.72-2.80 (m, 4 H), 2.64-2.69 (m, 5 H), 2.60 (s, 7 H), 2.00 (d, J=2.14 Hz, 3 H), 1.91 (s, 1 H), 1.87 (s, 2 H), 1.58 (s, 5 H), 1.42-1.50 (m, 2 H). MS (LC/MS) R.T.=0.48; [M+H]$^+$=298.13.

EXAMPLE 248

(R)-6-(4H-1'-Azaspiro[oxazole-5,3'-bicyclo[2.2.2] octane]-2-ylamino)-2,4-dimethylnicotinonitrile

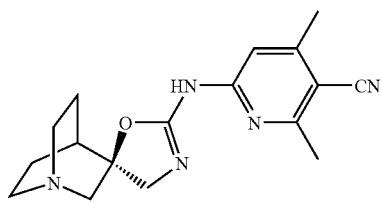

Step A: 6-Isothiocyanato-2,4-dimethylnicotinonitrile

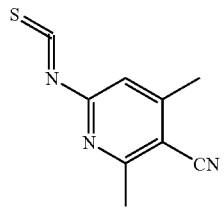

To 6-amino-2,4-dimethylnicotinonitrile (0.14 g, 0.95 mmol) in dichloromethane (20 mL) was added 1,1'-thiocarbonyldipyridin-2(1H)-one (0.23 g, 0.1 mmol). The reaction was stirred at 40° C. for 3 hours. The reaction was cooled to room temperature. The crude was purified by chromatography (Biotage: 25-100% ethyl acetate/hexane) to yield 6-isothiocyanato-2,4-dimethylnicotinonitrile (0.15 g, 0.79 mmol, 83% yield). 1H NMR (500 MHz, DMSO-D6) δ ppm 7.37 (s, 1 H), 2.63 (s, 3 H). MS (LC/MS) R.T.=2.40; [M+H]$^+$= 190.

Step B: (R)-6-(4H-1'-Azaspiro[oxazole-5,3'-bicyclo [2.2.2]octane]-2-ylamino)-2,4-dimethylnicotinonitrile

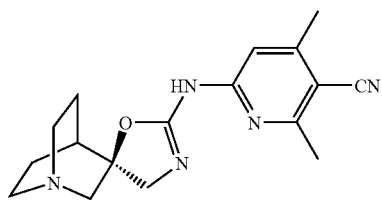

To 6-isothiocyanato-2,4-dimethylnicotinonitrile (0.09 g, 0.48 mmol) in N,N-dimethylformamide (20 mL) was added triethylamine (0.17 mL, 1.19 mmol) and 3-(aminomethyl) quinuclidin-3-ol dihydrochloride (0.11 g, 0.49 mmol) at room temperature. The reaction was stirred at 70° C. for 2 hours. The reaction was cooled to room temperature and concentrated in vacuo. The crude urea was purified by chromatography (Biotage: 85% CHCl$_3$, 14% MeOH, 1% NH$_4$OH). The product was then treated with N,N-dimethylformamide (20 mL) and N,N'-diisopropylcarbodiimide (0.22 mL, 1.43 mmol). The reaction was heated to 70° C. for 2 hours. The reaction was cooled to room temperature and concentrated in vacuo to yield the crude product. The crude product was purified by chromatography (Biotage: 85% CHCl$_3$, 14% MeOH, 1% NH$_4$OH) to yield (R)-6-(4H-1'-azaspiro[oxazole-5,3'-bicyclo[2.2.2]octane]-2-ylamino)-2,4-dimethylnicotinonitrile (0.10 g, 0.32 mmol, 66% yield) as a white powder. 1H NMR (500 MHz, DMSO-D6) δ ppm 9.08 (s, 1 H), 6.60 (s, 1 H), 3.88 (d, J=10.38 Hz, 1 H), 3.61 (d, J=10.38 Hz, 1 H), 2.98 (s, 2 H), 2.70-2.79 (m, 2 H), 2.63-2.69 (m, 2 H), 2.55-2.60 (m, 4 H), 2.31-2.39 (m, 4 H), 1.99 (s, 1 H), 1.89 (s, 1 H), 1.54-1.62 (m, 2 H), 1.41-1.49 (m, 1 H). MS (LC/MS) R.T.=0.78; [M+H]$^+$=312.1.

EXAMPLE 249

(R)—N-(6-Phenylpyridazin-3-yl)-4H-1'-azaspiro [oxazole-5,3'-bicyclo[2.2.2]octan]-2-amine

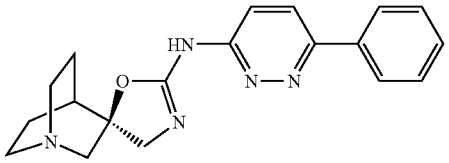

Step A: 3-Isothiocyanato-6-phenylpyridazine

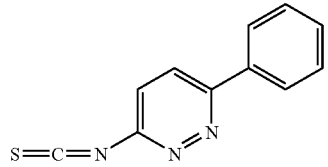

3-Isothiocyanato-6-phenylpyridazine was synthesized by the method of Example 23, Step B. Flash chromatography on a 120 g silica gel cartridge with 0 to 25% EtOAc in hexane, 25 min, at 35 mL/min afforded 420 mg (49% yield).

LCMS: RT=2.17 min, MH+=214.06.

Step B: (R)—N-(6-Phenylpyridazin-3-yl)-4H-1'-azaspiro[oxazole-5,3'-bicyclo[2.2.2]octan]-2-amine

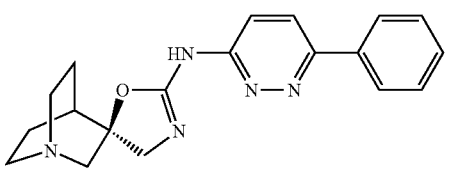

(R)—N-(6-Phenylpyridazin-3-yl)-4H-1'-azaspiro[oxazole-5,3'-bicyclo[2.2.2]octan]-2-amine was synthesized by the method of Example 23, Step B. Flash chromatography on a 160 g silica gel cartridge with 1-4% [9:1 MeOH/NH$_4$OH] in CHCl$_3$, 50 min, at 40 mL/min afforded 67 mg (R)—N-(6-phenylpyridazin-3-yl)-4H-1'-azaspiro[oxazole-5,3'-bicyclo [2.2.2]octan]-2-amine (17% yield).

1H NMR (400 MHz, CDCl$_3$) δ ppm 9.61 (1 H, br. s.), 7.95-7.99 (2 H, m), 7.74 (1 H, d, J=9.32 Hz), 7.39-7.52 (3 H, m), 7.22 (1 H, partial d), 3.97 (1 H, d, J=9.32 Hz), 3.64 (1 H, d, J=9.32 Hz), 3.37 (1 H, dd, J=14.73, 1.38 Hz), 2.69-3.06 (5 H, m), 2.16-2.26 (1 H, m), 2.14 (1 H, br. s.), 1.66-1.79 (1 H, m), 1.45-1.60 (2 H, m)

1H NMR (400 MHz, MeOD) δ ppm 7.87-8.02 (3 H, m), 7.44-7.55 (3 H, m), 7.13-7.29 (1 H, m), 4.05 (1 H, d, J=9.82 Hz), 3.74 (1 H, d, J=10.07 Hz), 3.17 (2 H, dd, J=49.35, 14.60 Hz), 2.73-3.04 (4 H, m), 2.16 (2 H, br. s.), 1.55-1.85 (3 H, m)

LCMS: RT=0.82 min, MH−=334.2, MH+=336.2.

EXAMPLE 250

(R)—N-(5-(Methylthio)pyrazin-2-yl)-4H-1'-azaspiro[oxazole-5,3'-bicyclo[2.2.2]octan]-2-amine

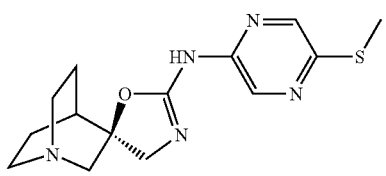

Step A: 5-(Methylthio)pyrazin-2-amine

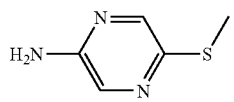

To a solution of 5-bromopyrazin-2-amine (2 g, 11.49 mmol) in N,N-dimethylformamide (20 ml) was added sodium thiomethoxide (1.611 g, 22.99 mmol). The mixture was stirred and heated at 100° C. under nitrogen for 18 h and concentrated. The residue was treated with water and the mixture was extracted with dichloromethane. The combined organics were dried with sodium sulfate, filtered and concentrated. The residue was purified by silica gel chromatography (0-10% 9:1 methanol:ammonium hydroxide-ethyl acetate) to afford 6-(pyridin-3-yl)pyrimidin-4-amine (0.15 g, 0.871 mmol, 35% yield) as a yellow solid. LCMS R.T.=0.91; [M+H]+=141.89.

Step B: 2-Isothiocyanato-5-(methylthio)pyrazine

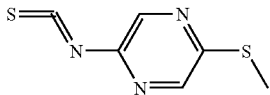

To a solution of 1,1'-thiocarbonyldipyridin-2(1H)-one (1.069 g, 4.60 mmol) in dichloromethane at room temperature was added 5-(methylthio)pyrazin-2-amine (0.50 g, 3.54 mmol). The reaction was stirred at room temperature for 18 hours. LC/MS showed the desired product peak as the major peak. The deep orange mixture was purified by silica gel chromatography (0-40% ethyl acetate-hexanes) to afford 2-isothiocyanato-5-(methylthio)pyrazine (0.545 g, 0.257 mmol, 84% yield) as an orange oil. LCMS R.T.=2.65; [M+H]+=184.02.

Step C: (R)—N-(5-(Methylthio)pyrazin-2-yl)-4H-1'-azaspiro[oxazole-5,3'-bicyclo[2.2.2]octan]-2-amine

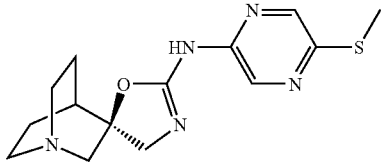

To (S)-3-(aminomethyl)quinuclidin-3-ol dihydrochloride (0.375 g, 1.637 mmol) in N,N-dimethylformamide (15 mL) was added Cs$_2$CO$_3$ (1.333 g, 4.09 mmol) and 2-isothiocyanato-5-(methylthio)pyrazine (0.3 g, 1.637 mmol),. The suspension was stirred at room temperature for 30 minutes. N,N'-diisopropylcarbodiimide (0.765 mL, 4.9 mmol) was then added and the mixture was continued to stir at room temperature for 18 hours. The mixture was concentrated and purified by silica gel chromatography (5-25% 9:1 methanol:ammonium hydroxide-ethyl acetate) to afford (R)—N-(5-(methylthio)pyrazin-2-yl)-4H-1'-azaspiro[oxazole-5,3'-bicyclo[2.2.2]octan]-2-amine (0.014 g, 0.04 mmol, 16% yield) as a yellow solid. M.P. 155-60° C. $^1$H NMR (400 MHz, MeOD) δ ppm 8.13 (1 H, d), 8.06 (1 H, s), 3.96 (1 H, d), 3.66 (1 H, d), 3.20 (1 H, d), 3.08 (1 H, d), 2.87-2.96 (2 H, m), 2.72-2.82 (2 H, m), 2.52 (3 H, s), 2.00-2.19 (2 H, m), 1.51-1.81 (3 H, m). LCMS R.T.=1.01; [M+H]+=306.12.

EXAMPLE 251

(R)—N-(5,6-Dichloropyridin-2-yl)-4H-1'-azaspiro[oxazole-5,3'-bicyclo[2.2.2]octan]-2-amine

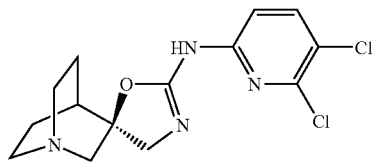

Step A: N-(5,6-Dichloropyridin-2-yl)pivalamide

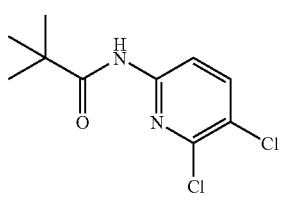

To a solution of N-(6-chloropyridin-2-yl)pivalamide, synthesized as in *J. Org. Chem* 2005, 70, 1771, (1.02 g, 4.80 mmol) in chloroform (25 mL) was added 1-chloropyrrolidine-2,5-dione (0.62 g, 4.67 mmol) and the mixture was refluxed in an oil bath for 3 hrs. It was allowed to cool to room temperature overnight. The reaction mixture was evaporated in vacuo and re-dissolved in DMF (15 mL). Another 480 mg 1-chloropyrrolidine-2,5-dione was added and the resulting solution was heated overnight in an oil bath at 95-100°, then cooled again to room temperature. The solvent was removed in vacuo and the residue was partitioned between water and ethyl acetate. The aqueous phase was washed twice more with ethyl acetate and the combined organic phases were washed with brine, dried over magnesium sulfate, and evaporated in vacuo. TLC (10% ethyl acetate/hexane) showed a robust spot at Rf 0.6 with smaller spots at Rf 0.4 and 0.2. The material was subjected to the Biotage in 5-10% ethyl acetate/hexane, collecting the Rf 0.6 fraction to give 790 mg (66%) white solid, N-(5,6-dichloropyridin-2-yl)pivalamide. 1H NMR (500 MHz, CDCl$_3$) δ ppm 8.17 (s, 1 H), 7.96 (s, 1 H), 7.72 (s, 1 H), 1.31 (s, 10 H). MS (LC/MS) R.T.=1.85; [M+H]$^+$=248.8.

Step B: 5,6-Dichloropyridin-2-amine

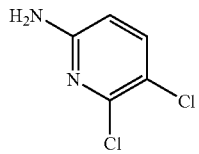

A mixture of N-(5,6-dichloropyridin-2-yl)pivalamide (790 mg, 3.20 mmol), hydrochloric acid, 37% (1.25 mL), water (1.25 mL), and EtOH (3 mL) was heated for 4 hrs in an oil bath at 85-90° C. LCMS showed nearly complete conversion to product. The reaction was cooled to room temperature and the reaction mixture was evaporated down to a small volume, then transferred to a separatory funnel where it was partitioned between aqueous sodium carbonate and ethyl acetate. The layers were separated, the aqueous phase was washed again with ethyl acetate, and the combined organic phases were washed with brine, dried over MgSO$_4$, filtered, and evaporated to give a white solid. The material was subjected to a Biotage column in 20% ethyl acetate/hexane, collecting the main component. 5,6-Dichloropyridin-2-amine (0.49 g, 2.98 mmol, 93%) was obtained as a white solid. 1H NMR (500 MHz, CDCl$_3$) δ ppm 7.44 (d, J=8.55 Hz, 1 H), 6.36 (d, J=8.24 Hz, 1 H), 4.58 (s, 2 H). MS (LC/MS) R.T.=1.28; [M+H]$^+$=164.8.

Step C: 5,6-Dichloro-2-isothiocyanatopyridine

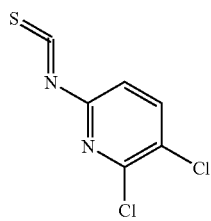

To 5,6-dichloropyridin-2-amine (0.47 g, 2.88 mmol) in dichloromethane (25 mL) was added 1,1'-thiocarbonyldipyridin-2(1 H)-one (0.68 g, 2.94 mmol). The reaction was stirred at 40° C. for 3 hours, then cooled to room temperature. The crude material was purified by chromatography (Biotage: 25-100% ethyl acetate/hexane) 2,3-dichloro-6-isothiocyanatopyridine (0.48 g, 2.34 mmol, 81% yield) as a white powder. 1H NMR (500 MHz, DMSO-D6) δ ppm 8.26 (d, J=8.55 Hz, 1 H), 7.47 (d, J=8.24 Hz, 1 H). MS (LC/MS) R.T.=2.83; [M+H]$^+$=204.8.

Step D: (R)—N-(5,6-Dichloropyridin-2-yl)-4H-1'-azaspiro[oxazole-5,3'-bicyclo[2.2.2]octan]-2-amine

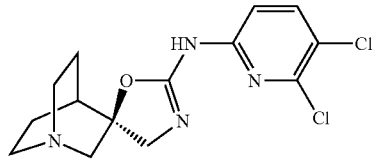

To 2,3-dichloro-6-isothiocyanatopyridine (0.47 g, 2.29 mmol) in N,N-dimethylformamide (20 mL) was added triethylamine (0.8 mL, 5.7 mmol) and 3-(aminomethyl)quinuclidin-3-ol dihydrochloride (0.54 g, 2.34 mmol) at room temperature. The reaction was stirred at 70° C. for 2 hours, cooled to room temperature and concentrated in vacuo. The crude urea was purified by chromatography (Biotage: 85% CHCl$_3$, 14% MeOH, 1% NH$_4$OH). The product was then treated with N,N-dimethylformamide (20 mL) and N,N'-diisopropylcarbodiimide (1.07 mL, 6.88 mmol). The reaction was heated to 70° C. for 2 hours. The reaction was cooled to room temperature and concentrated in vacuo. The crude product was purified by chromatography (Biotage: 85% CHCl$_3$, 14% MeOH, 1% NH$_4$OH) to yield (R)—N-(5,6-dichloropyridin-2-yl)-4H-1'-azaspiro[oxazole-5,3'-bicyclo[2.2.2]octan]-2-amine (0.36 g, 1.08 mmol, 47% yield) as a white powder. 1H NMR (500 MHz, DMSO-D6) δ ppm 8.31 (d, J=1.22 Hz, 1 H), 7.84 (s, 1 H), 6.80 (s, 1 H), 3.85 (d, J=10.07 Hz, 1 H), 3.57 (d, J=10.38 Hz, 2 H), 2.98 (s, 3 H), 2.69-2.78 (m, 3 H), 2.65 (t, J=7.78 Hz, 3 H), 2.00 (s, 2 H), 1.86 (s, 2 H), 1.58 (dd, J=7.48, 2.90 Hz, 2 H), 1.56 (s, 1 H), 1.41-1.49 (m, 2 H). MS (LC/MS) R.T.=0.81; [M+H]$^+$=327.1.

EXAMPLE 252

(R)—N-(4,5-Dichloropyridin-2-yl)-4H-1'-azaspiro[oxazole-5,3'-bicyclo[2.2.2]octan]-2-amine

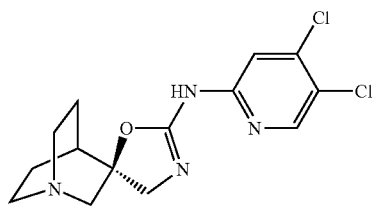

Step A: 4,5-Dichloro-2-isothiocyanatopyridine

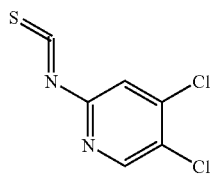

To 4,5-dichloropyridin-2-amine (0.25 g, 1.53 mmol) in dichloromethane (25 mL) was added 1,1'-thiocarbonyldipyridin-2(1H)-one (0.36 g, 1.56 mmol). The reaction was stirred at 40° C. for 3 hours, then cooled to room temperature. The crude material was purified by chromatography (Biotage: 25-100% ethyl acetate/hexane) to yield 4,5-dichloro-2-isothiocyanatopyridine (0.26 g, 1.27 mmol, 83% yield) as a yellow powder. The product was carried directly to the next step.

Step B: (R)—N-(4,5-Dichloropyridin-2-yl)-4H-1'-azaspiro[oxazole-5,3'-bicyclo[2.2.2]octan]-2-amine

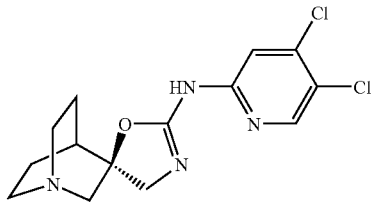

To 4,5-dichloro-2-isothiocyanatopyridine (0.25 g, 1.22 mmol) in N,N-dimethylformamide (20 mL) was added triethylamine (0.43 mL, 3.05 mmol) and (S)-3-(aminomethyl)quinuclidin-3-ol dihydrochloride (0.29 g, 1.24 mmol) at room temperature. The reaction was stirred at 70° C. for 2 hours. The reaction was cooled to room temperature and concentrated in vacuo. The crude urea was purified by chromatography (Biotage: 85% $CHCl_3$, 14% MeOH, 1% $NH_4OH$). The product was then treated with N,N-dimethylformamide (20 mL) and N,N'-diisopropylcarbodiimide (0.57 mL, 3.66 mmol). The reaction was heated to 70° C. for 2 hours. The reaction was cooled to room temperature and concentrated to yield the crude product. The crude product was purified by chromatography (Biotage: 85% $CHCl_3$, 14% MeOH, 1% $NH_4OH$) to yield (R)—N-(4,5-dichloropyridin-2-yl)-4H-1'-azaspiro[oxazole-5,3'-bicyclo[2.2.2]octan]-2-amine (0.09 g, 0.27 mmol, 22% yield) as a white powder. 1H NMR (500 MHz, DMSO-D6) δ ppm 8.81 (s, 1 H), 8.32 (d, J=6.10 Hz, 1 H), 7.03 (s, 1 H), 3.83 (d, J=9.46 Hz, 1 H), 3.57 (d, J=9.77 Hz, 1 H), 2.98 (s, 2 H), 2.71-2.79 (m, 2 H), 2.65 (t, J=7.78 Hz, 2 H), 1.99 (s, 1 H), 1.86 (s, 1 H), 1.53-1.61 (m, 2 H), 1.41-1.49 (m, 1 H). MS (LC/MS) R.T.=0.78; $[M+H]^+$=327.0.

EXAMPLE 253

(R)—N-(5-Chloro-4-methylpyridin-2-yl)-4H-1'-azaspiro[oxazole-5,3'-bicyclo[2.2.2]octan]-2-amine

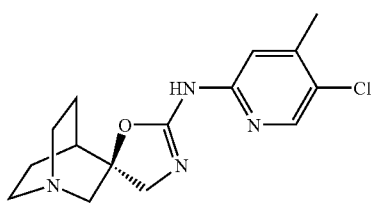

Step A: 5-Chloro-2-isothiocyanato-4-methylpyridine

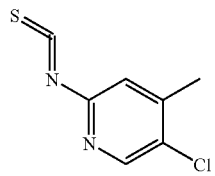

To 5-chloro-4-methylpyridin-2-amine (0.41 g, 2.88 mmol) in dichloromethane (25 mL) was added 1,1'-thiocarbonyldipyridin-2(1H)-one (0.70 g, 3.0 mmol). The reaction was stirred at 40° C. for 3 hours. The reaction was cooled to room temperature. The crude mixture was purified by chromatography (Biotage: 25-100% ethyl acetate/hexane) to yield 5-chloro-2-isothiocyanato-4-methylpyridine (0.45 g, 2.44 mmol, 85% yield). 1H NMR (500 MHz, DMSO-D6) δ ppm 8.45 (s, 1 H), 7.47 (s, 1 H), 2.37 (s, 3 H). LC/MS RT=2.79; $[M+H]^+$=184.9.

Step B: (R)—N-(5-Chloro-4-methylpyridin-2-yl)-4H-1'-azaspiro[oxazole-5,3'-bicyclo[2.2.2]octan]-2-amine

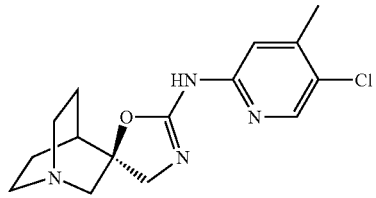

To 5-chloro-2-isothiocyanato-4-methylpyridine (0.37 g, 2.0 mmol) in N,N-dimethylformamide (20 mL) was added triethylamine (0.7 mL, 5.0 mmol) and (S)-3-(aminomethyl)quinuclidin-3-ol dihydrochloride (from Step B of Example 17) (0.47 g, 2.0 mmol) at room temperature. The reaction was stirred at 70° C. for 2 hours. The reaction was cooled to room temperature and concentrated in vacuo. The crude urea was purified by chromatography (Biotage: 85% $CHCl_3$, 14% MeOH, 1% $NH_4OH$). The product was then treated with N,N-dimethylformamide (20 mL) and N,N'-diisopropylcarbodiimide (0.94 mL, 6.0 mmol). The reaction was heated to 70° C. for 2 hours. The reaction was cooled to room temperature and concentrated to yield the crude product. The crude product was purified by chromatography (Biotage: 85% $CHCl_3$, 14% MeOH, 1% $NH_4OH$) to yield (R)—N-(5-chloro-4-methylpyridin-2-yl)-4H-1'-azaspiro[oxazole-5,3'-bicyclo[2.2.2]octan]-2-amine (0.19 g, 0.61 mmol, 30.3% yield) as a white powder. 1H NMR (500 MHz, DMSO-D6) δ ppm 8.79 (s, 1 H), 8.08-8.15 (m, 2 H), 6.78 (s, 1 H), 3.82 (d, J=8.55 Hz, 2 H), 3.55 (d, J=10.38 Hz, 2 H), 2.93-3.02 (m, 5 H), 2.71-2.80 (m, 5 H), 2.66 (t, J=7.63 Hz, 4 H), 2.23-2.29 (m, 7 H), 1.94-2.02 (m, 2 H), 1.92 (s, 1 H), 1.86 (s, 2 H), 1.53-1.62 (m, 5 H), 1.41-1.49 (m, J=12.55, 9.88, 7.02, 2.29 Hz, 2 H). MS (LC/MS) R.T.=0.72; $[M+H]^+$=307.1.

EXAMPLE 254

(R)—N-(6-Chloropyridazin-3-yl)-4H-1'-azaspiro[oxazole-5,3'-bicyclo[2.2.2]octan]-2-amine

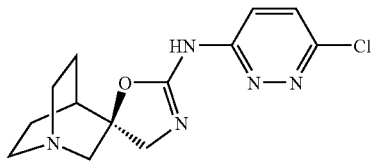

Step A: 3-Chloro-6-isothiocyanatopyridazine

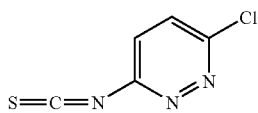

3-Chloro-6-isothiocyanatopyridazine was synthesized by the method of Example 218, Step D. Flash chromatography on a 120 g silica gel cartridge with 0 to 25% EtOAc in hexane, 25 min, at 35 mL/min afforded 213 mg (31% yield).
LCMS: RT=1.25 min, MH+=172.00.

Step B: (R)—N-(6-Chloropyridazin-3-yl)-4H-1'-azaspiro[oxazole-5,3'-bicyclo[2.2.2]octan]-2-amine

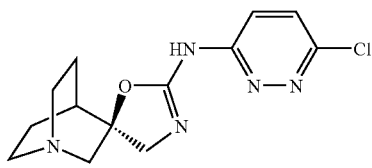

(R)—N-(6-Chloropyridazin-3-yl)-4H-1'-azaspiro[oxazole-5,3'-bicyclo[2.2.2]octan]-2-amine was synthesized by the method of Example 218, Step E. Flash chromatography on a 160 g silica gel cartridge with 1-3% [9:1 MeOH/NH4OH] in CHCl3, 50 min, at 40 mL/min afforded 29 mg (8% yield).
1H NMR (400 MHz, CDCl$_3$) δ ppm 9.27 (1 H, br. s.), 7.28 (1 H, d, J=9.07 Hz), 7.10 (1H, d, J=9.07 Hz), 3.95 (1 H, d, J=9.57 Hz), 3.62 (1 H, d, J=9.57 Hz), 3.34 (1 H, dd, J=14.98, 1.64 Hz), 2.67-3.04 (5 H, m), 2.14-2.21 (1 H, m), 2.12 (1 H, br. s.), 1.65-1.79 (1 H, m), 1.45-1.61 (2 H, m).
LCMS: RT=0.62 min, MH−=292.1, MH+=294.1.

EXAMPLE 255

(R)—N-(6-Bromopyridazin-3-yl)-4H-1'-azaspiro[oxazole-5,3'-bicyclo[2.2.2]octan]-2-amine

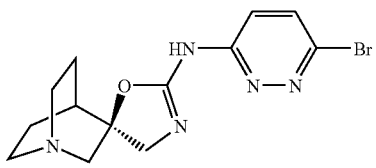

Step A: 3-Bromo-6-isothiocyanatopyridazine

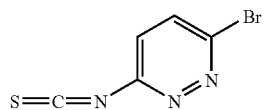

3-Bromo-6-isothiocyanatopyridazine was synthesized by the method of Example 218, Step D. Flash chromatography on a 120 g silica gel cartridge with 0 to 25% EtOAc in hexane, 25 min, at 35 mL/min afforded 364 mg (42% yield).
LCMS: RT=1.34 min, MH+=215.92.

Step B: (R)—N-(6-Bromopyridazin-3-yl)-4H-1'-azaspiro[oxazole-5,3'-bicyclo[2.2.2]octan]-2-amine

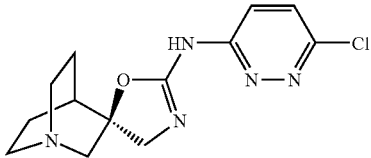

(R)—N-(6-Bromopyridazin-3-yl)-4H-1'-azaspiro[oxazole-5,3'-bicyclo[2.2.2]octan]-2-amine was synthesized by the method of Example 218, Step E. Flash chromatography on a 160 g silica gel cartridge with 1-3% [9:1 MeOH/NH4OH] in CHCl3, 50 min, at 40 mL/min afforded 211 mg (37% yield).
1H NMR (400 MHz, CDCl$_3$) δ ppm 9.23 (1 H, br. s.), 7.37 (1 H, d, J=9.07 Hz), 6.97 (1 H, d, J=9.07 Hz), 3.92 (1 H, d, J=9.57 Hz), 3.59 (1 H, d, J=9.82 Hz), 3.29 (1 H, dd, J=14.98, 1.64 Hz), 2.63-2.99 (5 H, m), 2.04-2.19 (2 H, m), 1.59-1.74(1 H, m), 1.39-1.58 (2 H, m)
LCMS: RT=0.64 min., MH− 336.1, MH+ 338.0.

EXAMPLE 256

(R)—N-(6-(4-Chlorophenyl)pyrimidin-4-yl)-4H-1'-azaspiro[oxazole-5,3'-bicyclo[2.2.2]octan]-2-amine

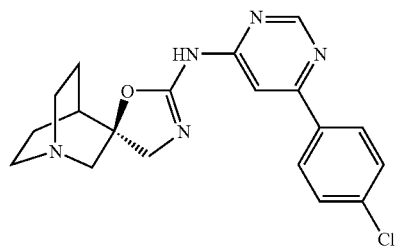

Step A: 6-(Pyridin-4-yl)pyrimidin-4-amine

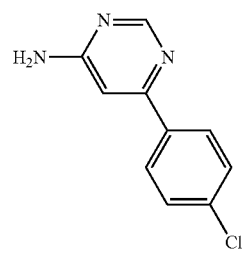

A mixture of 6-chloropyrimidin-4-amine (0.324 g, 2.5 mmol), 4-chlorophenylboronic acid (0.489 g, 3.13 mmol), Na₂CO₃ (0.795 g, 7.50 mmol) and bis(triphenylphosphine)palladium(II)chloride (0.035 g, 0.050 mmol) was suspended in a mixture of DME/EtOH/water (15:2:3 mL). The mixture was heated in the microwave synthesizer at 125° C. for 20 min and concentrated. The residue was purified by silica gel chromatography (2-15% 9:1 methanol:ammonium hydroxide-ethyl acetate) to afford:6-(pyridin-3-yl)pyrimidin-4-amine (0.3 g, 0.871 mmol, 58.4% yield) as an off-white solid. LCMS R.T.=1.42; [M+2H]$^+$=207.91.

Step B:
4-(4-Chlorophenyl)-6-isothiocyanatopyrimidine

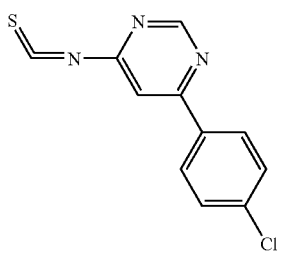

To a bright orange solution of 1,1'-thiocarbonyldipyridin-2(1H)-one(0.666 g, 2.87 mmol) dichloromethane/N,N-dimethylformamide at room temperature was added 6-(4-chlorophenyl)pyrimidin-4-amine (0.59 g, 2.87 mmol). The orange mixture was heated at 60° C. for 18 hours. The LC/MS showed the desired product peak as a major peak. The deep orange mixture was purified by silica gel chromatography (0-40% ethyl acetate-hexanes) to afford 4-(4-chlorophenyl)-6-isothiocyanatopyrimidine (0.322 g, 1.300 mmol, 45% yield) as an orange oil. LCMS R.T.=2.82; [M]$^+$=248.03.

Step C: (R)—N-(6-(4-Chlorophenyl)pyrimidin-4-yl)-4H-1'-azaspiro[oxazole-5,3'-bicyclo[2.2.2]octan]-2-amine

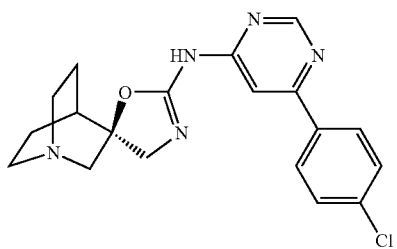

To (S)-3-(aminomethyl)quinuclidin-3-ol dihydrochloride (0.298 g, 1.300 mmol) in N,N-dimethylformamide (15 mL) was added Cs₂CO₃ (1.059 g, 3.25 mmol) and 4-(4-chlorophenyl)-6-isothiocyanatopyrimidine (0.322 g, 1.300 mmol). The suspension was stirred at room temperature for 30 minutes. N,N'-Diisopropylcarbodiimide (0.608 mL, 3.90 mmol) was then added and the mixture was stirred at room temperature for 18 hours. The mixture was concentrated and purified by silica gel chromatography (5-25% 9:1 methanol:ammonium hydroxide-ethyl acetate) to afford (R)—N-(6-(pyridin-4-yl)pyrimidin-4-yl)-4H-1'-azaspiro[oxazole-5,3'-bicyclo[2.2.2] octan]-2-amine (0.104 g, 0.276 mmol, 21% yield) as a yellow solid. $^1$H NMR (400 MHz, CDCl₃) δ ppm 9.54 (1 H, br. s.), 8.83 (1 H, d), 7.89-8.04 (2 H, m), 7.41-7.54 (2 H, m), 7.33 (1 H, br. s.), 4.02 (1 H, d), 3.71 (1 H, d), 3.42 (1 H, d), 2.73-3.15 (5 H, m), 2.10-2.31 (2 H, m), 1.46-1.89 (3 H, m). LCMS R.T.=1.92; [M]$^+$=370.35.

EXAMPLE 257

(R)—N-(6-(3-Chlorophenyl)pyrimidin-4-yl)-4H-1'-azaspiro[oxazole-5,3'-bicyclo[2.2.2]octan]-2-amine

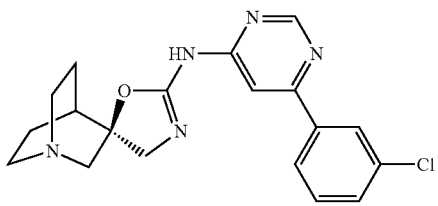

Step A: 6-(3-Chlorophenyl)pyrimidin-4-amine

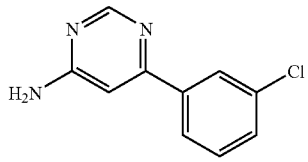

A mixture of 6-chloropyrimidin-4-amine (0.324 g, 2.5 mmol), 3-chlorophenylboronic acid (0.489 g, 3.13 mmol), Na₂CO₃ (0.795 g, 7.50 mmol) and bis(triphenylphosphine)palladium(II)chloride (0.035 g, 0.050 mmol) was suspended in a mixture of DME/EtOH/wate (15:2:3 mL). The mixture was heated in the microwave synthesizer at 125° C. for 20 min and concentrated. The residue was purified by silica gel chromatography (30-70% ethyl acetate in hexanes) to afford: 6-(3-chlorophenyl)pyrimidin-4-amine (0.47 g, 2.286 mmol, 91% yield) as a yellow solid. LCMS R.T.=1.45; [M+2H]$^+$= 208.05.

Step B:
4-(3-Chlorophenyl)-6-isothiocyanatopyrimidine

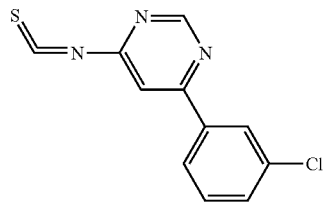

To a bright orange solution of 1,1'-thiocarbonyldipyridin-2(1H)-one (0.486 g, 2.091 mmol) in dichloromethane/N,N-dimethylformamide at room temperature was added 6-(3-chlorophenyl)pyrimidin-4-amine (0.43 g, 2.091 mmol). The orange mixture was heated at 60° C. for 18 hours. The LC/MS showed the desired product peak as a major peak. The deep orange mixture was purified by silica gel chromatography (0-40% ethyl acetate-hexanes) to afford 4-(3-chlorophenyl)-6-isothiocyanatopyrimidine (0.12 g, 0.484 mmol, 23% yield) as an orange oil. LCMS R.T.=2.15; [M]$^+$=248.31.

Step C: (R)—N-(6-(3-Chlorophenyl)pyrimidin-4-yl)-4H-1'-azaspiro[oxazole-5,3'-bicyclo[2.2.2]octan]-2-amine

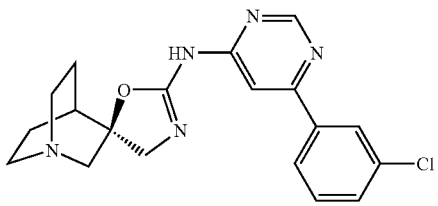

To (S)-3-(aminomethyl)quinuclidin-3-ol dihydrochloride (0.111 g, 0.484 mmol) in N,N-dimethylformamide (15 mL) was added Cs$_2$CO$_3$ (0.395 g, 1.211 mmol) and 4-(3-chlorophenyl)-6-isothiocyanatopyrimidine (0.12 g, 0.484 mmol). The suspension was stirred at room temperature for 30 minutes. N,N'-diisopropylcarbodiimide (0.226 mL, 1.453 mmol) was then added and the mixture was continued to stir at room temperature for 18 hours. The mixture was concentrated and purified by silica gel chromatography (5-25%, then, 2-10% 9:1 methanol:ammonium hydroxide-ethyl acetate) to afford (R)—N-(6-(3-chlorophenyl)pyrimidin-4-yl)-4H-1'-azaspiro[oxazole-5,3'-bicyclo[2.2.2]octan]-2-amine (0.086 g, 0.221 mmol, 46% yield) as a yellow solid. $^1$H NMR (400 MHz, MeOD) δ ppm 8.82 (1 H, d), 8.05 (1 H, d), 7.93 (1 H, ddd), 7.43-7.52 (2 H, m), 7.35 (1 H, br. s.), 4.13 (1 H, d), 3.93 (1 H, d), 3.63-3.81 (2 H, m), 3.42-3.53 (1 H, m), 3.30-3.40 (3 H, m), 2.46 (1 H, d), 2.26-2.40 (1 H, m), 1.88-2.16 (3 H, m). LCMS R.T.=1.90; [M]$^+$=370.28.

EXAMPLE 258

(R)—N-(5-Methyl-1,3,4-oxadiazol-2-yl)-4 H-1'-azaspiro[oxazole-5,3'-bicyclo[2.2.2]octan]-2-amine

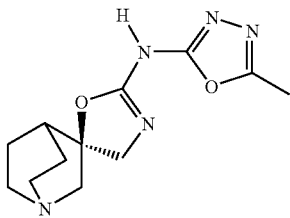

Step A: Dimethyl 5-methyl-1,3,4-oxadiazol-2-ylcarbonimidodithioate

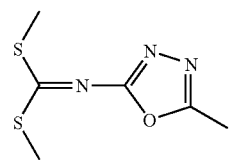

To a solution of 5-methyl-1,3,4-oxadiazol-2-amine (1.92 g, 20 mmol) in DMF (10 ml) was added NaOH (20M, 2 ml), CS$_2$ (3 ml), NaOH (20M, 2 ml) and iodomethane (3 ml) slowly over 10 minutes. The mixture was stirred at room temperature for 1 h and poured into 20 ml water. The precipitated solid was filtered, washed with water, and dried to obtain the desired product, dimethyl 5-methyl-1,3,4-oxadiazol-2-ylcarbonimidodithioate as a white solid (1.45 g, 35.7%). $^1$H NMR (500 MHz, CDCl$_3$) δ ppm 2.63 (s, 6H), 2.50 (s, 3H). LCMS R.T. 1.66 min; [M+H]=203.91.

Step B: (R)—N-(5-Methyl-1,3,4-oxadiazol-2-yl)-4H-1'-azaspiro[oxazole-5,3'-bicyclo[2.2.2]octan]-2-amine

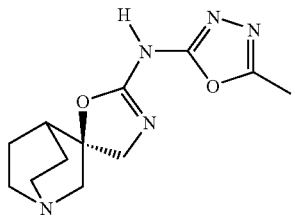

A mixture of dimethyl 5-methyl-1,3,4-oxadiazol-2-ylcarbonimidodithioate (260 mg, 1.28 mmol), (S)-3-(aminomethyl)quinuclidin-3-ol dihydrochloride (200 mg, 1.28 mmol) and cesium carbonate (876 mg, 2.69 mmol) in DMF (5 ml) was stirred overnight at room temperature. The mixture was concentrated and purified on a Biotage silica gel column (100% ethyl acetate, then 10-35% 9:1 methanol:ammonium hydroxide-chloroform) to obtain the desired product, (R)—N-(5-methyl-1,3,4-oxadiazol-2-yl)-4H-1'-azaspiro[oxazole-5,3'-bicyclo[2.2.2]octan]-2-amine (192 mg, 54.1%). $^1$H NMR (500 MHz, MeOD) δ ppm 4.05 (d, 1H), 3.74 (d, 1H), 3.25 (d, 1H), 3.15 (d, 1H), 2.94 (m, 2H), 2.85 (m, 2H), 2.43 (s, 3H), 2.19 (m, 1H), 2.10 (m, 1H), 1.6-1.8 (m, 3H). MS (LCMS) [M+H]=264.05. R.T. 0.16 min.

EXAMPLE 259

(R)—N-(3-Methyl-1,2,4-thiadiazol-5-yl)-4H-1'-azaspiro[oxazole-5,3'-bicyclo[2.2.2]octan]-2-amine

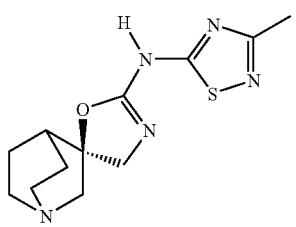

Step A: Dimethyl 3-methyl-1,2,4-thiadiazol-5-ylcarbonimidodithioate

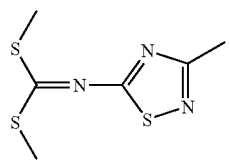

To a solution of 3-methyl-1,2,4-thiadiazol-5-amine (2.3 g, 20 mmol) in DMF (10 ml) was added NaOH (20M, 2 ml), CS$_2$ (3 ml), NaOH (20M, 2 ml) and iodomethane (3 ml) slowly over 10 minutes. The mixture was stirred at room temperature for 1 h and poured into 20 ml water. The precipitated solid was filtered and washed with water, and dried to obtain impure dimethyl 3-methyl-1,2,4-thiadiazol-5-ylcarbonimidodithioate, a yellow solid (2.3 g, 52.5%). ¹H NMR (500 MHz, CDCl3) δ ppm 2.67 (s), 2.62 (s). MS [M+H]=219.85.

Step B: (R)—N-(3-Methyl-1,2,4-thiadiazol-5-yl)-4H-1'-azaspiro[oxazole-5,3'-bicyclo[2.2.2]octan]-2-amine

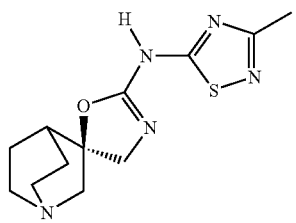

A mixture of dimethyl 3-methyl-1,2,4-thiadiazol-5-ylcarbonimidodithioate (281 mg, 1.28 mmol), (S)-3-(aminomethyl)quinuclidin-3-ol dihydrochloride (200 mg, 1.28 mmol) and cesium carbonate (876 mg, 2.69 mmol) in DMF (5 ml) was stirred overnight at room temperature. The mixture was concentrated and purified on a Biotage silica gel column (100% ethyl acetate, then 10-35% 9:1 methanol:ammonium hydroxide-chloroform) to obtain the desired product, (R)—N-(3-methyl-1,2,4-thiadiazol-5-yl)-4H-1'-azaspiro[oxazole-5,3'-bicyclo[2.2.2]octan]-2-amine (147.8 mg, 40.5%). ¹H NMR (500 MHz, MeOD) δ ppm 4.01-3.99 (d, 1H), 3.72-3.70 (d, 1H), 3.27 (d, 1H), 3.16 (d, 1H), 3.01-2.9 (m, 2H), 2.86-2.83 (m, 2H), 2.43 (s, 3H), 2.21-2.0(m, 2H), 1.81-1.75(m, 1H), 1.75-1.70 (m, 2H). MS (LCMS) [M+H]=279.99; R.T.=0.2 min.

EXAMPLE 260

(R)—N-(3-Methyl-1,2,4-oxadiazol-5-yl)-4H-1'-azaspiro[oxazole-5,3'-bicyclo[2.2.2]octan]-2-amine

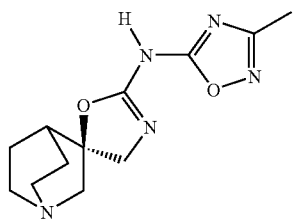

Step A: Dimethyl 3-methyl-1,2,4-oxadiazol-5-ylcarbonimidodithioate

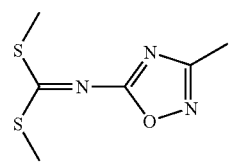

To a solution of 3-methyl-1,2,4-oxadiazol-5-amine (490 mg, 4.94 mmol) in DMF (5 ml) was added NaOH (20M, 0.5 ml), CS₂ (1 ml), NaOH (20M, 0.5 ml) and iodomethane (1 ml) slowly over 10 minutes. The mixture was stirred at room temperature for 1 hour. The mixture became very thick, and 20 ml water was added. The solid was filtered off, washed with water, and dried to obtain impure dimethyl 3-methyl-1,2,4-oxadiazol-5-ylcarbonimidodithioate, a yellow solid (770 mg, 77%). MS (LCMS) [M+H]=203.91; R.T.=1.84 min. The product was used directly in the next step.

Step B: (R)—N-(3-Methyl-1,2,4-oxadiazol-5-yl)-4H-1'-azaspiro[oxazole-5,3'-bicyclo[2.2.2]octan]-2-amine

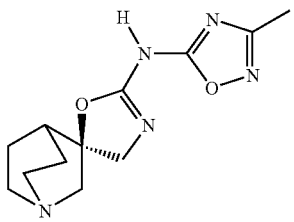

A mixture of dimethyl 3-methyl-1,2,4-oxadiazol-5-ylcarbonimidodithioate (280 mg, 1.37 mmol), (S)-3-(aminomethyl)quinuclidin-3-ol dihydrochloride (215 mg, 1.37 mmol) and cesium carbonate (942 mg, 2.89 mmol) in DMF (5 ml) was stirred overnight at room temperature. The mixture was concentrated and purified on a Biotage silica gel column (100% ethyl acetate, then 10-35% 9:1 methanol:ammonium hydroxide-chloroform) to obtain the desired product, (R)—N-(3-methyl-1,2,4-oxadiazol-5-yl)-4H-1'-azaspiro[oxazole-5,3'-bicyclo[2.2.2]octan]-2-amine (198 mg, 51.9%). ¹H NMR (500 MHz, MeOD) δ ppm 4.1-4.0 (d, 1H), 3.8-3.7 (d, 1H), 3.4-3.2 (d, 1H), 3.2-3.1 (d, 1H), 3.0-2.9 (m, 2H), 2.9-2.8 (m, 2H), 2.27 (s, 3H), 2.2 (m, 1H), 2.2-2.0 (m, 1H), 1.9-1.6 (m, 3H). MS (LCMS) [M+H]=264.05; R.T.=0.26 min.

EXAMPLE 261

(R)—N-(6-(Methylthio)pyrimidin-4-yl)-4H-1'-azaspiro[oxazole-5,3'-bicyclo[2.2.2]octan]-2-amine

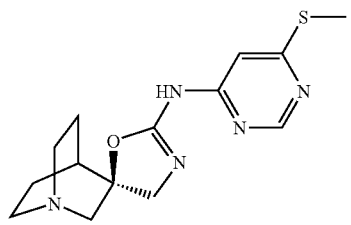

Step A: Dimethyl 6-chloropyrimidin-4-ylcarbonimidodithioate

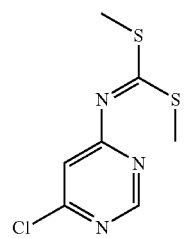

To a solution of 6-chloropyrimidin-4-amine (1.295 g, 10 mmol) in N,N-dimethylformamide (12 mL) was added dropwise NaOH (1 mL, 20.00 mmol, 20 M), CS2 (1.5 mL, 24.88 mmol), NaOH (1 mL, 20.00 mmol, 20 M) and iodomethane (1.5 mL, 23.99 mmol) at 15 min intervals. Stirring was continued for 1.5 h and the mixture was poured into water. The orange solid was separated washed with water, dried and recrystallised from methanol to afford dimethyl 6-chloropyrimidin-4-ylcarbonimidodithioate (0.966 g, 4.13 mmol, 41.3% yield) as a yellow solid. LCMS R.T.=2.39; [M+H]⁺= 234.08.

Step B: (R)—N-(6-(Methylthio)pyrimidin-4-yl)-4H-1'-azaspiro[oxazole-5,3'-bicyclo[2.2.2]octan]-2-amine

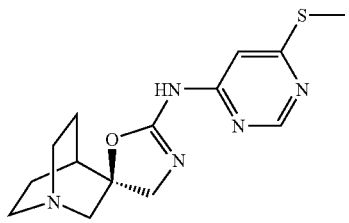

To (S)-3-(aminomethyl)quinuclidin-3-ol dihydrochloride (0.9 g, 3.93 mmol) in N,N-dimethylformamide (20 mL) was added Cs₂CO₃ (2.69 g, 8.25 mmol) and dimethyl 6-chloropyrimidin-4-ylcarbonimidodithioate (0.964 g, 4.12 mmol). The suspension was stirred at room temperature for 18 hours, then heated at 100 C for 3 hours. The mixture was concentrated and purified by silica gel chromatography (5-15% 9:1 methanol:ammonium hydroxide-ethyl acetate) to afford (R)—N-(6-(methylthio)pyrimidin-4-yl)-4H-1'-azaspiro[oxazole-5,3'-bicyclo[2.2.2]octan]-2-amine (0.21 g, 0.72 mmol, 48.2% yield) as a pale yellow solid. ¹H NMR (400 MHz, CDCl₃) δ ppm 9.43 (1 H, br. s.), 8.55 (1 H, d), 6.78 (1 H, br. s.), 3.98 (1 H, d), 3.64 (1 H, d), 3.37 (1 H, dd), 2.72-3.06 (5 H, m), 2.51 (3 H, s), 2.08-2.24 (2 H, m), 1.69-1.81 (1 H, m), 1.41-1.64 (2 H, m). LCMS R.T.=0.93; [M+H]⁺=306.29.

EXAMPLE 262

(R)—N-([1,2,4]Triazol[4,3-a]pyridine-3-yl)-4H-1'-azaspiro[oxazole-5,3'-bicyclo[2.2.2]octan]-2-amine

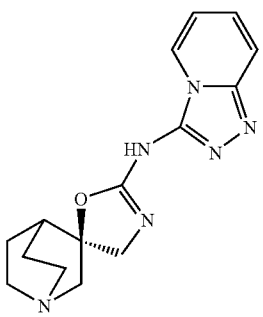

Step A: Di(1H-imidazol-1-yl)methanimine

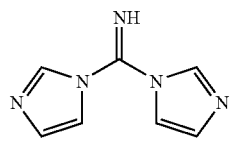

To a solution of 1H-imidazole (42 g, 617 mmol) in dichloromethane (1 L) was added cyanogen bromide (22.5, 212 mmol) and the mixture was heated to reflux for 30 minutes, allowed to cool to room temperature and the white solid was filtered off. The filtrate was concentrated to 100 ml and stored in the refrigerator for 3 days. The precipitated solid was filtered off to obtain 8 g di(1H-imidazol-1-yl)methanimine (49.6 mmol, 8%). ¹H NMR (500 MHz, DMSO) δ ppm 8.09 (s, 1H), 7.55 (s, 1H), 7.13 (s, 1H).

Step B: [1,2,4]Triazolo[4,3-a]pyridine-3-amine

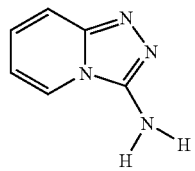

To a solution of 2-hydrazinylpyridine (5.2 g, 47.6 mmol) in THF (70 ml) was added di(1H-imidazol-1-yl)methanimine (7.8 g, 48.4 mmol). The mixture was heated to reflux overnight. The crude mixture was evaporated and purified on a Biotage silica gel column (0-25%, methanol-methylene chloride) collecting the purple-colored spot, [1,2,4]triazolo[4,3-a]pyridine-3-amine (4.7 g, 35 mmol, 73.5%). ¹H NMR (500 MHz, DMSO) δ ppm 8.05-8.0 (m, 1H), 7.44-7.40 (m, 1H), 7.08-7.0 (m, 1H), 6.74-6.70 (m, 1H), 6.35 (s, 2H). MS (LCMS) [M+H]=134.98; R.T.=0.1 min.

Step C: Dimethyl[1,2,4]triazol[4,3-a]pyridine-3-ylcarbonimidodithioate

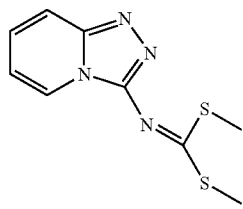

To a solution of [1,2,4]triazolo[4,3-a]pyridine-3-amine (300 mg, 2.24 mmol) in DMF (5 ml) was added NaOH (20M, 0.25 ml), CS₂ (0.5 ml), NaOH (20M, 0.25 ml) and iodomethane (0.5 ml) slowly over 10 minutes. The mixture was stirred at room temperature for 1 h and 10 ml water was added to the reaction mixture. The precipitated solid was filtered off, washed with water (100 ml), and dried to obtain 230 mg dimethyl[1,2,4]triazol[4,3-a]pyridine-3-ylcarbonimidodithioate (0.96 mmol, 43.1%), a white solid. ¹H NMR (500 MHz, CDCl3) δ ppm 8.17 (d, 1H), 7.7 (d, 1H), 7.24-7.22 (t, 1H), 6.84-6.80 (t, 1H), 2.71-2.68 (d, 6H). MS (LCMS) [M+H]=238.94; R.T.=1.26 min.

Step D: (R)—N-([1,2,4]Triazol[4,3-a]pyridine-3-yl)-4H-1'-azaspiro[oxazole-5,3'-bicyclo[2.2.2]octan]-2-amine

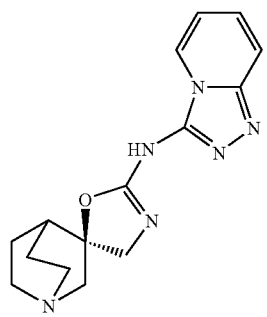

A mixture of dimethyl[1,2,4]triazol[4,3-a]pyridine-3-ylcarbonimidothioate (120 mg, 0.50 mmol), (S)-3-(aminomethyl)quinuclidin-3-ol dihydrochloride (120 mg, 0.76 mmol) and cesium carbonate (492 mg, 1.5 mmol) in DMF (5 ml) was heated at 70° C. for 6 hours. The mixture was concentrated and purified on a Biotage silica gel column (100% ethyl acetate, then 10-35% 9:1 methanol:ammonium hydroxide-chloroform) to obtain the desired product, (R)—N-([1,2,4]triazol[4,3-a]pyridine-3-yl)-4H-1'-azaspiro[oxazole-5,3'-bicyclo[2.2.2]octan]-2-amine (97.2 mg, 61.5%). $^{1}$H NMR (500 MHz, CDCl3) δ ppm 8.2-8.1 (d, 1H), 7.6-7.5 (d, 1H), 7.2-7.1 (t, 1H), 6.7-6.6 (t, 1H), 4.1-4.0 (d, 1H), 3.7-3.6 (d, 1H), 3.5-3.4 (m, 1H), 3.1-2.7(m, 5H), 2.4-2.2 (m, 2H), 1.8-1.7 (m, 1H), 1.7-1.5(m, 2H). MS (LCMS) [M+H]=299.3; R.T.=1.22 min.

EXAMPLE 263

(R)—N-(6-bromothiazolo[5,4-b]pyrazin-2-yl)-4H-1'-azaspiro[oxazole-5,3'-bicyclo[2.2.2]octan]-2-amine

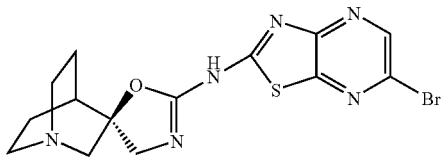

Step A: Dimethyl 6-bromothiazolo[5,4-b]pyrazin-2-ylcarbonimidodithioate

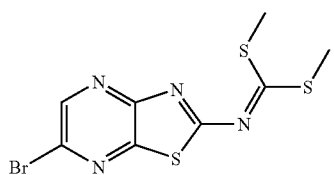

To a suspension of 6-bromothiazolo[5,4-b]pyrazin-2-amine (700 mg, 3.03 mmol) in DMF (3 mL) was added 16.0M sodium hydroxide (400 μL, 6.40 mmol). The mixture was allowed to stir 10 min at room temperature at which time carbon disulfide was added (450 μL, 7.57 mmol) and the resulting reddish brown mixture was stirred for 10 minutes. An additional portion of 16.0M sodium hydroxide (400 μL, 6.40 mmol) was added and the mixture was again stirred for 10 minutes. Finally, iodomethane (450 μL, 7.27 mmol) was added dropwise. The mixture was stirred for 5 minutes, at which time a voluminous yellow precipitate had formed. The mixture was poured into water and the solids were collected by filtration to afford dimethyl 6-bromothiazolo[5,4-b]pyrazin-2-ylcarbonimidodithioate (680 mg, 67% yield) as a yellow solid of sufficient purity to use without further purification. 1H NMR (400 MHz, CDCl$_3$) δ ppm 8.63 (s, 1 H) 2.68 (s, 6 H).

Step B: (R)—N-(6-bromothiazolo[5,4-b]pyrazin-2-yl)-4H-1'-azaspiro[oxazole-5,3'-bicyclo[2.2.2]octan]-2-amine

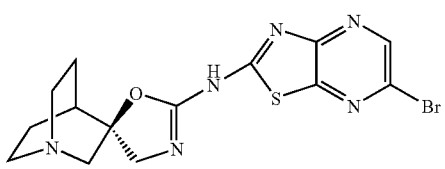

A mixture of dimethyl 6-bromothiazolo[5,4-b]pyrazin-2-ylcarbonimidodithioate (300 mg, 0.895 mmol), (S)-3-(aminomethyl)quinuclidin-3-ol dihydrochloride (210 mg, 0.895 mmol) and cesium carbonate (600 mg, 1.79 mmol) in acetonitrile (25 mL) was heated on a 100° C. oil bath for 2 hours in an open flask, with nitrogen bubbling through the solution the entire time to help in the removal of methanethiol. After 2 hours, TLC showed the reaction to be complete, so the mixture was cooled to ambient temperature, diluted with water and concentrated in vacuo. The mixture was extracted with chloroform (4×). The combined organics were washed with brine, dried over sodium sulfate, filtered, concentrated in vacuo, and the crude residue was purified by silica gel chromatography (2-40% 9:1 methanol:ammonium hydroxide-chloroform). The product fractions were combined and concentrated in vacuo to afford (R)—N-(6-bromothiazolo[5,4-b]pyrazin-2-yl)-4H-1'-azaspiro[oxazole-5,3'-bicyclo[2.2.2]octan]-2-amine (200 mg, 57% yield). 1H NMR (400 MHz, CDCl$_3$) δ ppm 9.39 (br. s., 1 H) 8.48 (s, 1 H) 4.05 (d, J=9.79 Hz, 1 H) 3.72 (d, J=9.79 Hz, 1 H) 3.42 (dd, J=15.06, 1.76 Hz, 1 H) 2.73-3.08 (m, 5 H) 2.10-2.22 (m, 2 H) 1.73-1.84 (m, J=14.09, 9.94, 4.17, 4.17 Hz, 1 H) 1.52-1.65 (m, 2 H). MS (LC/MS) R.T.=1.29; [M+H]$^{+}$=394.99.

EXAMPLE 264

(R)—N-(6-(methylthio)thiazolo[5,4-b]pyrazin-2-yl)-4H-1'-azaspiro[oxazole-5,3'-bicyclo[2.2.2]octan]-2-amine

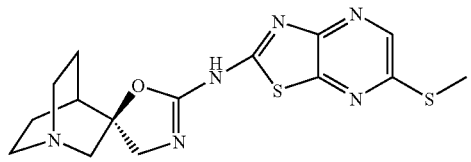

A mixture of dimethyl 6-bromothiazolo[5,4-b]pyrazin-2-ylcarbonimidodithioate from Step A of Example 263 (100 mg, 0.298 mmol), (S)-3-(aminomethyl)quinuclidin-3-ol dihydrochloride (68 mg, 0.298 mmol) and cesium carbonate (100 mg, 0.60 mmol) in DMF (1.5 mL) was placed in a 1 dram vial and heated on a 100° C. oil bath for 1 hour, at which time, sodium thiomethoxide (100 mg, 1.43 mmol) was added and the mixture was heated overnight. The mixture was cooled to ambient temperature and poured into water (20 mL) and the resulting solids were collected by filtration and then purified by silica gel chromatography (2-40% 9:1 methanol:ammonium hydroxide-chloroform). The product fractions were combined and concentrated in vacuo to afford (R)—N-(6-(methylthio)thiazolo[5,4-b]pyrazin-2-yl)-4H-1'-azaspiro[oxazole-5,3'-bicyclo[2.2.2]octan]-2-amine (52 mg, 46% yield). 1H NMR (500 MHz, CDCl$_3$) δ ppm 9.39 (br. s., 1 H) 8.31 (s, 1 H) 4.03 (d, J=9.77 Hz, 1 H) 3.70 (d, J=9.77 Hz, 1 H) 3.41 (dd, J=14.95, 1.83 Hz, 1 H) 2.73-3.10 (m, 5 H) 2.63 (s, 3 H) 2.10-2.25 (m, 2 H) 1.47-1.86 (m, 3 H). MS (LC/MS) R.T.=1.04; [M+H]$^{+}$=363.04.

EXAMPLE 265

(R)—N-(5-Methoxythiazolo[5,4-d]pyrimidin-2-yl)-4H-1'-azaspiro[oxazole-5,3'-bicyclo[2.2.2]octan]-2-amine

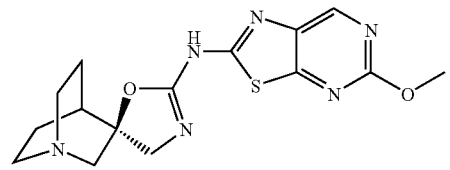

Step A: 5-Methoxythiazolo[5,4-d]pyrimidin-2-amine

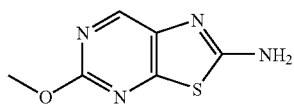

Ethyl 5-chlorothiazolo[5,4-d]pyrimidin-2-ylcarbamate (250 mg, 0.966 mmol) was suspended in MeOH (10 mL) and a 25% (w/w) solution of sodium methoxide in methanol was added (10 mL, 46.3 mmol). The resulting solution was refluxed overnight, cooled to ambient temperature, poured into an equal volume of water and extracted with chloroform (4×). A significant amount of compound was still present in the aqueous phase, so this was concentrated to residue, and then dissolved in a small amount of 1N HCl (not enough to make the resulting solution acidic) and extracted again with EtOAc (5×). The combined organics were washed with brine, dried over sodium sulfate, filtered and concentrated in vacuo. 5-Methoxythiazolo[5,4-d]pyrimidin-2-amine (144 mg, 0.790 mmol, 82% yield) was thus obtained as a white solid. 1H NMR (400 MHz, DMSO-$d_6$) δ ppm 8.43 (s, 1H) 7.81 (s, 2H) 3.90 (s, 3H). MS (LC/MS) R.T.=0.73; $[M+H]^+$=183.03.

Step B: Dimethyl 5-methoxythiazolo[5,4-d]pyrimidin-2-ylcarbonimidodithioate

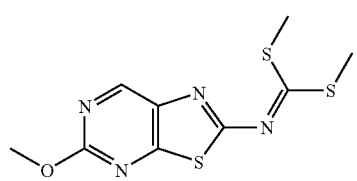

To a suspension of 5-methoxythiazolo[5,4-d]pyrimidin-2-amine (911 mg, 5.00 mmol) in DMF (5 mL) was added 20.0M sodium hydroxide (500 μL, 10.00 mmol). The mixture was allowed to stir 10 min at room temperature at which time carbon disulfide was added (750 μL, 12.50 mmol) and the resulting reddish brown mixture was stirred for 10 minutes. An additional portion of 20.0M sodium hydroxide (500 μL, 10.00 mmol) was added and the mixture was again stirred for 10 minutes. Finally, iodomethane (750 μL, 12.00 mmol) was added dropwise. The mixture was stirred for 5 minutes, at which time a voluminous yellow precipitate had formed. The mixture was poured into water and the solids were collected by filtration to afford a yellow solid that was further purified by silica gel chromatography (2-20% EtOAc/CHCl$_3$) to provide dimethyl 5-methoxythiazolo[5,4-d]pyrimidin-2-ylcarbonimidodithioate (380 mg, 27% yield). 1H NMR (400 MHz, CDCl$_3$) δ ppm 8.90 (s, 1H) 4.09 (s, 3H) 2.66 (s, 6H).

Step C: (R)—N-(5-methoxythiazolo[5,4-d]pyrimidin-2-yl)-4H-1'-azaspiro[oxazole-5,3'-bicyclo[2.2.2]octan]-2-amine

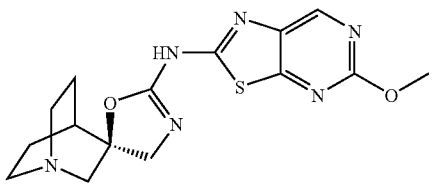

A mixture of dimethyl 5-methoxythiazolo[5,4-d]pyrimidin-2-ylcarbonimidodithioate (100 mg, 0.349 mmol), (S)-3-(aminomethyl)quinuclidin-3-ol dihydrochloride (80 mg, 0.349 mmol) and cesium carbonate (228 mg, 0.698 mmol) in DMF (1.7 mL) was heated to 100° C. for 2 hours. The reaction mixture was cooled to ambient temperature, poured into water and the solids were collected by filtration to afford (R)—N-(5-methoxythiazolo[5,4-d]pyrimidin-2-yl)-4H-1'-azaspiro[oxazole-5,3'-bicyclo[2.2.2]octan]-2-amine (78 mg, 64% yield). 1H NMR (500 MHz, CDCl$_3$) δ ppm 9.12 (br. s., 1 H) 8.63 (s, 1 H) 3.95-4.18 (m, 4 H) 3.71 (d, J=9.77 Hz, 1 H) 3.41 (d, J=15.26 Hz, 1 H) 2.74-3.10 (m, 5 H) 2.11-2.27 (m, 2 H) 1.71-1.86 (m, 1 H) 1.50-1.70 (m, 2 H). MS (LC/MS) R.T.=1.66; $[M+H]^+$=347.0.

EXAMPLE 266

(R)—N-(5-Ethyl-1,3,4-oxadiazol-2-yl)-4H-1'-azaspiro[oxazole-5,3'-bicyclo[2.2.2]octan]-2-amine

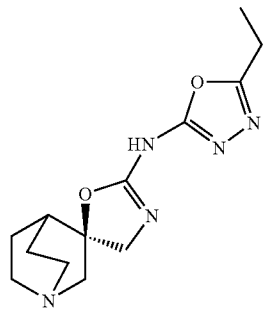

Step A: Dimethyl 5-ethyl-1,3,4-oxadiazol-2-ylcarbonimidodithioate

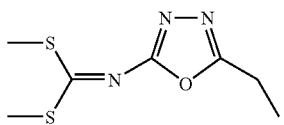

To a solution of 5-ethyl-1,3,4-oxadiazol-2-amine (2.26 g, 20 mmol) in DMF (10 ml) was added NaOH (20M, 2 ml), CS$_2$ (3 ml), NaOH (20M, 2 ml) and iodomethane (3 ml) slowly over 10 minutes. The mixture was stirred at room temperature for 2 h and poured into 30 ml water. The precipitated yellow solid was filtered off, washed with water, and dried to obtain the desired product, dimethyl 5-ethyl-1,3,4-oxadiazol-2-ylcarbonimidodithioate, a white solid (2.6 g, 59.8%). $^1$H NMR (500 MHz, CDCl3) δ ppm 2.86-2.83 (q, 2H), 2.63 (s, 6H), 1.3901.35 (t, 3H). MS (LCMS) [M+H]=217.95; R.T.=1.93 min.

Step B: (R)—N-(5-Ethyl-1,3,4-oxadiazol-2-yl)-4H-1'-azaspiro[oxazole-5,3'-bicyclo[2.2.2]octan]-2-amine

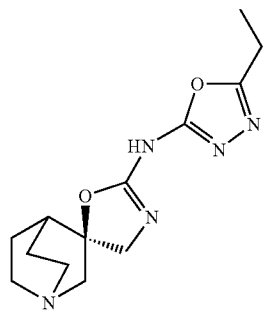

A mixture of dimethyl 5-ethyl-1,3,4-oxadiazol-2-ylcarbonimidodithioate (327 mg, 1.5 mmol), (S)-3-(aminomethyl)quinuclidin-3-ol dihydrochloride (235 mg, 1.5 mmol) and cesium carbonate (1000 mg, 3.16 mmol) in DMF (10 ml) was stirred overnight at room temperature. The mixture was concentrated and purified on a Biotage silica gel column (100% ethyl acetate, then 10-35% 9:1 methanol:ammonium hydroxide-chloroform) to obtain the desired product, (R)—N-(5-ethyl-1,3,4-oxadiazol-2-yl)-4H-1'-azaspiro[oxazole-5,3'-bicyclo[2.2.2]octan]-2-amine (290 mg, 66%). $^1$H NMR (500 MHz, MeOD) δ ppm 4.05 (d, 1H), 3.74 (d, 1H), 3.3-3.2 (d, 1H), 3.2-3.1 (d, 1H), 3.0-2.9(m, 2H), 2.9-2.8 (m, 5H), 2.2 (s, 1H), 2.15-2.0 (m, 1H), 1.9-1.6 (m, 3H), 1.4-1.3 (t, 3H). (m, 2H). MS (LCMS) [M+H]=278.09; R.T.=0.48 min.

EXAMPLE 267

(R)—N-(3,5-Dichloropyridin-2-yl)-4H-1'-azaspiro[oxazole-5,3'-bicyclo[2.2.2]octan]-2-amine

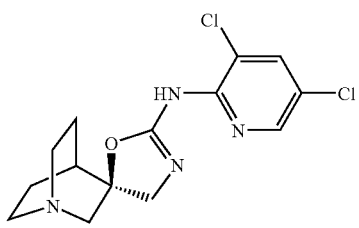

Step A: 3,5-Dichloro-2-isothiocyanatopyridine

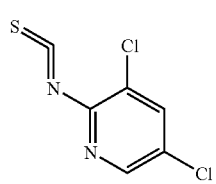

To 3,5-dichloropyridin-2-amine (0.36 g, 2.209 mmol) in dichloromethane (25 mL) was added 1,1'-thiocarbonyldipyridin-2(1H)-one (0.523 g, 2.253 mmol). The reaction was stirred at 40° C. for 3 hours. The reaction was cooled to room temperature and the crude was purified by chromatography (Biotage: 25-100% ethyl acetate/hexane) to yield to yield 3,5-dichloro-2-isothiocyanatopyridine (0.4 g, 1.951 mmol, 88% yield). 1H NMR (500 MHz, DMSO-D6) δ ppm 8.50 (t, J=2.59 Hz, 1 H), 8.45 (t, J=2.59 Hz, 1 H). MS (LC/MS) R.T.=2.07; [M+H]$^+$=204.8.

Step B: (R)—N-(3,5-Dichloropyridin-2-yl)-4H-1'-azaspiro[oxazole-5,3'-bicyclo[2.2.2]octan]-2-amine

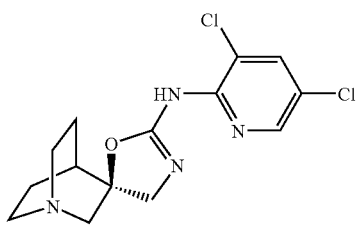

To 3,5-dichloro-2-isothiocyanatopyridine (0.11 g, 0.55 mmol) in N,N-dimethylformamide (10 mL) was added Et$_3$N (0.17 mL, 1.21 mmol) and (S)-3-(aminomethyl)quinuclidin-3-ol dihydrochloride (0.13 g, 0.56 mmol) at room temperature. The reaction was stirred at 70° C. for 2 hours. The reaction was cooled to room temperature and concentrated in vacuo. The crude urea was purified by chromatography (Biotage: 85% CHCl$_3$, 14% MeOH, 1% NH$_4$OH). The product was then treated with N,N-dimethylformamide (10 mL) and N,N'-diisopropylcarbodiimide (0.26 mL, 1.65 mmol). The reaction was heated to 70° C. for 2 hours. The reaction was cooled to room temperature and concentrated in vacuo to yield the crude product. The crude product was purified by chromatography (Biotage: 85% CHCl$_3$, 14% MeOH, 1% NH$_4$OH) to yield (R)—N-(3,5-dichloropyridin-2-yl)-4H-1'-azaspiro[oxazole-5,3'-bicyclo[2.2.2]octan]-2-amine (0.08 g, 0.24 mmol, 44% yield) as a white powder. 1H NMR (500 MHz, DMSO-D6) δ ppm 8.91 (s, 1 H), 8.11-8.17 (m, 1 H), 7.97 (d, J=2.44 Hz, 1 H), 3.84 (d, J=9.77 Hz, 1 H), 3.59 (d, J=9.77 Hz, 1 H), 2.95-3.04 (m, 2 H), 2.72-2.81 (m, 2 H), 2.66 (t, J=7.63 Hz, 2 H), 2.01 (s, 1 H), 1.89 (s, 1 H), 1.54-1.62 (m, 2 H), 1.42-1.50 (m, 1 H). MS (LC/MS) R.T.=0.78; [M+]$^+$=326.1.

EXAMPLE 268

(R)—N-(5-chlorothiazolo[5,4-b]pyridin-2-yl)-4H-1'-azaspiro[oxazole-5,3'bicyclo[2.2.2]octan]-2-amine

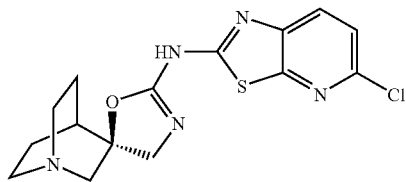

Step A: Dimethyl 5-chlorothiazolo[5,4-b]pyridin-2-ylcarbonimidodithioate

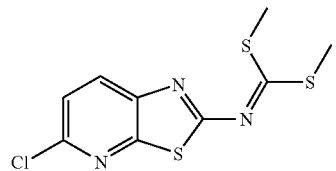

To a suspension of 5-chlorothiazolo[5,4-b]pyridin-2-amine (930 mg, 5.00 mmol) in DMF (5 mL) was added 20.0M sodium hydroxide (500 μL, 10.00 mmol). The mixture was allowed to stir 10 min at room temperature at which time carbon disulfide was added (750 μL, 12.50 mmol) and the mixture was stirred for 10 minutes. An additional portion of 20.0M sodium hydroxide (500 μL, 10.0 mmol) was added and the mixture was again stirred for 10 minutes. Finally, iodomethane (750 μL, 12.00 mmol) was added dropwise. An exotherm was noticed during this addition. The mixture was stirred for 15 minutes, at which time a voluminous precipitate had formed. The mixture was poured into water and the solids were collected by filtration. Most of the collected solids were pale yellow and crystalline. A few small clumps of a slightly darker gummy orange solid were also present, and these were manually removed and discarded. The remainder was the title compound, dimethyl 5-chlorothiazolo[5,4-b]pyridin-2-ylcarbonimidodithioate (1.00 g, 69% yield). 1H NMR (400 MHz, CDCl₃) δ ppm 8.04 (d, J=8.53 Hz, 1 H) 7.38 (d, J=8.53 Hz, 1 H) 2.66 (s, 6 H).

Step B: (R)—N-(5-chlorothiazolo[5,4-b]pyridin-2-yl)-4H-1'-azaspiro[oxazole-5,3'bicyclo[2.2.2]octan]-2-amine

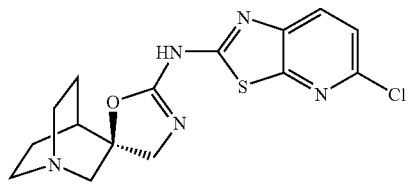

A mixture of dimethyl 5-chlorothiazolo[5,4-b]pyridin-2-ylcarbonimidodithioate (100 mg, 0.35 mmol), (S)-3-(aminomethyl)quinuclidin-3-ol dihydrochloride (79 mg, 0.35 mmol) and cesium carbonate (225 mg, 0.69 mmol) in DMF (1.7 mL) was heated to 100° C. for 2 hours. The reaction mixture was cooled to ambient temperature, poured into water and the solids collected by filtration. The crude solids were purified by silica gel chromatography (2-40% 9:1 methanol:ammonium hydroxide-chloroform) to afford (R)—N-(5-chlorothiazolo[5,4-b]pyridin-2-yl)-4H-1'-azaspiro[oxazole-5,3' bicyclo[2.2.2]octan]-2-amine (62 mg, 51% yield). 1H NMR (400 MHz, DMSO-d₆) δ ppm 9.13 (br. s., 1 H) 7.93 (d, J=8.53 Hz, 1 H) 7.45 (d, J=8.28 Hz, 1 H) 3.92 (d, J=10.29 Hz, 1 H) 3.67 (d, J=10.29 Hz, 1 H) 3.00-3.14 (m, 2 H) 2.77-2.93 (m, 2 H) 2.69 (t, J=7.65 Hz, 2 H) 2.12 (br. s., 1 H) 1.95 (br. s., 1 H) 1.43-1.72 (m, 3 H). MS (LC/MS) R.T.=1.10; [M+H]⁺=350.10.

EXAMPLE 269

(R)—N⁵,N⁵-dimethyl-N²-(4H-1'-azaspiro[oxazole-5,3'-bicyclo[2.2.2]octane]-2-yl)thiazolo[5,4-d]pyrimidine-2,5-diamine

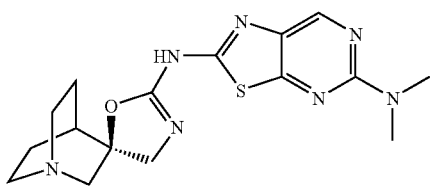

Step A: Ethyl 5-chlorothiazolo[5,4-d]pyrimidin-2-ylcarbamate

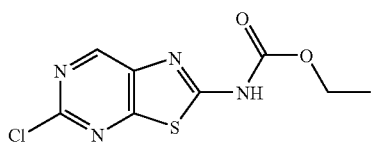

Ethoxycarbonyl isothiocyanate (4.32 mL, 36.6 mmol) and 2,4-dichloro-pyrimidin-5-ylamine (3.00 g, 18.29 mmol) were mixed neat and sonicated for 5 minutes to help dissolve. The mixture was stirred at ambient temperature for 10 minutes, at which time the entire mixture had solidified. Methanol (100 mL) was added and the mixture was refluxed for 30 minutes, cooled to ambient temperature and the solids were collected by filtration to afford ethyl 5-chlorothiazolo[5,4-d]pyrimidin-2-ylcarbamate (3.8 g, 80% yield). 1H NMR (400 MHz, DMSO-d₆) δ ppm 12.64 (s, 1 H) 9.05 (s, 1 H) 4.31 (q, J=7.19 Hz, 2 H) 1.32 (t, J=7.15 Hz, 3 H).

Step B: Ethyl 5-(dimethylamino)thiazolo[5,4-d]pyrimidin-2-ylcarbamate

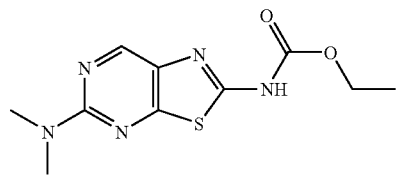

Ethyl 5-chlorothiazolo[5,4-d]pyrimidin-2-ylcarbamate (300 mg, 1.16 mmol) was suspended in a 2.0 M solution of dimethylamine in methanol (5.0 mL, 10.00 mmol) in a pressure vessel, which was sealed and heated overnight on a 75° C. oil bath. The mixture was cooled to ambient temperature, the solvent was evaporated and the residue was partitioned between aqueous bicarbonate and chloroform and extracted 3 times. The combined organics were washed with brine, dried over sodium sulfate, filtered and concentrated in vacuo to afford ethyl 5-(dimethylamino)thiazolo[5,4-d]pyrimidin-2-ylcarbamate (236 mg, 99% yield). 1H NMR (400 MHz, DMSO-d₆) δ ppm 11.97 (s, 1H) 8.67 (s, 1H) 4.26 (q, J=7.03 Hz, 2H) 3.17 (s, 6H) 1.16-1.40 (m, 3H). MS (LC/MS) R.T.=1.88; [M+H]⁺=268.09.

Step C: Ethyl N⁵,N⁵-dimethylthiazolo[5,4-d]pyrimidine-2,5-diamine

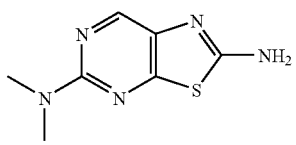

Ethyl 5-(dimethylamino)thiazolo[5,4-d]pyrimidin-2-ylcarbamate (236 mg, 0.88 mmol) was suspended in a 25% (w/w) solution of sodium methoxide in methanol (5 mL, 23.0 mmol) and the mixture was heated to reflux overnight. The reaction mixture was evaporated to dryness and the residue was partitioned between water and chloroform and extracted 3 times. The combined organics were washed with brine, dried over sodium sulfate, filtered and concentrated in vacuo to afford ethyl N⁵,N⁵-dimethylthiazolo[5,4-d]pyrimidine-2,5-diamine (170 mg, 99% yield) as a white solid. 1H NMR (400 MHz, DMSO-d₆) δ ppm 8.27 (s, 1 H) 7.44 (s, 2 H) 3.10 (s, 6 H).

Step D: Dimethyl 5-(dimethylamino)thiazolo[5,4-d]pyrimidin-2-ylcarbonimidodithioate

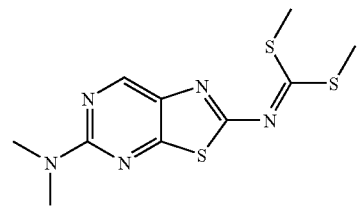

To a suspension of ethyl N$^5$,N$^5$-dimethylthiazolo[5,4-d]pyrimidine-2,5-diamine (160 mg, 0.819 mmol) in DMF (1 mL) was added 20.0 M sodium hydroxide (100 μL, 2.00 mmol). The mixture was allowed to stir 10 min at room temperature at which time carbon disulfide was added (120 μL, 2 mmol) and the resulting reddish brown mixture was stirred for 10 minutes. An additional portion of 20.0 M sodium hydroxide (100 μL, 2.0 mmol) was added and the mixture was again stirred for 10 minutes. Finally, iodomethane (120 μL, 1.9 mmol) was added dropwise. The mixture was stirred for 5 minutes, at which time a voluminous yellow precipitate had formed. The mixture was poured into water and the solids were collected by filtration to afford dimethyl 5-(dimethylamino)thiazolo[5,4-d]pyrimidin-2-ylcarbonimidodithioate (194 mg, 79% yield). 1H NMR (400 MHz, CDCl$_3$) δ ppm 8.75 (s, 1 H) 3.26 (s, 6 H) 2.64 (s, 6 H).

Step E: (R)—N$^5$,N$^5$-dimethyl-N$^2$-(4H-1'-azaspiro[oxazole-5,3'-bicyclo[2.2.2]octane]-2-yl)thiazolo[5,4-d]pyrimidine-2,5-diamine

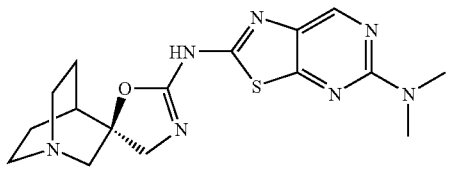

A mixture of dimethyl 5-(dimethylamino)thiazolo[5,4-d]pyrimidin-2-ylcarbonimidodithioate (90 mg, 0.301 mmol), (S)-3-(aminomethyl)quinuclidin-3-ol dihydrochloride (83 mg, 0.361 mmol) and cesium carbonate (196 mg, 0.60 mmol) in DMF (1.0 mL) was heated to 100° C. for 1.5 hours. The reaction mixture was cooled to ambient temperature, poured into water and extracted with chloroform (4×). The combined organics were washed with brine, dried over sodium sulfate, filtered, concentrated in vacuo, and the crude residue was purified by silica gel chromatography (2-40% 9:1 methanol:ammonium hydroxide-chloroform) to afford (R)—N$^5$,N$^5$-dimethyl-N$^2$-(4H-1'-azaspiro[oxazole-5,3'-bicyclo[2.2.2]octane]-2-yl)thiazolo[5,4-d]pyrimidine-2,5-diamine (81 mg, 71% yield) as a tan solid. 1H NMR (400 MHz, CDCl$_3$) δ ppm 9.07 (br. s., 1 H) 8.50 (s, 1 H) 4.01 (d, J=9.54 Hz, 1 H) 3.67 (d, J=9.54 Hz, 1 H) 3.39 (dd, J=14.93, 1.63 Hz, 1 H) 3.23 (s, 6 H) 2.71-3.10 (m, 5 H) 2.10-2.24 (m, 2 H) 1.68-1.84 (m, 1 H) 1.46-1.68 (m, 2 H). MS (LC/MS) R.T.=0.87; [M+H]$^+$=360.23.

EXAMPLE 270

(R)—N-([1,2,4]Triazol[1,5-a]pyrazin-2-yl)-4H-1'-azaspiro[oxazole-5,3'-bicyclo[2.2.2]octan]-2-amine

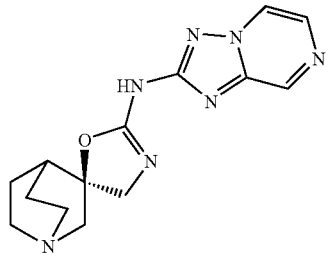

Step A: [1,2,4]Triazolo[1,5-a]pyrazin-2-amine

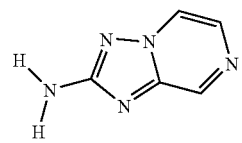

To a solution of pyrazin-2-amine (25 g, 260 mmol) in dioxane (300 ml) at room temperature was added ethoxycarbonyl-isothiocyanate (37.9 g, 289 mmol) slowly. The mixture was stirred for 18 hours and the solvent was evaporated under vacuum. The residual solid was dissolved in a mixture of methanol (150 ml) and ethanol (150 ml). To this solution was added TEA (109 ml, 780 mmol) and hydroxylamine hydrochloride (72.5 g, 1040 mmol). The mixture was stirred at room temperature for 2 hours and was heated to reflux for 4 hours. The crude mixture was cooled to room temperature and the solvent was evaporated. The residual solid was purified by column chromatography (0-20% methanol/CH$_2$Cl$_2$) to obtain a white solid (60 g). The solid was taken into EtOAc and water. The aqueous layer was extracted with EtOAc twice. The combined organic layer was washed with brine and dried over sodium sulfate to obtain [1,2,4]triazolo[1,5-a]pyrazin-2-amine as a white solid (12 g, 88 mmol, 33%). MS (LCMS) [M+H]=135.96; R.T.=0.21 min.

Step B: Dimethyl[1,2,4]triazol[1,5-a]pyrazin-2-ylcarbonimidodithioate

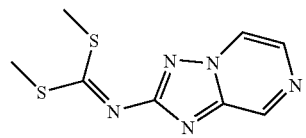

To a solution of [1,2,4]triazolo[1,5-a]pyrazin-2-amine (676 mg, 5 mmol) in DMF (10 ml) was added NaOH (20 M, 0.5 ml), CS$_2$ (1 ml), NaOH (20 M, 0.5 ml) and iodomethane (1 ml) slowly over 10 minutes. The mixture was stirred at room temperature for 1 h and 10 ml water was added to the reaction mixture, which became cloudy. The mixture was extracted with EtOAc (100 ml×3). The combined organic layers were washed with brine, dried over sodium sulfate, filtered, and evaporated. The residue was purified on a Biotage silica gel column (ethyl acetate-hexane 10-30%) to obtain dimethyl[1,2,4]triazol[1,5-a]pyrazin-2-ylcarbonimidodithioate as a yellow solid (720 mg, 3 mmol, 60%). $^1$H NMR (500 MHz, CDCl3) δ ppm 9.2 (2, 1H), 8.5 (d, 1H), 8.2 (d, 1H), 2.67 (s, 6H). MS (LCMS) [M+H]=239.92. [M+Na]=261.89; R.T.=1.55 min.

Step C: (R)—N-([1,2,4]Triazol[1,5-a]pyrazin-2-yl)-4H-1'-azaspiro[oxazole-5,3'-bicyclo[2.2.2]octan]-2-amine

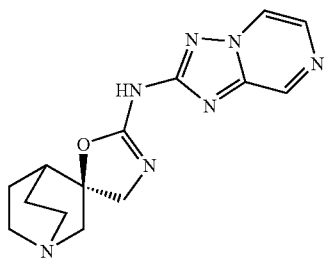

A mixture of dimethyl[1,2,4]triazol[1,5-a]pyrazin-2-ylcarbonimidodithioate (120 mg, 0.50 mmol), (S)-3-(aminomethyl)quinuclidin-3-ol dihydrochloride (120 mg, 0.76 mmol) and cesium carbonate (492 mg, 1.5 mmol) in DMF (5 ml) was heated at 70° C. for 6 hours. The mixture was concentrated and purified on a Biotage silica gel column (100% ethyl acetate, then 10-35% 9:1 methanol:ammonium hydroxide-chloroform) to obtain the desired product, (R)—N-([1,2,4]triazol[1,5-a]pyrazin-2-yl)-4H-1'-azaspiro[oxazole-5,3'-bicyclo[2.2.2]octan]-2-amine (85 mg, 26.7%) as a white solid. $^1$H NMR (500 MHz, MeOD) δ ppm 9.0 (m, 1H), 8.71-8.70 (m, 1H), 8.15-8.10 (m, 1H), 4.15-4.0 (d, 1H), 3.85-3.8 (d, 1H), 3.6-3.5 (d, 1H), 3.4-3.3 (d, 1H), 3.3-3.0 (m, 4H), 2.4-2.2 (m, 2H), 2.0-1.8 (m, 3H).
MS (LCMS) [M+H]=300.06; R.T.=0.2 min.

EXAMPLE 271

(R)—N-(Thiazolo[5,4-b]pyridin-2-yl)-4H-1'-azaspiro[oxazole-5,3'-bicyclo[2.2.2]octan]-2-amine

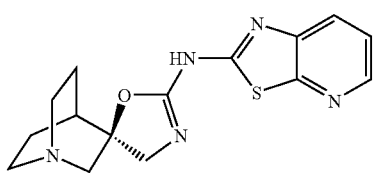

Step A: Dimethyl thiazolo[5,4-b]pyridin-2-ylcarbonimidodithioate

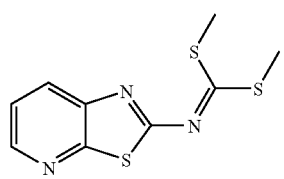

To a suspension of thiazolo[5,4-b]pyridin-2-amine (300 mg, 1.98 mmol) in DMF (2 mL) was added 20.0M sodium hydroxide (200 μL, 4.0 mmol). The mixture was allowed to stir 10 min at room temperature at which time carbon disulfide was added (300 μL, 4.96 mmol) and the resulting reddish brown mixture was stirred for 10 minutes. An additional portion of 20.0M sodium hydroxide (200 μL, 4.0 mmol) was added and the mixture was again stirred for 10 minutes. Finally, iodomethane (300 μL, 4.76 mmol) was added dropwise. The mixture was stirred for 5 minutes, at which time a voluminous yellow precipitate had formed. The mixture was poured into water and the solids were collected by filtration to afford dimethyl thiazolo[5,4-b]pyridin-2-ylcarbonimidodithioate (190 mg, 38% yield) as a yellow solid of sufficient purity to use without further purification. 1H NMR (500 MHz, CDCl$_3$) δ ppm 8.47 (d, J=4.58 Hz, 1 H) 8.11 (dd, J=8.24, 1.53 Hz, 1 H) 7.37 (dd, J=8.24, 4.88 Hz, 1 H) 2.66 (s, 6 H).

Step B: (R)—N-(Thiazolo[5,4-b]pyridin-2-yl)-4H-1'-azaspiro[oxazole-5,3'-bicyclo[2.2.2]octan]-2-amine

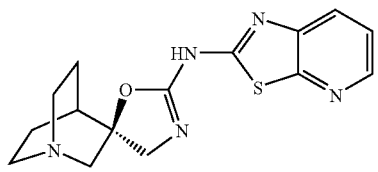

A mixture of dimethyl thiazolo[5,4-b]pyridin-2-ylcarbonimidodithioate (90 mg, 0.35 mmol), (S)-3-(aminomethyl)quinuclidin-3-ol dihydrochloride (97 mg, 0.42 mmol) and cesium carbonate (230 mg, 0.71 mmol) in DMF (1 mL) was heated to 100° C. for 2 hours. The reaction mixture was cooled to ambient temperature, poured into water and extracted with chloroform (4×). The combined organics were washed with brine, dried over sodium sulfate, filtered and concentrated in vacuo. The mixture was purified by silica gel chromatography (2-40% 9:1 methanol:ammonium hydroxide-chloroform). The product fractions were combined and concentrated in vacuo to afford (R)—N-(thiazolo[5,4-b]pyridin-2-yl)-4H-1'-azaspiro[oxazole-5,3'-bicyclo[2.2.2]octan]-2-amine (84 mg, 76% yield). 1H NMR (400 MHz, CDCl$_3$) δ ppm 9.30 (br. s., 1 H) 8.37 (dd, J=4.77, 1.51 Hz, 1 H) 7.82 (dd, J=8.03, 1.51 Hz, 1 H) 7.28 (dd, J=8.03, 4.77 Hz, 1 H) 4.05 (d, J=9.54 Hz, 1 H) 3.70 (d, J=9.54 Hz, 1 H) 3.42 (dd, J=15.06, 1.76 Hz, 1 H) 2.75-3.07 (m, 5 H) 2.14-2.26 (m, 2 H) 1.71-1.84 (m, J=13.99, 9.79, 4.17, 4.17 Hz, 1 H) 1.48-1.68 (m, 2 H). MS (LC/MS) R.T.=0.64; [M+H]$^+$=316.15.

EXAMPLE 272

(R)—N-(Thiazolo[5,4-b]pyrazin-2-yl)-4H-1'-azaspiro[oxazole-5,3'-bicyclo[2.2.2]octan]-2-amine

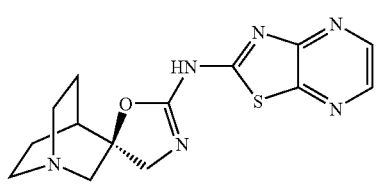

(R)—N-(6-Bromothiazolo[5,4-b]pyrazin-2-yl)-4H-1'-azaspiro[oxazole-5,3'-bicyclo[2.2.2]octan]-2-amine (44 mg, 0.111 mmol) was suspended in MeOH (50 mL) and 3N HCl was added until all solids had dissolved (~10 ml). The reaction flask was flushed with nitrogen and then 10% palladium on carbon (35 mg) was added, and the flask was fitted with a hydrogen balloon. The mixture was allowed to react overnight, at which time TLC showed consumption of the starting material. The flask was flushed with nitrogen, filtered through celite and washed with methanol. The combined filtrates were concentrated by ~90% to remove most of the methanol, and the solution was made basic by the addition of a saturated solution of sodium bicarbonate. The basic aqueous phase was extracted with chloroform (4×). The combined organics were washed with brine, dried over sodium sulfate, filtered and concentrated in vacuo. The mixture was purified by silica gel chromatography (2-40% [9:1 methanol:ammonium hydroxide]-chloroform). The product fractions were combined and concentrated in vacuo to afford (R)—N-(thiazolo[5,4-b]pyrazin-2-yl)-4H-1'-azaspiro[oxazole-5,3'-bicyclo[2.2.2]octan]-2-amine (24 mg, 0.075 mmol, 67.5% yield). 1H NMR (400 MHz, CDCl$_3$) δ ppm 9.50 (br. s., 1 H) 8.41 (d, J=2.76 Hz, 1 H) 8.27 (d, J=2.76 Hz, 1 H) 4.06 (d, J=9.79 Hz, 1 H) 3.72 (d, J=9.79 Hz, 1 H) 3.43 (dd, J=15.06, 1.76 Hz, 1 H) 2.74-3.09 (m, 5 H) 2.12-2.25 (m, 2 H) 1.71-1.86 (m, 1 H) 1.49-1.67 (m, 2 H). MS (LC/MS) R.T.=0.75; [M+H]$^+$=317.13.

EXAMPLE 273

(R)—N-(7-Methoxy-5-methylthiazolo[5,4-d]pyrimidin-2-yl)-4H-1'-azaspiro[oxazole-5,3'-bicyclo[2.2.2]octan]-2-amine

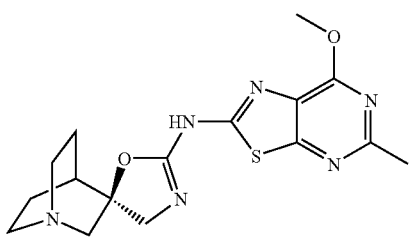

Step A: Ethyl 7-chloro-5-methylthiazolo[5,4-d]pyrimidin-2-ylcarbamate

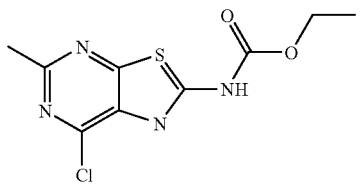

To a mixture of 4,6-dichloro-2-methylpyrimidin-5-amine (1 g, 5.62 mmol) and O-ethyl carbonisothiocyanatidate (0.66 mL, 5.62 mmol) was added toluene (2 mL) to wet the solids completely. The mixture was placed on 100° C. oil bath for 1.5 hours, at which time, the mixture had seized to give a solid mass. The solids were cooled to ambient temperature and triturated with ether, then the resulting solids were collected by filtration to give ethyl 7-chloro-5-methylthiazolo[5,4-d]pyrimidin-2-ylcarbamate (1.08 g, 3.96 mmol, 70.5% yield).

1H NMR (400 MHz, DMSO-d$_6$) δ ppm 12.70 (br. s., 1H) 4.30 (q, J=7.19 Hz, 2H) 2.69 (s, 3H) 1.30 (t, J=7.15 Hz, 3H).

Step B: 7-Methoxy-5-methylthiazolo[5,4-d]pyrimidin-2-amine

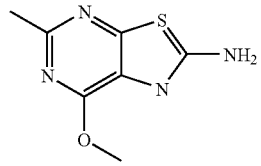

Ethyl 7-chloro-5-methylthiazolo[5,4-d]pyrimidin-2-ylcarbamate (300 mg, 1.100 mmol) was suspended in a 25% w/w solution of sodium methoxide in methanol (5 mL, 23.14 mmol) and the mixture was refluxed overnight. The mixture was cooled to ambient temperature, diluted with water and extracted with chloroform (4×). The combined organics were washed with brine, dried over sodium sulfate, filtered and concentrated in vacuo to afford 7-methoxy-5-methylthiazolo[5,4-d]pyrimidin-2-amine (120 mg, 0.612 mmol, 55.6% yield). 1H NMR (400 MHz, DMSO-d$_6$) δ ppm 7.71 (s, 2 H) 3.98 (s, 3 H) 2.52 (s, 3 H).

Step C: Dimethyl 7-methoxy-5-methylthiazolo[5,4-d]pyrimidin-2-ylcarbonimidodithioate

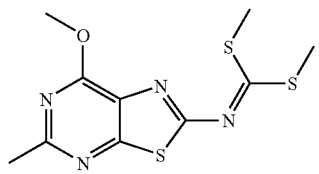

To a suspension of 7-methoxy-5-methylthiazolo[5,4-d]pyrimidin-2-amine (100 mg, 0.51 mmol) in DMF (0.5 mL) was added 16.0M sodium hydroxide (75 μL, 1.2 mmol). The mixture was allowed to stir 10 min at room temperature at which time carbon disulfide was added (80 μL, 1.27 mmol) and the resulting reddish brown mixture was stirred for 10 minutes. An additional portion of 16.0M sodium hydroxide (75 μL, 1.2 mmol) was added and the mixture was again stirred for 10 minutes. Finally, iodomethane (80 μL, 1.29 mmol) was added dropwise. The mixture was stirred for 5 minutes, at which time a voluminous yellow precipitate had formed. The mixture was poured into water and the solids were collected by filtration to afford a crude yellow solid that was further purified by silica gel chromatography (2-20% ethyl acetate-chloroform). The product fractions were combined and concentrated in vacuo to afford dimethyl 7-methoxy-5-methylthiazolo[5,4-d]pyrimidin-2-ylcarbonimidodithioate (90 mg, 59% yield) as a yellow solid. 1H NMR (400 MHz, CDCl$_3$) δ ppm 4.17 (s, 3 H) 2.71 (s, 3 H) 2.64 (s, 6 H).

Step D: (R)—N-(7-Methoxy-5-methylthiazolo[5,4-d]pyrimidin-2-yl)-4H-1'-azaspiro[oxazole-5,3'-bicyclo[2.2.2]octan]-2-amine

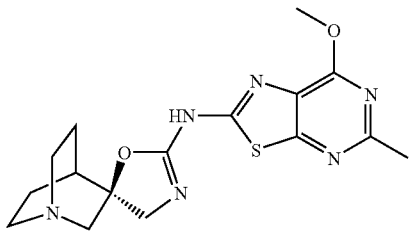

A mixture of dimethyl 7-methoxy-5-methylthiazolo[5,4-d]pyrimidin-2-ylcarbonimidodithioate (56 mg, 0.19 mmol), (S)-3-(aminomethyl)quinuclidin-3-ol dihydrochloride (51 mg, 0.22 mmol) and cesium carbonate (175 mg, 0.54 mmol) in DMF (0.5 mL) was heated to 100° C. for 2 hours. The reaction mixture was cooled to ambient temperature, poured into water and extracted with chloroform (4×). The combined organics were washed with brine, dried over sodium sulfate, filtered and concentrated in vacuo. The mixture was purified by silica gel chromatography (2-40% [9:1 methanol:ammonium hydroxide]-chloroform). The product fractions were combined and concentrated in vacuo to afford (R)—N-(7-methoxy-5-methylthiazolo[5,4-d]pyrimidin-2-yl)-4H-1'-azaspiro[oxazole-5,3'-bicyclo[2.2.2]octan]-2-amine (34 mg, 50% yield). 1H NMR (400 MHz, CDCl$_3$) δ ppm 9.10 (br. s., 1 H) 4.14 (s, 3 H) 4.03 (d, J=9.54 Hz, 1 H) 3.68 (d, J=9.54 Hz, 1 H) 3.39 (dd, J=14.93, 1.63 Hz, 1 H) 2.74-3.07 (m, 5 H) 2.68 (s, 3 H) 2.04-2.28 (m, 2 H) 1.70-1.86 (m, 1 H) 1.44-1.67 (m, 2 H). MS (LC/MS) R.T.=1.10; [M+H]$^+$=361.32.

EXAMPLE 274

(R)—N-(7-Methoxythiazolo[5,4-d]pyrimidin-2-yl)-4H-1'-azaspiro[oxazole-5,3'-bicyclo[2.2.2]octan]-2-amine

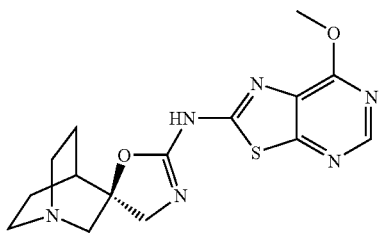

Step A: Dimethyl 7-methoxy-5-methylthiazolo[5,4-d]pyrimidin-2-ylcarbonimidodithioate

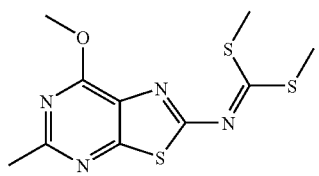

To a suspension of 7-methoxythiazolo[5,4-d]pyrimidin-2-amine (300 mg, 1.67 mmol) in DMF (1.5 mL) was added 16.0M sodium hydroxide (210 μL, 3.4 mmol). The mixture was allowed to stir 10 min at room temperature at which time carbon disulfide was added (250 μL, 4.15 mmol) and the resulting reddish brown mixture was stirred for 10 minutes. An additional portion of 16.0M sodium hydroxide (210 μL, 3.4 mmol) was added and the mixture was again stirred for 10 minutes. Finally, iodomethane (250 μL, 4.00 mmol) was added dropwise. The mixture was stirred for 10 minutes, at which time a voluminous yellow precipitate had formed. The mixture was poured into water and the solids were collected by filtration to afford dimethyl 7-methoxy-5-methylthiazolo[5,4-d]pyrimidin-2-ylcarbonimidodithioate (324 mg, 69% yield) as a yellow solid. 1H NMR (400 MHz, CDCl$_3$) δ ppm 8.60 (s, 1 H) 4.20 (s, 3 H) 2.65 (s, 6 H).

Step B: (R)-N-(7-Methoxythiazolo[5,4-d]pyrimidin-2-yl)-4H-1'-azaspiro[oxazole-5,3'-bicyclo[2.2.2]octan]-2-amine

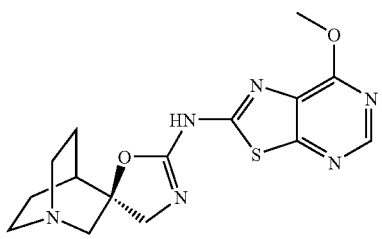

A mixture of dimethyl 7-methoxythiazolo[5,4-d]pyrimidin-2-ylcarbonimidodithioate (150 mg, 0.52 mmol), (S)-3-(aminomethyl)quinuclidin-3-ol dihydrochloride (132 mg, 0.58 mmol) and cesium carbonate (427 mg, 1.31 mmol) in DMF (3 mL) was heated to 100° C. for 2 hours. The reaction mixture was cooled to ambient temperature, poured into water and extracted with chloroform (4×). The combined organics were washed with brine, dried over sodium sulfate, filtered and concentrated in vacuo. The mixture was purified by silica gel chromatography (2-40% [9:1 methanol:ammonium hydroxide]-chloroform). The product fractions were combined and concentrated in vacuo to afford (R)—N-(7-methoxythiazolo[5,4-d]pyrimidin-2-yl)-4H-1'-azaspiro[oxazole-5,3'-bicyclo[2.2.2]octan]-2-amine (95 mg, 51% yield). 1H NMR (400 MHz, CDCl$_3$) δ ppm 9.12 (br. s., 1 H) 8.52 (s, 1 H) 4.16 (s, 3 H) 4.05 (d, J=9.54 Hz, 1 H) 3.70 (d, J=9.54 Hz, 1 H) 3.40 (dd, J=14.93, 1.88 Hz, 1 H) 2.70-3.07 (m, 5 H) 2.08-2.27 (m, 2 H) 1.68-1.85 (m, 1 H) 1.48-1.66 (m, 2 H). MS (LC/MS) R.T.=0.90; [M+H]$^+$=347.34.

EXAMPLE 275

(R)-2-(4H-1'-Azaspiro[oxazole-5,3'-bicyclo[2.2.2]octan]-2-ylamino)thiazole-5-carbonitrile

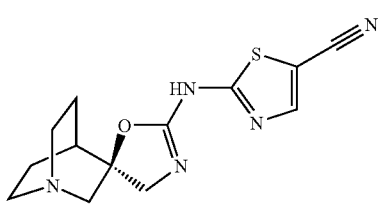

(R)-2-(4H-1'-Azaspiro[oxazole-5,3'-bicyclo[2.2.2]octan]-2-ylamino)thiazole-5-carbonitrile was synthesized by the method of Example 274, starting from 2-amino-5-cyanothiazole. 1H NMR (500 MHz, DMSO-D6) δ ppm 9.05 (s, 1 H), 8.13 (s, 1 H), 3.86 (d, J=10.38 Hz, 1 H), 3.61 (d, J=10.38 Hz, 1 H), 3.01-3.10 (m, 2 H), 2.83 (t, J=7.63 Hz, 2 H), 2.62-2.71 (m, 2 H), 2.09 (s, 1 H), 1.90-1.97 (m, 2 H), 1.54-1.62 (m, 3 H). MS (LC/MS) R.T.=0.52; [M+H]$^+$=290.0.

EXAMPLE 276

(R)—N-(7-Bromopyrrolo[1,2-f][1,2,4]triazin-4-yl)-4H-1'-azaspiro[oxazole-5,3'-bicyclo[2.2.2]octan]-2-amine

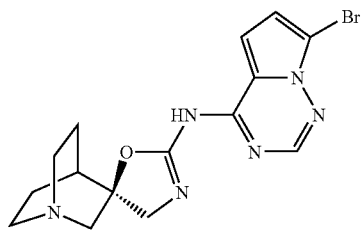

(R)—N-(7-bromopyrrolo[1,2-f][1,2,4]triazin-4-yl)-4H-1'-azaspiro[oxazole-5,3'-bicyclo[2.2.2]octan]-2-amine was synthesized by the method of Example 274 starting from 7-bromopyrrolo[1,2-f][1,2,4]triazin-4-amine. 1H NMR (400 MHz, MeOD) δ ppm 8.13 (1 H, s), 7.04 (1 H, d, J=4.53 Hz), 6.77 (1 H, d, J=4.53 Hz), 4.09 (1 H, D, J=10.32 Hz), 3.79 (1 H, d, J=10.58 Hz), 3.24 (1 H, d), 3.12 (1 H, d), 2.70-3.00 (4 H, m), 2.06-2.25 (2 H, m), 1.52-1.86 (3 H, m) MS (LC/MS) R.T.=1.62; [M+H]$^+$=377.2.

EXAMPLE 277

(R)—N-(1,6-Naphthyridin-2-yl)-4H-1'-azaspiro[oxazole-5,3'-bicyclo[2.2.2]octan]-2-amine

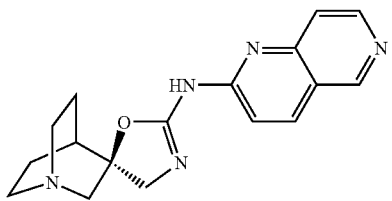

(R)—N-(1,6-Naphthyridin-2-yl)-4H-1'-azaspiro[oxazole-5,3'-bicyclo[2.2.2]octan]-2-amine was synthesized by the method of Example 274 starting from 1,6-naphthyridin-2-amine. 1H NMR (400 MHz, MeOD) δ ppm 8.99 (1 H, s), 8.48 (1 H, d, J=6.04 Hz), 8.20 (1 H, d, J=8.56 Hz), 7.77 (1 H, d, J=6.04 Hz), 7.12 (1 H, d, J=8.81 Hz), 4.12 (1 H, d, J=10.32 Hz), 3.82 (1 H, d, J=10.32 Hz), 3.36 (1 H, d), 3.21 (1 H, d), 2.79-3.09 (4 H, m), 2.08-2.30 (2 H, m), 1.56-1.95 (3 H, m). (LC/MS) R.T.=0.38; [M+H]$^+$=310.3.

EXAMPLE 278

(R)—N-(Quinazolin-2-yl)-4H-1'-azaspiro[oxazole-5,3'-bicyclo[2.2.2]octan]-2-amine

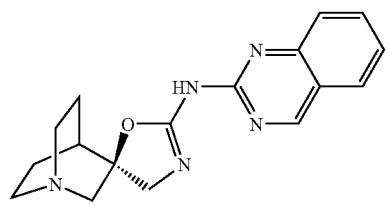

(R)—N-(Quinazolin-2-yl)-4H-1'-azaspiro[oxazole-5,3'-bicyclo[2.2.2]octan]-2-amine was synthesized by the method of Example 274 starting from 2-aminoquinazoline. $^1$H NMR (400 MHz, MeOD) δ ppm 9.27 (1 H, s), 7.72-7.99 (3 H, m), 7.47 (1 H, dd, J=7.55, 3.78 Hz), 4.07 (1 H, d, J=10.07 Hz), 3.76 (1 H, d, J=10.07 Hz), 3.26 (1 H, br. s.), 3.13 (1 H, d), 2.70-3.03 (4 H, m), 2.17 (2 H, br. s.), 1.50-1.88 (3 H, m). (LC/MS) R.T.=1.11; [M+H]$^+$=310.3.

EXAMPLE 279

(R)—N-(6,8-Dichloroisoquinolin-3-yl)-4H-1'-azaspiro[oxazole-5,3'-bicyclo[2.2.2]octan]-2-amine

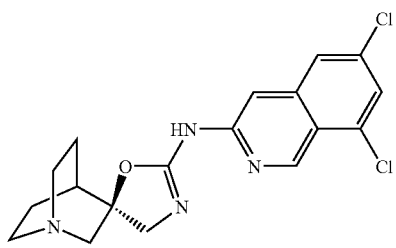

Step A:
N-(2,4-Dichlorobenzyl)-2,2-diethoxyacetimidamide

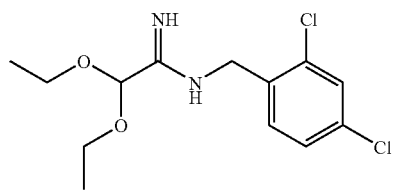

(2,4-Dichlorophenyl)methanamine (2 g, 11.4 mmol) was added to a solution of methyl 2,2-diethoxyacetimidate (2.04 g, 12.6 mmol) in methanol (10 ml). The mixture was heated at 70° C. for 1 h. The mixture was purified by chromatography (Biotage: 100% ethyl acetate). The desired fractions were concentrated to yield N-(2,4-dichlorobenzyl)-2,2-diethoxyacetimidamide (2.8 g, 9.2 mmol, 72.7% yield) as a colorless viscous oil. 1H NMR (500 MHz, DMSO-D$_6$) δ ppm 7.27-7.70 (m, 3 H), 4.77 (s, 1 H), 4.14-4.35 (m, 2 H), 3.45-3.68 (m, 4 H), 1.09-1.29 (m, 6 H). LC/MS RT=2.03; [M+H]$^+$=304.9.

Step B: 6,8-Dichloroisoquinolin-3-amine

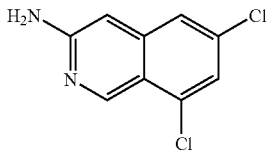

To sulfuric acid (4 mL, 75 mmol) was added N-(2,4-dichlorobenzyl)-2,2-diethoxyacetimidamide (2 g, 6.6 mmol) at room temperature. The reaction was heated to 40° C. for 18 hours. TLC and LC/MS indicated the presence of product. The reaction was cooled to room temperature and quenched with aq. NaOH (~15 M) until the reaction mixture was ~pH 7. The crude product was extracted with ethyl acetate (2×50 mL) and the organics were dried with MgSO$_4$, filtered, and concentrated in vacuo to yield the product. The crude product was purified by chromatography (Biotage: 10-80% ethyl acetate/hexanes) to yield 5,7-dichloroisoquinolin-1-amine (0.32 g, 1.50 mmol, 22.9% yield) as a dark yellow powder. 1H NMR (400 MHz, DMSO-D$_6$) δ ppm 8.99 (s, 1 H), 7.64-7.73 (m, 1 H), 7.30 (d, J=2.01 Hz, 1 H), 6.61 (s, 1 H), 6.43 (s, 2 H). MS (LC/MS) R.T.=1.40; [M+H]$^+$=213.1.

Step C: 6,8-Dichloro-3-isothiocyanatoisoquinoline

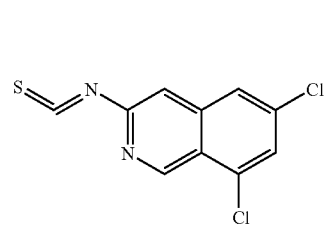

To 6,8-dichloroisoquinolin-3-amine (0.27 g, 1.28 mmol) in dichloromethane (20 mL) was added 1,1'-thiocarbonyldipyridin-2(1H)-one (0.30 g, 1.29 mmol) and the reaction mixture was stirred at 40° C. for 4 hours. The reaction was cooled to room temperature and chromatographed (Biotage: 10-100% ethyl acetate/hexanes) to yield 6,8-dichloro-3-isothiocyanatoisoquinoline (0.2 g, 0.78 mmol, 61.9% yield) as a powder. 1H NMR (500 MHz, DMSO-D$_6$) δ ppm 9.42 (s, 1H), 8.16 (d, J=1.83 Hz, 1H), 8.02 (d, J=2.14 Hz, 1H), 7.92 (s, 1H). MS (LC/MS) R.T.=3.63; [M+H]$^+$=255.0.

Step D: (R)—N-(6,8-Dichloroisoquinolin-3-yl)-4H-1'-azaspiro[oxazole-5,3'-bicyclo[2.2.2]octan]-2-amine

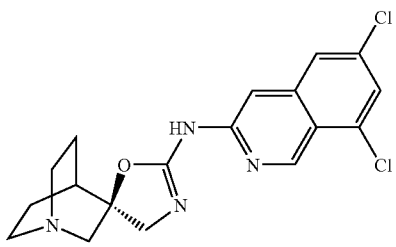

To 6,8-dichloro-3-isothiocyanatoisoquinoline (0.17 g, 0.67 mmol) in DMF (10 mL) was added cesium carbonate (0.543 g, 1.67 mmol) and (S)-3-(aminomethyl)quinuclidin-3-ol dihydrochloride (0.15 g, 0.67 mmol) at room temperature. The reaction was stirred at 70° C. for 2 hours. The reaction was cooled to room temperature and concentrated in vacuo. The product was treated with N,N'-diisopropylcarbodiimide (0.31 mL, 2.0 mmol). The reaction was heated to 90° C. for 4 hours. The reaction was cooled to room temperature and concentrated to yield the crude product. The crude product was purified by chromatography (Biotage: 85% CHCl$_3$, 14% MeOH, 1% NH$_4$OH). The product was taken up in a small amount of ethyl acetate, which resulted in the formation of a precipitate. It was filtered off, washed with a small amount of ethyl acetate, and dried in a vacuum oven to yield (R)—N-(6,8-dichloroisoquinolin-3-yl)-4H-1'-azaspiro[oxazole-5,3'-bicyclo[2.2.2]octan]-2-amine (0.094 g, 0.24 mmol, 36.6% yield) as a white powder. 1H NMR (400 MHz, DMSO-D$_6$) δ ppm 9.23 (s, 1H), 8.71-8.83 (m, 1H), 7.90-8.00 (m, 1H), 7.57-7.67 (m, 1H), 7.13-7.24 (m, 1H), 3.79-3.90 (m, 1H), 3.53-3.64 (m, 1H), 2.93-3.04 (m, 2H), 2.72-2.82 (m, 2H), 2.61-2.70 (m, 2H), 1.99 (s, 1H), 1.90 (s, 1H), 1.59 (d, J=4.78 Hz, 2H), 1.40-1.50 (m, 1H). MS (LC/MS) R.T.=1.68; [M+H]$^+$=377.1.

EXAMPLE 280

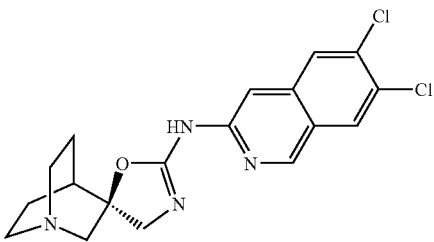

(R)—N-(6,7-Dichloroisoquinolin-3-yl)-4H-1'-azaspiro[oxazole-5,3'-bicyclo[2.2.2]octan]-2-amine

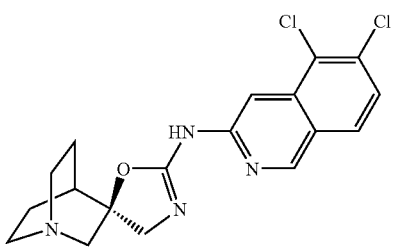

Step A:
N-(3,4-Dichlorobenzyl)-2,2-diethoxyacetimidamide

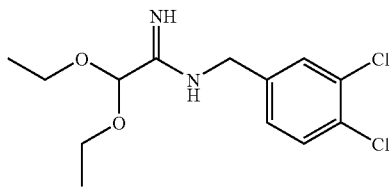

(3,4-Dichlorophenyl)methanamine (2 g, 11.4 mmol) was added to a solution of methyl 2,2-diethoxyacetimidate (2.04 g, 12.6 mmol) in methanol (10 ml). The mixture was heated at 70° C. for 1 h. The mixture was purified by chromatography (Biotage: 100% ethyl acetate). The desired fractions were concentrated to yield N-(3,4-dichlorobenzyl)-2,2-diethoxyacetimidamide (2.8 g, 9.2 mmol, 72.7% yield) as a colorless viscous oil. 1H NMR (500 MHz, CDCl$_3$) δ ppm 7.45 (m, 1 H), 7.40 (m, 1 H), 7.19 (dd, J=8.09, 1.98 Hz, 1 H), 4.94 (s, 1 H), 4.43 (s, 2 H), 3.47-3.77 (m, 4 H), 1.41-1.79 (m, 6 H). LC/MS RT=2.15; [M+H]$^+$=305.1.

Step B: 6,7-Dichloroisoquinolin-3-amine and 5,6-dichloroisoquinolin-3-amine

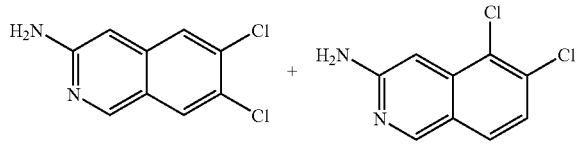

To sulfuric acid (4 mL, 75 mmol) was added N-(3,4-dichlorobenzyl)-2,2-diethoxyacetimidamide (2 g, 6.6 mmol) at room temperature. The reaction was heated to 40° C. for 49 hours. TLC and LC/MS indicated the presence of product. The reaction was cooled to room temperature and quenched with aq. NaOH (~15 M) until the reaction mixture was ~pH 7. The crude product was extracted with ethyl acetate (2×50 mL) and the organics were dried with $MgSO_4$, filtered, and concentrated in vacuo to yield the product. The crude product was purified by chromatography (Biotage: 100% ethyl acetate to [90/10% ethyl acetate/MeOH]) to yield approximately a 1:1 mixture of regioisomers 6,7-dichloroisoquinolin-1-amine and 5,6-dichloroisoquinolin-3-amine (1.2 g, 5.64 mmol, 86.0% yield) as a dark yellow powder. The regioisomers were carried on without separation. 1H NMR: 1H NMR (500 MHz, DMSO-$D_6$) δ ppm 8.90 (s, 1 H), 8.83 (s, 1 H), 8.12 (s, 1 H), 7.89 (s, 1 H), 7.84 (d, J=8.54 Hz, 1 H), 7.28 (d, J=8.85 Hz, 1 H), 6.83 (s, 1 H), 6.58 (s, 1 H), 6.48 (s, 2 H), 6.25 (s, 2 H). MS (LC/MS) R.T.=1.59; $[M+H]^+$=213.0.

Step C: 6,7-Dichloro-3-isothiocyanatoisoquinoline and 5,6-dichloro-3-isothiocyanatoisoquinoline

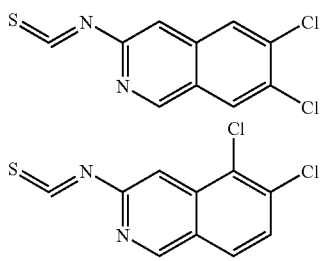

To 6,7-dichloroisoquinolin-3-amine and 5,6-dichloroisoquinolin-3-amine (0.410 g, 1.924 mmol) in dichloromethane (20 mL) was added 1,1'-thiocarbonyldipyridin-2(1H)-one (0.469 g, 2.021 mmol) and the reaction mixture was stirred at 40° C. for 4 hours. The reaction was cooled to room temperature and chromatographed (Biotage: 10-100% ethyl acetate/hexanes) to yield the separated regioisomers, 6,7-dichloro-3-isothiocyanatoisoquinoline (0.2 g, 0.784 mmol, 40.7% yield) and 5,6-dichloro-3-isothiocyanatoisoquinoline (0.23 g, 0.902 mmol, 46.8% yield) as yellow solids. 5,6-dichloro-3-isothiocyanatoisoquinoline: 1H NMR (500 MHz, $CDCl_3$) δ ppm 9.10 (s, 1 H), 7.87 (d, J=8.85 Hz, 1 H), 7.82 (s, 1 H), 7.66 (d, J=8.55 Hz, 1 H). MS (LC/MS) R.T.=3.63; $[M+H]^+$=255.0. 6,7-dichloro-3-isothiocyanatoisoquinoline: 1H NMR (500 MHz, $CDCl_3$) δ ppm 9.04 (s, 1 H), 8.11 (s, 1 H), 7.94 (s, 1 H), 7.37 (s, 1 H). MS (LC/MS) R.T.=3.42; $[M+H]^+$=255.0.

Step C: (R)—N-(6,7-Dichloroisoquinolin-3-yl)-4H-1'-azaspiro[oxazole-5,3'-bicyclo[2.2.2]octan]-2-amine

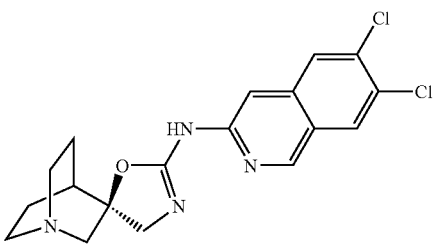

To 6,7-dichloro-3-isothiocyanatoisoquinoline (0.13 g, 0.510 mmol) in DMF (10 mL) was added cesium carbonate (0.42 g, 1.27 mmol) and (S)-3-(aminomethyl)quinuclidin-3-ol dihydrochloride (0.118 g, 0.515 mmol) at room temperature. The reaction was stirred at 70° C. for 2 hours. The reaction was cooled to room temperature and concentrated in vacuo. The crude urea was purified by chromatography (Biotage: 85% $CHCl_3$, 14% MeOH, 1% $NH_4OH$). The product was then treated with DMF (10 mL) and N,N'-diisopropylcarbodiimide (0.238 mL, 1.529 mmol). The reaction was heated to 90° C. for 18 hours. The reaction was cooled to room temperature and concentrated to yield the crude product, which was purified by chromatography (Biotage: 85% $CHCl_3$, 14% MeOH, 1% $NH_4OH$) to yield (R)—N-(6,7-dichloroisoquinolin-3-yl)-4H-1'-azaspiro[oxazole-5,3'-bicyclo[2.2.2]octan]-2-amine (0.12 g, 0.312 mmol, 61.2% yield). 1H NMR (500 MHz, $CDCl_3$) δ ppm 9.03 (s, 1 H), 8.87 (s, 1 H), 7.96 (s, 1 H), 7.83 (s, 1 H), 7.24 (s, 1 H), 3.88-4.06 (m, 1 H), 3.60-3.74 (m, 1 H), 3.42 (d, J=14.65 Hz, 1 H), 2.82-3.15 (m, 5 H), 2.23-2.34 (m, 1 H), 2.18 (s, 1 H), 1.72-1.87 (m, 1 H), 1.48-1.70 (m, 2 H). MS (LC/MS) R.T.=1.63; $[M+H]^+$=377.1.

EXAMPLE 281

(R)—N-(5,6-Dichloroisoquinolin-3-yl)-4H-1'-azaspiro[oxazole-5,3'-bicyclo[2.2.2]octan]-2-amine

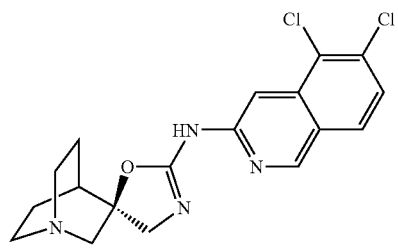

To 5,6-dichloro-3-isothiocyanatoisoquinoline (0.11 g, 0.431 mmol) in DMF (10 mL) was added cesium carbonate (0.351 g, 1.078 mmol) and (S)-3-(aminomethyl)quinuclidin-3-ol dihydrochloride (0.100 g, 0.435 mmol) at room temperature. The reaction was stirred at 70° C. for 2 hours. The reaction was cooled to room temperature and concentrated in vacuo. The crude urea was purified by chromatography (Biotage: 85% $CHCl_3$, 14% MeOH, 1% $NH_4OH$). The product was then treated with DMF (10 mL) and N,N'-diisopropylcarbodiimide (0.202 mL, 1.293 mmol). The reaction was heated to 90° C. for 18 hours. The reaction was cooled to room temperature and concentrated to yield the crude product. The crude product was purified by chromatography (Biotage: 85% CHCl$_3$, 14% MeOH, 1% NH$_4$OH) to yield (R)—N-(5,6-dichloroisoquinolin-3-yl)-4H-1'-azaspiro[oxazole-5,3'-bicyclo[2.2.2]octan]-2-amine (0.084 g, 0.218 mmol, 50.6% yield) as a yellow powder. 1H NMR (500 MHz, CDCl$_3$) δ ppm 9.09 (s, 1 H), 8.93 (s, 1 H), 7.63-7.82 (m, 2 H), 7.40 (d, J=8.55 Hz, 1 H), 3.99 (d, J=9.16 Hz, 1 H), 3.78 (d, J=8.85 Hz, 1 H), 3.51 (d, J=14.65 Hz, 1 H), 3.30 (d, J=14.65 Hz, 1 H), 2.90-3.23 (m, 4 H), 2.33-2.48 (m, 1 H), 2.29 (s, 1 H), 1.83-1.94 (m, 1 H), 1.62-1.83 (m, J=42.12 Hz, 2 H). MS (LC/MS) R.T.=1.57; [M+H]$^+$=377.1.

EXAMPLE 282

(R)—N-(3,4-Dichloropyridin-2-yl)-4H-1'-azaspiro[oxazole-5,3'-bicyclo[2.2.2]octan]-2-amine

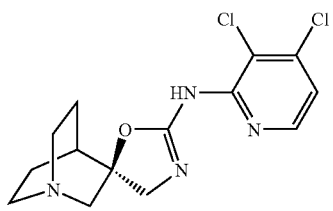

(R)—N-(3,4-Dichloropyridin-2-yl)-4H-1'-azaspiro[oxazole-5,3'-bicyclo[2.2.2]octan]-2-amine was prepared by the method of Example 267, starting from 2-amino-3,4-dichloropyridine. 1H NMR (500 MHz, DMSO-D$_6$) δ ppm 9.10 (s, 1 H), 8.08 (d, J=5.49 Hz, 1 H), 7.13 (d, J=5.49 Hz, 1 H), 3.86 (d, J=9.77 Hz, 1 H), 3.60 (d, J=9.77 Hz, 1 H), 2.96-3.05 (m, 2 H), 2.77 (t, J=7.63 Hz, 2 H), 2.66 (t, J=7.78 Hz, 2 H), 1.97-2.05 (m, 1 H), 1.86-1.94 (m, 1 H), 1.54-1.63 (m, 2 H), 1.43-1.51 (m, 1 H). MS (LC/MS) R.T.=0.78; [M+H]$^+$=327.0.

EXAMPLE 283

(R)—N-(3-Chloropyridin-2-yl)-4H-1'-azaspiro[oxazole-5,3'-bicyclo[2.2.2]octan]-2-amine

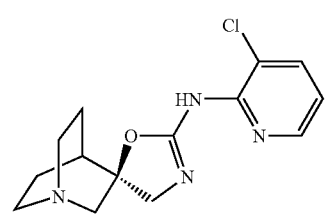

(R)—N-(3-Chloropyridin-2-yl)-4H-1'-azaspiro[oxazole-5,3'-bicyclo[2.2.2]octan]-2-amine was prepared by the method of Example 267, starting from 2-amino-3-chloropyridine. 1H NMR (500 MHz, DMSO-D$_6$) δ ppm 9.06 (s, 1 H), 8.14-8.19 (m, 1 H), 7.74-7.79 (m, J=7.78, 1.83, 1.83, 1.68 Hz, 1 H), 6.86-6.91 (m, 1 H), 3.81-3.89 (m, 1 H), 3.55-3.63 (m, 1 H), 2.96-3.04 (m, 2 H), 2.78 (t, J=7.63 Hz, 2 H), 2.67 (t, J=7.63 Hz, 2 H), 1.96-2.02 (m, 1 H), 1.86-1.92 (m, J=5.65, 3.20 Hz, 1 H), 1.54-1.63 (m, J=6.87, 3.66, 3.51 Hz, 2 H), 1.42-1.49 (m, 1 H). MS (LC/MS) R.T.=0.26; [M+H]$^+$=293.0.

EXAMPLE 284

(R)—N-(5-Chloro-3-fluoropyridin-2-yl)-4H-1'-azaspiro[oxazole-5,3'-bicyclo[2.2.2]octan]-2-amine

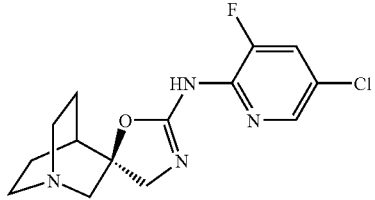

(R)—N-(5-Chloro-3-fluoropyridin-2-yl)-4H-1'-azaspiro[oxazole-5,3'-bicyclo[2.2.2]octan]-2-amine was prepared by the method of Example 267, starting from 2-amino-3-fluoro-5-chloropyridine. 1H NMR (500 MHz, DMSO-D$_6$) δ ppm 8.81 (s, 1 H), 8.05 (s, 1 H), 7.79 (d, J=10.07 Hz, 1 H), 3.83 (d, J=9.46 Hz, 1 H), 3.58 (d, J=9.46 Hz, 1 H), 2.99 (s, 2 H), 2.71-2.80 (m, 2 H), 2.61-2.70 (m, 2 H), 2.00 (s, 1 H), 1.83-1.92 (m, 1 H), 1.53-1.62 (m, 2 H), 1.41-1.50 (m, 1 H). MS (LC/MS) R.T.=0.52; [M+]$^+$=311.0

EXAMPLE 285

(R)—N-(6-Chloropyridin-2-yl)-4H-1'-azaspiro[oxazole-5,3'-bicyclo[2.2.2]octan]-2-amine

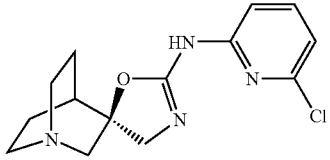

(R)—N-(6-Chloropyridin-2-yl)-4H-1'-azaspiro[oxazole-5,3'-bicyclo[2.2.2]octan]-2-amine was prepared by the method of Example 267, starting from 2-amino-6-chloropyridine. 1H NMR (500 MHz, DMSO-D$_6$) δ ppm 8.33-8.42 (m, 1 H), 7.60-7.68 (m, 1 H), 6.94 (d, J=7.02 Hz, 1 H), 6.72-6.81 (m, 1 H), 3.86 (d, J=9.46 Hz, 1 H), 3.57 (d, J=10.07 Hz, 1 H), 2.97 (s, 2 H), 2.69-2.78 (m, 2 H), 2.63-2.68 (m, J=7.63, 7.63 Hz, 2 H), 1.95-2.03 (m, 1 H), 1.83-1.92 (m, 1 H), 1.53-1.62 (m, 2 H), 1.41-1.49 (m, 1 H). MS (LC/MS) R.T.=0.43; [M+H]$^+$=293.0.

EXAMPLE 286

(R)—N-(4,6-Dichloropyridin-2-yl)-4H-1'-azaspiro[oxazole-5,3'-bicyclo[2.2.2]octan]-2-amine

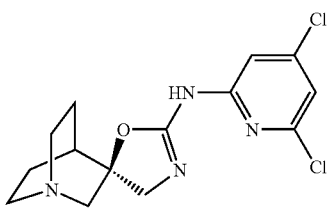

(R)—N-(4,6-Dichloropyridin-2-yl)-4H-1'-azaspiro[oxazole-5,3'-bicyclo[2.2.2]octan]-2-amine was prepared by the method of Example 267, starting from 2-amino-4,6-dichloropyridine. 1H NMR (500 MHz, DMSO-D6) δ ppm 8.43 (s, 1 H), 7.13 (s, 1 H), 6.84 (s, 1 H), 3.86 (d, J=9.77 Hz, 1 H), 3.59 (d, J=10.07 Hz, 1 H), 2.98 (s, 2 H), 2.58-2.86 (m, 4 H), 1.94-2.13 (m, 1 H), 1.78-1.95 (m, 1 H), 1.36-1.65 (m, 3 H). MS (LC/MS) R.T.=0.87; [M+H]⁺=327.0.

EXAMPLE 287

(R)—N-(2-Methoxy-3-4'-bipyridin-2'-yl)-4H-1'-azaspiro[oxazole-5,3'-bicyclo[2.2.2]octan]-2-amine

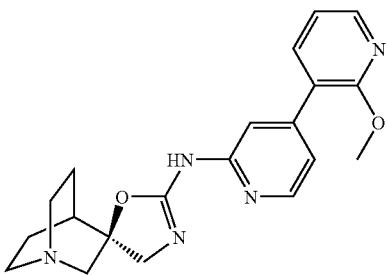

Step A:
N-(2,4-Dichlorobenzyl)-2,2-diethoxyacetimidamide

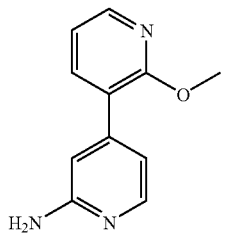

To 4-bromopyridin-2-amine (0.5 g, 2.8 mmol), 2-methoxypyridin-3-ylboronic acid (0.52 g, 3.4 mmol) in DMF (25 mL) was added 1N sodium carbonate (10 mL, 2.3 mmol), followed by 1,1'-bis(diphenylphosphino)ferrocene-palladium(II)dichloride dichloromethane complex (0.21 g, 0.26 mmol). The reaction mixture was stirred for 3 hours at 85° C. and then cooled to room temperature. The product was extracted with ethyl acetate (2×50 mL), dried with MgSO₄, filtered, and concentrated in vacuo. The crude product was purified by chromatography (Biotage: 100 to 90/10% ethyl acetate-ethyl acetate/methanol) to yield 2-methoxy-3,4'-bipyridin-2'-amine (0.53 g, 2.63 mmol, 93% yield) as a brown powder. The product was taken directly to the next step.

Step B: 2'-Isothiocyanato-2-methoxy-3,4'-bipyridine

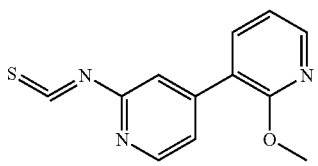

To 2-methoxy-3,4'-bipyridin-2'-amine (0.53 g, 2.63 mmol) in dichloromethane (20 mL) was added 1,1'-thiocarbonyldipyridin-2(1H)-one (0.62 g, 2.7 mmol) and the reaction mixture was stirred at 40° C. for 4 hours. The reaction was cooled to room temperature and chromatographed (Biotage: 10-100% ethyl acetate/hexanes) to yield 2'-isothiocyanato-2-methoxy-3,4'-bipyridine (0.46 g, 1.9 mmol, 71.8% yield). 1H NMR (500 MHz, DMSO-D6) δ ppm 8.67 (d, J=2.44 Hz, 1 H), 8.26 (dd, J=4.88, 1.53 Hz, 1 H), 8.15 (dd, J=8.24, 2.44 Hz, 1 H), 7.89 (dd, J=7.32, 1.53 Hz, 1 H), 7.48 (d, J=8.24 Hz, 1 H), 7.15 (dd, J=7.32, 4.88 Hz, 1 H), 3.91 (s, 3 H). MS (LC/MS) R.T.=2.87; [M+H]⁺=244.9.

Step D: (R)—N-(2-Methoxy-3-4'-bipyridin-2'-yl)-4H-1'-azaspiro[oxazole-5,3'-bicyclo[2.2.2]octan]-2-amine

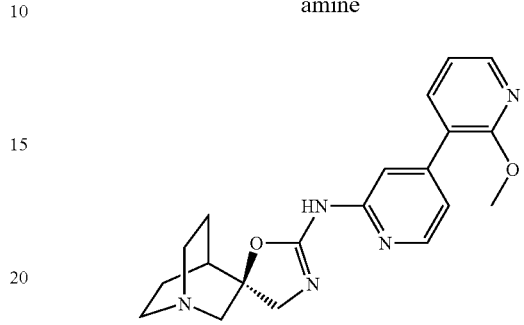

To 2'-isothiocyanato-2-methoxy-3,4'-bipyridine (0.09 g, 0.37 mmol) in DMF (20 mL) was added Et₃N (0.11 mL, 0.81 mmol) and (S)-3-(aminomethyl)quinuclidin-3-ol dihydrochloride (0.09 g, 0.37 mmol) at room temperature. The reaction was stirred at 70° C. for 2 hours. The reaction was cooled to room temperature and concentrated in vacuo. The crude urea was purified by chromatography (biotage: 85% CHCl₃, 14% MeOH, 1% NH₄OH) to yield the pure urea intermediate. The product was then treated with DMF (20 mL) and N,N'-diisopropylcarbodiimide (0.17 mL, 1.1 mmol). The reaction was heated to 90° C. for 18 hours. The reaction was cooled to room temperature and concentrated to yield the crude product. The crude product was purified by chromatography (Biotage: 85% CHCl₃, 14% MeOH, 1% NH₄OH) and the product-containing fractions were combined. LC/MS and 1HNMR indicated some impurities may be present. The impure product was subjected to reverse phase HPLC to yield (R)—N-(2-methoxy-3,4'-bipyridin-2'-yl)-4H-1'-azaspiro[oxazole-5,3'-bicyclo[2.2.2]octan]-2-amine (0.02 g, 0.05 mmol, 14.05% yield) as a white powder. 1H NMR (500 MHz, DMSO-D6) δ ppm 9.07 (s, 1H), 8.43 (s, 1H), 8.17 (dd, J=4.73, 1.68 Hz, 1H), 7.79 (d, J=7.32 Hz, 2H), 7.10 (dd, J=7.32, 4.88 Hz, 1H), 6.79-6.92 (m, 1H), 3.76-3.97 (m, 4H), 3.51-3.66 (m, 1H), 2.92-3.09 (m, 2H), 2.59-2.82 (m, 4H), 1.85-2.03 (m, 2H), 1.53-1.71 (m, 2H), 1.35-1.49 (m, 1H). MS (LC/MS) R.T.=1.05; [M+H]⁺=366.1.

EXAMPLE 288

(R)—N-(Benzo[d]oxazol-2-yl)-4H-1'-azaspiro[oxazole-5,3'-bicyclo[2.2.2]octan]-2-amine

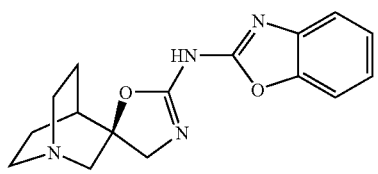

Step A: Benzo[d]oxazol-2-amine

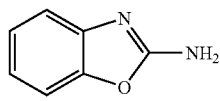

An oven dried round bottom flask was charged with di(1H-imidazol-1-yl)methanimine (500 mg, 3.10 mmol), 2-aminophenol (188 mg, 1.724 mmol) and anhydrous THF (20 ml) at room temperature. The resulting suspension was refluxed under $N_2$ for 2 hr to give complete conversion based on LC/MS. The solvent was removed in vacuo and the residue was purified on a Biotage Flash Collector, eluting with 30-80% EtOAc/Hexane (1200 ml) to afford the expected product, benzo[d]oxazol-2-amine (200 mg, 1.5 mmol, 87% yield), as a white solid. 1H NMR (400 MHz, CDCl$_3$) δ ppm 6.20 (br. s., 2H) 7.02-7.11 (m, 1H) 7.17-7.22 (m, 1H) 7.29 (d, J=7.53 Hz, 1H) 7.36 (d, J=7.03 Hz, 1H ). MS (LC/MS) R.T.=1.05; [M+H]$^+$=134.96.

Step B: Dimethyl benzo[d]oxazol-2-ylcarbonimidodithioate

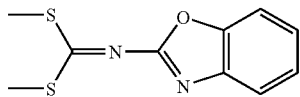

To a colorless solution of benzo[d]oxazol-2-amine (200 mg, 1.491 mmol) in DMF (10 ml) was added sodium hydroxide (20N, 149 μL, 2.98 mmol), to give a green suspension. The mixture was stirred for 15 min at room temperature. Carbon disulfide (225 μL, 3.73 mmol) was added to give a dark brown solution. The reaction was stirred for 15 min at room temperature, followed by the addition of sodium hydroxide (20N, 149 μL, 2.98 mmol) and stirred for an additional 10 min. Iodomethane (224 μL, 3.58 mmol) was then added dropwise. A green solid precipitated after 12 min. The reaction stirred for a further 2 hr. The solid was collected by filtration, washed with DMF (2×1 ml), H$_2$O (2×1 ml), dried under the house vacuum for 30 min and further dried in an oven in vacuo over night to afford the expected product, dimethyl benzo[d]oxazol-2-ylcarbonimidodithioate (258.5 mg, 1.085 mmol, 72.7% yield), as a white solid. 1H NMR (400 MHz, CDCl$_3$) δ ppm 2.70 (s, 6H) 7.24-7.34 (m, 2H) 7.45-7.50 (m, 1H) 7.66-7.74 (m, 1H). MS (LC/MS) R.T.=1.76, [M+H]$^+$=238.96.

Step C: (R)—N-(Benzo[d]oxazol-2-yl)-4H-1'-azaspiro[oxazole-5,3'-bicyclo[2.2.2]octan]-2-amine A 10 ml-vial was charged with (S)-3-(aminomethyl)quinuclidin-3-ol.2HCl salt (69.5 mg, 0.361 mmol), DMF (2 ml), DIEA (0.063 mL, 0.361 mmol) and Cs$_2$CO$_3$ (235 mg, 0.722 mmol) at room temperature, followed by dimethyl benzo[d]oxazol-2-ylcarbonimidodithioate (86 mg, 0.361 mmol). The resulting suspension was stirred at room temperature for 1 hr. LC/MS then indicated consumption of starting material. The mixture was diluted with MeOH and purified by preparative HPLC to afford the expected product, (R)—N-(benzo[d]oxazol-2-yl)-4H-1'-azaspiro[oxazole-5,3'-bicyclo[2.2.2]octan]-2-amine (101.5 mg, 0.323 mmol, 90% yield), as a tan gum. 1H NMR (400 MHz, Acetone-d$_6$) δ ppm 2.07-2.14 (m, 2H) 2.20 (ddd, J=8.78, 5.27, 3.26 Hz, 2H) 2.33-2.45 (m, 1H) 2.62 (d, J=2.26 Hz, 1H) 3.34-3.47 (m, 3H) 3.48-3.58 (m, 1H) 3.75-3.88 (m, 2H) 4.15 (d, J=10.54 Hz, 1H) 4.32 (d, J=10.54 Hz, 1H) 7.13-7.26 (m, 2H) 7.41 (td, J=3.70, 1.63 Hz, 1H) 9.24 (br, s, 1H). MS (LC/MS) R.T.=0.792, [M+H]$^+$=299.17.

EXAMPLE 289

(R)—N-(5-Chlorobenzo[d]oxazol-2-yl)-4H-1'-azaspiro[oxazole-5,3'-bicyclo[2.2.2]octan]-2-amine

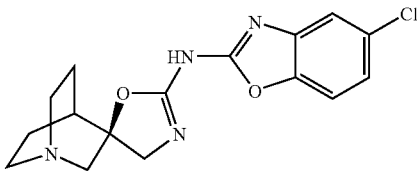

Step A: Dimethyl 5-chlorobenzo[d]oxazol-2-ylcarbonimidodithioate

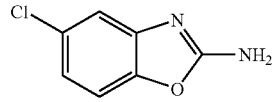

To a brown solution of 5-chlorobenzo[d]oxazol-2-amine (700 mg, 4.15 mmol) in DMF (5 ml) was added sodium hydroxide (20N, 415 μL, 8.30 mmol) to give a grey suspension. The mixture was stirred for 15 min at room temperature. Carbon disulfide (626 μL, 10.38 mmol) was added at room temperature to give a brown solution. The mixture was stirred for 15 min at room temperature, then sodium hydroxide (20N, 208 μL, 4.16 mmol) was added. After 10 min, iodomethane (623 μL, 9.97 mmol) was added dropwise. A grey solid came out from solution. The reaction was further stirred at room temperature for 2 hr. The solid was collected by filtration, washed with DMF/H$_2$O (50:50, 2×2 ml), dried under house vacuum for 30 min and further dried in an oven at 65° C. under vacuum for 1½ hr to afford the expected product, dimethyl 5-chlorobenzo[d]oxazol-2-ylcarbonimidodithioate (780 mg, 2.86 mmol, 68.9% yield), as an off-white solid which was pure enough to be used in next step. 1H NMR (400 MHz, DMSO-d$_6$) δ ppm 2.69 (s, 6H) 7.37 (dd, J=8.53, 2.26 Hz, 1H) 7.66 (d, J=9.03 Hz, 1H) 7.75 (d, J=1.76 Hz, 1H). MS (LC/MS) R.T.=1.44; [M+H]$^+$=272.9.

Step B: (R)—N-(5-Chlorobenzo[d]oxazol-2-yl)-4H-1'-azaspiro[oxazole-5,3'-bicyclo[2.2.2]octan]-2-amine

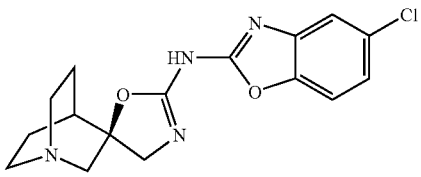

A 10 ml vial was charged with (S)-3-(aminomethyl)quinuclidin-3-ol.2HCl salt (106 mg, 0.550 mmol), DMF (2 ml), DIEA (0.096 mL, 0.550 mmol), and Cs$_2$CO$_3$ (358 mg, 1.100 mmol) at room temperature, followed by dimethyl 5-chlorobenzo[d]oxazol-2-ylcarbonimidodithioate (150 mg, 0.550 mmol). The resulting suspension was stirred at room temperature for 1 hr. LC/MS then indicated consumption of starting material. The reaction mixture was diluted with MeOH and purified by preparative HPLC to afford the expected product, (R)—N-(5-chlorobenzo[d]oxazol-2-yl)-4H-1'-azaspiro[oxazole-5,3'-bicyclo[2.2.2]octan]-2-amine (106.5 mg, 0.3 mmol, 53.0% yield), as a white solid. 1H NMR (400 MHz, Acetone-d$_6$) δ ppm 2.08-2.30 (m, 3H) 2.35-2.48 (m, 1H) 2.60-2.73 (m, 1H) 3.48 (qd, J=7.53, 7.28 Hz, 3H) 3.54-3.68 (m, 1H) 3.79-4.00 (m, 2H) 4.18 (d, J=10.54 Hz, 1H) 4.35 (d, J=10.54 Hz, 1H) 7.19 (dd, J=8.53, 2.01 Hz, 1H) 7.30-7.47 (m, 2H) 9.10 (br. s., 1H). MS(LC/MS) R.T.=1.56; [M+H]$^+$=333.13.

EXAMPLE 290

(R)—N-(Oxazolo[4,5-b]pyridin-2-yl)-4H-1'-azaspiro[oxazole-5,3'-bicyclo[2.2.2]octan]-2-amine

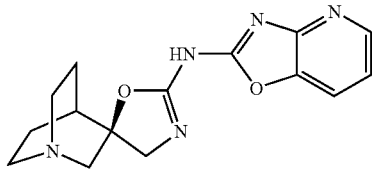

Step A: Oxazolo[4,5-b]pyridin-2-amine

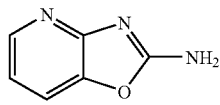

An oven dried round bottom flask was charged with di(1H-imidazol-1-yl)methanimine (500 mg, 3.10 mmol), 2-aminopyridin-3-ol (171 mg, 1.551 mmol) and anhydrous THF (20 ml) at room temperature. The resulting suspension was refluxed under N$_2$ for 1 hr. LC/MS indicated complete consumption of starting material. The solvent was removed in vacuo and the residue was used in the next step without further purification. MS(LC/MS) R.T.=0.235; [M+H]$^+$=136.09.

Step B: Dimethyl oxazolo[4,5-b]pyridin-2-ylcarbonimidodithioate

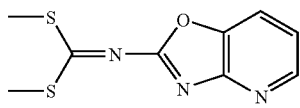

To the crude oxazolo[4,5-b]pyridin-2-amine (811 mg, 6 mmol) from step A, in DMF (12 ml), was added NaOH (20 N, 600 μL, 12.00 mmol) to give a tan solution which was stirred for 15 min at room temperature. Carbon disulfide (904 μL, 15.00 mmol) was then added to give an orange solution. The mixture was stirred for 15 min at room temperature, then NaOH (20 N, 600 μL, 12.00 mmol) was added and the stirring continued for 10 min to give a dark red solution. Iodomethane (900 μL, 14.40 mmol) was added dropwise, resulting in a yellow solid precipitating after 1 hr to give ~80% conversion. The mixture was diluted with MeOH and purified via preparative HPLC to afford the expected product, dimethyl oxazolo[4,5-b]pyridin-2-ylcarbonimidodithioate (35 mg, 0.146 mmol, 2.4% yield), as a white solid. 1H NMR (400 MHz, CDCl$_3$) δ ppm 2.71 (s, 6H) 7.22 (dd, J=8.03, 5.02 Hz, 1H) 7.72 (dd, J=8.03, 1.25 Hz, 1H) 8.49 (dd, J=5.02, 1.51 Hz, 1H). MS (LC/MS) R.T.=1.358; [M+H]=240.04.

Step C: (R)—N-(Oxazolo[4,5-b]pyridin-2-yl)-4H-1'-azaspiro[oxazole-5,3'-bicyclo[2.2.2]octan]-2-amine

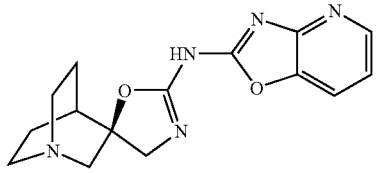

A 10 ml vial was charged with (S)-3-(aminomethyl)quinuclidin-3-ol.2HCl salt (8.53 mg, 0.044 mmol), DMF (2 ml), DIEA (7.74 μL, 0.04 mmol) and Cs$_2$CO$_3$ (28.9 mg, 0.089 mmol) at room temperature, followed by dimethyl oxazolo[4,5-b]pyridin-2-ylcarbonimidodithioate (10.6 mg, 0.044 mmol). The resulting suspension was stirred at room temperature for 1 hr. LC/MS indicated complete consumption of starting material. The reaction mixture was diluted with MeOH and purified via preparative HPLC to afford the expected product, (R)—N-(oxazolo[4,5-b]pyridin-2-yl)-4H-1'-azaspiro[oxazole-5,3'-bicyclo[2.2.2]octan]-2-amine (13 mg, 0.038 mmol, 86% yield), as a white solid. 1H NMR (400 MHz, Acetone-d$_6$) δ ppm 1.54-1.60 (m, 1H) 1.71-1.77 (m, 2H) 2.16-2.24 (m, 1H) 2.77-2.82 (m, 2H) 2.89 (t, J=7.91 Hz, 4H) 3.13-3.25 (m, 2H) 3.90 (d, J=10.29 Hz, 1H) 4.22 (d, J=10.29 Hz, 1H) 7.13 (dd, J=8.03, 5.02 Hz, 1H) 7.70 (dd, J=7.91, 1.13 Hz, 1H) 8.27 (dd, J=5.14, 1.13 Hz, 1H) 9.11 (br. s., 1H). MS (LC/MS) R.T.=0.443; [M+H]$^+$=300.16.

EXAMPLE 291

(2R)—N-(6,8-Dimethyl-3-isoquinolinyl)-4'H-spiro[4-azabicyclo[2.2.2]octane-2,5'-[1,3]oxazol]-2'-amine

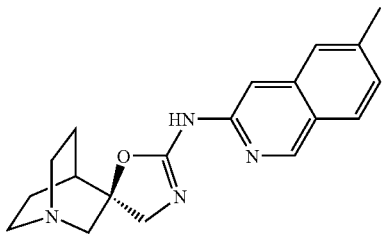

Step A: 6-Methylisoquinolin-3-amine

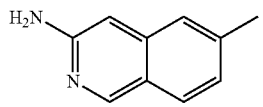

To a solution of methyl 2,2-diethoxyacetimidate (1.1 g, 6.82 mmol) in methanol (8 mL) was added p-tolylmethanamine (0.788 g, 6.50 mmol) dropwise at ambient temperature. The reaction flask was then placed into a preheated oil-bath and stirred at 70° C. for 16 h, then removed and allowed cooled. The volatiles were removed under reduced pressure and the crude material was added dropwise to sulfuric acid (5 mL) at ambient temperature. The reaction mixture was stirred for 72 h, then the flask was placed into an ice-water bath, diluted with water (50 mL), and slowly neutralized to pH=10 with sodium hydroxide (10 N). As the reaction mixture became basic, a grey precipitate formed. This precipitate was filtered, washed with water, and dried to afford 6-methylisoquinolin-3-amine (0.65 g, 63%), as a grey powder. 1H NMR (400 MHz, DMSO-$d_6$) δ ppm 8.73 (s, 1H), 7.69 (d, J=8.28 Hz, 1H), 7.29 (s, 1H), 7.00 (d, J=8.28 Hz, 1H), 5.81 (s, 1H), 2.40 (s, 3H). MS (LC/MS) R.T.=1.37; [M+H]$^+$=159.10.

Step B: 3-Isothiocyanato-6-methylisoquinoline

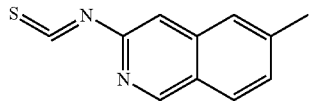

To a solution of 1,1'-thiocarbonyldipyridin-2(1H)-one (220 mg, 0.948 mmol) in dichloromethane (10 mL) at ambient temperature was added 6-methylisoquinolin-3-amine (125 mg, 0.790 mmol). The reaction mixture was placed into a preheated oil-bath and stirred at 40° C. for 18 h, then removed from the oil-bath and cooled to ambient temperature. The mixture was concentrated and the crude material was purified by silica gel chromatography (5-30% ethyl acetate in hexanes) to afford 3-isothiocyanato-6-methylisoquinoline (75 mg, 0.375 mmol, 47.4% yield), as an off-white solid. 1H NMR (400 MHz, CDCl$_3$) δ ppm 9.03 (s, 1H), 7.88 (d, J=8.24 Hz, 1H), 7.56 (s, 1H), 7.46 (dd, J=8.24, 1.53 Hz, 1H), 7.39 (s, 1H) 2.57 (s, 3H). MS (LC/MS) R.T.=1.92; [M+H]$^+$=201.13.

Step C: (R)—N-(6-Methylisoquinolin-3-yl)-4H-1'-azaspiro[oxazole-5,3'-bicyclo[2.2.2]octan]-2-amine

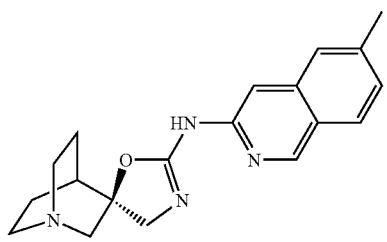

To (S)-3-(aminomethyl)quinuclidin-3-ol dihydrochloride (65.8 mg, 0.285 mmol) in N,N-dimethylformamide (6 mL) was added triethylamine (0.090 mL, 0.63 mmol) and 3-isothiocyanato-6-methylisoquinoline (57 mg, 0.285 mmol). The suspension was placed into a preheated oil-bath and stirred at 70° C. for 2 h and 30 min. N,N'-diisopropylcarbodiimide (0.177 mL, 1.14 mmol) was then added and the mixture was stirred at 85° C. for 16 h. The mixture was concentrated and purified by silica gel chromatography (0-40% [9:1 methanol:ammonium hydroxide] in chloroform) followed by purification by reverse phase preparatory HPLC (0-40% TFA-methanol-water). The solution of product was filtered through UCT Clean-up CHQAX15M25 cartridge with MeOH (3×10 ml) and concentrated to afford the expected product, (S)-1-((3-hydroxyquinuclidin-3-yl)methyl)-3-(6-methylisoquinolin-3-yl)thiourea, as a tan gum. 1H NMR (400 MHz, MeOD) δ ppm 9.11 (s, 1H), 8.02 (d, J=8.53 Hz, 1H), 7.80 (s, 1H), 7.74 (s, 1H), 7.47 (d, J=8.53 Hz, 1H), 4.47 (d, J=10.54 Hz, 1H), 4.31 (d, J=10.54 Hz, 1H), 4.10 (d, J=14.81 Hz, 1H), 3.92 (d, J=14.81 Hz, 1H), 3.53-3.71 (m, 2H), 3.27-3.51 (m, 3H), 2.84 (br.s, 1H), 2.55 (s, 3H), 2.48 (m, 1H), ) 2.10-2.30 (m, 3H). MS (LC/MS) R.T.=1.24; [M+H]$^+$=323.2.

EXAMPLE 292

(R)—N-(6-Bromoisoquinolin-3-yl)-4H-1'-azaspiro[oxazole-5,3'-bicyclo[2.2.2]octan]-2-amine

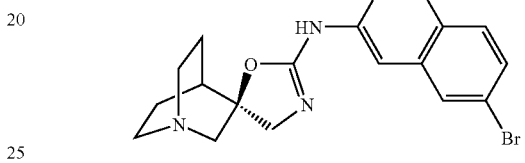

Step A:
N-(4-Bromobenzyl)-2,2-diethoxyacetimidamide

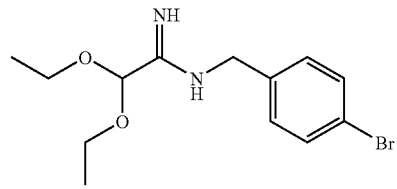

(4-Bromophenyl)methanamine hydrochloride (2.359 g, 10.39 mmol) and sodium methoxide (2.376 mL, 10.39 mmol) were added to a solution of methyl 2,2-diethoxyacetimidate (3.35 g, 20.78 mmol) in methanol (10 ml). The cloudy mixture was heated at 70 C for 1.5 h and the resulting yellow mixture was concentrated. The residue was purified by silica gel with 100% ethyl acetate to give a yellow viscous oil (2.04 g, 62%). $^1$H NMR (400 MHz, CDCl$_3$) δ ppm 7.47 (2H, d, J=8.56 Hz), 7.23 (2H, d, J=8.06 Hz), 6.76 (1H, br. s.), 5.31 (1H, br. s.), 4.94 (1H, br. s.), 4.45 (2H, br. s.), 3.47-3.77 (4H, m), 1.26 (6H, t, J=7.05 Hz). LCMS:R.T.=2.12; [M+2]$^+$=317.2.

Step B: 6-Bromoisoquinolin-3-amine

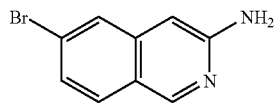

N-(4-bromobenzyl)-2,2-diethoxyacetimidamide (1.53 g, 4.85 mmol) in sulfuric acid (4 mL, 95-98%) was heated at 40 C for 14 h. The mixture was neutralized with 1M NaOH to pH 7 and the resulting suspension was filtered. The residue was purified by silica gel chromatography with 20-55% ethyl acetate in hexanes. The desired fractions were concentrated to give a brownish yellow solid (0.434 g, 40%). LCMS: R.T.=1.62; [M+2]⁺=225.1.

Step C: 6-Bromo-3-isothiocyanatoisoquinoline

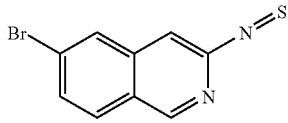

To a solution of 1,1'-thiocarbonyldipyridin-2(1H)-one (0.251 g, 1.080 mmol) in dichloromethane at room temperature was added 6-bromoisoquinolin-3-amine (0.241 g, 1.080 mmol). The solution was stirred at room temperature for 3 hours. LC/MS indicated formation of the desired product. The deep orange solution was purified by silica gel chromatography (0-10% ethyl acetate-hexanes) to afford: 6-bromo-3-isothiocyanatoisoquinoline (0.1 g, 0.377 mmol, 35% yield) as a yellow oil. R.T.=2.54; [M+H]⁺=267.04.

Step D: (R)—N-(6-bromoisoquinolin-3-yl)-4H-1'-azaspiro[oxazole-5,3'-bicyclo[2.2.2]octan]-2-amine

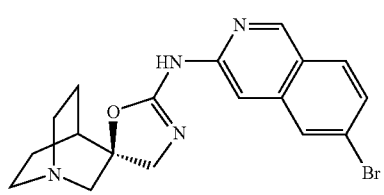

To (S)-3-(aminomethyl)quinuclidin-3-ol dihydrochloride (0.086 g, 0.377 mmol) in N,N-dimethylformamide (15 mL) was added Cs₂CO₃ (0.307 g, 0.943 mmol) and 6-bromo-3-isothiocyanatoisoquinoline (0.1 g, 0.377 mmol). The suspension was stirred at room temperature for 30 minutes. N,N'-Diisopropylcarbodiimide (0.176 mL, 1.132 mmol) was then added and the mixture was stirred for a further 18 hours. The mixture was concentrated and purified by silica gel chromatography (5-25% [9.5:0.5 methanol:ammonium hydroxide]-ethyl acetate) to afford (R)—N-(6-bromoisoquinolin-3-yl)-4H-1'-azaspiro[oxazole-5,3'-bicyclo[2.2.2]octan]-2-amine (0.054 g, 0.135 mmol, 36% yield) as a yellow solid. ¹H NMR (400 MHz, MeOD) δ ppm 9.04 (1H, s), 7.80-8.05 (2H, m), 7.55 (1H, dd, J=8.81, 1.76 Hz), 7.37 (1H, br. s.), 4.10 (1H, d, J=10.58 Hz), 3.87 (1H, d, J=10.83 Hz), 3.68-3.77 (1H, m), 3.56-3.67 (1H, m), 3.29-3.49 (4H, m), 2.45 (1H, br. s.), 2.28-2.41 (1H, m), 1.86-2.15 (3H, m). LCMS:R.T.=1.76; [M+]⁺=387.21.

EXAMPLE 293

(R)—N-(7-Bromoisoquinolin-3-yl)-4H-1'-azaspiro[oxazole-5,3'-bicyclo[2.2.2]octan]-2-amine

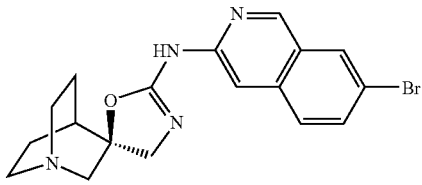

Step A:
N-(3-Bromobenzyl)-2,2-diethoxyacetimidamide

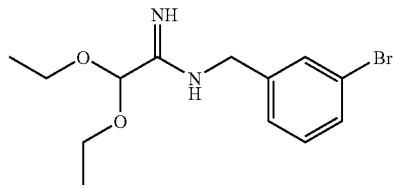

(3-Bromophenyl)methanamine hydrochloride (3.62 g, 15.64 mmol) and sodium methoxide (3.58 mL, 15.64 mmol) were added to a solution of methyl 2,2-diethoxyacetimidate (5.042 g, 31.3 mmol) in methanol (15 mL). The cloudy mixture was heated at 70 C for 1.5 h and the resulting yellow mixture was concentrated. The residue was purified by silica gel chromatography with 100% ethyl acetate. The desired fractions were concentrated to give a yellow viscous oil (2.5 g, 51%). LCMS:R.T.=2.11; [M+2]⁺=317.06.

Step B: 7-Bromoisoquinolin-3-amine and 5-bromoisoquinolin-3-amine

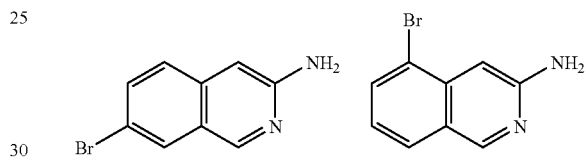

N-(3-Bromobenzyl)-2,2-diethoxyacetimidamide (2.5 g, 7.93 mmol) in sulfuric acid (5 mL, 95-98%) was heated at 40 C for 54 h. The mixture was neutralized with 10 M NaOH aqueous to pH 7 and the resulting suspension was filtered. The residue was purified by silica gel chromatography with 20-55% ethyl acetate in hexanes, then 100% ethyl acetate. The fractions were concentrated to give a brown solid containing a mixture of products. (1.0 g, 57%). LCMS: R.T.=1.56; [M+2]⁺=225.1. The mixture was used as is for the next step.

Step C: 7-Bromo-3-isothiocyanatoisoquinoline and 5-bromo-3-Isothiocyanatoisoquinoline

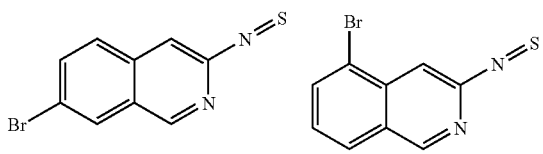

To a solution of 1,1'-thiocarbonyldipyridin-2(1H)-one 1.145 g, 4.93 mmol) in dichloromethane at room temperature was added the mixture of 7-bromoisoquinolin-3-amine and 5-bromoisoquinolin-3-amine from step B (1.0 g, 4.5 mmol). The orange solution was stirred at room temperature for 18 hours. LCMS indicated the formation of product. The deep orange solution was purified by silica gel chromatography (0-5% ethyl acetate-hexanes). The first product fractions were combined and concentrated in vacuo to afford 7-bromo-3-isothiocyanatoisoquinoline (0.27 g, 0.377 mmol, 22% yield) as a yellow solid. ¹H NMR (400 MHz, Acetone) δ ppm 9.19 (1H, s), 8.41 (1H, s), 7.86-8.02 (2H, m), 7.76 (1H, s). R.T.=4.28; [M+H]⁺=267.04. The second product fractions were combined and concentrated in vacuo to afford 5-bromo- 3-isothiocyanatoisoquinoline (0.25 g, 0.377 mmol, 21% yield) as a yellow solid. $^1$H NMR (400 MHz, Acetone) δ ppm 9.24 (1H, s), 8.23 (1H, d), 8.15 (1H, d), 7.81 (1H, s), 7.64 (1H, t). LCMS:R.T.=4.61; [M+H]$^+$=267.04.

Step D: (R)—N-(7-Bromoisoquinolin-3-yl)-4H-1'-azaspiro[oxazole-5,3'-bicyclo[2.2.2]octan]-2-amine

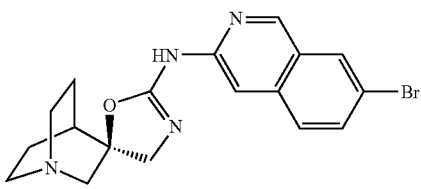

To (S)-3-(aminomethyl)quinuclidin-3-ol dihydrochloride (0.207 g, 0.905 mmol) in N,N-dimethylformamide (20 mL) was added Cs$_2$CO$_3$ (0.737 g, 2.263 mmol) and 7-bromo-3-isothiocyanatoisoquinoline (0.24 g, 0.905 mmol). The suspension was stirred at room temperature for 30 minutes. N,N'-Diisopropylcarbodiimide (0.423 mL, 2.72 mmol) was then added and the mixture was stirred at room temperature for 18 hours. The mixture was concentrated and purified by silica gel chromatography using 5-15% [9:1 methanol:ammonium hydroxide] in ethyl acetate. The desired fractions were concentrated and further purified using 5-15% [9.5:0.5 methanol:ammonium hydroxide] in ethyl acetate to afford ((R)—N-(7-bromoisoquinolin-3-yl)-4H-1'-azaspiro[oxazole-5,3'-bicyclo[2.2.2]octan]-2-amine (0.061 g, 0.156 mmol, 17% yield) as a yellow solid. $^1$H NMR (400 MHz, MeOD) δ ppm 8.96 (1H, s), 8.12 (1H, s), 7.66 (2H, s), 7.32 (1H, s), 4.01 (1H, d), 3.73 (1H, d), 3.35-3.42 (1H, m), 3.22-3.29 (1H, m), 2.84-3.17 (4H, m), 2.13-2.35 (2H, m), 1.62-1.96 (3H, m). LCMS: R.T.=1.76; [M+]$^+$=387.21.

EXAMPLE 294

((R)—N-(5-Bromoisoquinolin-3-yl)-4H-1'-azaspiro[oxazole-5,3'-bicyclo[2.2.2]octan]-2-amine

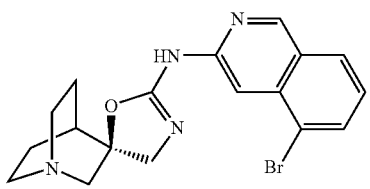

To (S)-3-(aminomethyl)quinuclidin-3-ol dihydrochloride (0.207 g, 0.905 mmol) in N,N-dimethylformamide (20 mL) was added Cs$_2$CO$_3$ (0.737 g, 2.263 mmol) and 5-bromo-3-isothiocyanatoisoquinoline (0.24 g, 0.905 mmol). The suspension was stirred at room temperature for 30 minutes. N,N'-Diisopropylcarbodiimide (0.423 mL, 2.72 mmol) was then added and the mixture was stirred at room temperature for 18 hours. The mixture was concentrated and purified by silica gel chromatography (5-15% [9.5:0.5 methanol:ammonium hydroxide]-ethyl acetate). The desired fractions were concentrated and further purified using 5-15% [9.5:0.5 methanol:ammonium hydroxide] in ethyl acetate to afford (R)—N-(5-bromoisoquinolin-3-yl)-4H-1'-azaspiro[oxazole-5,3'-bicyclo[2.2.2]octan]-2-amine (0.248 g, 0.634 mmol, 70% yield) as a yellow solid. $^1$H NMR (400 MHz, MeOD) δ ppm 8.99 (1H, s), 7.91 (2H, dd), 7.55 (1H, br. s.), 7.28 (1H, t), 3.96 (1H, d), 3.65 (1H, d), 3.17-3.26 (1H, m), 3.03-3.13 (1H, m), 2.70-2.99 (4H, m), 2.03-2.30 (2H, m), 1.47-1.87 (3H, m). LCMS:R.T.=1.69; [M+2]$^+$=389.21.

EXAMPLE 295

(2R)—N-(6,8-Dimethyl-3-isoquinolinyl)-4'H-spiro[4-azabicyclo[2.2.2]octane-2,5'-[1,3]oxazol]-2'-amine

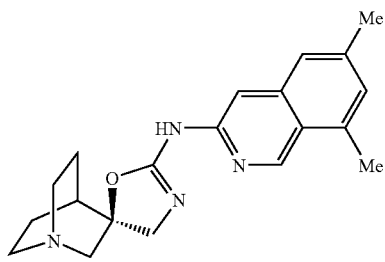

Step A: 6,8-Dimethylisoquinolin-3-amine

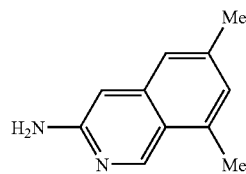

To a solution of methyl 2,2-diethoxyacetimidate (1.5 g, 9.3 mmol) in methanol (4.9 mL) was added (2,4-dimethylphenyl)methanamine (1.2 g, 8.9 mmol) dropwise at ambient temperature. The reaction flask was then placed into a preheated oil-bath and stirred at 70° C. for 16 h, then cooled and the volatiles removed under reduced pressure. The crude material was added dropwise to sulfuric acid (19.7 mL) at ambient temperature and stirred for 72 h. The flask was then placed into an ice-water bath, diluted with water (50 mL), and slowly neutralized to pH=10 with sodium hydroxide (10 N). As the reaction mixture became basic, an orange precipitate formed. This precipitate was filtered, washed with water, and dried to afford 6,8-dimethylisoquinolin-3-amine (1.37 g, 7.95 mmol, 90%). 1H NMR (400 MHz, MeOD) δ ppm 8.82 (s, 1H), 7.17 (s, 1H), 6.90 (s, 1H), 6.72 (s, 1H), 2.61 (s, 3H), 2.37 (s, 3H). MS (LC/MS) R.T.=0.77; [M+H]$^+$=173.15.

Step B: 3-Isothiocyanato-6,8-dimethylisoquinoline

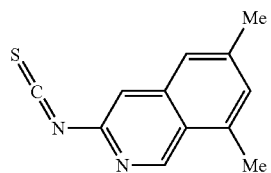

To a solution of 1,1'-thiocarbonyldipyridin-2(1H)-one (1.35 g, 5.8 mmol) in dichloromethane (19 mL) at ambient temperature was added 6,8-dimethylisoquinolin-3-amine (1 g, 5.8 mmol). The reaction mixture was placed into a preheated oil-bath and stirred at 40° C. for 18 h, then cooled, concentrated, and the crude material was purified by silica gel chromatography (10-35% ethyl acetate in hexanes) to afford 3-isothiocyanato-6,8-dimethylisoquinoline (93.7 mg, 0.437 mmol, 8%) as a yellow solid. 1H NMR (400 MHz, CDCl$_3$) δ ppm 9.20 (s, 1H), 7.36-7.44 (m, 2H), 7.23 (s, 1H), 2.75 (s, 3H), 2.51 (s, 3H). MS (LC/MS) R.T.=2.03; [M+H]$^+$=215.1.

Step C: (2R)—N-(6,8-Dimethyl-3-isoquinolinyl)-4'H-spiro[4-azabicyclo[2.2.2]octane-2,5'-[1,3]oxazol]-2'-amine

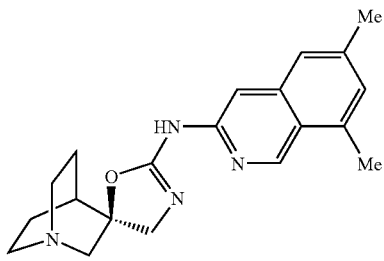

To (S)-3-(aminomethyl)quinuclidin-3-ol dihydrochloride (99 mg, 0.43 mmol) in N,N-dimethylformamide (1.4 mL) was added triethylamine (0.18 mL, 1.3 mmol) and 3-isothiocyanato-6,8-dimethylisoquinoline (93 mg, 0.43 mmol). The suspension was placed into a preheated oil-bath and stirred at 70° C. for 2 h and 30 min. N,N'-Diisopropylcarbodiimide (0.27 mL, 1.7 mmol) was then added and the mixture was stirred at 85° C. for 16 h. The mixture was concentrated and purified by silica gel chromatography (0-40% [9:1 methanol:ammonium hydroxide] in chloroform) followed by purification by reverse phase preparative HPLC (0-40% [0.1% TFA]-methanol-water) to afford (2R)—N-(6,8-dimethyl-3-isoquinolinyl)-4'H-spiro[4-azabicyclo[2.2.2]octane-2,5'-[1,3]oxazol]-2'-amine as the trifluoroacetic acid salt (24 mg, 0.053 mmol, 12% yield) as a white solid. 1H NMR (400 MHz, MeOD) δ ppm 9.29 (s, 1H), 7.54 (s, 1H), 7.43 (s, 1H), 7.34 (s, 1H), 4.38 (d, J=11.04 Hz, 1H), 4.17 (d, J=11.04 Hz, 1H), 3.94-4.10 (m, 1H), 3.86 (dd, J=15.06, 2.26 Hz, 1H), 3.51-3.67 (m, 1H), 3.37-3.51 (m, 3H), 2.77 (s, 3H), 2.73 (d, J=3.51 Hz, 1H), 2.48-2.57 (m, 3H), 2.30-2.46 (m, 1H), 1.94-2.28 (m, 3H). MS (LC/MS) R.T.=0.90; [M+H]$^+$=337.38.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula I, or a stereoisomer thereof,

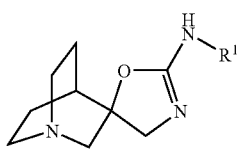

I wherein

R$^1$ is selected from the group consisting of isoxazolyl, pyrazolyl, oxazolyl, thiazolyl, imidazolyl, oxadiazolyl, thiadiazolyl, triazolyl, pyridinyl, pyrazinyl, pyridazinyl, pyrimidinyl, triazinyl, quinolinyl, isoquinolinyl, quinoxalinyl, quinazolinyl, naphthyridinyl, indazolyl, indolyl, 2-indolonyl, benzisoxazolyl, benzoisothiazolyl, benzoxazolyl, benzothiazolyl, benzimidazolyl, furopyridinyl, thienopyridinyl, thienopyrimidinyl, isothiazolopyridinyl, thiazolopyridinyl, thiazolopyridinonyl, thiazolopyrazinyl, thiazolopyrimidinyl, triazolopyridinyl, triazolopyrazinyl, pyrrolotriazinyl, 5,6-dihydrobenzo[h]quinazolinyl, 5H-chromeno[4,3-d]pyrimidinyl, 6,7-dihydro-5H-cyclopenta[d]pyrimidinyl, 5,6,7,8-tetrahydroquinazolinyl, 7,8-dihydroquinazolin-5(6H)-onyl, and tetrahydrobenzothiazolyl, and is substituted with 0-3 substituents independently selected from the group consisting of C$_{1-4}$alkyl, C$_{3-7}$cycloalkyl, C$_{1-4}$haloalkyl, C$_{1-4}$alkoxy, C$_{1-4}$haloalkoxy, C$_{3-7}$cycloalkoxy, C$_{1-4}$alkylthio, phenoxy, benzyloxy, halo, hydroxy, cyano, C$_{1-4}$alkylsulfonyl, NR$^2$R$^3$, pyrrolidinonyl, methylenedioxy, furyl, thienyl, triazolyl, pyrimidinyl, naphthyl, C$_{1-4}$alkylamido, CONR$^2$R$^3$, pyridyl, phenyl, and benzyl, and where pyridyl, phenyl and benzyl are substituted with 0-2 substituents independently selected from the group consisting of halo, C$_{1-4}$alkyl, C$_{1-4}$alkoxy, C$_{1-4}$haloalkyl, C$_{1-4}$haloalkoxy, and NR$^2$R$^3$;

R$^2$ is hydrogen, C$_{1-4}$alkyl, C$_{1-4}$hydroxyalkyl, or C$_{1-4}$aminoalkyl;

R$^3$ is hydrogen, C$_{1-4}$alkyl, C$_{1-4}$hydroxyalkyl, or C$_{1-4}$aminoalkyl;

or R$_2$ and R$_3$ taken together with the nitrogen atom to which they are attached is azetidinyl, pyrrolidinyl, piperidinyl, piperazinyl, N-(C$_{1-4}$alkyl)piperazinyl, morpholinyl, or homopiperidinyl;

or a pharmaceutically acceptable salt thereof.

2. A compound of claim 1 where R$^1$ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, pyrrolidinoylthiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, methoxypyridinylpyridazinyl, pyrimidinyl, (bromo)(isopropyl)pyrimidinyl, (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, phenylpyrazinyl, and dimethyltriazinyl;

or a pharmaceutically acceptable salt thereof.

3. A compound of claim 1 where $R^1$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, pyrrolidinoylbenzothiazolyl, methylsulfonylbenzothiazolyl, chlorothiazolopyridinyl, dimethylthiazolopyridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, chlorotriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy)thiazolopyrimidinyl, quinolinyl, bromoquinolinyl, fluoroquinolinyl, methylquinolinyl, (methyl)(methoxy)quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo [h] quinazolinyl, 5 H-chromeno[4,3-d]pyrimidinyl, 6,7-dihydro-5 H-cyclopenta[d]pyrimidinyl, 5,6,7,8-tetrahydroquinazolinyl, and 7,8-dihydroquinazolin-5(6H)-onyl;

or a pharmaceutically acceptable salt thereof.

4. A compound of claim 1 where $R^1$ is selected from the group consisting of phenylthiazolyl, (chloro)(methyl)pyridinyl, (bromo)(phenyl)pyrimidinyl, methoxypyrimidinyl, difluoromethoxypyrimidinyl, difluoroethoxypyrimidinyl, cyclopentoxypyrimidinyl, (methylphenyl)pyrimidinyl, (methoxyphenyl)pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinoinyl, and quinazolinyl;

or a pharmaceutically acceptable salt thereof.

5. The stereoisomer of claim 1 according to Formula Ia;

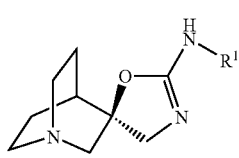

Ia or a pharmaceutically acceptable salt thereof.

6. A compound of claim 5 where $R^1$ is selected from the group consisting of dimethylisoxazolyl, (methyl)(phenyl)isoxazolyl, methylpyrazolyl, dimethylpyrazolyl, thienylpyrazolyl, methoxyphenylpyrazolyl, thiazolyl, bromothiazolyl, cyanothiazolyl, methylthiazolyl, dimethylthiazolyl, (methyl)(phenyl)thiazolyl, isopropylthiazolyl, butylthiazolyl, benzylthiazolyl, methoxyphenylmethylthiazolyl, phenylthiazolyl, chlorophenylthiazolyl, methoxyphenylthiazolyl, (methoxyphenyl)(methyl)thiazolyl, pyridinylthiazolyl, (phenyl)(methyl)imidazolyl, methyloxadiazolyl, ethyloxadiazolyl, methylthiadiazolyl, fluorophenylthiadiazolyl, furylthiadiazolyl, (dimethylcarboxamido)(methyl)thiazolyl, pyrrolidinoylthiazolyl, phenyltriazolyl, pyridinyl, bromopyridinyl, chloropyridinyl, (chloro)(fluoro)pyridinyl, (chloro)(methyl)pyridinyl, dichloropyridinyl, fluoropyridinyl, cyanopyridinyl, (cyano)(methyl)pyridinyl, (cyano)(dimethyl)pyridinyl, methoxypyridinyl, (methylpyrrolidinyl)pyridinyl, phenylpyridinyl, methoxypyridinylpyridinyl, pyridazinyl, bromopyridazinyl, chloropyridazinyl, methylpyridazinyl, methoxypyridazinyl, methylthiopyridazinyl, pyrrolidinylpyridazinyl, pyrrolidinonylpyridazinyl, phenylpyridazinyl, pyridinylpyridazinyl, methoxypyridinylpyridazinyl, pyrimidinyl, (bromo)(isopropyl)pyrimidinyl (bromo)(dimethyl)pyrimidinyl, (bromo)(cyclopropyl)pyrimidinyl, (bromo)(methoxy)pyrimidinyl, (bromo)(phenyl)pyrimidinyl, (bromo)(pyridinyl)pyrimidinyl, chloropyrimidinyl, (chloro)(dimethyl)pyrimidinyl, (methyl)(methoxy)pyrimidinyl, methylpyrimidinyl, ethylpyrimidinyl, (methyl)(phenyl)pyrimidinyl, dimethylpyrimidinyl, butylpyrimidinyl, isopropylpyrimidinyl, cyclopropylpyrimidinyl, methoxypyrimidinyl, dimethoxypyrimidinyl, isopropoxypyrimidinyl, cyclopentoxypyrimidinyl, difluoromethoxypyrimidinyl, trifluoroethoxypyrimidinyl, phenoxypyrimidinyl, methylthiopyrimidinyl, phenylpyrimidinyl, chlorophenylpyrimidinyl, methylphenylpyrimidinyl, methoxyphenylpyrimidinyl, (phenyl)(triazolyl)pyrimidinyl, pyridinylpyrimidinyl, methoxypyridinylpyrimidinyl, methoxypyrimidinylpyrimidinyl, naphthylpyrimidinyl, pyrazinyl, bromopyrazinyl, (bromo)(methoxy)pyrazinyl, chloropyrazinyl, methylpyrazinyl, dimethylpyrazinyl, butylpyrazinyl, cyanopyrazinyl, methoxypyrazinyl, isopropoxypyrazinyl, trifluoromethylpyrazinyl, phenylpyrazinyl, and dimethyltriazinyl;

or a pharmaceutically acceptable salt thereof.

7. A compound of claim 5 where $R^1$ is selected from the group consisting of dimethylpyridinoisoxazolyl, benzoxazolyl, chlorobenzoxazolyl, fluorophenylbenzoxazolyl, ethylphenylbenzoxazolyl, dimethylaminophenylbenzoxazolyl, pyridinylbenzoxazolyl, benzothiazolyl, acetamidobenzothiazolyl, bromobenzothiazolyl, chlorobenzothiazolyl, (chloro)(methyl)benzothiazolyl, (chloro)(methoxy)benzothiazolyl, fluorobenzothiazolyl, difluorobenzothiazolyl, cyanobenzothiazolyl, methylbenzothiazolyl, dimethylbenzothiazolyl, (methyl)(methoxy)benzothiazolyl, ethylbenzothiazolyl, trifluoromethylbenzothiazolyl, hydroxybenzothiazolyl, methoxybenzothiazolyl, ethoxybenzothiazolyl, isopropoxybenzothiazolyl, trifluoromethoxybenzothiazolyl, difluoromethoxybenzothiazolyl, dimethoxybenzothiazolyl, morpholinylbenzothiazolyl, pyrrolidinoylbenzothiazolyl, methylsulfonylbenzothiazolyl, chlorothiazolopyridinyl, dimethylthiazolopyridinyl, benzyloxythiazolopyridinyl, difluoromethoxythiazolopyridinyl, benzotriazolyl, indolonyl, indazolyl, bromoindazolyl, chloroindazolyl, fluoroindazolyl, (methyl)(methoxy)indazolyl, methoxyindazolyl, trifluoromethylindazolyl, trifluoromethoxyindazolyl, difluoromethoxyindazolyl, benzimidazolyl, fluorobenzimidazolyl, methylbenzimidazolyl, (methyl)(methoxy)benzimidazolyl, methoxybenzimidazolyl, tetrahydrobenzothiazolyl, furopyridinyl, dimethylfuropyrimidinyl, thienopyrimidinyl, isopropylthienopyrimidinyl, dimethylthienopyrimidinyl, chlorotriazolopyridinyl, methyltriazolopyridinyl, trifluoromethyltriazolopyridinyl, methoxytriazolopyridinyl, triazolopyrazinyl, bromopyrrolotriazinyl, dimethylaminothiazolopyrimidinyl, thiazolopyazinyl, bromothiazolopyazinyl, methoxythiazolopyazinyl, methylthiothiazolopyazinyl, methoxythiazolopyrimidinyl, (methyl)(methoxy)thiazolopyrimidinyl, quinolinyl, bromoquinolinyl, fluoroquinolinyl, methylquinolinyl, (methyl)(methoxy)quinolinyl, isoquinolinyl, bromoisoquinolinyl, dichloroisoquinolinyl, methylisoquinolinyl, dimethylisoquinolinyl, quinoxalinyl, chloroquinoxalinyl, methylquinoxalinyl, methoxyquinoxalinyl, quinazolinyl, bromoquinazolinyl, naphthyridinyl, 5,6-dihydrobenzo [h]quinazolinyl, 5H-chromeno[4,3-d]pyrimidinyl, 6,7-dihydro-5H-cyclopenta [d]pyrimidinyl, 5,6,7,8-tetrahydroquinazolinyl, and 7,8-dihydroquinazolin-5(6H)-onyl;

or a pharmaceutically acceptable salt thereof.

8. A compound of claim 5 where $R^1$ is selected from the group consisting of phenylthiazolyl, (chloro)(methyl)pyridinyl, (bromo)(phenyl)pyrimidinyl, methoxypyrimidinyl, difluoromethoxypyrimidinyl, difluoroethoxypyrimidinyl, cyclopentoxypyrimidinyl, (methylphenyl)pyrimidinyl, (methoxyphenyl)pyrimidinyl, bromopyrazinyl, chloropyrazinyl, methylthiopyrazinyl, methoxybenzothiazolyl, ethoxybenzothiazolyl, difluoromethoxybenzothiazolyl, thiazolopyridinonyl, trifluoromethylindazolyl, benzimidazolyl, isoquinolinyl, and quinazolinyl;

or a pharmaceutically acceptable salt thereof.

9. A compound of claim 5 where $R^1$ is selected from the group consisting of thiazolyl, pyridinyl, pyridazinyl, pyrimidinyl, pyrazinyl, benzothiazolyl, thiazolopyridinyl, indazolyl, benzimidazolyl, isoquinolinyl, and quinazolinyl, and is substituted with 0-3 substituents independently selected from the group consisting of $C_{1-4}$alkyl, $C_{3-7}$cycloalkyl, $C_{1-4}$haloalkyl, $C_{1-4}$ alkoxy, $C_{1-4}$haloalkoxy, $C_{3-7}$ cycloalkoxy, $C_{1-4}$ alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$ alkyl, $C_{1-4}$ alkoxy, $C_{1-4}$haloalkyl, $C_{1-4}$haloalkoxy, and $NR^2R^3$;

or a pharmaceutically acceptable salt thereof.

10. A compound of claim 9 where $R^1$ is selected from the group consisting of pyridinyl, pyrimidinyl, pyrazinyl, thiazolopyridinyl, and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$ alkoxy, $C_{1-4}$haloalkoxy, $C_{3-7}$ cycloalkoxy, $C_{1-4}$ alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$ alkyl, $C_{1-4}$ alkoxy, $C_{1-4}$haloalkyl, $C_{1-4}$haloalkoxy, and $NR^2R^3$;

or a pharmaceutically acceptable salt thereof.

11. A compound of claim 10 where $R^1$ is selected from the group consisting of pyridinyl and isoquinolinyl, and is substituted with 0-3 substituents independently selected from the group consisting of $C_{1-4}$alkyl, $C_{3-7}$cycloalkyl, $C_{1-4}$haloalkyl, $C_{1-4}$alkoxy, $C_{1-4}$haloalkoxy, $C_{3-7}$cycloalkoxy, $C_{1-4}$alkylthio, phenoxy, benzyloxy, halo, hydroxy, cyano, $C_{1-4}$alkylsulfonyl, $NR^2R^3$, pyrrolidinonyl, methylenedioxy, furyl, thienyl, triazolyl, pyrimidinyl, naphthyl, $C_{1-4}$alkylamido, $CONR^2R^3$, pyridyl, phenyl, and benzyl, and where pyridyl, phenyl and benzyl are substituted with 0-2 substituents independently selected from the group consisting of halo, $C_{1-4}$alkyl, $C_{1-4}$alkoxy, $C_{1-4}$haloalkyl, $C_{1-4}$haloalkoxy, and $NR^2R^3$;

or a pharmaceutically acceptable salt thereof.

12. A compound selected from the group consisting of

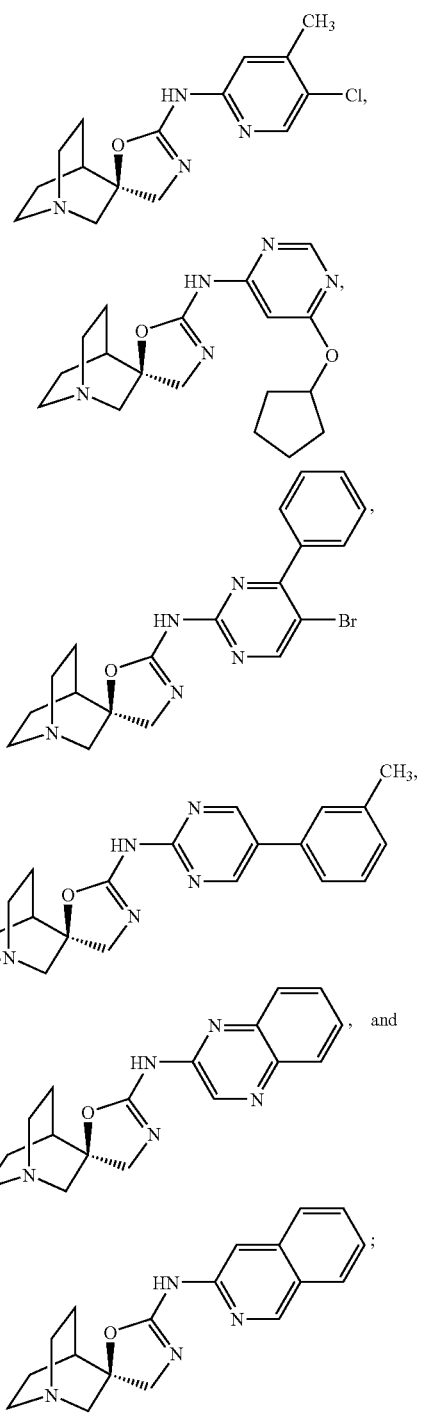

or a pharmaceutically acceptable salt thereof.

13. A pharmaceutical composition comprising a therapeutically effective amount of a compound of claim 1, or a pharmaceutically acceptable salt thereof, and a pharmaceutically acceptable carrier.

14. A method for the treatment of schizophrenia or Alzheimer's Disease which comprises administering to a patient a therapeutically affective amount of a compound of claim 1.

* * * * *

UNITED STATES PATENT AND TRADEMARK OFFICE
CERTIFICATE OF CORRECTION

PATENT NO. : 7,863,291 B2  Page 1 of 1
APPLICATION NO. : 12/423299
DATED : January 4, 2011
INVENTOR(S) : James H. Cook, II et al.

It is certified that error appears in the above-identified patent and that said Letters Patent is hereby corrected as shown below:

In the Claims:

Claim 6:

Column 326, line 24, after "pyrimidinyl", insert -- , --.

Signed and Sealed this
Twenty-ninth Day of November, 2011

David J. Kappos
*Director of the United States Patent and Trademark Office*